United States Patent
Bruce et al.

(10) Patent No.: US 10,588,980 B2
(45) Date of Patent: Mar. 17, 2020

(54) FATTY ACIDS AND THEIR USE IN CONJUGATION TO BIOMOLECULES

(71) Applicant: Novartis AG, Basel (CH)

(72) Inventors: Alexandra Marshall Bruce, Cambridge, MA (US); Aimee Richardson Usera, Winchester, MA (US); Frederic Zecri, Brookline, MA (US); Jun Yuan, Boston, MA (US); Changgang Lou, Portage, MI (US); Aaron Kanter, Somerville, MA (US)

(73) Assignee: Novartis AG, Basel (CH)

( * ) Notice: Subject to any disclaimer, the term of this patent is extended or adjusted under 35 U.S.C. 154(b) by 522 days.

(21) Appl. No.: 14/738,272

(22) Filed: Jun. 12, 2015

(65) Prior Publication Data
US 2016/0030585 A1 Feb. 4, 2016

Related U.S. Application Data

(60) Provisional application No. 62/107,016, filed on Jan. 23, 2015, provisional application No. 62/082,327, filed on Nov. 20, 2014, provisional application No. 62/015,862, filed on Jun. 23, 2014.

(51) Int. Cl.

| | | |
|---|---|---|
| A61K 47/54 | (2017.01) | |
| A61K 38/08 | (2019.01) | |
| A61K 38/16 | (2006.01) | |
| A61K 38/17 | (2006.01) | |
| A61K 38/18 | (2006.01) | |
| A61K 38/22 | (2006.01) | |
| A61K 45/06 | (2006.01) | |
| C07C 55/02 | (2006.01) | |
| C07C 55/22 | (2006.01) | |
| C07C 57/02 | (2006.01) | |
| C07C 57/18 | (2006.01) | |
| C07C 59/245 | (2006.01) | |
| C12N 15/113 | (2010.01) | |

(52) U.S. Cl.
CPC ............ *A61K 47/543* (2017.08); *A61K 38/08* (2013.01); *A61K 38/164* (2013.01); *A61K 38/1709* (2013.01); *A61K 38/1825* (2013.01); *A61K 38/1841* (2013.01); *A61K 38/2221* (2013.01); *A61K 45/06* (2013.01); *A61K 47/542* (2017.08); *C07C 55/02* (2013.01); *C07C 55/22* (2013.01); *C07C 57/02* (2013.01); *C07C 57/18* (2013.01); *C07C 59/245* (2013.01); *C12N 15/113* (2013.01); *C12N 2310/14* (2013.01); *C12N 2310/351* (2013.01)

(58) Field of Classification Search
None
See application file for complete search history.

(56) References Cited

U.S. PATENT DOCUMENTS

| 6,420,543 B1 | 7/2002 | Lee et al. |
| 6,500,638 B2 | 12/2002 | Hudson et al. |
| | (Continued) | |

FOREIGN PATENT DOCUMENTS

| CN | 101852804 B1 | 12/2013 |
| EP | 0 837 881 B1 | 9/2004 |
| | (Continued) | |

OTHER PUBLICATIONS

Amaya et al. ('Solid-phase synthesis of carbohydrate cluster on tree-type linker with three types of orthogonally cleavable part' SYNLETT No. 3 2004 pp. 503-507).*

(Continued)

*Primary Examiner* — Ronald T Niebauer
(74) *Attorney, Agent, or Firm* — Judith D. Kuntz

(57) ABSTRACT

The invention provides a conjugate comprising a biomolecule linked to a fatty acid via a linker wherein the fatty acid has the following Formulae A1, A2 or A3:

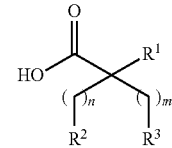

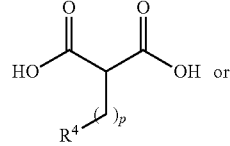

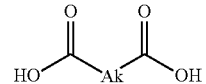

wherein $R^1$, $R^2$, $R^3$, $R^4$, Ak, n, m and p are defined herein. The invention also relates to a method for manufacturing the conjugate of the invention such as GDF15 conjugate, and its therapeutic uses such as treatment or prevention of metabolic disorders or diseases, type 2 diabetes mellitus, obesity, pancreatitis, dyslipidemia, alcoholic and nonalcoholic fatty liver disease/steatohepatitis and other progressive liver diseases, insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, diabetic complications (including but not limited to chronic kidney disease), neuropathy, gastroparesis and other metabolic disorders. The present invention further provides a combination of pharmacologically active agents and a pharmaceutical composition.

24 Claims, 1 Drawing Sheet

Specification includes a Sequence Listing.

(56) References Cited

U.S. PATENT DOCUMENTS

| | | |
|---|---|---|
| 6,521,227 B1 | 2/2003 | Hudson et al. |
| 6,974,684 B2 | 12/2005 | Anderson et al. |
| 7,157,235 B2 | 1/2007 | Breit et al. |
| 8,192,735 B2 | 6/2012 | Breit et al. |
| 8,673,848 B2 | 3/2014 | Zecri et al. |
| 8,921,307 B2 | 12/2014 | Zecri et al. |
| 8,946,146 B2 | 2/2015 | Breit et al. |
| 9,067,971 B2 | 6/2015 | Zecri et al. |
| 9,161,966 B2 | 10/2015 | Matern et al. |
| 9,175,076 B2 | 11/2015 | Lerner et al. |
| 9,266,925 B2 | 2/2016 | Zecri et al. |
| 9,272,019 B2 | 3/2016 | Shaw et al. |
| 9,399,676 B2 | 7/2016 | Schurpf et al. |
| 9,550,819 B2 | 1/2017 | Lindhout et al. |
| 9,573,995 B2 | 2/2017 | Schurpf et al. |
| 9,580,500 B2 | 2/2017 | Schurpf et al. |
| 9,683,018 B2 | 6/2017 | Zecri et al. |
| 9,683,019 B2 | 6/2017 | Zecri et al. |
| 9,714,276 B2 | 7/2017 | Xiong et al. |
| 9,725,505 B2 | 8/2017 | Lerner et al. |
| 9,758,576 B2 | 9/2017 | Schurpf et al. |
| 9,758,577 B2 | 9/2017 | Schurpf et al. |
| 9,827,291 B2 | 11/2017 | Matern et al. |
| 9,828,415 B2 | 11/2017 | Matern et al. |
| 9,834,586 B2 | 12/2017 | Lindhout et al. |
| 9,862,752 B2 | 1/2018 | Xiong et al. |
| 9,908,919 B2 | 3/2018 | Zecri et al. |
| 9,920,118 B2 | 3/2018 | Shen et al. |
| 9,931,372 B2 | 4/2018 | Kanter et al. |
| 9,956,264 B2 | 5/2018 | Shaw et al. |
| 9,982,017 B2 | 5/2018 | Zecri et al. |
| 9,993,494 B2 | 6/2018 | Appleman et al. |
| 10,005,829 B2 | 6/2018 | Zecri et al. |
| 10,172,948 B2 | 1/2019 | Hu et al. |
| 2003/0166903 A1 | 9/2003 | Astromoff et al. |
| 2009/0004181 A1 | 1/2009 | Breit |
| 2009/0142338 A1* | 6/2009 | Levetan ............ A61K 39/39558 424/133.1 |
| 2010/0179093 A1* | 7/2010 | Danho ............... A61K 38/2271 514/1.1 |
| 2010/0317048 A1* | 12/2010 | Fujimoto ......... G01N 33/54393 435/29 |
| 2011/0123454 A1 | 5/2011 | Breit et al. |
| 2011/0257022 A1 | 10/2011 | Hess et al. |
| 2011/0263443 A1 | 10/2011 | Hess et al. |
| 2011/0286976 A1 | 11/2011 | Nielsen et al. |
| 2011/0319324 A1 | 12/2011 | Lin et al. |
| 2013/0040884 A1 | 2/2013 | Lau et al. |
| 2013/0137763 A1 | 5/2013 | van Delft et al. |
| 2013/0196899 A1 | 8/2013 | Zecri et al. |
| 2014/0193427 A1 | 7/2014 | Lerner et al. |
| 2014/0213511 A1 | 7/2014 | Matern et al. |
| 2014/0378665 A1 | 12/2014 | Xiong et al. |
| 2015/0017166 A1 | 1/2015 | Baker et al. |
| 2015/0017192 A1 | 1/2015 | Usera et al. |
| 2015/0023960 A1 | 1/2015 | Lindhout et al. |
| 2015/0030594 A1 | 1/2015 | Yuan et al. |
| 2015/0031604 A1 | 1/2015 | Zecri et al. |
| 2015/0183861 A1 | 7/2015 | Breit et al. |
| 2015/0224132 A1 | 8/2015 | Appleman et al. |
| 2015/0307575 A1 | 10/2015 | Xiong |
| 2015/0337034 A1 | 11/2015 | Schurpf et al. |
| 2015/0361175 A1 | 12/2015 | Schurpf et al. |
| 2015/0361421 A1 | 12/2015 | Schurpf et al. |
| 2016/0015784 A1 | 1/2016 | Shaw et al. |
| 2016/0030585 A1 | 2/2016 | Barnes et al. |
| 2016/0031960 A1 | 2/2016 | Lindhout et al. |
| 2016/0031980 A1 | 2/2016 | Schurpf et al. |
| 2016/0083465 A1 | 3/2016 | Lerner et al. |
| 2016/0120999 A1 | 5/2016 | Shen et al. |
| 2016/0129082 A1 | 5/2016 | Matern et al. |
| 2016/0129083 A1 | 5/2016 | Shaw et al. |
| 2016/0166634 A1 | 6/2016 | Caplan et al. |
| 2016/0168213 A1 | 6/2016 | Xiong et al. |
| 2016/0200787 A1 | 7/2016 | Matern et al. |
| 2016/0213743 A1 | 7/2016 | Kanter et al. |
| 2016/0289292 A1 | 10/2016 | Kumar et al. |
| 2016/0289298 A1 | 10/2016 | Kumar et al. |
| 2016/0289318 A1 | 10/2016 | Schurpf et al. |
| 2016/0289320 A1 | 10/2016 | Breit et al. |
| 2016/0298093 A1 | 10/2016 | Kumar et al. |
| 2017/0073406 A1 | 3/2017 | Schurpf et al. |
| 2017/0095572 A1 | 4/2017 | Hu et al. |
| 2017/0107248 A1 | 4/2017 | Lou et al. |
| 2017/0137506 A1 | 5/2017 | Gyuris et al. |
| 2017/0190767 A1 | 7/2017 | Schurpf et al. |
| 2017/0204149 A1 | 7/2017 | Chopra et al. |
| 2017/0210798 A1 | 7/2017 | Schurpf et al. |
| 2017/0233443 A1 | 8/2017 | Zecri et al. |
| 2017/0246249 A1 | 8/2017 | Lindhout et al. |
| 2017/0291929 A1 | 10/2017 | Xiong et al. |
| 2017/0334971 A1 | 11/2017 | Shaw |
| 2018/0016332 A1 | 1/2018 | Schurpf et al. |
| 2018/0022798 A1 | 1/2018 | Schurpf et al. |
| 2018/0079790 A1 | 3/2018 | Xiong et al. |
| 2018/0099025 A1 | 4/2018 | Matern et al. |
| 2018/0100003 A1 | 4/2018 | Matern et al. |
| 2018/0134761 A1 | 5/2018 | Lindhout et al. |
| 2019/0000923 A1 | 1/2019 | Chuktow et al. |

FOREIGN PATENT DOCUMENTS

| | | |
|---|---|---|
| EP | 0833912 B1 | 2/2009 |
| EP | 2694092 B1 | 1/2017 |
| EP | 2830646 B1 | 3/2018 |
| EP | 2950807 B1 | 3/2018 |
| KR | 101727506 A1 | 5/2017 |
| WO | 9618730 A1 | 6/1996 |
| WO | 1996/041815 A2 | 12/1996 |
| WO | 9700958 A1 | 1/1997 |
| WO | 9811224 A1 | 3/1998 |
| WO | 0177288 A2 | 10/2001 |
| WO | WO 01/81928 A1 | 11/2001 |
| WO | 2005068663 A1 | 7/2005 |
| WO | 2005099747 A1 | 10/2005 |
| WO | WO 2005/099746 A1 | 10/2005 |
| WO | 2007062526 A1 | 6/2007 |
| WO | WO 2009/021293 A1 | 2/2009 |
| WO | 2009042798 A1 | 4/2009 |
| WO | 2011146902 A1 | 11/2011 |
| WO | WO 2012/138919 A2 | 10/2012 |
| WO | WO 2012/140647 A2 | 10/2012 |
| WO | WO 2013/113008 A1 | 8/2013 |
| WO | 2013130684 A1 | 9/2013 |
| WO | WO 2013/148117 A1 | 10/2013 |
| WO | 2014100689 A1 | 6/2014 |
| WO | WO 2014/083505 A1 | 6/2014 |
| WO | WO 2014/120619 A2 | 8/2014 |
| WO | 2014182676 A2 | 11/2014 |
| WO | 2015003122 A1 | 1/2015 |
| WO | 2015013168 | 1/2015 |
| WO | WO 2015/006728 A2 | 1/2015 |
| WO | WO 2015/013168 A1 | 1/2015 |
| WO | WO 2015/013169 A2 | 1/2015 |
| WO | WO 2015/017710 A1 | 2/2015 |
| WO | 2015120350 A2 | 8/2015 |
| WO | 2015171691 A1 | 11/2015 |
| WO | 2015196145 A1 | 12/2015 |
| WO | 2015197446 A1 | 12/2015 |
| WO | 2015200078 A1 | 12/2015 |
| WO | WO 2015/198199 A1 | 12/2015 |
| WO | WO 2015/200080 A1 | 12/2015 |
| WO | 2016018931 A1 | 2/2016 |
| WO | 2016069921 A1 | 5/2016 |
| WO | 2016069925 A1 | 5/2016 |
| WO | 2016102580 A1 | 6/2016 |
| WO | 2016164089 A2 | 10/2016 |
| WO | 2016164497 A1 | 10/2016 |
| WO | 2016164501 A1 | 10/2016 |
| WO | 2016164503 A1 | 10/2016 |
| WO | 2017066525 A1 | 4/2017 |
| WO | 2017108941 A1 | 6/2017 |
| WO | 2017109706 A1 | 6/2017 |

(56) References Cited

FOREIGN PATENT DOCUMENTS

| WO | 2017121865 A1 | 7/2017 |
|---|---|---|
| WO | 2017147742 A1 | 9/2017 |
| WO | 2017152105 A1 | 9/2017 |

OTHER PUBLICATIONS

Correa et al. ('A graph-structural method for prediction of polymer properties' Brazilian Journal of Chemical Engineering v21(4) Oct.-Dec. 2004 pp. 621-628).*
Folda et al. ('Polyreactions in oriented systems: Formation of oriented polypeptides and polyamides in monolayers and liposomes' Macromolecular Rapid Communications v3 1982 pp. 167-174) (Year: 1982).*
CAS Registry No. 4371-64-6 (2005).
CAS Registry No. 4475-23-4 (2005).
CAS Registry No. 4475-04-1 (2005).
CAS Registry No. 3578-47-0 (2005).
CAS Registry No. 4371-74-8 (2005).
CAS Registry No. 78651-82-8 (2004).
CAS Registry No. 760-54-3 (2005).
CAS Registry No. 3974-36-5 (2005).
CAS Registry No. 4475-27-8 (2005).
Ceder, Olof, "Pimaricin. II. High Pressure—High Temperature Hydrogenation Studies," *Acta Chem. Scand.* 18(1):93-97, XP055223487 (1964).
Chae, Su Young, et al., "The fatty acid conjugated exendin-4 analogs for type 2 antidiabetic therapeutics," *Journal of Controlled Release* 144:10-16 (2010).
Hackett, Michael J., et al., "A Dicarboxylic Fatty Acid Derivative of Paclitaxel for Albumin-Assisted Drug Delivery," *Journal of Pharmaceutical Sciences* 101(9):3292-3304 (2012).
International Search Report and Written Opinion for International Application No. PCT/US2015/036328, dated Nov. 2, 2015 (13 pages).
Lefort, D., et al., "Free-radical addition of alcohols and acids to 10-undecenoic esters," *Bulletin of the Academy of the USSR, Division of Chemical Sciences*, 16(3):623-627, XP055223363 (1967).
Lim, Sung in, et al., "Site-specific fatty acid-conjugation to prolong protein half-life in vivo," *Journal of Controlled Release* 170:219-225 (2013).
Mädler, Stefanie, et al., "Chemical cross-linking with NHS esters: a systematic study on amino acid reactivities," *J. Mass. Spectrom.* 44(5):694-706 (May 2009).
Mentinova, Marija, et al., "Solution versus Gas-Phase Modification of Peptide Cations with NHS-Ester Reagents," *J. Am. Soc. Mass. Spectrom.* 23(2):282-289 (Feb. 2012).
Registry No. 4371-72-6, entered into Registry file on STN on Nov. 16, 1984.
Registry No. 4423-21-6, entered into Registry file on STN on Nov. 16, 1984.
Registry No. 4471-14-1, entered into Registry file on STN on Nov. 16, 1984.
Registry No. 4472-96-2, entered into Registry file on STN on Nov. 16, 1984.
Registry No. 5860-64-0, entered into Registry file on STN on Nov. 16, 1984.
Registry No. 60398-89-2, entered into Registry file on STN on Nov. 16, 1984.
Registry No. 74965-69-8, entered into Registry file on STN on Nov. 16, 1984.
Registry No. 74965-70-1, entered into Registry file on STN on Nov. 16, 1984.
Registry No. 1352061-05-2, entered into Registry file on STN on Dec. 29, 2011.
Registry No. 96873-04-0, entered into Registry file on STN on Jun. 23, 1985.
Registry No. 96976-48-6, entered into Registry file on STN on Jul. 1, 1985.
Registry No. 183602-08-6, entered into Registry file on STN on Dec. 5, 1996.
Registry No. 859201-82-4, entered into Registry file on STN on Aug. 9, 2005.
Registry No. 1026947-38-5, entered into Registry file on STN on Jun. 10, 2008.
Wang, Qin, et al., "Pharmacological properties of hydrophilic and lipophilic derivatives of octreotate," *Nuclear Medicine and Biology* 31(1):21-30 (2004).
Hsiao, E.C., et al., "Characterization of Growth-Differentiation Factor 15, a Transforming Growth Factor Beta Superfamily Member Induced Following Liver Injury," Molecular and Cellular Biology, 20(10), 3743-3751, (2000).
Cong "Site specific PEGylation at Histidine Tags", Bioconjugate Chemistry, 23(2):248-263, (2012).
Marti-Centelles et al.: "Recognition of Free Tryptophan in Water by Synthetic Pseudopeptides: Fluorescence and Thermodynamic Studies", Chemistry—A European Journal, 20(24):7465-7478, (2014).
Hudak et al.: "Synthesis of heterobifunctional protein fusions using copper-free click chemistry and the aldehyde tag", Angewandte Chemie, International Edition, 51(17):4161-4165, S4161/1-S4161116, (2012).
Strekowski et al: "Synthesis of a functionalized cyanine dye for covalent labeling of biomolecules with a pH-sensitive chromophore", Heterocyclic Communications, 10(6):381-382 (full text of previously reviewed abstract), (2004).
Bootcov, et al., "MIC-1, a novel marcophage inhibitory cytokine, is a divergent member of the TGF-Beta superfamily", Proc. Natl. Acad. Sci. USA, 94:11514-11519, (1997).
Zimmers et al., "Growth Differentiation Factor-15:Induction in Liver Injury Through p53 and Tumor Necrosis Factor-Independent Mechanisms", Journal of Surgical Research, 130(1):45-51, (2006).
Knock et al.: "N-acylation of Aplysia Egg-laying Hormone with Biotin", The Journal of Biological Chemistry, 266 (36):24413-24419, (1991).
Baker et al.: "N-terminally PEGylated Human interferon-beta-1a with Improved pharmacokinetic properties and in Vivo Efficacy in a Melanoma Angiogenesis Model", Bioconjugate Chem., 17:179-188, (2006).
Novak et al.: "A top-down method for determination of residue-specific solvent accessibility in proteins", Journal of Mass Spectrometry, 39:322-328, (2004).
"Preferentially biotinylated N-terminal alpha-amino groups in peptides", Thermos Scientific, 2009, XP002742982; URL: https://tools.lifetechnologies.com/content/sfs/brochures/TR0046-Biotynylate-N-terminus.pdf.
Jia et al.: "Cardiovascular effects of a Pegylated apelin", Peptides, vol. 28(1):181-188, (2012).
Lee et al.: "N-terminal site specific mono-PEGylation of epidermal growth factor", Pharmaceutical Research, 20 (5):818-825, (2003).
Chan et al.: "Modification of N-terminal [alpha]-amino groups of peptides and proteins using ketenes", JACS, 134 (5):2589-2598, (2012).
Harris et al., "Effect of pegylation on pharmaceuticals," Nat Rev. Drug Discov., 2(3):214-21, (2003).
Zhao et al., "Linear and branched bicin linkers for releasable PEGylation of macromolecules: controlled release in vivo and in vitro from mono- and multi-PEGylated proteins," Bioconjug Chem., 17(2):341-51, (2006).
Delgado et al., "The uses and properties of PEG-linked proteins," Crit. Rev. Ther. Drug Carrier Syst., 9(3-4):249-304, (1992).
Chatrath, et al., "Dyslipidemia in Patients with nonalcoholic Fatty Liver Disease", Seminars in Liver Disease, 32:22-29, (2012).
Chitturi et al., "NASH and Insulin Resistance: Insulin Hypersecretion and Specific Association with the Insulin Resistance Syndrome", Hepatology, 35(2):373-379, (2002).
Chuang et al., "Pharmaceutical Strategies Utilizing Recombinant Human Serum Albumin", Pharmaceutical Research, 19(5):569-577, (2002).
Correa et al., "A Graph-Structural Method for Prediction of Polymer Properties", Brazilian Journal of Chemical Engineering, 21(4):621-628, (2004).

(56) References Cited

OTHER PUBLICATIONS

Amaya et al., "Solid-Phase synthesis of Carbohydrate Cluster on Tree-Type Linker with Three Types of Orthogonally Cleavable Part", Synlett, 3:503-507, (2004).
Folda et al., "Polyreactions in Oriented Systems, 29: Formation of Oriented Polypeptides and Polyamides in Monolayers and Liposomes", Macromolecular Rapd Communications, 3(3):167-174, (1982).

* cited by examiner

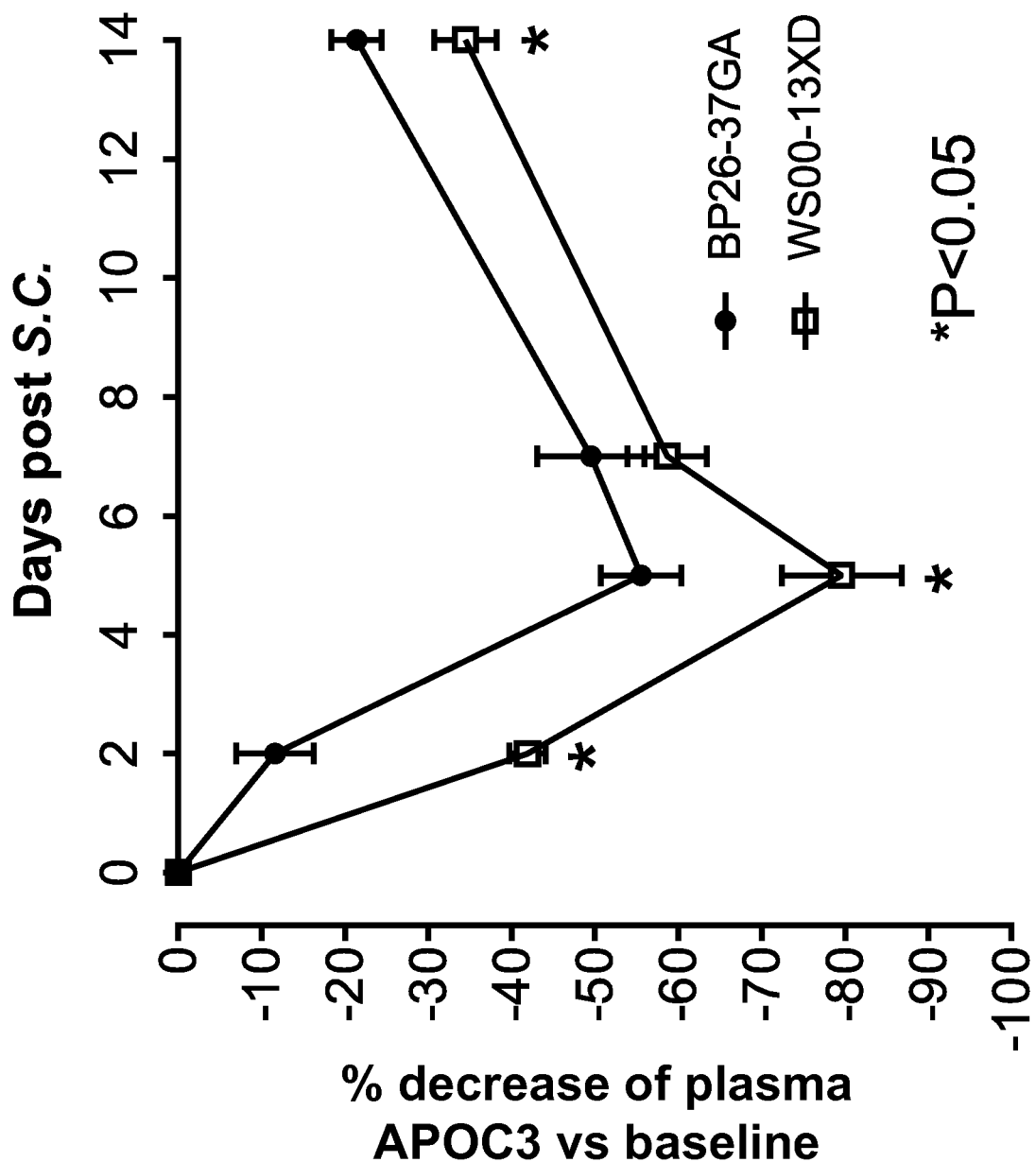

SEQUENCE LISTING

<160> NUMBER OF SEQ ID NOS: 36

<210> SEQ ID NO 1
<211> LENGTH: 119
<212> TYPE: PRT
<213> ORGANISM: Artificial Sequence
<220> FEATURE:
<223> OTHER INFORMATION: His-hGDF15

<400> SEQUENCE: 1

Met His His His His His His Ala Arg Asn Gly Asp His Cys Pro Leu
1               5                   10                  15

Gly Pro Gly Arg Cys Cys Arg Leu His Thr Val Arg Ala Ser Leu Glu
            20                  25                  30

Asp Leu Gly Trp Ala Asp Trp Val Leu Ser Pro Arg Glu Val Gln Val
        35                  40                  45

```
Thr Met Cys Ile Gly Ala Cys Pro Ser Gln Phe Arg Ala Ala Asn Met
    50                  55                  60

His Ala Gln Ile Lys Thr Ser Leu His Arg Leu Lys Pro Asp Thr Val
 65                  70                  75                  80

Pro Ala Pro Cys Cys Val Pro Ala Ser Tyr Asn Pro Met Val Leu Ile
                85                  90                  95

Gln Lys Thr Asp Thr Gly Val Ser Leu Gln Thr Tyr Asp Asp Leu Leu
            100                 105                 110

Ala Lys Asp Cys His Cys Ile
            115

<210> SEQ ID NO 2
<211> LENGTH: 120
<212> TYPE: PRT
<213> ORGANISM: Artificial Sequence
<220> FEATURE:
<223> OTHER INFORMATION: GDF15 mutant, Intermediate 52:
      M-(His)6-M-hGDF15

<400> SEQUENCE: 2

Met His His His His His His Met Ala Arg Asn Gly Asp His Cys Pro
 1               5                  10                  15

Leu Gly Pro Gly Arg Cys Cys Arg Leu His Thr Val Arg Ala Ser Leu
                20                  25                  30

Glu Asp Leu Gly Trp Ala Asp Trp Val Leu Ser Pro Arg Glu Val Gln
            35                  40                  45

Val Thr Met Cys Ile Gly Ala Cys Pro Ser Gln Phe Arg Ala Ala Asn
 50                  55                  60

Met His Ala Gln Ile Lys Thr Ser Leu His Arg Leu Lys Pro Asp Thr
 65                  70                  75                  80

Val Pro Ala Pro Cys Cys Val Pro Ala Ser Tyr Asn Pro Met Val Leu
                85                  90                  95

Ile Gln Lys Thr Asp Thr Gly Val Ser Leu Gln Thr Tyr Asp Asp Leu
            100                 105                 110

Leu Ala Lys Asp Cys His Cys Ile
            115                 120

<210> SEQ ID NO 3
<211> LENGTH: 120
<212> TYPE: PRT
<213> ORGANISM: Artificial Sequence
<220> FEATURE:
<223> OTHER INFORMATION: GDF15 mutant, Intermediate 53: His-dGDF15

<400> SEQUENCE: 3

Met His His His His His His Ala His Ala Arg Asp Gly Cys Pro Leu
 1               5                  10                  15

Gly Glu Gly Arg Cys Cys Arg Leu Gln Ser Leu Arg Ala Ser Leu Gln
                20                  25                  30

Asp Leu Gly Trp Ala Asn Trp Val Val Ala Pro Arg Glu Leu Asp Val
            35                  40                  45

Arg Met Cys Val Gly Ala Cys Pro Ser Gln Phe Arg Ser Ala Asn Thr
 50                  55                  60

His Ala Gln Met Gln Ala Arg Leu His Gly Leu Asn Pro Asp Ala Ala
 65                  70                  75                  80

Pro Ala Pro Cys Cys Val Pro Ala Ser Tyr Glu Pro Val Val Leu Met
                85                  90                  95
```

His Gln Asp Ser Asp Gly Arg Val Ser Leu Thr Pro Phe Asp Asp Leu
            100                 105                 110

Val Ala Lys Asp Cys His Cys Val
        115                 120

<210> SEQ ID NO 4
<211> LENGTH: 112
<212> TYPE: PRT
<213> ORGANISM: Artificial Sequence
<220> FEATURE:
<223> OTHER INFORMATION: GDF15 mutant, Intermediate 54:
      MH-(199-308)-hGDF15

<400> SEQUENCE: 4

Met His Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 5
<211> LENGTH: 112
<212> TYPE: PRT
<213> ORGANISM: Artificial Sequence
<220> FEATURE:
<223> OTHER INFORMATION: GDF15 mutant, Intermediate 55:
      AH-(199-308)-hGDF15

<400> SEQUENCE: 5

Ala His Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 6
<211> LENGTH: 112
<212> TYPE: PRT
<213> ORGANISM: Artificial Sequence
<220> FEATURE:
<223> OTHER INFORMATION: GDF15 mutant, Intermediate 56:
      MHA-(200-308)-hGDF15

<400> SEQUENCE: 6

```
Met His Ala Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 7
<211> LENGTH: 112
<212> TYPE: PRT
<213> ORGANISM: Artificial Sequence
<220> FEATURE:
<223> OTHER INFORMATION: GDF15 mutant, Intermediate 57:
    AHA-(200-308)-hGDF15

<400> SEQUENCE: 7

```
Ala His Ala Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 8
<211> LENGTH: 226
<212> TYPE: PRT
<213> ORGANISM: Artificial Sequence
<220> FEATURE:
<223> OTHER INFORMATION: Fragment of FGF23 peptide

<400> SEQUENCE: 8

```
Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80
```

```
Ser His Tyr Phe Asp Pro Glu Asn Cys Arg Phe Gln His Gln Thr Leu
                 85                  90                  95

Glu Asn Gly Tyr Asp Val Tyr Ser Pro Gln Tyr His Phe Leu Val
            100                 105                 110

Ser Leu Gly Arg Ala Lys Arg Ala Phe Leu Pro Gly Met Asn Pro Pro
            115                 120                 125

Pro Tyr Ser Gln Phe Leu Ser Arg Arg Asn Glu Ile Pro Leu Ile His
            130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
            195                 200                 205

Asn Thr His Ala Gly Gly Thr Gly Pro Glu Gly Cys Arg Pro Phe Ala
            210                 215                 220

Lys Phe
225

<210> SEQ ID NO 9
<211> LENGTH: 250
<212> TYPE: PRT
<213> ORGANISM: Homo sapiens

<400> SEQUENCE: 9

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
            130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
            195                 200                 205

Glu Leu Pro Ser Ala Glu Asp Asn Ser Pro Met Ala Ser Asp Pro Leu
            210                 215                 220
```

```
Gly Val Val Arg Gly Gly Arg Val Asn Thr His Ala Gly Gly Thr Gly
225                 230                 235                 240

Pro Glu Gly Cys Arg Pro Phe Ala Lys Phe
            245                 250

<210> SEQ ID NO 10
<211> LENGTH: 227
<212> TYPE: PRT
<213> ORGANISM: Artificial Sequence
<220> FEATURE:
<223> OTHER INFORMATION: FGF23 variant

<400> SEQUENCE: 10

Met Tyr Pro Asn Ala Ser Pro Leu Leu Gly Ser Ser Trp Gly Gly Leu
1               5                   10                  15

Ile His Leu Tyr Thr Ala Thr Ala Arg Asn Ser Tyr His Leu Gln Ile
            20                  25                  30

His Lys Asn Gly His Val Asp Gly Ala Pro His Gln Thr Ile Tyr Ser
        35                  40                  45

Ala Leu Met Ile Arg Ser Glu Asp Ala Gly Phe Val Val Ile Thr Gly
    50                  55                  60

Val Met Ser Arg Arg Tyr Leu Cys Met Asp Phe Arg Gly Asn Ile Phe
65                  70                  75                  80

Gly Ser His Tyr Phe Asp Pro Glu Asn Cys Arg Phe Gln His Gln Thr
                85                  90                  95

Leu Glu Asn Gly Tyr Asp Val Tyr His Ser Pro Gln Tyr His Phe Leu
            100                 105                 110

Val Ser Leu Gly Arg Ala Lys Arg Ala Phe Leu Pro Gly Met Asn Pro
        115                 120                 125

Pro Pro Tyr Ser Gln Phe Leu Ser Arg Arg Asn Glu Ile Pro Leu Ile
    130                 135                 140

His Phe Asn Thr Pro Ile Pro Arg Arg His Thr Gln Ser Ala Glu Asp
145                 150                 155                 160

Asp Ser Glu Arg Asp Pro Leu Asn Val Leu Lys Pro Arg Ala Arg Met
                165                 170                 175

Thr Pro Ala Pro Ala Ser Cys Ser Gln Glu Leu Pro Ser Ala Glu Asp
            180                 185                 190

Asn Ser Pro Met Ala Ser Asp Pro Leu Gly Val Val Arg Gly Gly Arg
        195                 200                 205

Val Asn Thr His Ala Gly Gly Thr Gly Pro Glu Gly Cys Arg Pro Phe
    210                 215                 220

Ala Lys Phe
225

<210> SEQ ID NO 11
<211> LENGTH: 146
<212> TYPE: PRT
<213> ORGANISM: Homo sapiens

<400> SEQUENCE: 11

Met Arg Leu Leu Gln Leu Leu Phe Arg Ala Ser Pro Ala Thr Leu Leu
1               5                   10                  15

Leu Val Leu Cys Leu Gln Leu Gly Ala Asn Lys Ala Gln Asp Asn Thr
            20                  25                  30

Arg Lys Ile Ile Ile Lys Asn Phe Asp Ile Pro Lys Ser Val Arg Pro
        35                  40                  45
```

```
Asn Asp Glu Val Thr Ala Val Leu Ala Val Gln Thr Glu Leu Lys Glu
     50                  55                  60

Cys Met Val Val Lys Thr Tyr Leu Ile Ser Ser Ile Pro Leu Gln Gly
 65                  70                  75                  80

Ala Phe Asn Tyr Lys Tyr Thr Ala Cys Leu Cys Asp Asp Asn Pro Lys
                 85                  90                  95

Thr Phe Tyr Trp Asp Phe Tyr Thr Asn Arg Thr Val Gln Ile Ala Ala
            100                 105                 110

Val Val Asp Val Ile Arg Glu Leu Gly Ile Cys Pro Asp Ala Ala
        115                 120                 125

Val Ile Pro Ile Lys Asn Asn Arg Phe Tyr Thr Ile Glu Ile Leu Lys
    130                 135                 140

Val Glu
145

<210> SEQ ID NO 12
<211> LENGTH: 118
<212> TYPE: PRT
<213> ORGANISM: Artificial Sequence
<220> FEATURE:
<223> OTHER INFORMATION: Example of synthetic Prolactin-Inducible
      Peptide

<400> SEQUENCE: 12

Gln Asp Asn Thr Arg Lys Ile Ile Ile Lys Asn Phe Asp Ile Pro Lys
  1               5                  10                  15

Ser Val Arg Pro Asn Asp Glu Val Thr Ala Val Leu Ala Val Gln Thr
             20                  25                  30

Glu Leu Lys Glu Cys Met Val Val Lys Thr Tyr Leu Ile Ser Ser Ile
         35                  40                  45

Pro Leu Gln Gly Ala Phe Asn Tyr Lys Tyr Thr Ala Cys Leu Cys Asp
     50                  55                  60

Asp Asn Pro Lys Thr Phe Tyr Trp Asp Phe Tyr Thr Asn Arg Thr Val
 65                  70                  75                  80

Gln Ile Ala Ala Val Val Asp Val Ile Arg Glu Leu Gly Ile Cys Pro
                 85                  90                  95

Asp Asp Ala Ala Val Ile Pro Ile Lys Asn Asn Arg Phe Tyr Thr Ile
            100                 105                 110

Glu Ile Leu Lys Val Glu
        115

<210> SEQ ID NO 13
<211> LENGTH: 125
<212> TYPE: PRT
<213> ORGANISM: Artificial Sequence
<220> FEATURE:
<223> OTHER INFORMATION: M-His-hPIP (29-146) Sequence

<400> SEQUENCE: 13

Met His His His His His His Gln Asp Asn Thr Arg Lys Ile Ile Ile
  1               5                  10                  15

Lys Asn Phe Asp Ile Pro Lys Ser Val Arg Pro Asn Asp Glu Val Thr
             20                  25                  30

Ala Val Leu Ala Val Gln Thr Glu Leu Lys Glu Cys Met Val Val Lys
         35                  40                  45

Thr Tyr Leu Ile Ser Ser Ile Pro Leu Gln Gly Ala Phe Asn Tyr Lys
     50                  55                  60
```

```
Tyr Thr Ala Cys Leu Cys Asp Asp Asn Pro Lys Thr Phe Tyr Trp Asp
 65                  70                  75                  80

Phe Tyr Thr Asn Arg Thr Val Gln Ile Ala Ala Val Val Asp Val Ile
                 85                  90                  95

Arg Glu Leu Gly Ile Cys Pro Asp Asp Ala Ala Val Ile Pro Ile Lys
            100                 105                 110

Asn Asn Arg Phe Tyr Thr Ile Glu Ile Leu Lys Val Glu
        115                 120                 125

<210> SEQ ID NO 14
<211> LENGTH: 9
<212> TYPE: PRT
<213> ORGANISM: Artificial Sequence
<220> FEATURE:
<223> OTHER INFORMATION: Partial sequence of human oxytocin

<400> SEQUENCE: 14

Cys Tyr Ile Gln Asn Cys Pro Leu Gly
1               5

<210> SEQ ID NO 15
<211> LENGTH: 8
<212> TYPE: PRT
<213> ORGANISM: Artificial Sequence
<220> FEATURE:
<223> OTHER INFORMATION: A tag for the N-terminus of hGDF15

<400> SEQUENCE: 15

Met His His His His His His Met
1               5

<210> SEQ ID NO 16
<211> LENGTH: 7
<212> TYPE: PRT
<213> ORGANISM: Artificial Sequence
<220> FEATURE:
<223> OTHER INFORMATION: A tag for the N-terminus of hGDF15

<400> SEQUENCE: 16

Met His His His His His His
1               5

<210> SEQ ID NO 17
<211> LENGTH: 7
<212> TYPE: PRT
<213> ORGANISM: Artificial Sequence
<220> FEATURE:
<223> OTHER INFORMATION: His Tag ARN-(200-308)-hGDF15

<400> SEQUENCE: 17

Met His His His His His His
1               5

<210> SEQ ID NO 18
<211> LENGTH: 19
<212> TYPE: RNA
<213> ORGANISM: Artificial Sequence
<220> FEATURE:
<223> OTHER INFORMATION: TTR siRNA Antisense strand
<220> FEATURE:
<221> NAME/KEY: modified_base
<222> LOCATION: (1)..(2)
<223> OTHER INFORMATION: a 2'-F modified nucleotide
<220> FEATURE:
<221> NAME/KEY: modified_base
<222> LOCATION: (4)..(4)
<223> OTHER INFORMATION: a 2'-F modified nucleotide
```

```
<220> FEATURE:
<221> NAME/KEY: modified_base
<222> LOCATION: (6)..(6)
<223> OTHER INFORMATION: a 2'-F modified nucleotide
<220> FEATURE:
<221> NAME/KEY: modified_base
<222> LOCATION: (8)..(8)
<223> OTHER INFORMATION: a 2'-F modified nucleotide
<220> FEATURE:
<221> NAME/KEY: modified_base
<222> LOCATION: (10)..(10)
<223> OTHER INFORMATION: a 2'-F modified nucleotide
<220> FEATURE:
<221> NAME/KEY: modified_base
<222> LOCATION: (12)..(12)
<223> OTHER INFORMATION: a 2'-F modified nucleotide
<220> FEATURE:
<221> NAME/KEY: modified_base
<222> LOCATION: (14)..(14)
<223> OTHER INFORMATION: a 2'-F modified nucleotide
<220> FEATURE:
<221> NAME/KEY: modified_base
<222> LOCATION: (16)..(16)
<223> OTHER INFORMATION: a 2'-F modified nucleotide
<220> FEATURE:
<221> NAME/KEY: modified_base
<222> LOCATION: (17)..(19)
<223> OTHER INFORMATION: a 2'-MOE modified nucleotide
<220> FEATURE:
<221> NAME/KEY: misc_RNA
<222> LOCATION: (19)..(19)
<223> OTHER INFORMATION: abasic ribitol

<400> SEQUENCE: 18
uagagcaaga acacuguur                                                  19

<210> SEQ ID NO 19
<211> LENGTH: 19
<212> TYPE: RNA
<213> ORGANISM: Artificial Sequence
<220> FEATURE:
<223> OTHER INFORMATION: TTR siRNA Sense strand
<220> FEATURE:
<221> NAME/KEY: modified_base
<222> LOCATION: (4)..(4)
<223> OTHER INFORMATION: a 2'-F modified nucleotide
<220> FEATURE:
<221> NAME/KEY: modified_base
<222> LOCATION: (6)..(6)
<223> OTHER INFORMATION: a 2'-F modified nucleotide
<220> FEATURE:
<221> NAME/KEY: modified_base
<222> LOCATION: (8)..(8)
<223> OTHER INFORMATION: a 2'-F modified nucleotide
<220> FEATURE:
<221> NAME/KEY: modified_base
<222> LOCATION: (10)..(10)
<223> OTHER INFORMATION: a 2'-F modified nucleotide
<220> FEATURE:
<221> NAME/KEY: modified_base
<222> LOCATION: (12)..(12)
<223> OTHER INFORMATION: a 2'-F modified nucleotide
<220> FEATURE:
<221> NAME/KEY: modified_base
<222> LOCATION: (14)..(14)
<223> OTHER INFORMATION: a 2'-F modified nucleotide
<220> FEATURE:
<221> NAME/KEY: modified_base
<222> LOCATION: (16)..(16)
<223> OTHER INFORMATION: a 2'-F modified nucleotide
<220> FEATURE:
<221> NAME/KEY: modified_base
<222> LOCATION: (17)..(17)
<223> OTHER INFORMATION: a 2'-MOE modified nucleotide
```

```
<220> FEATURE:
<221> NAME/KEY: misc_RNA
<222> LOCATION: (19)..(19)
<223> OTHER INFORMATION: abasic ribitol

<400> SEQUENCE: 19
aacaguguuc uugcucuar                                                        19

<210> SEQ ID NO 20
<211> LENGTH: 500
<212> TYPE: PRT
<213> ORGANISM: Artificial Sequence
<220> FEATURE:
<223> OTHER INFORMATION: CRM197 Sequence

<400> SEQUENCE: 20
```

| Gly | Ala | Asp | Asp | Val | Val | Asp | Ser | Ser | Lys | Ser | Phe | Val | Met | Glu | Asn |
|---|---|---|---|---|---|---|---|---|---|---|---|---|---|---|---|
| 1 | | | | 5 | | | | | 10 | | | | | 15 | |

| Phe | Ser | Ser | Tyr | His | Gly | Thr | Lys | Pro | Gly | Tyr | Val | Asp | Ser | Ile | Gln |
|---|---|---|---|---|---|---|---|---|---|---|---|---|---|---|---|
| | | | 20 | | | | | 25 | | | | | 30 | | |

| Lys | Gly | Ile | Gln | Lys | Pro | Lys | Ser | Gly | Thr | Gln | Gly | Asn | Tyr | Asp | Asp |
|---|---|---|---|---|---|---|---|---|---|---|---|---|---|---|---|
| | | 35 | | | | | 40 | | | | | 45 | | | |

| Asp | Trp | Lys | Glu | Phe | Tyr | Ser | Thr | Asp | Asn | Lys | Tyr | Asp | Ala | Ala | Gly |
|---|---|---|---|---|---|---|---|---|---|---|---|---|---|---|---|
| 50 | | | | | 55 | | | | | 60 | | | | | |

| Tyr | Ser | Val | Asp | Asn | Glu | Asn | Pro | Leu | Ser | Gly | Lys | Ala | Gly | Gly | Val |
|---|---|---|---|---|---|---|---|---|---|---|---|---|---|---|---|
| 65 | | | | | 70 | | | | | 75 | | | | | 80 |

| Val | Lys | Val | Thr | Tyr | Pro | Gly | Leu | Thr | Lys | Val | Leu | Ala | Leu | Lys | Val |
|---|---|---|---|---|---|---|---|---|---|---|---|---|---|---|---|
| | | | | 85 | | | | | 90 | | | | | 95 | |

| Asp | Asn | Ala | Glu | Thr | Ile | Lys | Lys | Glu | Leu | Gly | Leu | Ser | Leu | Thr | Glu |
|---|---|---|---|---|---|---|---|---|---|---|---|---|---|---|---|
| | | | 100 | | | | | 105 | | | | | 110 | | |

| Pro | Leu | Met | Glu | Gln | Val | Gly | Thr | Glu | Glu | Phe | Ile | Lys | Arg | Phe | Gly |
|---|---|---|---|---|---|---|---|---|---|---|---|---|---|---|---|
| | | 115 | | | | | 120 | | | | | 125 | | | |

| Asp | Gly | Ala | Ser | Arg | Val | Val | Leu | Ser | Leu | Pro | Phe | Ala | Glu | Gly | Ser |
|---|---|---|---|---|---|---|---|---|---|---|---|---|---|---|---|
| | 130 | | | | | 135 | | | | | 140 | | | | |

| Ser | Ser | Val | Glu | Tyr | Ile | Asn | Asn | Trp | Glu | Gln | Ala | Lys | Ala | Leu | Ser |
|---|---|---|---|---|---|---|---|---|---|---|---|---|---|---|---|
| 145 | | | | | 150 | | | | | 155 | | | | | 160 |

| Val | Glu | Leu | Glu | Ile | Asn | Phe | Glu | Thr | Arg | Gly | Lys | Arg | Gly | Gln | Asp |
|---|---|---|---|---|---|---|---|---|---|---|---|---|---|---|---|
| | | | | 165 | | | | | 170 | | | | | 175 | |

| Ala | Met | Tyr | Glu | Tyr | Met | Ala | Gln | Ala | Cys | Ala | Gly | Asn | Arg | Val | Arg |
|---|---|---|---|---|---|---|---|---|---|---|---|---|---|---|---|
| | | | 180 | | | | | 185 | | | | | 190 | | |

| Arg | Ser | Val | Gly | Ser | Ser | Leu | Ser | Cys | Ile | Asn | Leu | Asp | Trp | Asp | Val |
|---|---|---|---|---|---|---|---|---|---|---|---|---|---|---|---|
| | | 195 | | | | | 200 | | | | | 205 | | | |

| Ile | Arg | Asp | Lys | Thr | Lys | Thr | Lys | Ile | Glu | Ser | Leu | Lys | Glu | His | Gly |
|---|---|---|---|---|---|---|---|---|---|---|---|---|---|---|---|
| | 210 | | | | | 215 | | | | | 220 | | | | |

| Pro | Ile | Lys | Asn | Lys | Met | Ser | Glu | Ser | Pro | Asn | Lys | Thr | Val | Ser | Glu |
|---|---|---|---|---|---|---|---|---|---|---|---|---|---|---|---|
| 225 | | | | | 230 | | | | | 235 | | | | | 240 |

| Glu | Lys | Ala | Lys | Gln | Tyr | Leu | Glu | Glu | Phe | His | Gln | Thr | Ala | Leu | Glu |
|---|---|---|---|---|---|---|---|---|---|---|---|---|---|---|---|
| | | | | 245 | | | | | 250 | | | | | 255 | |

| His | Pro | Glu | Leu | Ser | Glu | Leu | Lys | Thr | Val | Thr | Gly | Thr | Asn | Pro | Val |
|---|---|---|---|---|---|---|---|---|---|---|---|---|---|---|---|
| | | | 260 | | | | | 265 | | | | | 270 | | |

| Phe | Ala | Gly | Ala | Asn | Tyr | Ala | Ala | Trp | Ala | Val | Asn | Val | Ala | Gln | Val |
|---|---|---|---|---|---|---|---|---|---|---|---|---|---|---|---|
| | | 275 | | | | | 280 | | | | | 285 | | | |

| Ile | Asp | Ser | Glu | Thr | Ala | Asp | Asn | Leu | Glu | Lys | Thr | Thr | Ala | Ala | Leu |
|---|---|---|---|---|---|---|---|---|---|---|---|---|---|---|---|
| | 290 | | | | | 295 | | | | | 300 | | | | |

| Ser | Ile | Leu | Pro | Gly | Ile | Gly | Ser | Val | Met | Gly | Ile | Ala | Asp | Gly | Ala |
|---|---|---|---|---|---|---|---|---|---|---|---|---|---|---|---|
| 305 | | | | | 310 | | | | | 315 | | | | | 320 |

```
Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser
                485                 490                 495

Glu Lys Ile His
            500

<210> SEQ ID NO 21
<211> LENGTH: 50
<212> TYPE: PRT
<213> ORGANISM: Artificial Sequence
<220> FEATURE:
<223> OTHER INFORMATION: AgRP(83-132)  Sequence

<400> SEQUENCE: 21

Ser Ser Arg Arg Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
            20                  25                  30

Ala Phe Cys Tyr Cys Arg Lys Leu Gly Thr Ala Met Asn Pro Cys Ser
        35                  40                  45

Arg Thr
    50

<210> SEQ ID NO 22
<211> LENGTH: 20
<212> TYPE: PRT
<213> ORGANISM: Artificial Sequence
<220> FEATURE:
<223> OTHER INFORMATION: AgRP (1-20) peptide sequence

<400> SEQUENCE: 22

Ser Ser Arg Arg Cys Val Arg Leu His Glu Ser Cys Leu Gly Gln Gln
1               5                   10                  15

Val Pro Cys Cys
            20

<210> SEQ ID NO 23
<211> LENGTH: 30
<212> TYPE: PRT
<213> ORGANISM: Artificial Sequence
```

```
<220> FEATURE:
<223> OTHER INFORMATION: AgRP (21-50) peptide sequence

<400> SEQUENCE: 23

Asp Pro Cys Ala Thr Cys Tyr Cys Arg Phe Phe Asn Ala Phe Cys Tyr
1               5                   10                  15

Cys Arg Lys Leu Gly Thr Ala Met Asn Pro Cys Ser Arg Thr
            20                  25                  30

<210> SEQ ID NO 24
<211> LENGTH: 53
<212> TYPE: PRT
<213> ORGANISM: Artificial Sequence
<220> FEATURE:
<223> OTHER INFORMATION: Serelaxin Sequence

<400> SEQUENCE: 24

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Cys Phe Arg
            20                  25                  30

Ala Leu Ser Arg Lys Thr Cys Gly Val His Cys Cys Lys Asn Ala Leu
        35                  40                  45

Ala Ser Tyr Leu Glu
        50

<210> SEQ ID NO 25
<211> LENGTH: 145
<212> TYPE: PRT
<213> ORGANISM: Artificial Sequence
<220> FEATURE:
<223> OTHER INFORMATION: Artificial expressed M-His-HPIP (29-146)
      protein sequence

<400> SEQUENCE: 25

Met Glu Thr Asp Thr Leu Leu Leu Trp Val Leu Leu Leu Trp Val Pro
1               5                   10                  15

Gly Ser Thr Gly Met His His His His His His Gln Asp Asn Thr Arg
            20                  25                  30

Lys Ile Ile Ile Lys Asn Phe Asp Ile Pro Lys Ser Val Arg Pro Asn
        35                  40                  45

Asp Glu Val Thr Ala Val Leu Ala Val Gln Thr Glu Leu Lys Glu Cys
    50                  55                  60

Met Val Val Lys Thr Tyr Leu Ile Ser Ser Ile Pro Leu Gln Gly Ala
65                  70                  75                  80

Phe Asn Tyr Lys Tyr Thr Ala Cys Leu Cys Asp Asp Asn Pro Lys Thr
                85                  90                  95

Phe Tyr Trp Asp Phe Tyr Thr Asn Arg Thr Val Gln Ile Ala Ala Val
            100                 105                 110

Val Asp Val Ile Arg Glu Leu Gly Ile Cys Pro Asp Asp Ala Ala Val
        115                 120                 125

Ile Pro Ile Lys Asn Asn Arg Phe Tyr Thr Ile Glu Ile Leu Lys Val
    130                 135                 140

Glu
145

<210> SEQ ID NO 26
<211> LENGTH: 454
<212> TYPE: DNA
<213> ORGANISM: Artificial Sequence
```

```
<220> FEATURE:
<223> OTHER INFORMATION: Artificial M-His-hPIP (29-146) nucleotide
      sequence

<400> SEQUENCE: 26
gctagccacc atggagactg atactttgtt gttgtgggta ctgttgcttt gggtgcccgg    60
tagtaccggt atgcatcacc accaccatca ccaggacaac acccggaaga tcatcatcaa   120
gaacttcgac atccctaaga gcgtgcgccc aaacgatgaa gtcaccgcgg tgctggcagt   180
gcagactgag ctgaaggagt gcatggtggt caagacgtac ctgatttcgt ccatcccgct   240
gcaaggcgcc ttcaactaca gtacactgc ctgcctctgt gacgcaacc ccaagacctt    300 ttactgggac ttctacacca atagaactgt ccagattgct gccgtggtgg atgtgatcag   360
ggaattggga atttgccccg acgatgcggc cgtgattccg atcaagaaca accgcttcta   420
taccatcgag atccttaaag tggaatgaga attc                              454

<210> SEQ ID NO 27
<211> LENGTH: 6
<212> TYPE: PRT
<213> ORGANISM: Artificial Sequence
<220> FEATURE:
<223> OTHER INFORMATION: His Tag

<400> SEQUENCE: 27

Met His His His His His
1               5

<210> SEQ ID NO 28
<211> LENGTH: 11
<212> TYPE: PRT
<213> ORGANISM: Artificial Sequence
<220> FEATURE:
<223> OTHER INFORMATION: APJ agonist-conjugate
<220> FEATURE:
<221> NAME/KEY: MOD_RES
<222> LOCATION: (11)..(11)
<223> OTHER INFORMATION: D-Nle

<400> SEQUENCE: 28

Glu Arg Pro Cys Leu Ser Cys Lys Gly Pro Leu
1               5                   10

<210> SEQ ID NO 29
<211> LENGTH: 13
<212> TYPE: PRT
<213> ORGANISM: Artificial Sequence
<220> FEATURE:
<223> OTHER INFORMATION: APJ agonist-conjugate
<220> FEATURE:
<221> NAME/KEY: MOD_RES
<222> LOCATION: (11)..(11)
<223> OTHER INFORMATION: Nle

<400> SEQUENCE: 29

Glu Arg Pro Arg Leu Cys His Lys Gly Pro Leu Cys Phe
1               5                   10

<210> SEQ ID NO 30
<211> LENGTH: 18
<212> TYPE: PRT
<213> ORGANISM: Artificial Sequence
<220> FEATURE:
<223> OTHER INFORMATION: Intermediate of pE-R-P-C*-L-S-C*-K-G-P-(D-Nle)-
      NH(Phenethyl) (disulfide C4-C7) Acetate
```

```
<220> FEATURE:
<221> NAME/KEY: MISC_FEATURE
<222> LOCATION: (9)..(14)
<223> OTHER INFORMATION: [[(1alpha,8alpha,9alpha)-bicyclo[6.1.0]non-4-
      yn-9-ylmethoxy]carbonyl]
<220> FEATURE:
<221> NAME/KEY: MOD_RES
<222> LOCATION: (18)..(18)
<223> OTHER INFORMATION: D-Nle

<400> SEQUENCE: 30

Glu Arg Pro Cys Leu Ser Cys Pro Asn Asn Asn Asn Asn Lys Gly
1               5                   10                  15

Pro Leu

<210> SEQ ID NO 31
<211> LENGTH: 19
<212> TYPE: PRT
<213> ORGANISM: Artificial Sequence
<220> FEATURE:
<223> OTHER INFORMATION: Apelin cyclic peptide BCN intermediate
<220> FEATURE:
<221> NAME/KEY: MISC_FEATURE
<222> LOCATION: (8)..(13)
<223> OTHER INFORMATION: [[(1alpha,8alpha,9alpha)-bicyclo[6.1.0]non-4-
      yn-9-ylmethoxy]carbonyl]
<220> FEATURE:
<221> NAME/KEY: MOD_RES
<222> LOCATION: (17)..(17)
<223> OTHER INFORMATION: Nle

<400> SEQUENCE: 31

Glu Arg Pro Arg Leu Cys His Asn Asn Asn Asn Asn Asn Lys Gly Pro
1               5                   10                  15

Leu Cys Phe

<210> SEQ ID NO 32
<211> LENGTH: 13
<212> TYPE: PRT
<213> ORGANISM: Artificial Sequence
<220> FEATURE:
<223> OTHER INFORMATION: A-H-Q-R-P-C-L-S-C-K-G-P-Dnle-Phenethyl amine
      Intermediate 21B1
<220> FEATURE:
<221> NAME/KEY: MOD_RES
<222> LOCATION: (13)..(13)
<223> OTHER INFORMATION: Nle

<400> SEQUENCE: 32

Ala His Gln Arg Pro Cys Leu Ser Cys Lys Gly Pro Leu
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Oxytocin derivative
<220> FEATURE:
<221> NAME/KEY: MISC_FEATURE
<222> LOCATION: (6)..(6)
<223> OTHER INFORMATION: N-CH2CH2CH2NH2

<400> SEQUENCE: 33

Tyr Ile Gln Asn Cys Gly Leu Gly
1               5
```

```
<210> SEQ ID NO 34
<211> LENGTH: 15
<212> TYPE: PRT
<213> ORGANISM: Artificial Sequence
<220> FEATURE:
<223> OTHER INFORMATION: Serelaxin peptide
<220> FEATURE:
<221> NAME/KEY: MISC_FEATURE
<222> LOCATION: (8)..(8)
<223> OTHER INFORMATION: Site of the fatty acid addition to serelaxin
      (Lysine K17)

<400> SEQUENCE: 34

Cys Cys His Val Gly Cys Thr Lys Arg Ser Leu Ala Arg Phe Cys
1               5                   10                  15

<210> SEQ ID NO 35
<211> LENGTH: 13
<212> TYPE: PRT
<213> ORGANISM: Artificial Sequence
<220> FEATURE:
<223> OTHER INFORMATION: MH6-PIP peptide with fatty acid addition site
<220> FEATURE:
<221> NAME/KEY: MISC_FEATURE
<222> LOCATION: (1)..(1)
<223> OTHER INFORMATION: Fatty acid adition site
<220> FEATURE:
<221> NAME/KEY: MISC_FEATURE
<222> LOCATION: (1)..(1)
<223> OTHER INFORMATION: Fatty acid addition site

<400> SEQUENCE: 35

Met His His His His His His Gln Asp Asn Thr Arg Lys
1               5                   10

<210> SEQ ID NO 36
<211> LENGTH: 25
<212> TYPE: PRT
<213> ORGANISM: Artificial Sequence
<220> FEATURE:
<223> OTHER INFORMATION: MH6-PIP peptide fragment; fatty acid addition
      site
<220> FEATURE:
<221> NAME/KEY: MISC_FEATURE
<222> LOCATION: (19)..(19)
<223> OTHER INFORMATION: Fatty acid addition at lysine K42

<400> SEQUENCE: 36

Ser Val Arg Pro Asn Asp Glu Val Thr Ala Val Leu Ala Val Gln Thr
1               5                   10                  15

Glu Leu Lys Glu Cys Met Val Val Lys
            20                  25
```

FATTY ACIDS AND THEIR USE IN CONJUGATION TO BIOMOLECULES

This application claims benefit under 35 U.S.C. § 119(e) of U.S. Provisional Application No. 62/015862, filed Jun. 23, 2014; U.S. Application No. 62/082327 filed Nov. 20, 2014; and U.S. Provisional Application No. 62/107016 filed Jan. 23, 2015; the contents of which are incorporated herein by reference in their entirety.

FIELD OF THE INVENTION

The present invention relates to novel conjugates of GDF15 which have improved half-life and duration of action, method of making them and using them. The invention further relates to novel fatty acids and their use in extending the half-life of biomolecules via conjugation.

BACKGROUND OF THE INVENTION

Peptides and proteins are widely used in medical practice, and since they can be produced by recombinant DNA technology it can be expected that their importance will increase also in the years to come. The number of known endogenous peptides and proteins with interesting biological activities is growing rapidly, also as a result of the ongoing exploration of the human genome. Due to their biological activities, many of these polypeptides and proteins could in principle be used as therapeutic agents. Endogenous peptides or proteins are, however, not always suitable as drug candidates because they often have half-lives of few minutes due to rapid degradation by peptidases and/or due to renal filtration and excretion in the urine. The half-life of polypeptides or proteins in human plasma varies strongly (from a few minutes to more than one week).

A high clearance of a therapeutic agent is inconvenient in cases where it is desired to maintain a high blood level thereof over a prolonged period of time. One way which has been currently used to overcome this disadvantage is to administer large dosage of therapeutic peptide or proteins of interest to the patient so that even if some therapeutic peptide or protein is degraded, enough remains to be therapeutically effective. However, this method is uncomfortable to patients. Since most therapeutic peptides or proteins cannot be administered orally, the therapeutic peptide or proteins would have to be either constantly infused, frequently infused by intravenous injection or administered frequently by the inconvenient route of subcutaneous injections. The need for frequent administration also results in much potential peptide or protein therapeutics having an unacceptable high projected cost of treatment. The presence of large amounts of degraded peptide or protein may also generate undesired side effects.

Discomfort in administration and high costs are two reasons why most therapeutic peptides or proteins with attractive bioactivity profiles may not be developed as drug candidates.

Therefore, one approach to prolong half-life of peptides or proteins is to modify the therapeutic peptides or proteins in such a way that their degradation is slowed down while still maintaining biological activity. Serum albumin has a half-life of more than one week, and one approach to increasing the plasma half-life of peptides or proteins has been to derivatize them with a chemical entity that binds to serum albumin or other plasma proteins.

However, there is still a need to identify new half-life extending moieties to modify therapeutic biomolecules such as peptides and proteins in order to provide longer duration of action in vivo while maintaining low toxicity and therapeutic advantages.

SUMMARY OF THE INVENTION

The present invention relates to a conjugate comprising a biomolecule linked to a fatty acid via a linker wherein the fatty acid has the following Formulae A1, A2 or A3:

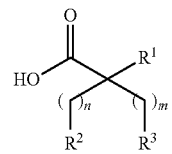

A1

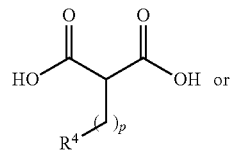

A2

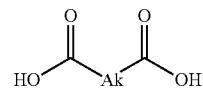

A3

$R^1$ is $CO_2H$ or H;
$R^2$, $R^3$ and $R^4$ are independently of each other H, OH, $CO_2H$, —CH=$CH_2$ or —C≡CH;
Ak is a branched $C_6$-$C_{30}$alkylene;
n, m and p are independently of each other an integer between 6 and 30, or an amide, an ester or a pharmaceutically acceptable salt thereof.

The fatty acid of Formulae A1, A2 and A3 when conjugated to a biomolecule of interest via a linker have been found to increase the half-life of said biomolecule to a much greater extent than more commonly used fatty acid residues.

In another embodiment, the invention pertains to a conjugate comprising a biomolecule liked to a fatty acid of Formulae A1 wherein at least one of R2 and R3 is CO2H.

In another embodiment of the present invention, the biomolecule of interest is a therapeutic peptide, a therapeutic protein or a RNA. In yet another aspect of this embodiment, the biomolecule of interest is a peptide or polypeptide. In yet a further aspect of this embodiment, the peptide or polypeptide is an APJ agonist peptide, an oxytocin receptor agonist peptide, serelaxin, NPFF, a PIP peptide, an FGF23 peptide, an AgRP peptide or a Growth Differentiation Factor 15 (GDF15) protein, homologs, variants, fragments and other modified forms thereof.

In yet another embodiment, the invention pertains to pharmaceutical compositions, comprising a conjugate of the invention and one or more pharmaceutically acceptable carriers.

In still another embodiment, the invention pertains to combinations including, a conjugate of the invention, and pharmaceutical combinations of one or more therapeutically active agents.

In another embodiment, the invention pertains to the fatty acid of Formulae A1, A2 or A3.

In another embodiment, the present invention contemplates the use of the conjugates described herein, and composition thereof, to treat and/or prevent various diseases, disorders and conditions, and/or the symptoms thereof.

For example, the invention pertains to a method for activation of the APJ receptor in a subject in need thereof, comprising: administering to the subject a therapeutically effective amount of a conjugate of the invention wherein the biomolecule is an APJ agonist. The conjugates of the invention, via activation of the APJ receptor, have utility in the treatment of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia. In a preferred aspect of this embodiment the conjugates of the invention are useful in the treatment of acute decompensated heart failure (ADHF) or chronic heart failure.

In another embodiment, the invention pertains to a method for activation of the oxytocin receptor in a subject in need thereof; comprising: administering to the subject a therapeutically effective amount of a conjugate of the invention wherein the biomolecule is an oxytocin receptor agonist peptide. The conjugates of the invention, via activation of the oxytocin receptor, have utility in the treatment of autism (therapeutic or prophylactic), migraine, attention deficit hyperactivity disorder (ADHD), oppositional defiant disorder (ODD), stress, including post traumatic stress disorder, anxiety, including anxiety disorders and depression, schizophrenia, psychiatric disorders and memory loss, alcohol withdrawal, drug addiction, Prader-Willi Syndrome, metabolic disorders or diseases, type 2 diabetes mellitus, obesity, dyslipidemia, elevated glucose levels, elevated insulin levels and diabetic nephropathy, fibromyalgia, sleep disorder, sleep apnea, diastolic heart failure, urine incontinence, atherosclerosis, hypertension, erectile dysfunction, prostatic hypertrophy symptoms, non-alcoholic fatty liver disease, compromised lactation conditions, labor induction impairment, uterine conditions, excessive bleeding, inflammation, pain, abdominal pain, back pain, male and female sexual dysfunction, irritable bowel syndrome (IBS), constipation, gastrointestinal obstruction, surgical blood loss, postpartum haemorrhage, wound healing, infection, mastitis, placenta delivery impairment, osteoporosis; and for the diagnosis of cancer and placental insufficiency. In a preferred aspect of this embodiment the conjugates of the invention are useful in the treatment of autism, anxiety, including anxiety disorders and depression, Migraine, ADHD, Oppositional Defiant Disorder, schizophrenia, psychiatric disorders, obesity, compromised lactation conditions, labor induction impairment, uterine atony conditions, excessive bleeding, postpartum hemorrhage. Yet in a more preferred embodiment, the conjugates of the invention are useful for the treatment of Prader-Willi Syndrome.

In yet another embodiment, the invention pertains to a method of treating Cushing's syndrome, Hypercortisolism, the ectopic ACTH syndrome, the change in adrenocortical mass, primary pigmented nodular adrenocortical disease (PPNAD) Carney complex (CNC), the cortisol-induced mineralocorticoid excess, Conditions associated with post-traumatic stress disorder, hirsutism, thin skin, myopathy, osteoporosis, increased tissue fragility, poor wound healing, hypertension, diabetes mellitus, low serum potassium, low eosinophils and lymphopenia, comprising: administering to the subject a therapeutically effective amount of a conjugate of the invention wherein the biomolecule is an AgRP peptide. In a preferred aspect of this embodiment the conjugates of the invention are useful in the treatment of Cushing's syndrome, Hypercortisolism, the ectopic ACTH syndrome, osteoporosis.

In yet another embodiment, the invention pertains to a method of treating or preventing FGF23-related diseases such as age-related conditions (selected from the group consisting of sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss), a metabolic disorder (selected from the group consisting of Type II Diabetes, Metabolic Syndrome, hyperglycemia, and obesity), hyperphosphatemia (tumoral calcinosis, hyperphosphatemic hyperostosis syndrome), chronic renal disease, chronic renal failure, cancer, breast cancer, and/or muscle atrophy; comprising: administering to the subject a therapeutically effective amount of a conjugate of the invention wherein the biomolecule is a FGF23 peptide.

In yet another embodiment, the invention pertains to a method of treating acute heart failure, chronic heart failure with reduced ejection fraction (HFrEF), chronic heart failure with preserved ejection fraction (HFpEF), diastolic dysfunction, post myocardial remodeling, angina, hypertension, pulmonary hypertension, pulmonary artery hypertension, fibrosis (diffuse, cardiac, renal, pulmonary, liver), scleroderma, wound healing, critical limb ischemia, peripheral vascular disease, intermittent claudication, renal dysfunction and chronic kidney disease; comprising: administering to the subject a therapeutically effective amount of a conjugate of the invention wherein the biomolecule is a serelaxin peptide. In a preferred aspect of this embodiment, the serelaxin conjugates of the invention are useful in the treatment of acute heart failure, chronic heart failure with reduced ejection fraction (HFrEF), chronic heart failure with preserved ejection fraction (HFpEF), diastolic dysfunction, post myocardial remodeling, angina, hypertension, pulmonary hypertension or pulmonary artery hypertension.

In yet another embodiment, the invention pertains to a method of treating or preventing metabolic disorders such as type 2 diabetes mellitus (T2DM), pancreatic beta cell impairment, glucose intolerance, hyperglycemia, insulin resistance, obesity, dyslipidemia, nonalcoholic steatohepatitis (NASH), metabolic syndrome, and other metabolic disorders; comprising: administering to the subject a therapeutically effective amount of a conjugate of the invention wherein the biomolecule is a PIP peptide.

In yet another embodiment, the invention pertains to a method of treating or preventing metabolic disorders or diseases, type 2 diabetes mellitus, obesity, pancreatitis, dyslipidemia, nonalcoholic steatohepatitis, insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, diabetic complications (including but not limited to chronic kidney disease), neuropathy, gastroparesis, urge incontinence, sedation, neuropathic and inflammatory pain, memory loss, and other metabolic disorders; comprising: administering to the subject a therapeutically effective amount of a conjugate of the invention wherein the biomolecule is NPFF peptide.

In still another aspect of the present invention, the invention pertains to a method of treating metabolic disorders or diseases, diabetes, type 2 diabetes mellitus, obesity, alcoholic and nonalcoholic fatty liver disease/steatohepatitis and other progressive liver diseases, pancreatitis, dyslipidemia, insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, diabetic complications (including but not limited to chronic kidney disease), neuropathy, gastroparesis and other metabolic disorders, in a subject in need thereof, comprising: administering to the subject a therapeutically effective amount of a conjugate of the invention wherein the biomolecule is human Growth Differentiation Factor 15 (GDF15), homologs, variants, mutants, fragments and other modified forms thereof.

These and other aspects of the invention will be elucidated in the following detailed description of the invention.

BRIEF DESCRIPTION OF THE DRAWING

FIG. 1 shows that Example 24 decreased plasma APOC3 levels more effectively than reference example 3.

DETAILED DESCRIPTION

Definition:

For purposes of interpreting this specification, the following definitions will apply unless specified otherwise and whenever appropriate, terms used in the singular will also include the plural and vice versa.

It must be noted that as used herein and in the appended claims, the singular forms "a", "an" and "the" include plural referents unless the context clearly dictates otherwise. Thus, for example, reference to "the conjugate" includes reference to one or more conjugates; reference to "the polypeptide" includes reference to one or more polypeptides; and so forth.

The term alkyl refers to a fully saturated branched or unbranched (or straight chain or linear) hydrocarbon moiety, comprising 1 to 30 carbon atoms. Preferably the alkyl comprises 5 to 20 carbon atoms, and more preferably 10 to 15 carbon atoms. $C_{10-15}$alkyl refers to an alkyl chain comprising 10 to 15 carbons. The term "alkylene" refer to a divalent alkyl as defined supra.

The term "alkenyl" refers to a branched or unbranched hydrocarbon having at least one carbon-carbon double bond. The term "$C_{2-30}$-alkynyl" refers to a hydrocarbon having two to seven carbon atoms and comprising at least one carbon-carbon triple The term "alkynyl" refers to a branched or unbranched hydrocarbon having at least one carbon-carbon triple bond. The term "$C_{2-30}$-alkynyl" refers to a hydrocarbon having two to seven carbon atoms and comprising at least one carbon-carbon triple bond.

The term aryl refers to monocyclic or bicyclic aromatic hydrocarbon groups having 6-10 carbon atoms in the ring portion. Representative examples of aryl are phenyl or naphthyl.

The term heteroaryl includes monocyclic or bicyclic heteroaryl, containing from 5-10 ring members selected from carbon atoms and 1 to 5 heteroatoms, and each heteroatoms is independently selected from O, N or S wherein S and N may be oxidized to various oxidation states. For bicyclic heteroaryl system, the system is fully aromatic (i.e. all rings are aromatic).

The term cycloalkyl refers to saturated or unsaturated but non-aromatic monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic. For example, cycloalkyl encompasses cycloalkenyl and cycloalkynyl. The term "cycloalkenyl" refers to a bicyclic or tricyclic hydrocarbon group of 3-12 carbon atoms, having at least one carbon-carbon double bond. The term "cycloalkynyl" refers to a bicyclic or tricyclic hydrocarbon group of 3-12 carbon atoms, having at least one carbon-carbon triple bond.

The term heterocyclyl refers to a saturated or unsaturated non-aromatic (partially unsaturated but non-aromatic) monocyclic, bicyclic or tricyclic ring system which contains at least one heteroatom selected from O, S and N, where the N and S can also optionally be oxidized to various oxidation states. In one embodiment, heterocyclyl moiety represents a saturated monocyclic ring containing from 5-7 ring atoms and optionally containing a further heteroatom, selected from O, S or N. The heterocyclic ring may be substituted with alkyl, halo, oxo, alkoxy, haloalkyl, haloalkoxy. In other embodiment, heterocyclyl is di- or tricyclic. For polycyclic system, some ring may be aromatic and fused to saturated or partially saturated ring or rings. The overall fused system is not fully aromatic. For example, a heterocyclic ring system can be an aromatic heteroaryl ring fused with saturated or partially saturated cycloalkyl ring system.

The term "conjugate" is intended to refer to the entity formed as a result of a covalent attachment of biomolecule and a fatty acid moiety, via a linker. The term "conjugation" refers to the chemical reaction resulting in the covalent attachment of the biomolecule and the fatty acid moiety.

Biomolecule:

As used herein the term biomolecule includes, but is not limited to, antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, enzymatic nucleic acids, antisense nucleic acids, triplex forming oligonucleotides, antisense DNA or RNA compositions, chimeric DNA:RNA compositions, allozymes, aptamers, ribozyme, decoys and analogs thereof, plasmids and other types of expression vectors, and small nucleic acid molecules, RNAi agents, short interfering nucleic acid (siNA), messenger ribonucleic acid" (messenger RNA, mRNA), short interfering RNA (siRNA), double-stranded RNA (dsRNA), micro-RNA (miRNA), and short hairpin RNA (shRNA) molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (asymmetrical interfering RNA), and siRNA with 1, 2 or more mismatches between the sense and anti-sense strand to relevant cells and/or tissues, such as in a cell culture, subject or organism. Such compounds may be purified or partially purified, and may be naturally occurring or synthetic, and may be chemically modified.

In one embodiment the biomolecule is a polypeptide, peptide, proteins or a RNAi agent, short interfering nucleic acid (siNA), short interfering RNA (siRNA), double-stranded RNA (dsRNA), micro-RNA (miRNA), or a short hairpin RNA (shRNA) molecule.

In other embodiment the biomolecule is a polypeptide (or protein), or peptide. Examples of polypeptides or peptides are APJ agonist peptides, oxytocin peptides, serelaxin, NPFF, a PIP peptide, an FGF23 peptide, AgRP peptides and GDF15 peptide. In a preferred embodiment, the biomolecule is GDF15 polypeptide, homolog, variant, mutant, fragment and other modified forms thereof.

A "ribonucleic acid" (RNA) is a polymer of nucleotides linked by a phosphodiester bond, where each nucleotide contains ribose or a modification thereof as the sugar component. Each nucleotide contains an adenine (A), a guanine (G), a cytosine (C), a uracil (U) or a modification thereof as the base. The genetic information in a mRNA molecule is encoded in the sequence of the nucleotide bases of the mRNA molecule, which are arranged into codons consisting of three nucleotide bases each. Each codon encodes for a specific amino acid of the polypeptide, except for the stop codons, which terminate translation (protein synthesis). Within a living cell, mRNA is transported to a ribosome, the site of protein synthesis, where it provides the genetic information for protein synthesis (translation). For a fuller description, see, Alberts B et al. (2007) *Molecular Biology of the Cell, Fifth Edition*, Garland Science.

The terms "RNAi agent," "short interfering RNA", "siRNA", "short interfering nucleic acid", "siNA" and the like as used herein refers to any nucleic acid molecule capable of inhibiting or down regulating gene expression or viral replication by mediating RNA interference (RNAi) or gene silencing in a sequence-specific manner. The terms include short interfering RNA (siRNA), short hairpin RNA (shRNA), microRNA (miRNA), short interfering oligo-nucleotides, chemically-modified short interfering nucleic acid molecules, sisiRNA (small internally segmented interfering RNA), aiRNA (asymmetrical interfering RNA), siRNA with 1, 2 or more mismatches between the sense and anti-sense strand to relevant cells and/or tissues, RNAi agents wherein one or more mismatches exist between the sense and antisense strands, RNAi agents wherein the sense strand is very short relative to the antisense strand and/or has one or more single-stranded nicks, or any other molecule capable of mediating RNA interference. RNAi agents can comprise ribonucleotides, or be modified or substituted at one or more sugar, base and/or phosphate. As non-limiting examples, the RNAi agents can be modified at the 2' position with a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one embodiment, all pyrimidines (uridine and cytidine) are 2'-O-methyl-modified nucleosides. In various embodiments, one or more phosphate can be substituted with a modified internucleoside linker, selected from phosphorothioate, phosphorodithioate, phosphoramidate, boranophosphonoate, and an amide linker. In various embodiments, one or more nucleotides can be modified, or substituted with DNA, a peptide nucleic acid (PNA), locked nucleic acid (LNA), morpholino nucleotide, threose nucleic acid (TNA), glycol nucleic acid (GNA), arabinose nucleic acid (ANA), 2"-fluoroarabinose nucleic acid (FANA), cyclohexene nucleic acid (CeNA), anhydrohexitol nucleic acid (HNA), unlocked nucleic acid (UNA). Various modifications and substitutions of RNAi agents are known in the art and can be used in the context of the instant disclosure. siRNAs are responsible for RNA interference, the process of sequence-specific post-transcriptional gene silencing in animals and plants. siRNAs are generated naturally by ribonuclease III cleavage from longer double-stranded RNA (dsRNA) which are homologous to, or specific to, the silenced gene target; artificial RNAi agents can be produced by any method known in the art.

As used herein, the term "polypeptide" refers to a polymer of amino acid residues linked by peptide bonds, whether produced naturally or synthetically. Polypeptides of less than about 10 amino acid residues are commonly referred to as "peptides." The term "peptide" is intended to indicate a sequence of two or more amino acids linked by peptide bonds, wherein said amino acids may be natural or unnatural. The term encompasses the terms polypeptides and proteins, which may consist of two or more peptides held together by covalent interactions, such as for instance cysteine bridges, or non-covalent interactions. The art-recognized three letter or one letter abbreviations are used to represent amino acid residues that constitute the peptides and polypeptides of the invention. Except when preceded with "D", the amino acid is an L-amino acid. When the one letter abbreviation is a capital letter, it refers to the D-amino acid. When the one letter abbreviation is a lower case letter, it refers to the L-amino acid. Groups or strings or amino acid abbreviations are used to represent peptides. Peptides are indicated with the N-terminus on the left and the sequence is written from the N-terminus to the C-terminus.

Peptides of the invention contain non-natural amino acids (i.e., compounds that do not occur in nature) and other amino acid analogs as are known in the art may alternatively be employed.

Certain non-natural amino acids can be introduced by the technology described in Deiters et al., J Am Chem Soc 125:11782-11783, 2003; Wang and Schultz, Science 301: 964-967, 2003; Wang et al., Science 292:498-500, 2001; Zhang et al., Science 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the non-natural amino acid of choice. Particular non-natural amino acids that are beneficial for purpose of conjugating moieties to the polypeptides of the invention include those with acetylene and azido side chains.

A "protein" is a macromolecule comprising one or more polypeptide chains. Each of those polypeptide chains may be conjugated with a fatty acid molecule of Formula A1, A2 or A3. A protein may also comprise non-peptidic components, such as carbohydrate groups. Carbohydrates and other nonpeptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless. A protein or polypeptide encoded by a non-host DNA molecule is a "heterologous" protein or polypeptide.

An "isolated polypeptide or isolated protein" is a polypeptide or protein (for example GDF15) that is essentially free from cellular components, such as carbohydrate, lipid, or other proteinaceous impurities associated with the polypeptide in nature. Typically, a preparation of isolated polypeptide or protein contains the polypeptide or protein in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide or protein is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide or protein in alternative physical forms, such as dimers or alternatively glycosylated or derivatized forms. Preferably, the isolated polypeptide is substantially free from any other contaminating polypeptides or other contaminants that are found in its natural environment that would interfere with its therapeutic, diagnostic, prophylactic or research use.

One of ordinary skill in the art will appreciate that various amino acid substitutions, e.g, conservative amino acid substitutions, may be made in the sequence of any of the polypeptide or protein described herein, without necessarily decreasing its activity. As used herein, "amino acid commonly used as a substitute thereof" includes conservative substitutions (i.e., substitutions with amino acids of comparable chemical characteristics). For the purposes of conservative substitution, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Examples of amino acid substitutions include substituting an L-amino acid for its corresponding D-amino acid, substituting cysteine for homocysteine or other non-natural amino acids having a thiol-containing side chain, substituting a lysine for homolysine, diaminobutyric acid, diaminopropionic acid, ornithine or other non-natural amino acids having an amino containing side chain, or substituting an alanine for norvaline or the like.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

The term "naturally occurring" refers to materials which are found in nature and are not manipulated by man. Similarly, "non-naturally occurring," "un-natural," and the like, as used herein, refers to a material that is not found in nature or that has been structurally modified or synthesized by man. When used in connection with amino acids, the term "naturally occurring" refers to the 20 conventional amino acids (i.e., alanine (A or Ala), cysteine (C or Cys), aspartic acid (D or Asp), glutamic acid (E or Glu), phenylalanine (F or Phe), glycine (G or Gly), histidine (H or His), isoleucine (I or Ile), lysine (K or Lys), leucine (L or Leu), methionine (M or Met), asparagine (N or Asn), proline (P or Pro), glutamine (Q or Gln), arginine (R or Arg), serine (S or Ser), threonine (T or Thr), valine (V or Val), tryptophan (W or Trp), and tyrosine (Y or Tyr)).

The terms "non-natural amino acid" and "unnatural amino acid," as used herein, are interchangeably intended to represent amino acid structures that cannot be generated biosynthetically in any organism using unmodified or modified genes from any organism, whether the same or different. The terms refer to an amino acid residue that is not present in the naturally occurring (wild-type) protein sequence or the sequences of the present invention. These include, but are not limited to, modified amino acids and/or amino acid analogues that are not one of the 20 naturally occurring amino acids, selenocysteine, pyrrolysine (Pyl), or pyrrolinecarboxy-lysine (Pcl, e.g., as described in PCT patent publication WO2010/48582). Such non-natural amino acid residues can be introduced by substitution of naturally occurring amino acids, and/or by insertion of non-natural amino acids into the naturally occurring (wild-type) protein sequence or the sequences of the invention. The non-natural amino acid residue also can be incorporated such that a desired functionality is imparted to the molecule, for example, the ability to link a functional moiety (e.g., PEG). When used in connection with amino acids, the symbol "U" shall mean "non-natural amino acid" and "unnatural amino acid," as used herein.

The term "analogue" as used herein referring to a polypeptide or protein means a modified peptide or protein wherein one or more amino acid residues of the peptide/protein have been substituted by other amino acid residues and/or wherein one or more amino acid residues have been deleted from the peptide/protein and/or wherein one or more amino acid residues have been added the peptide/protein. Such addition or deletion of amino acid residues can take place at the N-terminal of the peptide and/or at the C-terminal of the peptide.

As used herein, the term "ester of the conjugate" refers to a conjugate which comprises a peptide or polypeptide wherein an ester derivative of a carboxylic acid group is present (e.g —$CO_2H$ at the C-terminus has been converted to —COOR) form wherein R of the ester refers to $C_{1-6}$ alkyl groups such as methyl, ethyl, n-propyl, isopropyl, n-butyl, etc., $C_{3-8}$ cycloalkyl groups such as cyclopentyl, cyclohexyl, etc., $C_{6-10}$ aryl groups such as phenyl, α-naphthyl, etc., $C_{6-10}$ aryl-$C_{1-6}$ alkyl groups, for example phenyl-$C_{1-2}$ alkyl groups such as benzyl, phenethyl, benzhydryl, etc., and α-naphthyl-$C_{1-2}$ alkyl groups such as α-naphthylmethyl and the like. When the peptide or polypeptide moiety of the conjugate possess additional carboxyl or carboxylate groups in positions other than the C terminus, those polypeptides in which such groups are amidated or esterified also fall under the category of the polypeptide of the invention. In such cases, the esters may for example be the same kinds of esters as the C-terminal esters mentioned above.

As used herein the term "amide of the conjugate" refers to a conjugate which comprises a peptide or polypeptide wherein an amide derivative of a carboxylic acid group is present (e.g. —$CO_2H$ has been converted to —CO(NR'R') wherein R' is H or R and R is defined above. the term "amide of the conjugate" also refers to a conjugate which comprises a peptide or polypeptide wherein an amide derivative of an amino group is present (i.e. other than the amino group conjugated to a fatty acid) (e.g. —$NH_2$ has been converted to —NH—C(O)R) wherein R is defined supra. In a preferred embodiment, an "amide of the conjugate"is a conjugate which comprises a peptide or polypeptide wherein the carboxylic group at the C-terminus has been amidated (e.g. —$CO_2H$ has been converted to —C(O)$NH_2$, —C(O)NH—$C_{1-6}$alkyl, —C(O)NH—$C_{1-2}$alkylphenyl, or —C(O)N($C_{1-6}$ alkyl)$_2$).

The term "APJ" (also referred to as "apelin receptor," "angiotensin-like-1 receptor," "angiotensin II-like-1 receptor," and the like) indicates a 380 residue, 7 transmembrane domain, Gi coupled receptor whose gene is localized on the long arm of chromosome 11 in humans (NCBI Reference Sequence: NP_005152.1, and encoded by NCBI Reference Sequence: NM_005161). APJ was first cloned in 1993 from genomic human DNA using degenerate oligonucleotide primers (O'Dowd et al. Gene, 136:355-60, 1993) and shares significant homology with angiotensin II receptor type 1. Despite this homology however, angiotensin II does not bind APJ. Although orphan for many years, the endogenous ligand has been isolated and named apelin (Tatemoto et al., Biochem Biophys Res Commun 251, 471-6 (1998)).

The term "APJ agonist" includes apelin polypeptides: Apelin indicates a 77 residue preprotein (NCBI Reference Sequence: NP_0059109.3, and encoded by NCBI Reference Sequence: NM_017413.3), which gets processed into biologically active forms of apelin peptides, such as apelin-36, apelin-17, apelin-16, apelin-13, apelin-12. The full length mature peptide, referred to as "apelin-36," comprises 36 amino acids, but the most potent isoform is the pyroglutamated form of a 13mer of apelin (apelin-13), referred to as "Pyr-1-apelin-13 or Pyr¹-apelin-13" Different apelin forms are described, for instance, in U.S. Pat. No. 6,492,324B1. Apelin peptide agonists are also described in patent application numbers WO 2013/111110, U.S. application Ser. No. 14/082,771, and provisional U.S. application Nos. 61/858, 263, 61/858,280 and 61/858290 which are incorporated by reference herein.

The term "oxytocin receptor agonist peptide" or "oxytocin peptide" are used interchangeably and includes oxytocin and its analogs. Oxytocin is a nine amino acid cyclic peptide hormone with two cysteine residues that form a disulfide bridge between position 1 and 6. Human oxytocin comprises the sequence Cys-Tyr-Ile-Gln-Asn-Cys-Pro-Leu-Gly (SEQ ID NO: 14). The term "oxytocin receptor agonist peptide" also includes analogs of oxytocin that retain bioactivity. Such analog molecules are capable of acting in a similar manner to endogenous oxytocin, including binding the oxytocin receptor. Analogs of oxytocin of particular interest are those disclosed in PCT application No. WO 2014/095773 (particularly Example 13); those disclosed in US patent application No. US2011/044905 (particularly Example 49); and those disclosed in Kazimierz Wisniewski et al., Journal of Medicinal Chemistry 2014, 57, 5306-5317 and Zbigniew Grzonka et al., Journal of Medicinal Chemistry 1983, 26, 1786-1787; which are all incorporated by reference herein.

By "PIP" or "Prolactin-Inducible Peptide" is meant the protein with GenBank Accession No. NP_002643 that exhibits roles in diverse biological processes. PIP is also known in the art as gross cystic disease fluid protein-15 (GCDFP-15); secretory actin-binding protein (SABP); extraparotid glycoprotein (EP-GP); and 17-kDa CD4-binding protein (GP17). PIP is expressed in exocrine organs, and in benign and malignant human breast tumors. The mature secreted PIP protein has a molecular mass of 13 kDa and it runs as a 17-20 kDa polypeptide in SDS-PAGE suggesting a glycosylation event. PIP is expressed in most organs that contribute to human body fluids; the expression of PIP is highest in salivary gland followed by lacrimal, prostrate, muscle, trachea and mammary glands. The PIP gene encodes the PIP polypeptide.

By "PIP peptide" as used herein is meant human PIP or a homolog, variant, fragment or modified form thereof, which retains at least one activity of human PIP.

The sequence of a non-limiting example of human PIP is presented in SEQ ID NO: 11:

```
                                                    (SEQ ID NO: 11)
  1 MRLLQLLFRA SPATLLLVLC LQLGANKAQD NTRKIIIKNF DIPKSVRPND EVTAVLAVQT

61 ELKECMVVKT YLISSIPLQG AFNYKYTACL CDDNPKTFYW DFYTNRTVQI AAVVDVIREL

121 GICPDDAAVI PIKNNRFYTI EILKVE
```

SEQ ID NO:11 represents the full length human wild-type PIP, including the signal peptide (amino acids 1-28), which is not required for function.

Another non-limiting example of the term "PIP" as used herein is amino acids (aa) 29-146 of SEQ ID NO: 11, which thus lacks the signal peptide (amino acids 1-28) and is presented below as SEQ ID NO: 12.

```
                                                    (SEQ ID NO: 12)
  1 QDNTRKIIIK NFDIPKSVRP NDEVTAVLAV QTELKECMVV KTYLISSIPL QGAFNYKYTA

61 CLCDDNPKTF YWDFYTNRTV QIAAVVDVIR ELGICPDDAA VIPIKNNRFY TIEILKVE
```

By a "homolog," "variant", "fragment" or "modified form" of PIP or the like is meant a polypeptide similar but non-identical to a human PIP, but which retains at least one activity of human PIP. Such a polypeptide can have a sequence not identical to that of human PIP (e.g., SEQ ID NO: 12), or have a sequence identical to that of human PIP (e.g., SEQ ID NO: 12), but vary in some other manner (e.g., a post-translational modification). Such a polypeptide can comprise, for example, at least 70%, at least 80%, at least 90% or at least 95% sequence identity to SEQ ID NO: 12, or have, for example, a maximum of 5, 10, 15, 20, 25, 30, 35, 40, 45 or 50 amino acid differences (e.g., substitutions, deletions and/or additions) from the amino acid sequence of SEQ ID NO: 12. In some embodiments, the PIP homolog, variant, fragment or modified form thereof retains at least 90% sequence identity or have a maximum of 25 amino acid differences from SEQ ID NO:12. A PIP homolog, variant, fragment or modified form retains at least one activity of human PIP.

By "FGF23" or "Fibroblast Growth Factor 23" is meant the polypeptide also known as FGF-23, ADHR; FGFN; HPDR2; HYPF; PHPTC; External IDs: OMIM: 605380 MGI: 1891427 HomoloGene: 10771 GeneCards: FGF23 Gene; Species: Human; Entrez 8074; Ensembl ENSG00000118972; UniProt: Q9GZV9; RefSeq (mRNA): NM_020638; RefSeq (protein): NP_065689; Location (UCSC): Chr 12: 4.48-4.49 Mb; Species: Mouse; Entrez: 64654; Ensembl: ENSMUSG00000000182; UniProt: Q9EPC2; RefSeq (mRNA): NM_022657; RefSeq (protein): NP_073148; Location (UCSC): Chr 6: 127.07-127.08 Mb. The FGF23 gene encodes the FGF23 polypeptide.

By "FGF23 peptide" as used herein is meant human FGF23 or a homolog, variant, fragment or modified form thereof, which retains at least one activity of human FGF23.

The sequence of a non-limiting example of human FGF23, including the signal peptide, is presented in SEQ ID NO: 9:

```
                                          (SEQ ID NO: 9)
        10         20         30         40
   MLGARLRLWV CALCSVCSMS VLRAYPNASP LLGSSWGGLI 50         60         70         80
   HLYTATARNS YHLQIHKNGH VDGAPHQTIY SALMIRSEDA 90        100        110        120
   GFVVITGVMS RRYLCMDFRG NIFGSHYFDP ENCRFQHQTL 130        140        150        160
   ENGYDVYHSP QYHFLVSLGR AKRAFLPGMN PPPYSQFLSR 170        180        190        200
   RNEIPLIHFN TPIPRRHTRS AEDDSERDPL NVLKPRARMT 210        220        230        240
   PAPASCSQEL PSAEDNSPMA SDPLGVVRGG RVNTHAGGTG 250        260
   PEGCRPFAKF I
```

SEQ ID NO: 9 represents a full-length, human wild-type FGF23, including the signal peptide (amino acids 1-24), which is not required for function. Yamashita et al. 2000 Biochem. Biophys. Res. Comm. 277: 494-498; Shimada et al. 2001 Proc. Natl. Acad. Sci. USA 98: 6500-6505; and Zhang et al. 2004 Protein Sci. 13: 2819-2824.

A non-limiting example of the term "FGF23" as used herein is amino acids (aa) 25-251 of SEQ ID NO: 9, which thus lacks the signal peptide (amino acids 1-24) and is presented below as SEQ ID NO: 8.

```
                                          (SEQ ID NO: 8)
        10         20         30         40
                        YPNASP LLGSSWGGLI 50         60         70         80
   HLYTATARNS YHLQIHKNGH VDGAPHQTIY SALMIRSEDA 90        100        110        120
   GFVVITGVMS RRYLCMDFRG NIFGSHYFDP ENCRFQHQTL 130        140        150        160
   ENGYDVYHSP QYHFLVSLGR AKRAFLPGMN PPPYSQFLSR 170        180        190        200
   RNEIPLIHFN TPIPRRHTRS AEDDSERDPL NVLKPRARMT 210        220        230        240
   PAPASCSQEL PSAEDNSPMA SDPLGVVRGG RVNTHAGGTG 250        260
   PEGCRPFAKF I
```

By a "homolog," "variant", "fragment" or "modified form" of FGF23 or the like is meant a polypeptide similar but non-identical to a human FGF23 (e.g., SEQ ID NO: 8), but which retains at least one activity of human FGF23. Such a polypeptide can comprise, for example, at least 70%, at least 80%, at least 90% or at least 95% sequence identity to SEQ ID NO: 8, or have, for example, a maximum of 5, 10, 15, 20, 25, 30, 35, 40, 45 or 50 amino acid differences (e.g., substitutions, deletions and/or additions) from the amino acid sequence of SEQ ID NO: 8. In some embodiments, the FGF23 homolog, variant, fragment or modified form thereof retains at least 90% sequence identity or have a maximum of 25 amino acid differences from SEQ ID NO: 8. A FGF23 homolog, variant, fragment or modified form retains at least one activity of human FGF23. Such activities (or functions) include, as non-limiting examples, those known for human FGF23, including roles in binding to a FGF23 receptor, interacting with Klotho protein, cellular proliferation, and cell signaling; and activity in various in vitro assays of FGF23 activity, including the Egr-1-luciferase assay; and an activity related to a FGF23-related disease such as an age-related condition (selected from the group consisting of sarcopenia, skin atrophy, muscle wasting, brain atrophy, atherosclerosis, arteriosclerosis, pulmonary emphysema, osteoporosis, osteoarthritis, immunoincompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss), a metabolic disorder (selected from the group consisting of Type II Diabetes, Metabolic Syndrome, hyperglycemia, and obesity), hyperphosphatemia (tumoral calcinosis, hyperphosphatemic hyperostosis syndrome), chronic renal disease, chronic renal failure, cancer, breast cancer, and/or muscle atrophy. Yamashita et al. 2000 Biochem. Biophys. Res. Comm. 277: 494-498; Shimada et al. 2001 Proc. Natl. Acad. Sci. USA 98: 6500-6505; Urakawa et al. 2006 Nature 444: 770-774; Zhang et al. 2004 Protein Sci. 13: 2819-2824; WO 2013/027191, WO 2011/092234 and WO 2009/095372. In some embodiments, the invention provides a conjugate comprising a fatty acid described herein and a FGF23 peptide, wherein the FGF23 peptide retains at least one activity of FGF23; and in some embodiments, the activity of FGF23 retained is function in the in vitro Egr-1-luciferase assay.

By a "homolog" of FGF23 is meant a polypeptide corresponding to human FGF23, but from a different source, such as a mammal, such as mouse, rat, cynomolgus monkey, cow, pig, sheep, horse, dog, etc., yet retains at least one function of human FGF23.

By a "variant" of FGF23 is meant a FGF23 which comprises one or more mutation (e.g., deletion, substitution or addition), e.g., relative to SEQ ID NO: 8, yet retains at least one function of human FGF23. Mutations in FGF23 include those at positions Y154, Q156, R176, R179, C206 and C244. Such mutations have previously been described. A mutation at R179 confers proteolysis resistance on FGF23; in ADHR, mutations of the 176RXXR179 site prevent cleavage and inactivation of FGF23. White et al. 2000 Nat. Genet. 26: 345-348; Liu et al. 2003 J. Biol. Chem. 278: 37419-37426. The mutation at Y154 decreases degradation; mutation at Q156 eliminates a cleavage site; and mutations at C206 and C244 reduce dimerization and aggregation. WO 2013/027191 and WO 2011/092234. A FGF23 homolog, variant, or modified form can further comprise one or more additional amino acids (which are not normally found in wild-type human FGF23).

A non-limiting example of a FGF23 variant is shown here:

```
                                         (SEQ ID NO: 10)
        10         20         30         40
                        MYPNASP LLGSSWGGLI 50         60         70         80
   HLYTATARNS YHLQIHKNGH VDGAPHQTIY SALMIRSEDA 90        100        110        120
   GFVVITGVMS RRYLCMDFRG NIFGSHYFDP ENCRFQHQTL 130        140        150        160
   ENGYDVYHSP QYHFLVSLGR AKRAFLPGMN PPPYSQFLSR 170        180        190        200
   RNEIPLIHFN TPIPRRHTQS AEDDSERDPL NVLKPRARMT 210        220        230        240
   PAPASCSQEL PSAEDNSPMA SDPLGVVRGG RVNTHAGGTG 250        260
   PEGCRPFAKF I
```

SEQ ID NO: 10 shows a variant of FGF23 in which the signal peptide (aa 1-24) has been deleted, but an initial M at position 1 has been re-introduced; and the amino acid corresponding to R179 has been mutated to Q. SEQ ID NO: 10 is also designated "hFGF23 R 179Q", "FGF23 R179", "hFGF23(R179Q)" and the like and represents a FGF23 variant which is used in Example 28C.

Additional FGF23 variants include, as non-limiting examples, those which have the sequence of SEQ ID NO: 8 or SEQ ID NO: 10, but also have a mutation at one or more of: Y154, Q156, R176, R179, C206 and C244. Additional FGF23 variants include, as non-limiting examples, those which have the sequence of SEQ ID NO: 8 or SEQ ID NO: 10, but also have a mutation at one or more of: Y154, Q156, R176, R179, C206 and C244 and further comprise one or more additional amino acids (which are not normally found in wild-type human FGF23).

By a "fragment" of FGF23 is meant a FGF23 which comprises one or more deleted amino acids, e.g., relative to SEQ ID NO: 8, yet retains at least one function of human FGF23. Functional fragments of FGF23 include amino acids 180-251 of SEQ ID NO: 8, Goetz et al. 2010 Proc. Natl. Acad. Sci. USA 107: 407-412. A FGF23 fragment can also have one or mutations, e.g., at any one or more of positions Y154, Q156, R176, R179, C206 and C244, but can retain at least one activity of human FGF23.

By "modified form" of FGF23 is meant a FGF23 which comprises a sequence similar or identical to that of FGF23, e.g., SEQ ID NO: 8, but which has one or more modification, and which retains at least one activity of human FGF23. Such a modification can include, as non-limiting examples, a post-translational modification (phosphorylation, methylation, or addition of a carbohydrate), or conjugation to a second moiety, which is not FGF23. Such a second moiety can be, as non-limiting examples, a signal peptide, alpha or beta Klotho or a fragment thereof (e.g., soluble Klotho or sKlotho), a Fc (e.g., FcLALA), or other modification. WO 2011/092234 and WO 2009/095372.

As used herein, the term "AgRP peptide or polypeptide," and like terms refer to the Agouti-Related Peptide, i.e., a signaling molecule made up of 132 amino acids that is post-translationally processed into its active or mature form, AgRP (83-132), which contains 10 cysteine residues and forms a network of five disulfide bonds. AgRP plays a role as an inverse agonist of the melanocortin receptors MC3R and MC4R. The term "AgRP peptide" in all instances includes salts thereof. In some embodiments, AgRP can be in an amide form, e.g., amidation of C-terminus —CO2H to form C(O)—NH2. In other embodiments, AgRP can be in an acid form.

The term "AgRP peptide" also includes shorter biologically active fragments of AgRP. A fragment is a portion of the parent sequence which is identical in sequence but shorter in length than the parent sequence and retain biological activity (i.e. inverse agonism). Fragments of AgRP polypeptides as well as variants thereof have also been described in Jackson, P. J. et al., Biochemistry 41, 7565-7572, which is incorporated by reference herein. For example AgRP (87-120) and AgRP(87-132) possess approximately the same MC3R and MC4R affinity as AgRP (83-132) and exhibit equivalent inverse agonism. Additional fragments of AgRP polypeptide have been described in Christine G. Joseph et al., Peptides 24 (2003), 263-270; which is incorporated by reference herein. Examples of fragments are AgRP(86-132) and monocyclic AgRP (109-118) as well as elongation thereof at the N- and/or C-terminus.

The term "AgRP polypeptides" also encompasses "AgRP mutant polypeptide" which are AgRP polypeptide in which a naturally occurring AgRP polypeptide sequence has been modified. Such modifications have been described in PCT application No. WO2013/006656, which is incorporated by reference herein.

The terms "GDF15 peptide", "GDF15 polypeptide" and "GDF15 protein" are used interchangeably and mean a naturally-occurring wild-type polypeptide expressed in a mammal, such as a human or a mouse. For purposes of this disclosure, the term "GDF15 protein" can be used interchangeably to refer to any full-length GDF15 polypeptide, which consists of 308 amino acid residues; (NCI Ref. Seq. NP_004855.2) containing a 29 amino acid signal peptide (amino acids 1-29), a 167 amino acid pro-domain (amino acids 30-196), and a mature domain of 112 amino acids (amino acids 197-308) which is excised from the prodomain by furin-like proteases. A 308-amino acid GDF15 polypeptide is referred to as "full-length" GDF15 polypeptide; a 112 amino acids GDF15 polypeptide (e.g. amino acids 197-308) is a "mature" GDF15 polypeptide. The mature GDF15 peptide contains the seven conserved cysteine residues required for the formation of the cysteine knot motif (having three intrachain disulfide bonds) and the single interchain disulfide bond that are typical for TGF~superfamily members. The mature GDF15 peptide contains two additional cysteine residues that form a fourth intrachain disulfide bond. Therefore, biologically active GDF15 is a homodimer of the mature peptide covalently linked by one interchain disulfide bond. A GDF15 protein or polypeptide therefore also includes multimer, more particularly dimer of the protein. Each monomeric unit which constitute the homodimer GDF15 may be linked to a fatty acid of Formulae A1, A2 or A3.

By "GDF15" or "GDF15 protein" as used herein is also meant human GDF15 or a homolog, variant, mutant, fragment or modified form thereof, which retains at least one activity of human GDF15.

The term "GDF15 mutant polypeptide" or "GDF15 variant polypeptide" encompasses a GDF15 polypeptide in which a naturally occurring GDF15 polypeptide sequence has been modified. Such modifications include, but are not limited to, one or more amino acid substitutions, including substitutions with non-naturally occurring amino acids non-naturally-occurring amino acid analogs and amino acid mimetics.

In one aspect, the term "GDF15 mutant protein" or "GDF15 variant polypeptide" refers to a GDF15 protein sequence in which at least one residue normally found at a given position of a native GDF15 polypeptide is deleted or is replaced by a residue not normally found at that position in the native GDF15 sequence. In some cases it will be desirable to replace a single residue normally found at a given position of a native GDF15 polypeptide with more than one residue that is not normally found at the position; in still other cases it may be desirable to maintain the native GDF15 polypeptide sequence and insert one or more residues at a given position in the protein; in still other cases it may be desirable to delete a given residue entirely; all of these constructs are encompassed by the term "GDF 15 mutant protein" or "GDF15 variant protein". In one aspect of the invention, the GDF15 mutant protein or "GDF15 variant protein" has a sequence selected from any one of SEQ ID NO 1 to SEQ ID No 7. The present invention also encompasses nucleic acid molecules encoding such GDF15 mutant polypeptide sequences or GDF15 variant polypeptide sequences.

By a "homolog," "variant", "fragment" or "modified form" of GDF15 or the like is meant a polypeptide similar but non-identical to a human GDF15, but which retains at least one activity of human GDF15.

By "modified form" of GDF15 is meant a GDF15 which comprises a sequence similar or identical to that of GDF15, but which has one or more modification, and which retains at least one activity of human GDF15. Such a modification can include, as non-limiting examples, a post-translational modification (phosphorylation, methylation, or addition of a carbohydrate).

By a "homolog" of GDF15 is meant a polypeptide corresponding to human GDF15, but from a different source, such as a mammal, such as cynomolgous monkeys, mice and rats etc., yet retains at least one function of human GDF15. In some instances, a GDF15 homolog can be used to treat or ameliorate a metabolic disorder in a subject in a mature form of a GDF15 mutant polypeptide that is derived from the same species as the subject.

In various embodiments, a GDF15 polypeptide, homolog, variant, mutant, fragment or modified form thereof comprises an amino acid sequence that is at least about 85 percent identical to a naturally-occurring GDF15 protein. In other embodiments, a GDF15 polypeptide comprises an amino acid sequence that is at least about 90 percent, or about 95, 96, 97, 98, or 99 percent identical to a naturally-occurring GDF15 polypeptide amino acid sequence. Such GDF15 polypeptide, homolog, variant, mutant, fragment or modified form thereof possess at least one activity of a wild-type GDF15 mutant polypeptide, such as the ability to lower blood glucose, insulin, triglyceride, or cholesterol levels; the ability to reduce body weight; or the ability to improve glucose tolerance, energy expenditure, or insulin sensitivity.

In various respective embodiments, a GDF15 polypeptide or homolog, variant, mutant, fragment or modified form thereof has a biological activity that is equivalent to, greater to or less than that of the naturally occurring form of the mature GDF15 protein. Examples of biological activities include the ability to lower blood glucose, insulin, triglyceride, or cholesterol levels; the ability to reduce body weight; or the ability to improve glucose tolerance, lipid tolerance, or insulin sensitivity; the ability to lower urine glucose and protein excretion.

As used herein in the context of the structure of a polypeptide or protein, the term"N-terminus" (or "amino terminus") and "C-terminus" (or "carboxyl terminus") refer to the extreme amino and carboxyl ends of the polypeptide, respectively.

The term "therapeutic polypeptide" or "therapeutic protein" as used herein means a polypeptide or protein which is being developed for therapeutic use, or which has been developed for therapeutic use.

The linker separates the biomolecule and the fatty acid moiety. Its chemical structure is not critical, since it serves primarily as a spacer.

The linker is a chemical moiety that contains two reactive groups/functional groups, one of which can react with the biomolecule and the other with the fatty acid moiety. The two reactive/functional groups of the linker are linked via a linking moiety or spacer, structure of which is not critical as long as it does not interfere with the coupling of the linker to the biomolecule and the fatty acid moiety of Formula A1, A2 or A3.

The linker can be made up of amino acids linked together by peptide bonds. In some embodiments of the present invention, the linker is made up of from 1 to 20 amino acids linked by peptide bonds, wherein the amino acids are selected from the 20 naturally occurring amino acids. In various embodiments, the 1 to 20 amino acids are selected from the amino acids glycine, serine, alanine, methionine, asparagine, glutamine, cysteine and lysine. In some embodiments, a linker is made up of a majority of amino acids that are sterically unhindered, such as glycine and alanine. In some embodiments, linkers are polyglycines, polyalanines, combinations of glycine and alanine (such as poly(Gly-Ala)), or combinations of glycine and serine (such as poly(Gly-Ser)). In some embodiments, a linker is made up of a majority of amino acids selected from histidine, alanine, methionine, glutamine, asparagine and glycine. In some embodiments, linkers contain poly-histidine moiety.

In some embodiments, the linker comprises 1 to 20 amino acids which are selected from unnatural amino acids. While a linker of 1-10 amino acid residues is preferred for conjugation with the fatty acid moiety, the present invention contemplates linkers of any length or composition. An example of non-natural amino acid linker is 8-Amino-3,6-dioxaoctanoic acid having the following formula:

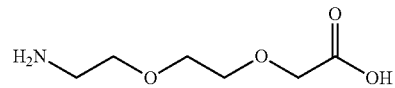 [SMILES: NCCOCCOCC(=O)O]

or its repeating units.

The linkers described herein are exemplary, and linkers that are much longer and which include other residues are contemplated by the present invention. Non-peptide linkers are also contemplated by the present invention.

In other embodiments, the linker comprise one or more alkyl groups, alkenyl groups, cycloalkyl groups, aryl groups, heteroaryl groups, heterocyclic groups, polyethylene glycol and/or one or more natural or unnatural amino acids, or combination thereof, wherein each of the alkyl, alkenyl, cycloalkyl, aryl, heteroaryl, heterocyclyl, polyethylene glycol and/or the natural or unnatural amino acids are optionally combined and linked together, or linked to the biomolecule and/or to the fatty acid moiety, via a chemical group selected from —C(O)O—, —OC(O)—, —NHC(O)—, —C(O)NH—, —O—, —NH—, —S—, —C(O)—, —OC(O)NH—, —NHC(O)—O—, =NH—O—, =NH—NH— or =NH—N(alkyl)-.

Linkers containing alkyl spacer are for example —NH—(CH$_2$)$_z$—C(O)— or —S—(CH$_2$)$_z$—C(O)— or —O—(CH$_2$)$_z$—C(O)—, —NH—(CH$_2$)$_z$—NH—, —O—C(O)—(CH$_2$)$_z$—C(O)—O—, —C(O)—(CH$_2$)$_z$—O—, —NHC(O)—(CH$_2$)$_z$—C(O)—NH— and the like wherein z is 2-20 can be used. These alkyl linkers can further be substituted by any non-sterically hindering group, including, but not limited to, a lower alkyl (e.g., C$_1$-C$_6$), lower acyl, halogen (e.g., Cl, Br), CN, NH$_2$, or phenyl.

The linker can also be of polymeric nature. The linker may include polymer chains or units that are biostable or biodegradable. Polymers with repeat linkage may have varying degrees of stability under physiological conditions depending on bond lability. Polymers may contain bonds such as polycarbonates (—O—C(O)—O—), polyesters (—C(O)—O—), polyurethanes (—NH—C(O)—O—), polyamide (—C(O)—NH—). These bonds are provided by way of examples, and are not intended to limit the type of bonds employable in the polymer chains or linkers of the invention. Suitable polymers include, for example, polyethylene glycol (PEG), polyvinyl pyrrolidone, polyvinyl alcohol, polyamino acids, divinylether maleic anhydride, N-(2-hydroxypropyl)-methacrylicamide, dextran, dextran derivatives, polypropylene glycol, polyoxyethylated polyol, heparin, heparin fragments, polysaccharides, cellulose and cellulose derivatives, starch and starch derivatives, polyalkylene glycol and derivatives thereof, copolymers of polyalkylene glycols and derivatives thereof, polyvinyl ethyl ether, and the like and mixtures thereof. A polymer linker is for example polyethylene glycol (PEG). The PEG linker can be linear or branched. A molecular weight of the PEG linker in the present invention is not restricted to any particular size, but certain embodiments have a molecular weight between 100 to 5000 Dalton for example 500 to 1500 Dalton.

The linker contains appropriate functional-reactive groups at both terminals that form a bridge between the amino group of the peptide or polypeptide/protein and a functional/reactive group on the fatty acid moiety (e.g the carboxylic acid functionality of the fatty acid moiety of formula A1, A2 and A3).

The linker may comprise several linking moieties (or spacer) of different nature (for example a combination of amino acids, heterocyclyl moiety, PEG and/or alkyl moieties). In this instance, each linking moiety contains appropriate functional-reactive groups at both terminals that form a bridge between the amino group of the peptide or polypeptide/protein and the next linking moiety of different nature and/or contains appropriate functional-reactive groups that form a bridge between the prior linking moiety of different nature and the fatty acid moiety.

The modified peptides or polypeptides and/or peptide-polypeptide partial construct (i.e. peptide/polypeptide attached to a partial linker) include reactive groups which can react with available reactive functionalities on the fatty acid moiety (or modified fatty acid moiety: i.e. already attached a partial linker) to form a covalent bond. Reactive groups are chemical groups capable of forming a covalent bond. Reactive groups are located at one site of conjugation and can generally be carboxy, phosphoryl, acyl group, ester or mixed anhydride, maleimide, N-hydroxysuccinimide, tetrazine, alkyne, imidate, pyridine-2-yl-disulfanyl, thereby capable of forming a covalent bond with functionalities like amino group, hydroxyl group, alkene group, hydrazine group, hydroxylamine group, an azide group or a thiol group at the other site of conjugation.

Reactive groups of particular interest for conjugating a biomolecule or modified biomolecule to a linker and/or a linker to the fatty acid moiety and/or to conjugate various linking moieties of different nature together are N-hydroxysuccinimide, alkyne (more particularly cyclooctyne).

Functionalities include: 1. thiol groups for reacting with maleimides, tosyl sulfone or pyridine-2-yldisulfanyl; 2. amino groups (for example amino functionality of an amino acid) for bonding to carboxylic acid or activated carboxylic acid (e.g. amide bond formation via N-hydroxysuccinamide chemistry), phosphoryl groups, acyl group or mixed anhydride; 3. Azide to undergo a Huisgen cycloaddition with a terminal alkyne and more particularly cyclooctyne (more commonly known as click chemistry); 4. carbonyl group to react with hydroxylamine or hydrazine to form oxime or hydrazine respectively; 5. Alkene and more particularly strained alkene to react with tetrazine in an aza[4+2] addition. While several examples of linkers and functionalities/reactive group are described herein, the invention contemplates linkers or any length and composition.

Embodiments

Various embodiments of the invention are described herein. It will be recognized that features specified in each embodiment may be combined with other specified features to provide further embodiments.

In embodiment 1, the invention pertains to a conjugate comprising a biomolecule linked to an fatty acid moiety via a linker wherein the fatty acid moiety has the following Formulae A1, A2 or A3:

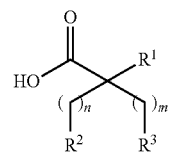

A1

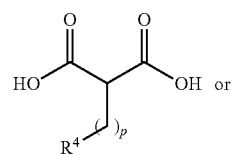

A2

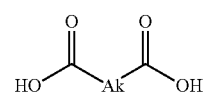

A3

$R^1$ is $CO_2H$, H;
$R^2$, $R^3$ and $R^4$ are independently of each other H, OH, $CO_2H$, —CH=$CH_2$ or —C≡CH;
Ak is a branched $C_6$-$C_{30}$alkylene;
n, m and p are independently of each other an integer between 6 and 30; or an amide, an ester or a pharmaceutically acceptable salt thereof.

In a further aspect of embodiment 1, the conjugate according to embodiment 1 may further comprise a fatty acid of Formula A1, A2 or A3 as described supra. In view of the difficulties of achieving selective conjugation and/or achieving mono conjugation of a fatty acid to a biomolecule, the conjugates of the invention, may comprise a biomolecule which is linked to one or more fatty acid moieties of Formula A1, A2 or A3. Additionally, in view of the multimeric nature of some proteins, each monomeric unit which constitutes a multimeric protein, may be linked to a fatty acid moiety, but not all monomeric units have to necessarily be linked to a fatty acid moiety as long as at least one of the monomeric unit is linked to a fatty acid moiety. In a further aspect, the invention relates to mixtures of the conjugates of the invention. For example, the mixture may comprise a biomolecule, for example a multimeric biomolecule, for example a dimeric biomolecule, which is linked to one fatty acid moieties of Formula A1, A2 or A3, and a biomolecule, for example a multimeric biomolecule, for example a dimeric biomolecule, which is linked to more than one fatty acid moieties of Formula A1, A2 or A3. Examples of the invention below further highlight this aspect of selective or non-selective multiconjugation of fatty acids to a protein or polypeptide.

In embodiment 1A, the invention pertains to a conjugate according to embodiment 1 wherein the fatty acid moiety is of Formula A1. In a particular aspect of this embodiment, the conjugate comprises a fatty acid moiety of Formula A1 wherein n and m are independently 8 to 20, preferably 10 to 16. In another aspect of this embodiment, the invention pertains to a conjugate according to embodiment 1 or 1A wherein the fatty acid moiety is of Formula A1 and wherein at least one of $R^2$ and $R^3$ is $CO_2H$.

In embodiment 2, the invention pertains to a conjugate according to embodiment 1 or 1A, wherein the fatty acid moiety is selected from the following Formulae:

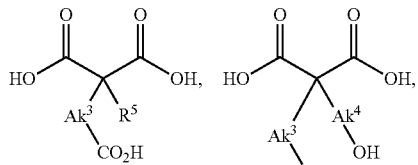

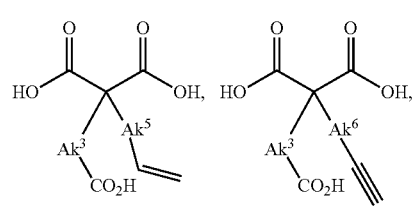

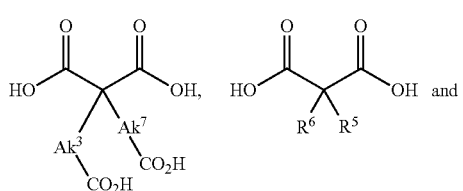

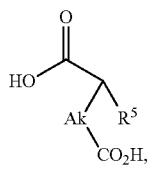

wherein $Ak^3$, $Ak^4$, $Ak^5$, $Ak^6$ and $Ak^7$ are independently a $(C_{8-20})$alkylene, $R^5$ and $R^6$ are independently $(C_{8-20})$alkyl.

In embodiment 3, the invention pertains to a conjugate according to embodiment 1, 1A or 2 wherein the fatty acid moiety is selected from the following Formulae:

-continued

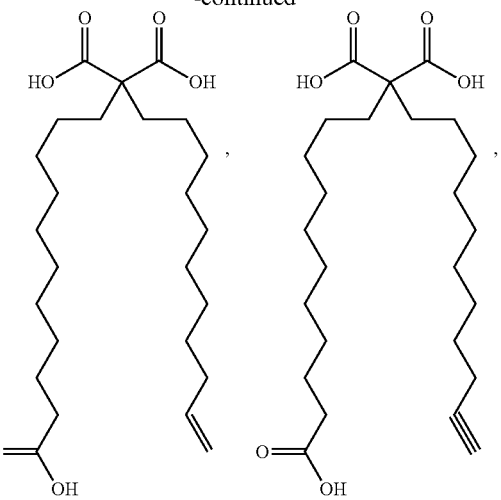

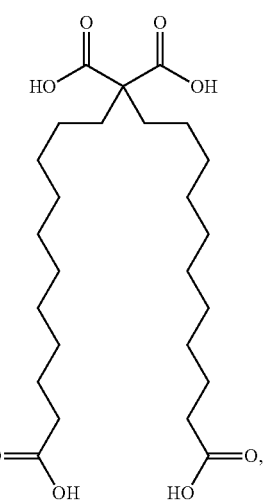

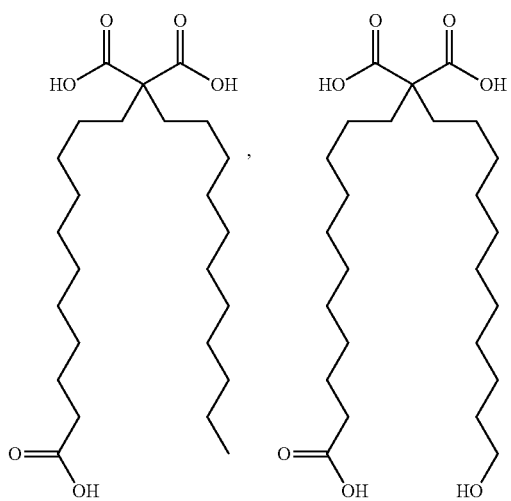

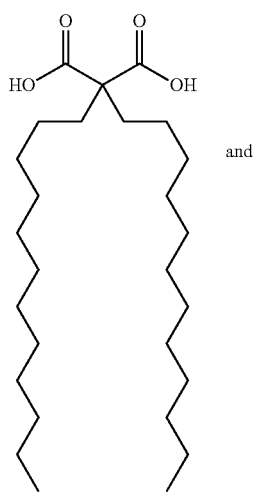

and

-continued

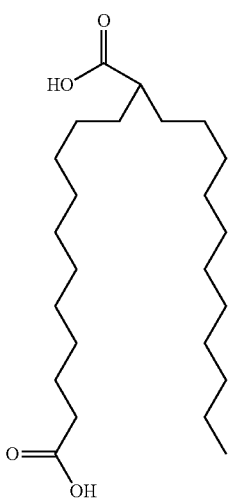

In embodiment 3A, the invention pertains to a conjugate according to embodiment 1, 1A or 2 wherein the fatty acid moiety is selected from the following Formulae:

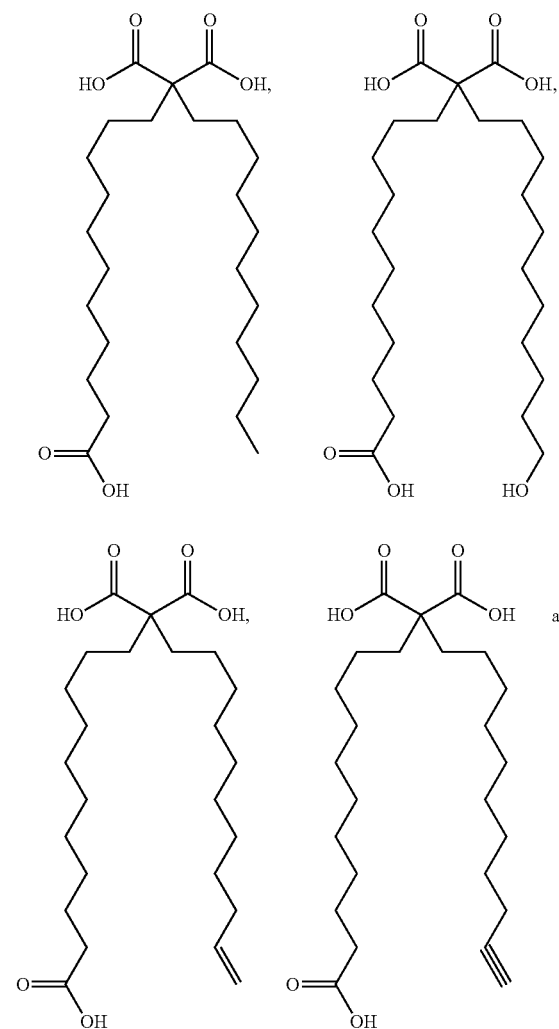

and

-continued

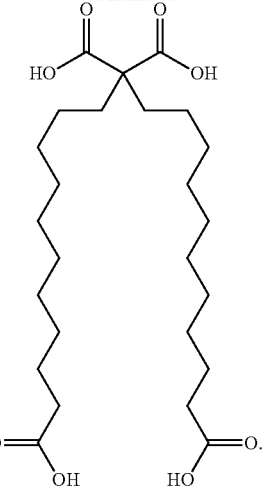

In embodiment 3B, the invention pertains to a conjugate according to embodiment 1 wherein the fatty acid moiety is of Formula A2 or A3. In a particular aspect of this embodiment, the conjugate comprises an fatty acid moeity of Formula A2 wherein p is 8 to 20, or a fatty acid moeity of Formula A3 wherein Ak is $C_{8-20}$alkylene.

In embodiment 3C, the invention pertains to a conjugate according to embodiment 1 or 3B wherein the fatty acid moiety is selected from the following Formulae:

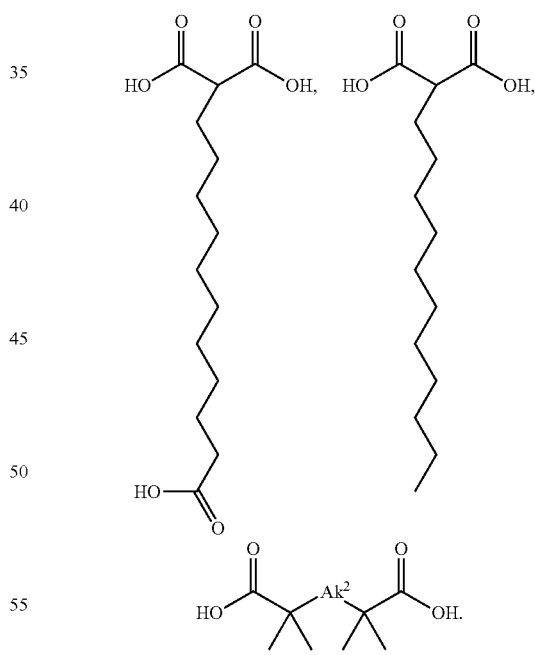

wherein $Ak^2$ is $C_{8-20}$alkylene.

In embodiment 4, the invention pertains to a conjugate according to any of the preceeding embodiments wherein the linker comprise one or more alkyl groups, alkenyl groups, cycloalkyl groups, aryl groups, heteroaryl groups, heterocyclic groups, polyethylene glycol, one or more natural or unnatural amino acids, or combination thereof, wherein each of the alkyl, alkenyl, cycloalkyl, aryl, heteroaryl, heterocyclyl, polyethylene glycol and/or the natural or unnatural amino acids are optionally combined and linked together or linked to the biomolecule and/or to the fatty acid moiety via a chemical group selected from —C(O)O—, —OC(O)—, —NHC(O)—, —C(O)NH—, —O—, —NH—, —S—, —C(O)—, —OC(O)NH—, —NHC(O)—O—, =NH—O—, =NH—NH— or =NH—N(alkyl)-.

In embodiment 5, the invention pertains to a conjugate according to any of the preceeding embodiment, wherein the linker comprises an unbranched oligo ethylene glycol moiety of Formula:

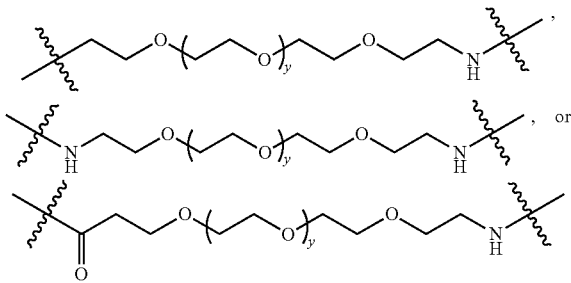

wherein y is 0 to 34.

In embodiment 6, the invention pertains to conjugate according to any of the preceeding embodiments wherein the linker comprises (or further comprises) a heterocyclic moiety selected from the following Formulae:

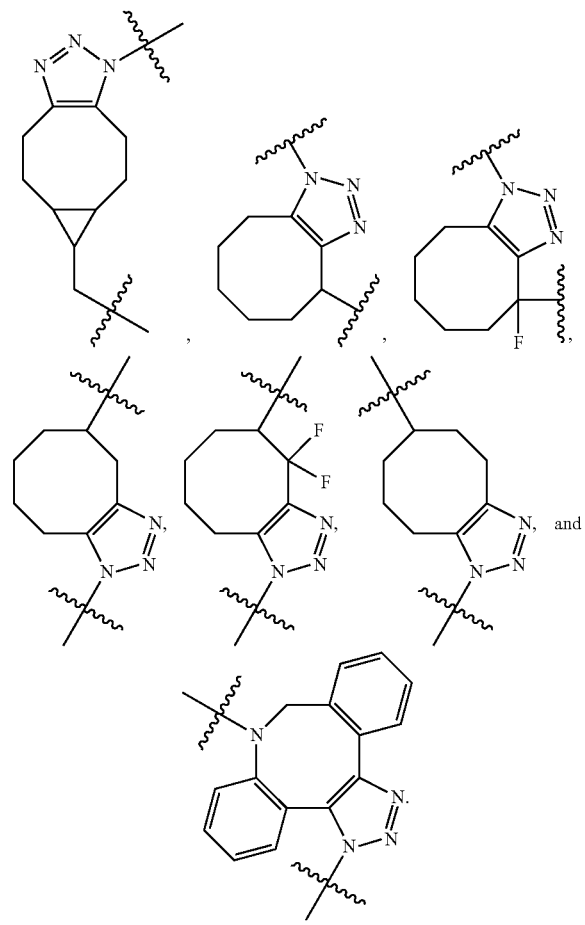

Such heterocyclyl containing linkers are obtained for example by azide-alkyne Huisgen cycloaddition, which more commonly known as click chemistry. More particularly, some of the heterocyclyl depicted supra result from the reaction of a cycloalkyne with an azide-containing moiety.

Cycloalkyne are readily available from commercial sources and can therefore be functionalized via cycloaddition with a moiety containing an azide functionality (e.g. a linker containing a terminal azide functionality). Examples of the use of cyclic alkyne click chemistry in protein labeling has been described in US 2009/0068738 which is herein incorporated by reference.

Non-limiting examples of cycloakyne agents which can be used in Huisgen cycloaddition are:

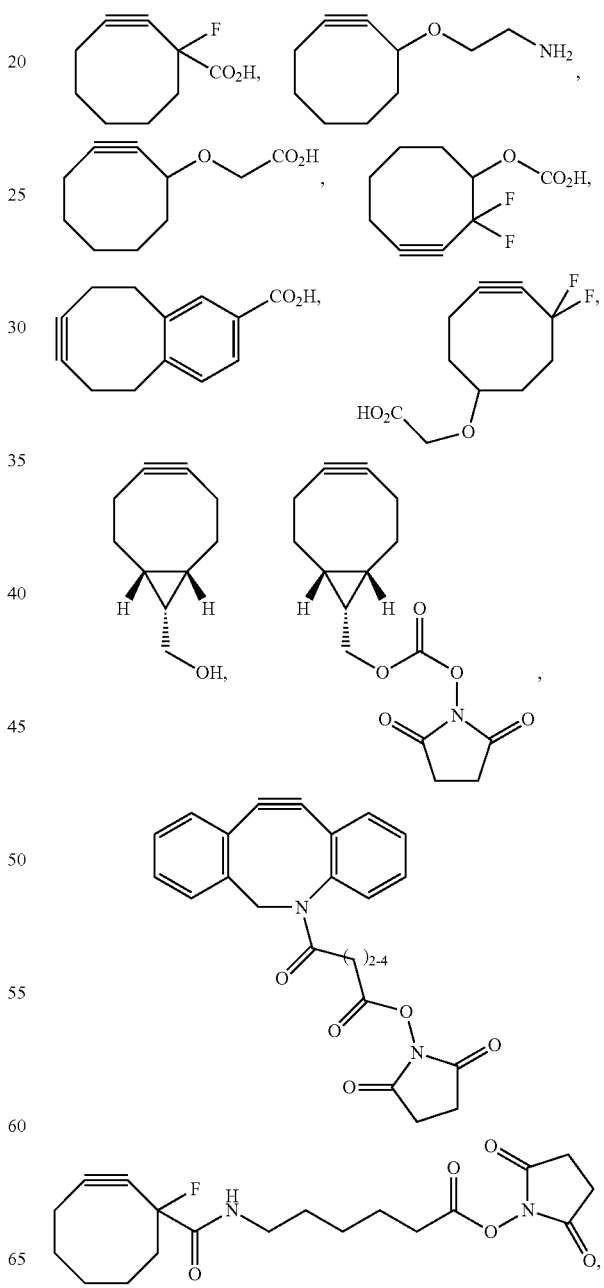

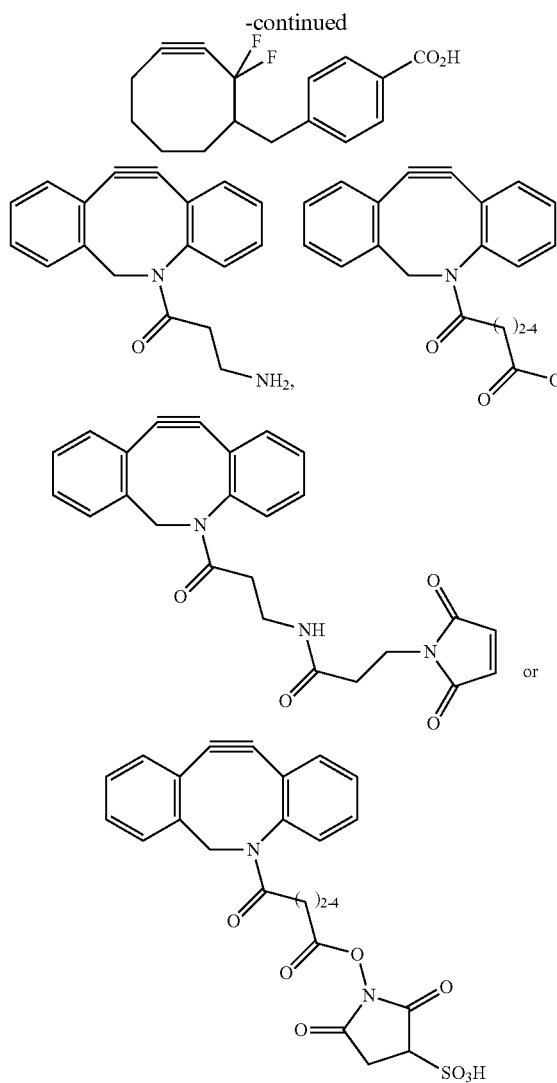

In embodiment 6A, the invention pertains to a conjugate according to any one of embodiments 1 to 5, wherein the linker comprises (or further comprises) a heterocyclyl selected from the following Formulae:

wherein r is an integer of 0 to 2 and s is an integer of 0 to 3.

Such heterocyclic linkers can be obtained via an aza[4+2] cycloadditon of an alkene, or preferably a strained alkene such as cycloalkane, with the following moiety:

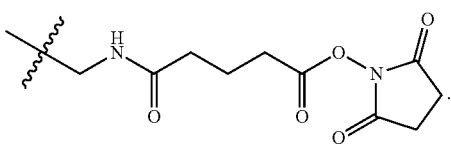

wherein Rf is for example —CH$_2$NH$_2$, —OH, —CH$_2$—CO$_2$H, —S—CH$_2$—CO$_2$H, —(O—CH$_2$)$_{4-6}$—C(O)—OH— or

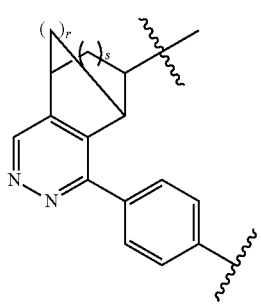

Such tetrazine moieties are readily available from commercial sources and can react with an alkene-containing moiety, for example a linker containing terminal alkene functionality.

In embodiment 6B, the invention pertains to a conjugate according to any one of embodiments 1 to 5 wherein the linker comprises (or further comprises) a heterocyclyl of Formula:

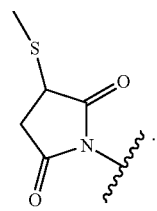 [SMILES: *N1C(=O)CC(SC)C1=O]

Such heterocyclic moiety can be obtained by reacting a maleimide with a thiol containing moiety, such as for example a linker containing a terminal thiol functionality.

These reagents which are readily available and/or commercially available are attached directly or via a linker as described supra to the peptide or polypeptide of interest. The alkyne, maleimide or tetrazine reactive groups are reacted with a functional group (azide, thiol and alkene respectively) which is present on the fatty acid moiety or on a linker-fatty acid construct (such as for example a PEG-fatty acid construct).

In embodiment 7, the invention pertains to a conjugate according to any of the preceeding embodiments wherein the linker comprises or further comprises one or more amino acids independently selected from histidine, methionine, alanine, glutamine, asparagine and glycine. In one particular aspect of this embodiment, the linker comprises 1 to 6 amino acid selected from histidine, alanine and methionine.

In embodiment 8, the invention pertains to a conjugate according to any one of the preceeding embodiments wherein the biomolecule is a peptide or polypeptide. In one particular aspect of embodiment 8, the invention pertains to a conjugate according to any one of the preceeding embodiments wherein the peptide or polypeptide is 1) human Growth Differentiation Factor 15 (GDF15), homologs, variants, mutants, fragments and other modified forms thereof; 2) an APJ agonist peptide, 3) an oxytocin receptor agonist peptide, 4) serelaxin, 5) NPFF, 6) a PIP peptide, 7) an FGF23 peptide 8) an AgRP peptide or 9) a siRNA.

In embodiment 8A, the invention pertains to a conjugate according to any one of the preceeding embodiments wherein the biomolecule is human Growth Differentiation Factor 15 (GDF15), homologs, variants, mutants, fragments and other modified forms thereof; or a dimer thereof. In one aspect of this embodiment, the biomolecule is human Growth Differentiation Factor 15 (GDF15) mutant or variant. In a preferred embodiment, the biomolecule is a dimer of GDF15 or a variant or mutant thereof. In view of the homodimer nature of the GDF15 polypeptide or mutant or variant thereof, each of the two polypeptide chains (i.e. each monomeric unit) which constitute the homodimer, may be linked to a fatty acid molecule of Formula A1, A2 or A3 via a linker. Therefore the GDF15 homodimer may be linked to one or two fatty acids via a linker. The structure of the GDF15 linked to a fatty acid moiety via a linker may be represented as follow:

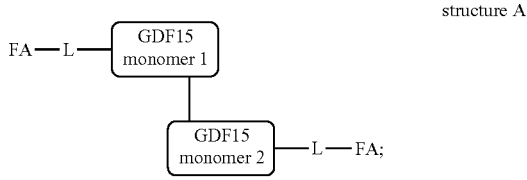

structure A wherein FA represent the fatty acid moiety and L the linker, and GDF15 monomer unit 1 and monomer unit 2 are both linked to a fatty acid moiety via a linker; or

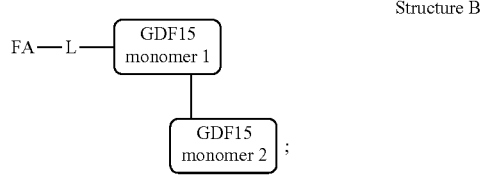

Structure B wherein FA is the fatty acid moiety and L the linker and only one of the monomer unit is linked to a fatty acid moiety via the linker and wherein the line between the 2 monomeric units represent a disulfide bond. Furthermore, the invention also relates to a mixture comprising a conjugate of structure A and a conjugate of structure B.

In embodiment 8B, the invention contemplates a conjugate according to embodiment 8A wherein the human GDF15 mutant is obtained by replacement of one or more amino acid residues of the mature polypeptide with another residue. In one particular aspect of this embodiment, the last two amino acid residues at the N-terminal of human GDF15 (i.e Arginine 198 and Alanine 197) have been replaced with an amino acid sequence XH- wherein H is histidine and X is an amino acid selected from methionine, alanine, glutamine, asparagine and glycine. In a preferred aspect of this embodiment, the hGDF15 mutant is MH(199-308)hGDF15 or AH(199-308)hGDF15.

In embodiment 8C, the last three amino acid residues at the N-terminal of human GDF15 (i.e. Asparagine 199, Arginine 198 and Alanine 197) have been replaced with an amino acid sequence XHX'- wherein H is histidine and X' and X are amino acids independently selected from selected from methionine, alanine, glutamine, asparagine and gly-cine. In another aspect of this embodiment, the last three amino acid residues at the N-terminal of human GDF15 (i.e. Asparagine 199, Arginine 198 and Alanine 197) have been replaced with an amino acid sequence AHX'- wherein H is histidine and X' is an amino acids independently selected from selected from methionine, alanine, glutamine, asparagine and glycine. In a preferred aspect of this embodiment, the modified GDF15 protein is MHA(200-308)hGDF15 or AHA(200-308)hGDF15 (SEQ ID NO: 7).

Compared to the native GDF15 protein, the GDF15 mutant enables the selective labeling of the protein at the N-terminus (i.e. conjugation of the fatty acid at the preferred N-terminus of the GDF15). The selective labeling of peptide and protein is described in further details in co-filed US application Nos. 62/015,858 and 62/082,337 .

In embodiment 8D, the invention pertains to a conjugate according to any one of embodiments 1 to 8 wherein the biomolecule is an APJ agonist peptide. In a particular aspect of this embodiment, the APJ agonist peptide is a peptide described in patent PCT application numbers WO 2013/111110, WO 2014/081702, WO 2015/013168, WO 2015/013165, WO 2015/013167 and WO 2015/013169 which are herein incorporated by reference.

In embodiment 8E, the invention pertains to a conjugate according to any one of embodiments 1 to 8 wherein the biomolecule is an oxytocin receptor agonist peptide. In a particular aspect of this embodiment, the oxytocin receptor agonist peptide is a peptide described in patent PCT application numbers WO 2009/122285 (Ferring B.V.) and WO 2014/095773 (Hoffman-La Roche) which are herein incorporated by reference.

In embodiment 8F, the invention pertains to a conjugate according to any one of embodiments 1 to 8 wherein the biomolecule is an AgRP peptide. In a particular aspect of this embodiment, the AgRP peptide is AgRP(83-132) wherein the C-terminus is in the form of a —free $CO_2H$ or an amide thereof (e.g. —C(O)$NH_2$).

In embodiment 8G, the invention pertains to a conjugate according to any one of embodiments 1 to 8 wherein the biomolecule is an FGF23 peptide. In a particular aspect of this embodiment, the FGF23 peptide is a FGF23 variant of SEQ ID NO: 8 having a mutation at R179 and optionally one or more additional mutations at Y154, Q156, R176, R179, C206 and C244. In another particular aspect of this embodiment, the FGF23 peptide is a FGF23 variant of SEQ ID NO: 8 having mutations at R179, Q156, C206 and C244.

In embodiment 8H, the invention pertains to a conjugate according to any one of embodiments 1 to 8 wherein the biomolecule is Serelaxin.

In embodiment 8I, the invention pertains to a conjugate according to any one of embodiments 1 to 8 wherein the biomolecule is NPFF peptide.

In embodiment 8J, the invention pertains to a conjugate according to any one of embodiments 1 to 8 wherein the biomolecule is a PIP peptide. In a particular aspect of this embodiment, the PIP peptide is the histagged protein MHH-HHHHH-PIP wherein PIP is of SEQ ID NO: 12.

In embodiment 8K, the invention pertains to a conjugate according to any one of embodiments 1 to 8 wherein the biomolecule is a siRNA.

In embodiment 8L, the invention pertains to a conjugate according to any one of the proceeding embodiments, further comprising a second fatty acid moiety linked to the biomolecule via a linker. Preferably the two fatty acid-linker moieties are of the same structure.

In embodiment 9, the invention pertains to a conjugate according to embodiment 1, 2, 8, 8A, 8B or 8C having the following structure:

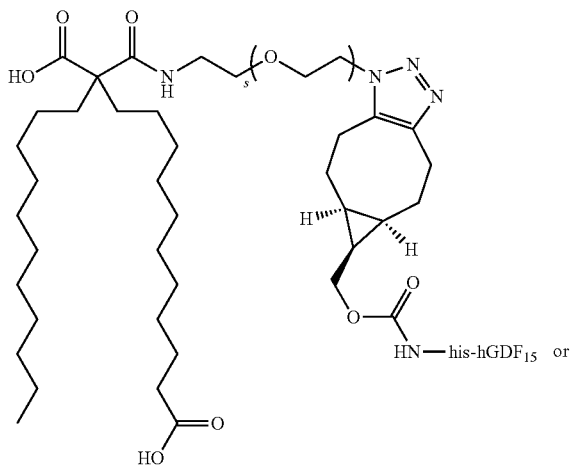

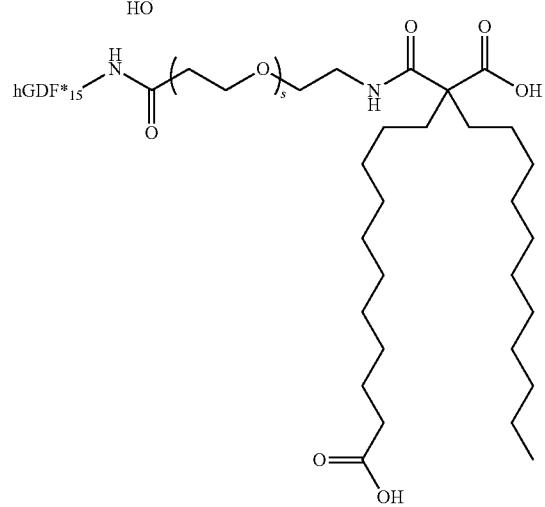

wherein hGDF15* is hGDF15 wherein the 2 or 3 amino acid at the N-terminus have been replaced with an amino acid sequence XH- or XHX'- respectively, wherein H is histidine and X and X' are independently selected from M and A; or a dimer thereof; and wherein his-hGDF15 is hGDF15 wherein a tag, comprising 1 to 6 histidine amino acids and optionally 1 or 2 methionine amino acids, has been added to the N-terminus of hGDF15; or a dimer thereof; and s is an integer between 20-30.

In one aspect of this embodiment the tag comprises histidine amino acids and 1 or 2 non-adjacent methionine amino acids. In another aspect of this embodiment, the arrangement of histidine and methionine amino acids is so that the amino acid at the position adjacent to the N-terminus amino acid is a histidine. In a further aspect of this embodiment the tag is selected from MHHHHHHM-(SEQ ID NO: 15) and MHHHHHH-(SEQ ID NO: 16).

In a particular aspect of embodiment 9, in view of the homodimer nature of hGDF15* and his-hGDF15, one or two polypeptide chains (monomeric unit) which constitute the homodimer may be linked the fatty acid molecule via a linker. As a result, the homodimer may be linked to one or may be linked to two fatty acid molecules via a linker at the N-terminus. Such embodiment may be represented by the GDF15 biomolecule linked to the fatty acid via a linker having the Formulae below:

FORMULA C

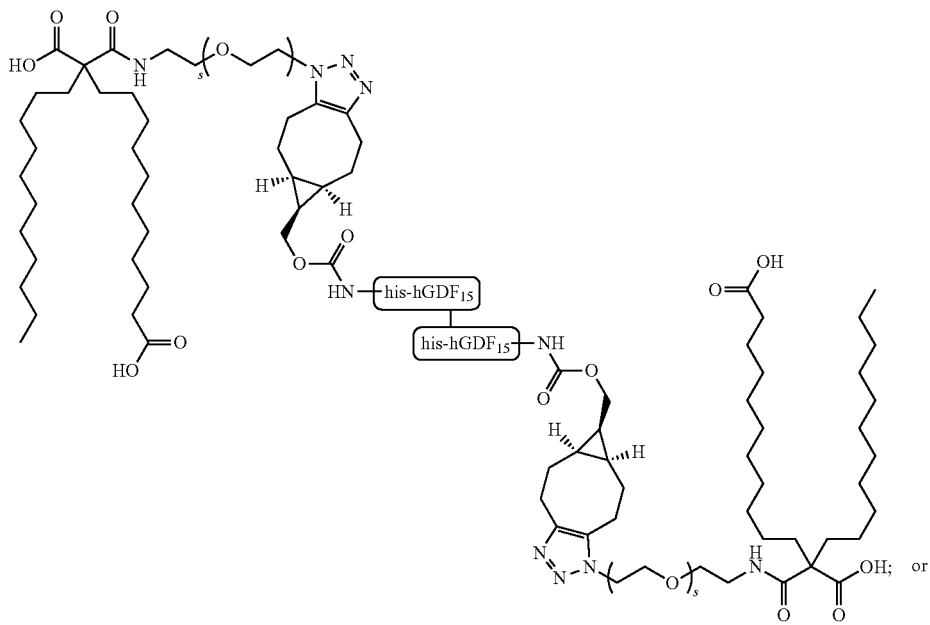

-continued

FORMULA D

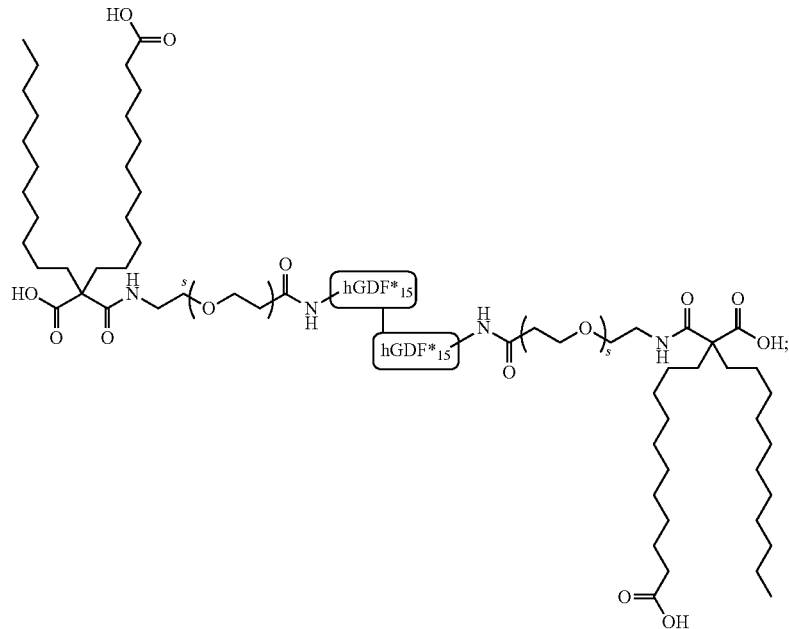

wherein both monomeric units of his-hGDF15 or of hGDF15* (as defined above) are linked to the fatty acid moiety via a linker at both N-terminus; or

FORMULA E

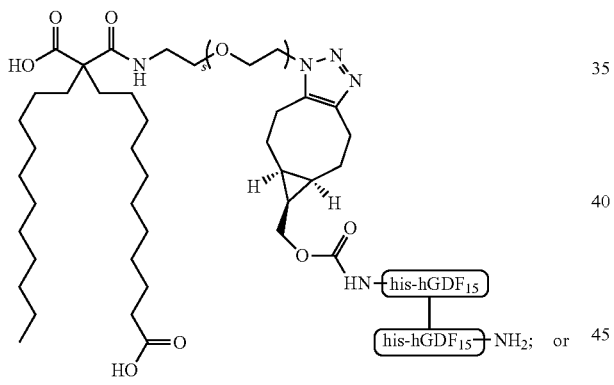

FORMULA F

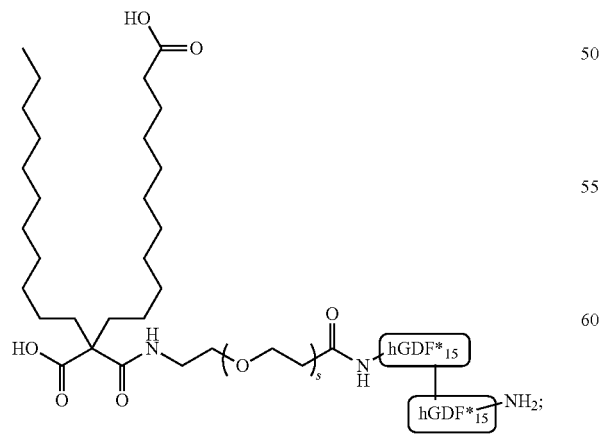

wherein only one of the monomer unit of his-hGDF15 or of hGDF15* (as defined above) is linked to the fatty acid moiety via a linker at the N-terminus. Furthermore, the invention also contemplates mixtures of conjugates of the invention; for example a mixture comprising a conjugate of Formula C and a conjugate of Formula E, or a mixture comprising a conjugate of formula D and a conjugate of Formula F.

In embodiment 10, the invention pertains to a composition comprising a mixture of a conjugate of Formula C and a conjugate of Formula E. In embodiment 10A, the invention pertains to a composition comprising a mixture of a conjugate of Formula D and a conjugate of Formula F. Therefore, in embodiment 10B, the invention relates to a conjugate according to claim 1, 2, 9 or 10, comprising:

1. a variant of homodimer hGDF15 wherein the 2 or 3 amino acid at the N-terminus have been replaced with an amino acid sequence XH- or XHX'- respectively, wherein H is histidine and X and X' are independently selected from M and A; or
   a homodimer hGDF15 wherein a tag, comprising 1 to 6 histidine amino acids and optionally 1 or 2 methionine amino acids, has been added at the N-terminus of hGDF15; and
2. one or two fatty acid of Formula:

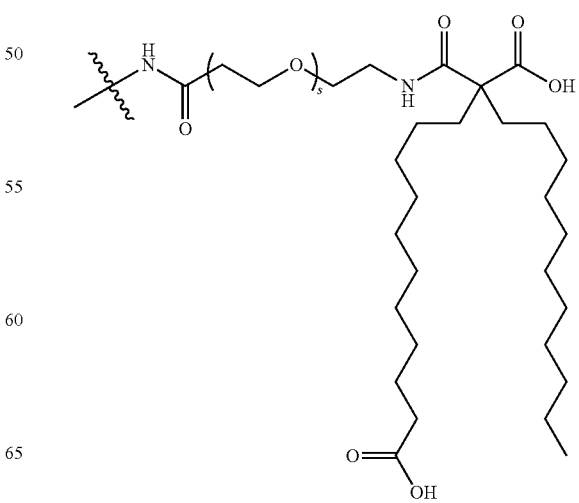

wherein the fatty acid is linked to the N-terminus of the polypeptide chain via a linker; or a mixture of conjugates.

In embodiment 10C, the invention pertains to a conjugate of embodiment 9, 10, 10A or 10B, wherein hGDF15* is hGDF15 wherein the 2 or 3 amino acid at the N-terminus have been replaced with an amino acid sequence XH- or XHX'- respectively,
wherein H is histidine and X and X' are independently selected from M and A; or a dimer thereof; and
wherein his-hGDF15 is hGDF15 wherein a tag, comprising 4 to 6 histidine amino acids and 1 or 2 methionine amino acids, has been added to the N-terminus of hGDF15; or a dimer thereof; and s is an integer between 22 and 28. In one aspect of this embodiment the tag comprises histidine amino acids and 1 or 2 non-adjacent methionine amino acids. In another aspect of this embodiment, the arrangement of histidine and methionine amino acids is so that the amino acid at the position adjacent to the N-terminus amino acid is a histidine. In a further aspect of this embodiment the tag is selected from MHHHHHHM-(SEQ ID NO: 15) and MHH-HHHH-(SEQ ID NO: 16).

In embodiment 11, the invention pertains to a conjugate according to any one of the preceeding embodiments wherein the biomolecule is selected from M-(His)6-hGDF15 (SEQ ID No 1), M-(his)6-M-hGDF15 (SEQ ID NO: 2), MH(199-308)hGDF15 (SEQ ID NO: 4), MHA(200-308)hGDF15(SEQ ID NO: 6), AHA(200-308)hGDF15 (SEQ ID NO: 7) and AH(199-308)GDF15 (SEQ ID NO: 5); or a dimer thereof.

In embodiment 11A, the invention pertains to a conjugate according to embodiment 11 wherein the biomolecule is selected from MH(199-308)hGDF15 (SEQ ID NO: 4), MHA(200-308)hGDF15 (SEQ ID NO: 6), AHA(200-308) hGDF15 (SEQ ID NO: 7) and AH(199-308)GDF15 (SEQ ID NO: 5); or a dimer thereof.

In embodiment 11B, the invention pertains to a conjugate according to embodiment 11 wherein the biomolecule is selected AHA(200-308)hGDF15 (SEQ ID NO: 7); or a dimer thereof.

In embodiment 12, the invention pertains to a conjugate according to embodiment 11B wherein the biomolecule linked to the fatty acid via a linker is of Formula G or of Formula H:

FORMULA G

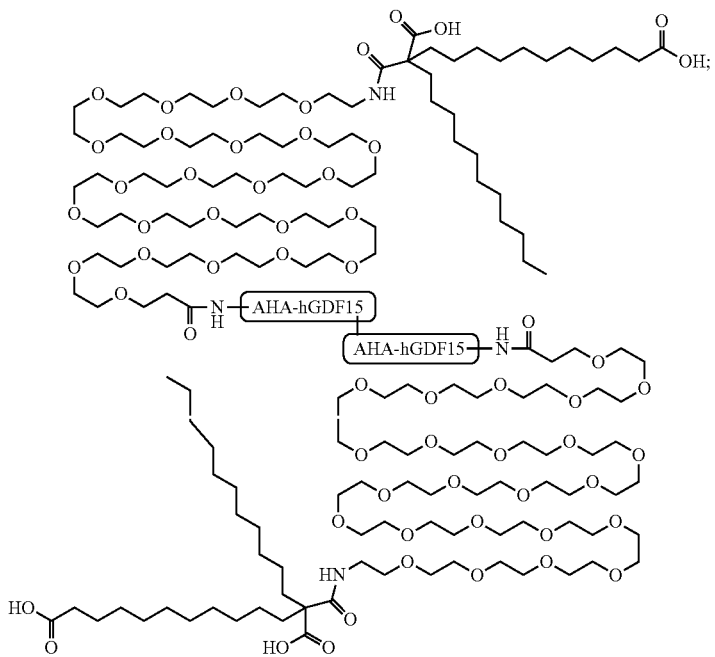

FORMULA H

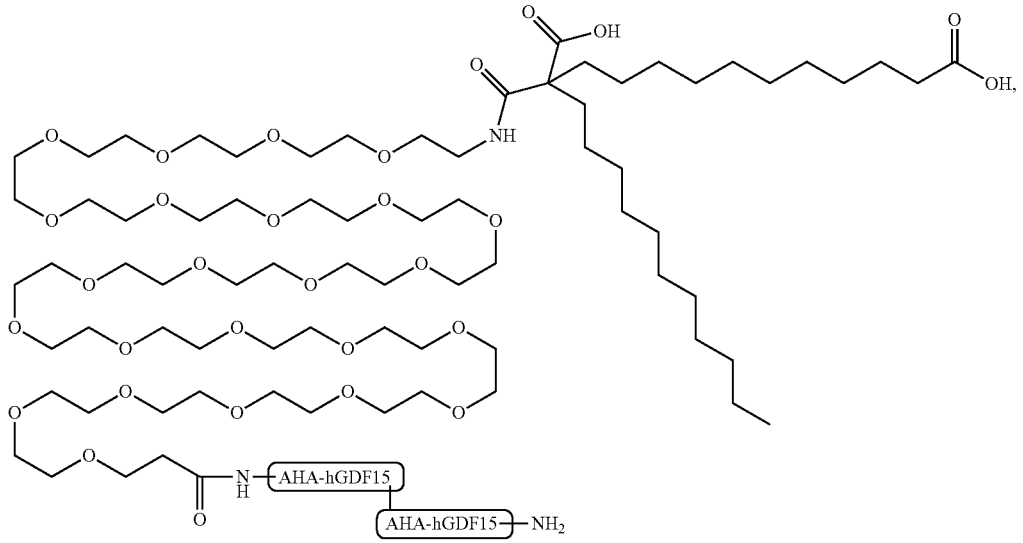

wherein AHA-hGDF15 is SEQ ID NO: 7 and the fatty acid is linked at the N-terminus of one or of the 2 monomeric units. Furthermore, the invention contemplates a mixture comprising the conjugate of Formula G and the conjugate of Formula H.

In embodiment 13, the invention pertains to a composition comprising a mixture of a conjugate according to embodiment 12 having Formula G and a conjugate according to embodiment 12 having Formula H. In a particular aspect of this embodiment, the mixture is a 1:1 molar ratio of a conjugate of Formulae G and a conjugate of Formula H.

The AHA-(200-308)-hGDF15 (SEQ ID NO: 7) was designed to remove the clipping site observed within the native protein as well as to remove the potential methioinine (M1) formylation site and the N-199 deamidation site. The superior quality and homogeneity of the AHA was confirmed by a material quality check showing no clipping, deamidation, or methionine oxidation which was observed with the hGDF15 native sequence.

|  | MHHHHHH-ARN-(200-308)-hGDF15 (SEQ ID NO: 17) | AHA-(200-308)-hGDF15 (SEQ ID NO: 7) |
| --- | --- | --- |
| clipping | R9/N10 (<1%) N10/G11 (<1%) | None detected |
| Methionine oxidation | M1: 12.0% oxidation | N/A |
| N-199 deamidation | N10: 50.1% deamidation | N/A |

In embodiment 14, the invention pertains to a conjugate according to any one of preceeding embodiments wherein the fatty acid residue is attached the N-terminus of the peptide or protein via a linker. In embodiment 15, the invention pertains to a conjugate according to any one of the preceeding embodiments wherein the conjugate has a plasma stability half-life of more than 5 h. In one aspect of this embodiment, the conjugate has a plasma stability half-life of more than 10 h. In another aspect of this embodiment, the conjugate has a plasma stability half-life of more than 20 h or more than 30 h. In yet another aspect of this embodiment, the conjugate has a plasma stability half-life of more than 40 h or more than 50 h.

In embodiment 16, the invention pertains to a conjugate according to any one of the preceeding embodiments where the improvement of plasma stability half-life compared to the non-conjugated biomolecule is 2 fold, 5 fold, 10 fold, 20 fold, 30 fold, 40 fold, 50 fold or 75 fold.

In another embodiment, the biomolecule, the linker and the fatty acid moiety (R1 to R4, n, m p and Ak) are those defined by in the Examples section below.

In one embodiment, the invention pertains to a compound of Formula:

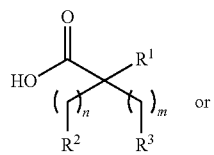

A1

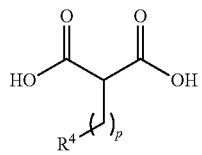

A2

$R^1$ is $CO_2H$ or H;

$R^2$ and $R^3$ are independently of each other H, OH, $CO_2H$, —CH=$CH_2$ or —C≡CH; with the proviso that $R^2$ and $R^3$ are not identical;

$R^4$ is $CO_2H$;

n and m are independently of each other an integer between 6 and 30; or an amide, ester or pharmaceutically acceptable salt thereof. In another aspect of this embodiment, the invention pertains to a compound of Formula A1 wherein at least one of $R^2$ and $R^3$ is $CO_2H$. In yet a further aspect of this embodiment, the invention pertains to a compound selected from the group consisting of:

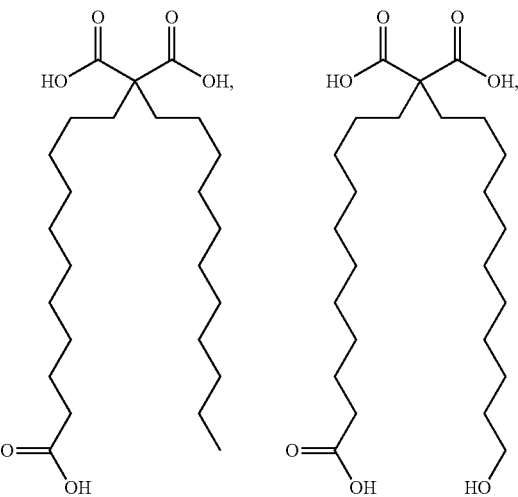

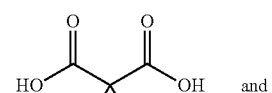 and

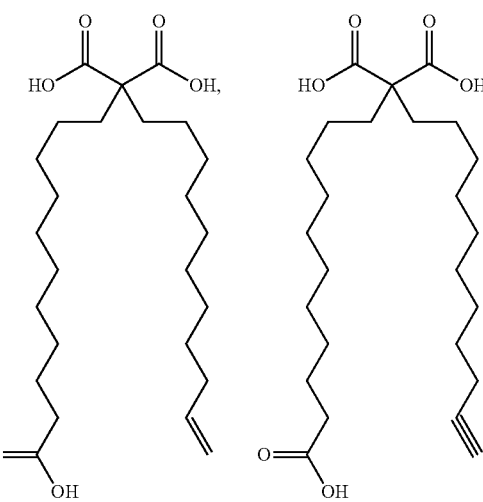

-continued

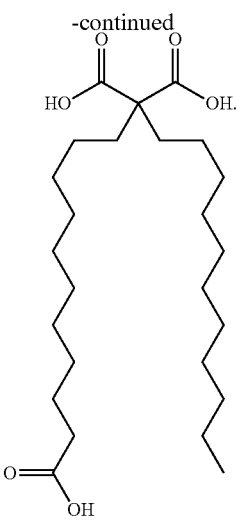

Synthesis of Peptide/polypeptide and/or Modified Form Thereof

The peptides or polypeptides of the invention may be produced by either synthetic chemical processes or by recombinant methods or combination of both methods. The peptides or polypeptides/protein constructs may be prepared as full-length or may be synthesized as non-full length fragments and joined. The peptides and polypeptides of the present invention can be produced by the per se known procedures for peptide synthesis. The methods for peptide synthesis may be any of a solid-phase synthesis and a liquid-phase synthesis. Thus, the peptide and polypeptide of interest can be produced by condensing a partial peptide or amino acid capable of constituting the protein with the residual part thereof and, when the product has a protective group, the protective group is detached whereupon a desired peptide can be manufactured. The known methods for condensation and deprotection include the procedures described in the following literature (1)-(5).

(1) M. Bodanszky and M. A. Ondetti, Peptide Synthesis, Interscience Publishers, New York, 1966,
(2) Schroeder and Luebke, The Peptide, Academic Press, New York, 1965,
(3) Nobuo Izumiya et al. Fundamentals and Experiments in Peptide Synthesis, Maruzen, 1975,
(4) Haruaki Yajima and Shumpei Sakakibara, Biochemical Experiment Series 1, Protein Chemistry IV, 205, 1977, and
(5) Haruaki Yajima (ed.), Development of Drugs-Continued, 14, Peptide Synthesis, Hirokawa Shoten.

After the reaction, the peptide or polypeptide can be purified and isolated by a combination of conventional purification techniques such as solvent extraction, column chromatography, liquid chromatography, size exclusion chromatography and ion exchange chromatography and recrystallization. Where the peptide isolated as above is a free compound, it can be converted to a suitable salt by the known method. Conversely where the isolated product is a salt, it can be converted to the free peptide by the known method.

The amide of polypeptide can be obtained by using a resin for peptide synthesis which is suited for amidation. The resin includes chloromethyl resin, hydroxymethyl resin, benzhydrylamine resin, aminomethyl resin, 4-benzyloxybenzyl alcohol resin, 4-methylbenz-hydrylamine resin, PAM resin, 4-hydroxymethylmethylphenylacetamidomethyl resin, polyacrylamide resin, 4-(2',4'-dimethoxyphenyl-hydroxymethyl)phenoxy resin, 4-(2',4'-dimethoxyphenyl-Fmoc-aminomethyl)phenoxy resin, 2-chlorotrityl chloride resin, and so on. Using such a resin, amino acids whose α-amino groups and functional groups of side-chain have been suitably protected are condensed on the resin according to the sequence of the objective peptide by various condensation techniques which are known per se. At the end of the series of reactions, the peptide or the protected peptide is removed from the resin and the protective groups are removed and if necessary, disulfide bonds are formed to obtain the objective polypeptide.

For the condensation of the above-mentioned protected amino acids, a variety of activating reagents for peptide synthesis can be used such as HATU, HCTU or e.g. a carbodiimide. The carbodiimide includes DCC, N,N'-diisopropylcarbodiimide, and N-ethyl-N'-(3-dimethylaminopropyl)carbodiimide. For activation with such a reagent, a racemization inhibitor additive, e.g. HOBt or Oxyma Pure can be used. The protected amino acid can be directly added to the resin along with the activation reagents and racemization inhibitor or be pre-activated as symmetric acid anhydride, HOBt ester, or HOOBt ester then added to the resin. The solvent for the activation of protected amino acids or condensation with the resin can be properly selected from among those solvents which are known to be useful for peptide condensation reactions. For example, N,N-dimethylformamide, N-methylpyrrolidone, chloroform, trifluoroethanol, dimethyl sulfoxide, DMF, pyridine, dioxane, methylene chloride, tetrahydrofuran, acetonitrile, ethyl acetate, or suitable mixtures of them can be mentioned. The reaction temperature can be selected from the range hitherto-known to be useful for peptide bond formation and is usually selected from the range of about −20° C.-50° C. The activated amino acid derivative is generally used in a proportion of 1.5-4 fold excess. If the condensation is found to be insufficient by a test utilizing the ninhydrin reaction, the condensation reaction can be repeated to achieve a sufficient condensation without removing the protective group. If repeated condensation still fails to provide a sufficient degree of condensation, the unreacted amino group can be acetylated with acetic anhydride or acetylimidazole.

The protecting group of amino group for the starting material amino acid includes Z, Boc, tertiary-amyloxycarbonyl, isobornyloxycarbonyl, 4-methoxybenzyloxycarbonyl, Cl—Z, Br—Z, adamantyloxycarbonyl, trifluoroacetyl, phthalyl, formyl, 2-nitrophenylsulfenyl, diphenylphosphinothioyl, or Fmoc. The carboxy-protecting group that can be used includes but is not limited to the above-mentioned $C_{1-6}$ alkyl, $C_{3-8}$ cycloalkyl and $C_{6-10}$aryl-$C_{1-2}$alkyl as well as 2-adamantyl, 4-nitrobenzyl, 4-methoxybenzyl, 4-chlorobenzyl, phenacyl, benzyloxycarbonylhydrazido, tertiary-butoxycarbonylhydrazido, and tritylhydrazido.

The hydroxy group of serine and threonine can be protected by esterification or etherification. The group suited for said esterification includes carbon-derived groups such as lower alkanoyl groups, e.g. acetyl etc., aroyl groups, e.g. benzoyl etc., benzyloxycarbonyl, and ethoxycarbonyl. The group suited for said etherification includes benzyl, tetrahydropyranyl, and tertiary-butyl. The protective group for the phenolic hydroxyl group of tyrosine includes Bzl, $Cl_2$-Bzl, 2-nitrobenzyl, Br—Z, and tertiary-butyl.

The protecting group of imidazole for histidine includes Tos, 4-methoxy-2,3,6-tri ethylbenzenesulfonyl, DNP, benzyloxymethyl, Bum, Boc, Trt, and Fmoc.

The activated carboxyl group of the starting amino acid includes the corresponding acid anhydride, azide and active esters, e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc. The activated amino group of the starting amino acid includes the corresponding phosphoramide.

The method for elimination of protective groups includes catalytic reduction using hydrogen gas in the presence of a catalyst such as palladium black or palladium-on-carbon, acid treatment with anhydrous hydrogen fluoride, methanesulfonic acid, trifluoromethanesulfonic acid, trifluoroacetic acid, or a mixture of such acids, base treatment with diisopropylethylamine, triethylamine, piperidine, piperazine, reduction with sodium metal in liquid ammonia. The elimination reaction by the above-mentioned acid treatment is generally carried out at a temperature of −20° C.-40° C. and can be conducted advantageously with addition of a cation acceptor such as anisole, phenol, thioanisole, m-cresol, p-cresol, dimethyl sulfide, 1,4-butanedithiol, 1,2-ethanedithiol. The 2,4-dinitrophenyl group used for protecting the imidazole group of histidine can be eliminated by treatment with thiophenol, while the formyl group used for protecting the indole group of tryptophan can be eliminated by alkali treatment with dilute sodium hydroxide solution or dilute aqueous ammonia as well as the above-mentioned acid treatment in the presence of 1,2-ethanedithiol, 1,4-butanedithiol.

The method for protecting functional groups which should not take part in the reaction of the starting material, the protective groups that can be used, the method of removing the protective groups, and the method of activating the functional groups that are to take part in the reaction can all be selected judicially from among the known groups and methods.

An another method for obtaining the amide form of the polypeptide comprises amidating the -carboxyl group of the C-terminal amino acid at first, then extending the peptide chain to the N-side until the desired chain length, and then selectively deprotecting the α-amino group of the C-terminal peptide and the α-carboxy group of the amino acid or peptide that is to form the remainder of the objective polypeptide and condensing the two fragments whose α-amino group and side-chain functional groups have been protected with suitable protective groups mentioned above in a mixed solvent such as that mentioned hereinbefore. The parameters of this condensation reaction can be the same as described hereinbefore. From the protected peptide obtained by condensation, all the protective groups are removed by the above-described method to thereby provide the desired crude peptide. This crude peptide can be purified by known purification procedures and the main fraction be lyophilized to provide the objective amidated polypeptide. To obtain an ester of the polypeptide, the α-carboxyl group of the C-terminal amino acid is condensed with a desired alcohol to give an amino acid ester and then, the procedure described above for production of the amide is followed.

Alternatively, recombinant expression methods are particularly useful. Recombinant protein expression using a host cell (a cell artificially engineered to comprise nucleic acids encoding the sequence of the peptide and which will transcribe and translate, and optionally, secrete the peptide into the cell growth medium) is used routinely in the art. For recombinant production process, a nucleic acid coding for amino acid sequence of the peptide would typically be synthesized by conventionally methods and integrated into an expression vector. Such methods is particularly preferred for manufacture of the polypeptide compositions comprising the peptides fused to additional peptide sequences or other proteins or protein fragments or domains. The host cell can optionally be at least one selected from *E. coli*, COS-1, COS-7, HEK293, BHT21, CHO, BSC-1, Hep G2, 653, SP2/0, 293, heLa, myeloma, lymphoma, yeast, insect or plant cells, or any derivative, immortalized or transformed cell thereof.

The invention also encompasses polynucleotides encoding the above-described variants that may be in the form of RNA or in the form of DNA, which DNA includes cDNA, genomic DNA, and synthetic DNA. The DNA may be double-stranded or single-stranded. The coding sequences that encode the compositions of the present invention may vary as a result of the redundancy or degeneracy of the genetic code.

The polynucleotides that encode for the compositions of the present invention may include the following: only the coding sequence for the variant, the coding sequence for the variant and additional coding sequence such as a functional polypeptide, or a leader or secretory sequence or a pro-protein sequence; the coding sequence for the variant and non-coding sequence, such as introns or non-coding sequence 5' and/or 3' of the coding sequence for the variant. Thus the term "polynucleotide encoding a variant" encompasses a polynucleotide that may include not only coding sequence for the variant but also a polynucleotide, which includes additional coding and/or non-coding sequence.

The invention further relates to variants of the described polynucleotides that encode for fragments, analogs and derivatives of the polypeptide that contain the indicated substitutions. The variant of the polynucleotide may be a naturally occurring allelic variant of the human GDF15 sequence, a non-naturally occurring variant, or a truncated variant as described above. Thus, the present invention also includes polynucleotides encoding the variants described above, as well as variants of such polynucleotides, which variants encode for a fragment, derivative or analog of the disclosed variant. Such nucleotide variants include deletion variants, substitution variants, truncated variants, and addition or insertion variants as long as at least one of the indicated amino acid substitutions of the first or second embodiments is present.

The polynucleotides of the invention can be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences. The GDF15 variant can be expressed in mammalian cells, insect, yeast, bacterial or other cells under the control of appropriate promoters. Cell free translation systems can also be employed to produce such proteins using RNAs derived from DNA constructs of the present invention.

*Escherichia Coli* (*E. coli*) is a prokaryotic host useful particularly for cloning the polynucleotides of the present invention. Other microbial hosts suitable for use include *Bacillus subtilus, Salmonella typhimurium*, and various species of *Serratia, Pseudomonas, Streptococcus*, and *Staphylococcus*, although others may also be employed as a matter of choice. In these prokaryotic hosts, one can also make expression vectors, which will typically contain expression control sequences compatible with the host cell (e.g., an origin of replication). In addition, any of a number of well-known promoters may be present, such as the lactose promoter system, a tryptophan (Trp) promoter system, a beta-lactamase promoter system, or a promoter system from phages lambda or T7. The promoters will typically control expression, optionally with an operator sequence, and have ribosome binding site sequences and the like, for initiating and completing transcription and translation.

One skilled in the art of expression of proteins will recognize that methionine or methionine-arginine sequence can be introduced at the N-terminus of the mature sequence for expression in *E. coli* and are contemplated within the context of this invention. Thus, unless otherwise noted, compositions of the present invention expressed in *E. coli* have a methionine sequence introduced at the N-terminus.

Other microbes, such as yeast or fungi, may also be used for expression. *Pichia pastoris, Saccharomyces cerevisiae, Schizosaccharomyces pombe*, and *Pichia angusta* are examples of preferred yeast hosts, with suitable vectors having expression control sequences, such as promoters, including 3-phosphoglycerate kinase or other glycolytic enzymes, and an origin of replication, termination sequences and the like as desired. *Aspergillus niger, Trichoderma reesei*; and *Schizophyllum commune*, are examples of fungi hosts, although others may also be employed as a matter of choice.

Mammalian tissue cell culture may also be used to express and produce the polypeptides of the present invention. A number of suitable host cell lines capable of secreting intact variants have been developed in the art, and include the CHO cell lines, various COS cell lines, NSO cells, Syrian Hamster Ovary cell lines, HeLa cells, or human embryonic kidney cell lines (i.e. HEK293, HEK293EBNA).

Expression vectors for mammalian cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from SV40, adenovirus, bovine papilloma virus, cytomegalovirus, Raus sarcoma virus, and the like. Preferred polyadenylation sites include sequences derived from SV40 and bovine growth hormone.

The vectors containing the polynucleotide sequences of interest (e.g., that encode the compositions of the present invention and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Various methods of protein purification may be employed and such methods are known in the art and described, for example, in Deutscher, Methods in Enzymology 182: 83-9 (1990) and Scopes, Protein Purification: Principles and Practice, Springer-Verlag, NY (1982). The purification step(s) selected will depend, for example, on the nature of the production process used for the compositions of the present invention.

The polypeptides may be prepared in substantially pure or isolated form (e.g., free from other polypeptides). The polypeptides can be present in a composition that is enriched for the polypeptide relative to other components that may be present (e.g., other polypeptides or other host cell components). For example, purified polypeptide may be provided such that the polypeptide is present in a composition that is substantially free of other expressed proteins, e.g., less than 90%, less than 60%, less than 50%, less than 40%, less than 30%, less than 20%, less than 10%, less than 5%, or less than 1%, of the composition is made up of other expressed proteins Synthesis of Fatty Acid Moiety Scheme 1 describes the synthesis of a fatty acid moiety of Formula A2.

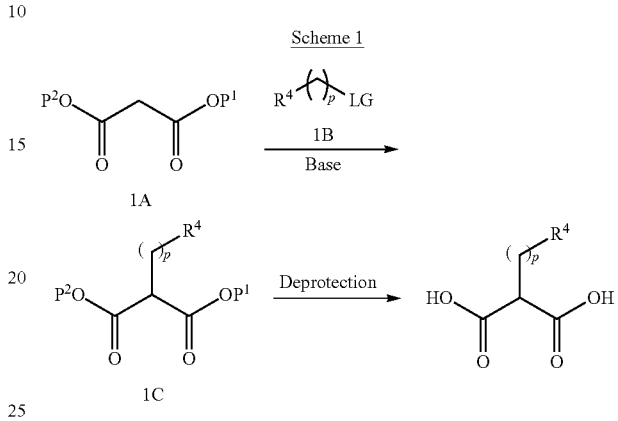

wherein $P^1$ and $P^2$ are carboxylic acid protective group such as for example methyl, ethyl, tert-butyl, methoxybenzyl, benzyl, benzyloxy, methoxymethyl, methylthiomethyl, tetrahydropyranyl, phenacyl, N-Phthalimide, cinnamyl, triphenylmethyl, 9-anthrylmethyl, piperonyl, trimethylsilyl, t-butyldimethylsilyl or 2-alkyl 1,3 oxazolines; wherein LG is a leaving group such as for example halo (e.g. Br, Cl, I) or trifluoromethanesulfonyloxy and wherein $R^4$ and p are as described in embodiment 1.

Alkylation of protected malonic acid (1A) with an alkylating agent (1B) in the presence of a base (e.g. sodium hydride, potassium or cesium carbonates, sodium hydroxide, lithium diisopropyl amide, sodium bis(trimethylsilyl)amide, potassium bis(trimethylsilyl)amide, lithium tertamethylpiperidide, 1,8-Diaazacycloundec-7-ene, N,N-diisopropyl ethyl amine or 2,6-dit-butylputridine), in a solvent such as DMF, THF or dimethyl acetamide, generates the protected fatty acid moiety (1C). When $R^4$ is OH or $CO_2H$, protection of these functional groups may be required prior to the alkylation step. Protective groups for hydroxyl are known in the art and are for example 1. ethers such as Methyl ether, methoxymethyl ether (MOM), Tetrahydropyranyl ether (THP), t-Butyl ether, allyl ether, benzyl ether, t-butyldimathylsilyl ether, t-butyldiphenyl silyl ether, tribenzyl silyl ether, isopropyldimethylsilyl ether, triphenylmethyl ether, nitrobenzyl ether, 2. Esters and carbonates such as acetic acid ester, formate ester, trichloroacetate ester, phenoxyacetate ester, pivaloate ester, benzoate ester, methyl carbonate, benzyl carbonate, allyl carbonate, nitrate ester, adamanoate ester, notrophenyl carbonate.

The fatty acid moiety of Formula A2 is obtained by deprotection using appropriate deprotection method. Standard methods can be applied for the hydrolysis of the intermediate (1C) using a base selected from, but not limited to, NaOH, KOH, or LiOH, or an acid selected from, but not limited to, TFA, HCl, or $BCl_3$. When $P^1$ or $P^2$ is benzyl or methoxybenzyl, a preferable method of the deprotection is hydrogenation in the presence of a catalyst such as, but not limited to, palladium-on-carbon.

Scheme 2 illustrates the synthesis of an fatty acid moiety of Formula $A^1$ wherein $R^1$ is $C(O)_2H$.

Scheme 2

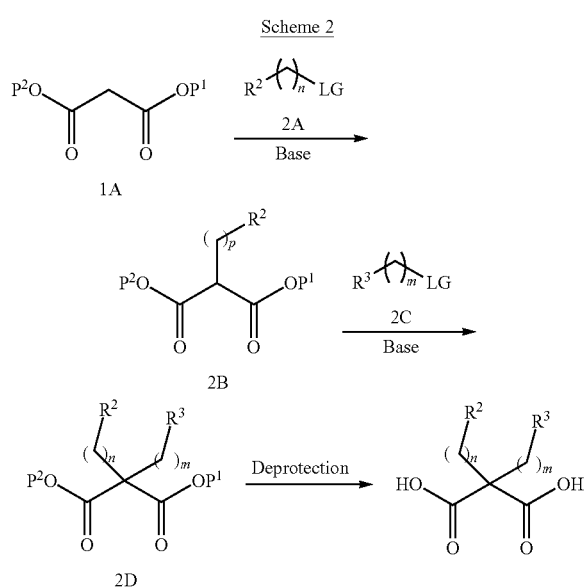

wherein $P^1$ and $P^2$, LG are as defined supra and $R^2$, $R^3$, n and m are as defined in embodiment 1.

Protected malonic acid (1A) undergoes 2 subsequent alkylations with alkylating agent (2A) and (2C), order of which can be reversed, prior to deprotection using appropriate method as described supra in Scheme 1. When $R^2$ and $R^3$ are OH or $CO_2H$, protection of these functional groups may be required prior to the alkylation steps.

The fatty acid moiety of Formula $A^1$ wherein $R^1$ is H can be prepared by decarboxylation of the corresponding fatty acid moiety of Formula $A^1$ wherein R1 is CO2H. Decarboxylation conditions are well known in the art such as for example decarboxylation under basic condition (e.g. Ammonium hydroxide).

Synthesis of Biomolecule-linker Construct

Scheme 3

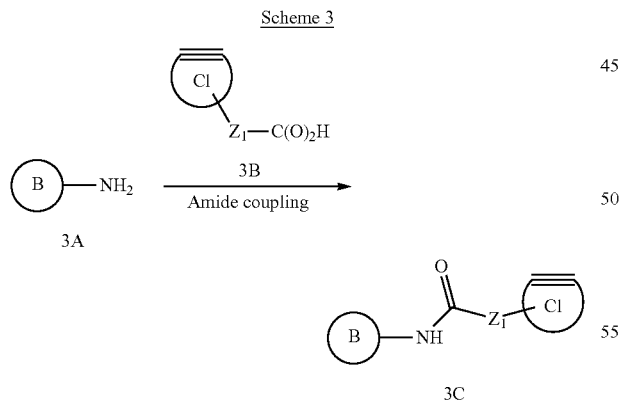

wherein B is biomolecule or a modified form thereof, $Z^1$ is a $C_1$-$C_{20}$ alkylene linker wherein the alkylene chain is optionally substituted with oxo (=O), and wherein one or more carbon is replaced with O or NH; and wherein Cl is a mono, di or tricyclic carbocyclic or heterocyclic ring system optionally substituted with fluorine.

The cycloalkyne (3B) is attached to an amino residue of the biomolecule (3A) (for example to the amino functionality of the N-terminus or the side chain of a lysine) via its carboxylic acid reactive group using standard amide coupling methods. Known coupling methods may be applied including, but not limited to, conversion of the intermediate (3B) to an activated form thereof, [e.g. to a corresponding pyrrolidine-2,5-dione (using standard N-hydrosuccinimide chemistry), or converting acid (3B) using reagents such as triphosgene, carbonyldiimidazole, 4-nitrophenyl chloroformate, or disuccinimidyl carbonate, conversion of the acid (3B) to a corresponding acid halide, using reagents such as thionyl chloride or oxalyl chloride, or conversion of the acid (3B) to a corresponding mixed anhydride using reagents such as ClC(O)O-isobutyl, 2,4,6-trichlorobenzoyl chloride or propyl phosphonic acid anhydride cyclic trimer (T3P), followed by reaction of the oxazolidine-2,5-dione, the acid halide, or the mixed anhydride] with the biomolecule (3A) in a presence or absence of a base such as tertiary amine (e.g. triethylamine or N,N-diisoproplyl ethylamine) or $K_2CO_3$. Alternatively, the biomolecule 3A can be coupled with the acid 3B using peptide condensation reagents including, but not limited to, dicyclohexylcarbodiimide (DCC), diisopropylcarbodiimide (DIC), 1-ethyl-3-(3-dimethylaminopropyl) carbodiimide hydrochloride (EDC HCl), benzotriazole-1-yl-oxy-tris-pyrrolidino-phosphonium hexafluorophosphate (PyBOP), or benzotriazole-1-yl-oxy-tris-(dimethylamino)-phosphonium hexafluorophosphate (BOP) in presence of or absence of a reagent such as 1-hydroxybenzotriazole, 1-hydroxy-7-azabenzotriazole, or dimethylaminopyridine. Preferably, the cycloalkyne/acid intermediate (3B) is converted to its activated form thereof using NHS chemistry prior to reacting with the amino functionality on the biomolecule.

A selective acylation of the amino functionality at the N-terminus of the biomolecule has been developed and reported in a co-filed US application Nos. 62/015,858 and 62/082,337.

The selective acylation involves the reaction of NHS activated cyclooctyne analog (NHS derivatives of (3B)) with a biomolecule where the N-terminus has been modified to include a histidine amino acid adjacent to the N-terminus amino acid. The reaction is highly selective for the amino functionality at the N-terminus when carried out at pH 4, due to the presence of a neighboring effect of the histidine amino acid.

Synthesis of Fatty Acid Residue Linker Construct
Fatty Acid-linker Construct for Click Chemistry Scheme 4 describes the synthesis of a fatty acid-PEG linker construct with a terminal azido functional group.

Scheme 4

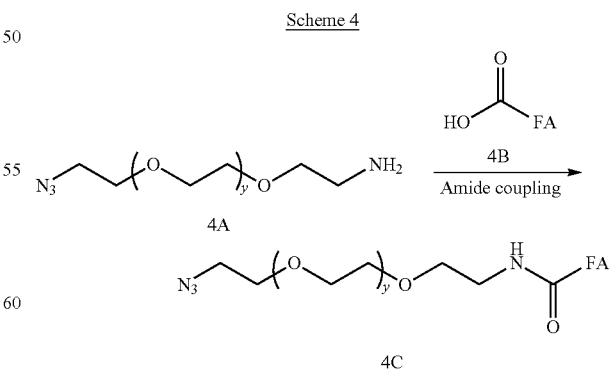

wherein y is 0 to 34 and FA is an fatty acid moiety as described in Formula A1, A2 or A3 which is attached via one of its carboxylic acid functionality to the PEG linker, FA has the following Formulae:

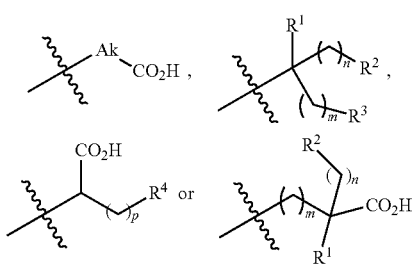

The fatty acid moiety (4B) is attached to a PEG containing linker (4A) via an amide coupling reaction. Known coupling methods have been described in detail supra in Scheme 3.

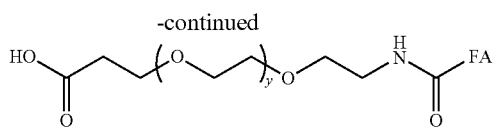

wherein FA is as defined supra in Scheme 4 and y is 0 to 34.

The fatty acid (4B) may be attached to a PEG containing linker (5A) using amide coupling described supra.

Fatty Acid-linker Construct for Attachment to a Biomolecule of Interest Using Transglutaminase Enzyme Scheme 5A describes the preparation of a Fatty acid-linker construct containing a glutamic acid amino acid allowing for site selective modification of a lysine when using transglutaminase enzyme.

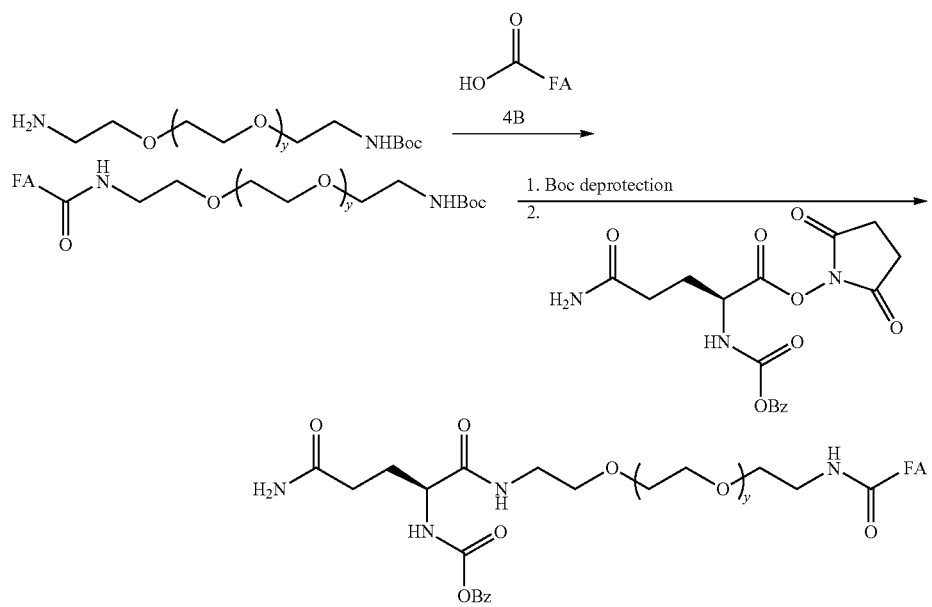

Preferably the acid functionality on the fatty acid moiety is activated using NHS chemistry.

Where $R^1$ is $CO_2H$, $R_2$, $R_3$ and $R_4$ are $CO_2H$ or OH, protecting groups may need to be introduced prior to the coupling reaction in order to control the reactive site. Protecting group for carboxylic acid and hydroxy groups have been described supra in scheme 1. Alternatively, selective activation of carboxylic acid can be achieved using NHS chemistry.

Fatty Acid-linker for Direct Attachment to the Biomolecule of Interest

Scheme 5 describes the synthesis of an fatty acid-PEG linker construct with a terminal CO2H functional group.

wherein y and FA are as previously defined. Such constructs allow for selective site modification of an amino group on the side chain of a lysine. This transglutaminase selective site modification of protein has been described in U.S. application Nos. 61/845,273 filed on Jul. 11 2013.

Synthesis of Conjugate of the Invention

Conjugation Using Click Chemistry

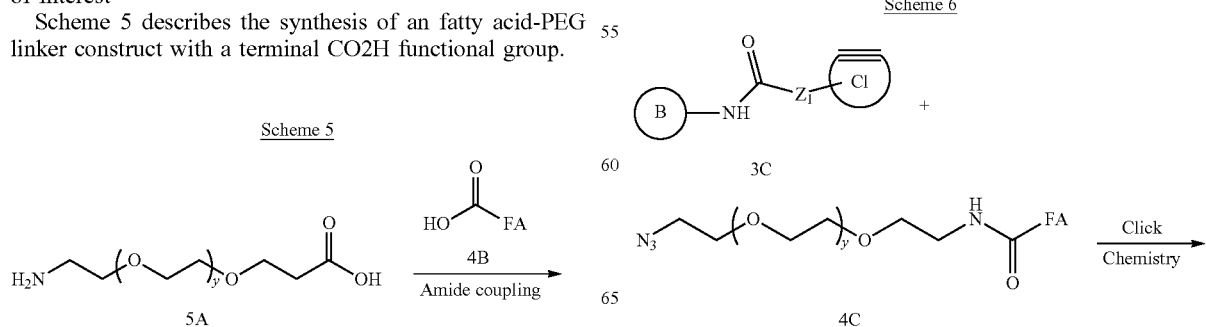

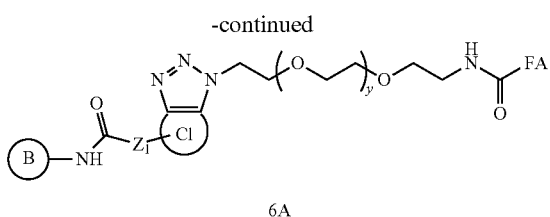

6A wherein B is a biomolecule of interest or a modified form thereof (for example mutant or a biomolecule containing a histidine tag) and y, C1, $Z_1$, FA and y are defined supra.

Cycloalkyne construct (3C) undergoes a Huisgen cycloaddition with a terminal azide of the Fatty acid-linker construct (4C) as commonly known as click chemistry. Example of click chemistries have been described in US 2009/0068738.

The fatty acid-linker construct (5B) is attached to an amino residue of the biomolecule (3A) (for example to the amino functionality of the N-terminus or the side chain of a lysine) via its carboxylic acid reactive group using standard amide coupling methods. Known coupling methods have been described in detail supra in Scheme 3. Preferably the acid functionality on the fatty acid-linker construct is activated using NHS chemistry.

A selective acylation of the amino functionality at the N-terminus of the biomolecule has been developed and reported in a co-filed US application Nos. 62/015,858 and 62/082,337. The selective acylation involves the reaction of a NHS activated compound (NHS derivatives of (5B)) with a biomolecule where the N-terminus has been modified to include a histidine amino acid adjacent to the N-terminus amino acid. The reaction is highly selective for the amino functionality at the N-terminus when carried out at pH 4, due to the presence of a neighboring effect of the histidine amino acid.

Conjugation Using Transglutaminase Enzyme

Scheme 7B

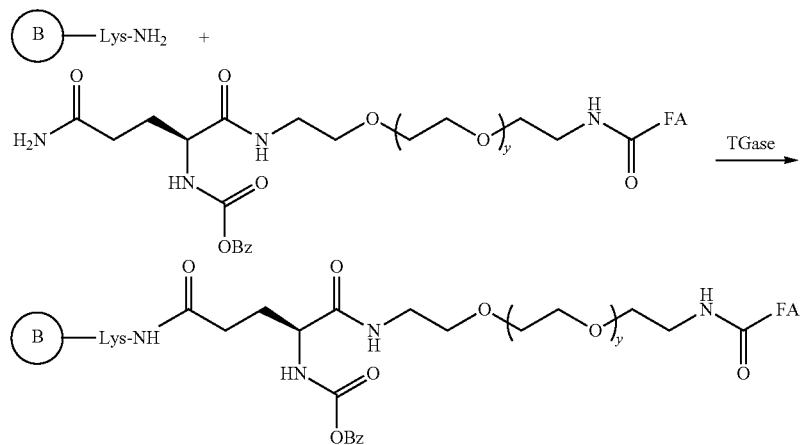

Conjugation Via Direct Attachment Using Coupling Conditions

Scheme 7

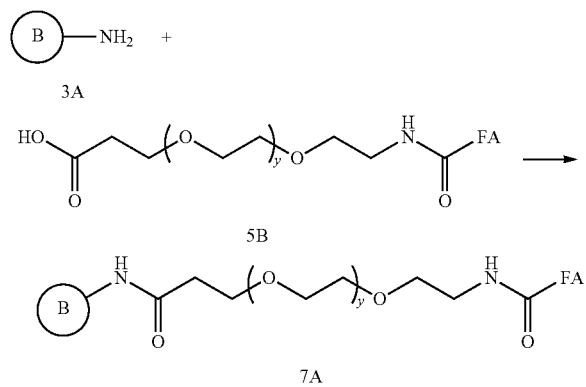

wherein B is a biomolecule of interest or a modified form thereof (such as for example mutant and/or a biomolecule containing a histidine tag) and the fatty acid-linker construct is attached to the N-terminus of the biomolecule.

Selective modification of the biomolecule at its lysine side chain can be achieved using transglutaminase enzyme. Such modification has been reported in U.S. application No. 61/845,273 filed Jul. 11 2013 or WO 2015/006728 (in example 25 of this application).

Pharmaceutical Composition

The conjugate of the instant invention may be administered in any of a variety of ways, including subcutaneously, intramuscularly, intravenously, intraperitoneally, inhalationally, intranasally, orally etc. Particularly preferred embodiments of the invention employ continuous intravenous administration of the conjugates of the instant invention, or an amide, ester, or salt thereof. The conjugates on the instant invention may be administered as a bolus or as a continuous infusion over a period of time. An implantable pump may be used. In certain embodiments of the invention, intermittent or continuous conjugates administration is continued for one to several days (e.g., 2-3 or more days), or for longer periods of time, e.g., weeks, months, or years. In some embodiments, intermittent or continuous conjugates administration is provided for at least about 3 days, preferably at least about 6 days. In other embodiments, intermittent or continuous conjugate administration is provided for at least about one week. In other embodiments, intermittent or continuous conjugate administration is provided for at least about two weeks. It may be desirable to maintain an average plasma conjugate concentration above a particular threshold value either during administration or between administration of multiple doses. A desirable concentration may be determined, for example, based on the subject's physiological condition, disease severity, etc. Such desirable value(s) can be identified by performing standard clinical trials. Alternatively, the peptides and conjugates thereof could be delivered orally via FcRn mechanism. (Nat Rev Immunol. 7(9), 715-25, 2007; Nat Commun. 3; 3:610, 2012, Am J Physiol Gastrointest Liver Physiol 304: G262-G270, 2013).

In another aspect, the present invention provides a pharmaceutical composition comprising a conjugate of the present invention or an amide, an ester or a salt thereof and one or more pharmaceutically acceptable carriers. The pharmaceutical composition can be formulated for particular routes of administration such as oral administration, subcutaneous administration, parenteral administration, and rectal administration, etc. In addition, the pharmaceutical compositions of the present invention can be made up in a solid form (including without limitation capsules, tablets, pills, granules, lyophilizates, powders or suppositories), or in a liquid form (including without limitation solutions, suspensions or emulsions). The pharmaceutical compositions can be subjected to conventional pharmaceutical operations such as aseptic manufacturing, sterilization and/or can contain conventional inert diluents, cake forming agents, tonicity agents, lubricating agents, or buffering agents, as well as adjuvants, such as preservatives, stabilizers, wetting agents, emulsifers and buffers, etc.

Pharmaceutical compositions suitable for injectable use typically include sterile aqueous solutions (where water soluble) or dispersions and sterile powders for the extemporaneous preparation of sterile injectable solutions or dispersion.

For intravenous administration, suitable carriers include physiological saline, bacteriostatic water, Cremophor ELTM (BASF, Parsippany, N.J.) or phosphate buffered saline (PBS). In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, amino acids, sorbitol, sodium chloride in the composition. Prolonged absorption of the injectable compositions can be brought about by including in the composition an agent which delays absorption, for example, aluminum monostearate and gelatin. In some embodiments, a multifunctional excipient such as recombinant albumin may be incorporated into the formulation process to facilitate the stabilization of the conjugate product from degradation or aggregation, to improve solubility and assist in the administration and release of the active component. (BioPharm International, 2012, Vol 23, Issue 3, pp 40-44).

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Sterile injectable solutions can be prepared by incorporating the active compound in the required amount in an appropriate solvent with one or a combination of ingredients enumerated above, as required, followed by filtration sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive therapeutic agents are preferably delivered in the form of an aerosol spray from pressured container or dispenser which contains a suitable propellant, e.g., a gas such as carbon dioxide, or a nebulizer. It is noted that the lungs provide a large surface area for systemic delivery of therapeutic agents.

The agents may be encapsulated, e.g., in polymeric microparticles such as those described in U.S. publication 20040096403, or in association with any of a wide variety of other drug delivery vehicles that are known in the art. In other embodiments of the invention the agents are delivered in association with a charged lipid as described, for example, in U.S. publication 20040062718. It is noted that the latter system has been used for administration of a therapeutic polypeptide, insulin, demonstrating the utility of this system for administration of peptide agents.

Systemic administration can also be by transmucosal or transdermal means.

Suitable compositions for transdermal application include an effective amount of a conjugate of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

In certain embodiments, the pharmaceutical composition is for subcutaneous administration. Suitable formulation components and methods for subcutaneous administration of polypeptide therapeutics (e.g., antibodies, fusion proteins and the like) are known in the art. See, e.g., Published United States Patent Application No 2011/0044977 and U.S. Pat. Nos. 8,465,739 and 8,476,239. Typically, the pharmaceutical compositions for subcutaneous administration contain suitable stabilizers (e.g, amino acids, such as methionine, and or saccharides such as sucrose), buffering agents and tonicifying agents.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, recombinant Albumin.

As used herein, the term "pharmaceutically acceptable salts" refers to salts that retain the biological effectiveness and properties of the conjugates of this invention and, which typically are not biologically or otherwise undesirable. In many cases, the conjugates of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.
Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, multifunctional excipient such as recombinant albumin and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

Method of the Invention

GDF15 circulating levels have been reported to be elevated in multiple pathological and physiological conditions, most notably pregnancy (Moore AG 2000. *J Clin Endocrinol Metab* 85: 4781-4788), β-thalassemia (Tanno T 2007, Nat Med 13:1096-101) (Zimmermann MB, 2008 *Am J Clin Nutr* 88:1026-31), and congenital dyserythropoietic anemia (Tamary H 2008, *Blood*. 112:5241-4). GDF15 has also been linked to multiple biological activities in literature reports. Studies of GDF15 knockout and transgenic mice suggested that GDF15 may be protective against ischemic/reperfusion- or overload-induced heart injury (Kempf T, 2006, *Circ Res*. 98:351-60) (Xu J, 2006, *Circ Res*. 98:342-50), protective against aging-associated motor neuron and sensory neuron loss (Strelau J, 2009, *J Neurosci*. 29: 13640-

8), mildly protective against metabolic acidosis in kidney, and may cause cachexia in cancer patients (Johnen H 2007 *Nat Med.* 11: 1333-40). Many groups also studied the role of GDF15 in cell apoptosis and proliferation and reported controversial results using different cell culture and xenograft models. Studies on transgenic mice showed that GDF15 is protective against carcinogen or Ape mutation induced neoplasia in intestine and lung (Baek S J 2006, *Gastroenterology.* 131:1553-60; Cekanova M 2009, *Cancer Prev Res* 2:450-8).

GDF15 has also been reported to play a role in inflammation, cancer and metabolism (Samule Breit et al. Growth Factors, October 2011; 29(5): 187-195). GDF15 has further been implicated in the regulation of physiological appetite and body weight (Vicky Wang-Wei Tsai et al. Public Library of Science: PLOS ONE 2013, Vol. 8, Issue 2, e55174)

The present invention provides methods for treating or preventing metabolic disorders or diseases, diabetes, type 2 diabetes mellitus, obesity, pancreatitis, dyslipidemia, alcoholic and nonalcoholic fatty liver disease/steatohepatitis and other progressive liver diseases, insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, diabetic complications (including but not limited to chronic kidney disease), neuropathy, gastroparesis and other metabolic disorders, in a subject in need thereof, comprising: administering to the subject a therapeutically effective amount of a conjugate of the invention, or an amide, ester or salt thereof or a mixture of conjugates, wherein the biomolecule is human Growth Differentiation Factor 15 (GDF15), homologs, variants, mutants, fragments and other modified forms thereof.

Such methods may have an advantageous effect such as for example decreasing the frequency of administration.

Thus, as a further embodiment, the present invention provides the use of a conjugate as described herein, or an amide, ester or a pharmaceutically acceptable salt thereof or a mixture of the conjugates described therein, wherein the biomolecule is human Growth Differentiation Factor 15 (GDF15), homologs, variants, mutants, fragments and other modified forms thereof, for the treatment of metabolic disorders or diseases, type 2 diabetes mellitus, obesity, pancreatitis, dyslipidemia, alcoholic and nonalcoholic fatty liver disease/steatohepatitis and other progressive liver diseases, insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, diabetic complications (including but not limited to chronic kidney disease), neuropathy, gastroparesis and other metabolic disorders.

Thus, as a further embodiment, the present invention provides the use of a conjugate or an amide, an ester or a pharmaceutically acceptable salt thereof, or a mixture of conjugates, in therapy.

The effective amount of a pharmaceutical composition or combination of the invention to be employed therapeutically will depend, for example, upon the therapeutic context and objectives. One skilled in the art will appreciate that the appropriate dosage levels for treatment will thus vary depending, in part, upon the molecule delivered, the indication for which the conjugate is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg. In a further aspect of this embodiment, the dosage can range from 5 µg/kg to 25 µg/kg. In yet a further aspect of this embodiment, the dosage can range from 10 µg/kg to 20 µg/kg.

The frequency of dosing will depend upon the pharmacokinetic parameters of the dual function protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The terms "therapeutically effective dose" and "therapeutically effective amount," as used herein, means an amount of conjugate that elicits a biological or medicinal response in a tissue system, animal, or human being sought by a researcher, physician, or other clinician, which includes alleviation or amelioration of the symptoms of the disease or disorder being treated, i.e., an amount of GDF15 (or GDF15 mutant) polypeptide conjugate that supports an observable level of one or more desired biological or medicinal response, for example lowering blood glucose, insulin, triglyceride, or cholesterol levels; reducing body weight; reducing food intake or improving glucose tolerance, energy expenditure, or insulin sensitivity).

The terms "patient" or "subject" are used interchangeably to refer to a human or a non-human animal (e.g., a mammal).

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. Thus, treatment includes inhibiting (i.e., arresting the development or further development of the disease, disorder or condition or clinical symptoms association therewith) an active disease (e.g. for example in the case of GDF15 conjugate, so as to decrease body weight, to decrease food intake, to decrease the level of insulin and/or glucose in the bloodstream, to increase glucose tolerance so as to minimize fluctuation of glucose levels, and/or so as to protect against diseases caused by disruption of glucose homeostasis).

In yet another embodiment, "treat", "treating" or "treatment" refers to preventing or delaying the onset or development or progression of the disease or disorder.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering a conjugate of the invention or a pharmaceutical composition comprising a conjugate) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "metabolic disease or disorder" refers to an associated cluster of traits that includes, but is not limited to, hyperinsulinemia, abnormal glucose tolerance, obesity, redistribution of fat to the abdominal or upper body compartment, hypertension, dyslipidemia characterized by high triglycerides, low high density lipoprotein (HDL)-cholesterol, and high small dense low density lipoprotein (LDL) particles. Subjects having metabolic disease or disorder are at risk for development of Type 2 diabetes and, for example, atherosclerosis.

The phrase "glucose metabolism disorder" encompasses any disorder characterized by a clinical symptom or a combination of clinical symptoms that is associated with an elevated level of glucose and/or an elevated level of insulin in a subject relative to a healthy individual. Elevated levels of glucose and/or insulin may be manifested in the following diseases, disorders and conditions: hyperglycemia, type II diabetes, gestational diabetes, type I diabetes, insulin resistance, impaired glucose tolerance, hyperinsulinemia, impaired glucose metabolism, pre-diabetes, metabolic disorders (such as metabolic disease or disorder, which is also referred to as syndrome X), and obesity, among others. The GDF15 conjugates of the present disclosure, and compositions thereof, can be used, for example, to achieve and/or maintain glucose homeostasis, e.g., to reduce glucose level in the bloodstream and/or to reduce insulin level to a range found in a healthy subject.

The term "insulin resistance" as used herein refers to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

The phrase "glucose tolerance", as used herein, refers to the ability of a subject to control the level of plasma glucose and/or plasma insulin when glucose intake fluctuates. For example, glucose tolerance encompasses the subject's ability to reduce, within about 120 minutes, the level of plasma glucose back to a level determined before the intake of glucose.

The term "Glucose intolerance, or 'Impaired Glucose Tolerance (IGT) is a pre-diabetic state of dysglycemia that is associated with increased risk of cardiovascular pathology. The pre-diabetic condition prevents a subject from moving glucose into cells efficiently and utilizing it as an efficient fuel source, leading to elevated glucose levels in blood and some degree of insulin resistance.

The term "Type 2 diabetes Mellitus" is a condition characterized by excess glucose production and circulating glucose levels remain excessively high as a result of inadequate glucose clearance and the inability of the pancreas to produce enough insulin.

The term "hyperglycemia", as used herein, refers to a condition in which an elevated amount of glucose circulates in the blood plasma of a subject relative to a healthy individual. Hyperglycemia can be diagnosed using methods known in the art, including measurement of fasting blood glucose levels as described herein.

The term "Hypoglycemia", also called low blood sugar, occurs when blood glucose level drops too low to provide enough energy for the body's activities.

The term "hyperinsulinemia", as used herein, refers to a condition in which there are elevated levels of circulating insulin when, concomitantly, blood glucose levels are either elevated or normal. Hyperinsulinemia can be caused by insulin resistance which is associated with dyslipidemia such as high triglycerides, high cholesterol, high low-density lipoprotein (LDL) and low high-density lipoprotein (HDL); high uric acids levels; polycystic ovary syndrome; type II diabetes and obesity. Hyperinsulinemia can be diagnosed as having a plasma insulin level higher than about 2 pU/mL.

The term "Pancreatitis" is inflammation of the pancreas.

The term "Dyslipidemia" is a disorder of lipoprotein metabolism, including lipoprotein overproduction or deficiency. Dyslipidemias may be manifested by elevation of the total cholesterol, low-density lipoprotein (LDL) cholesterol and triglyceride concentrations, and a decrease in high-density lipoprotein (HDL) cholesterol concentration in the blood.

The term "Fatty liver disease (FLD)", also known as fatty liver, is a condition wherein large vacuoles of triglyceride fat accumulate in liver cells via the process of steatosis (i.e., abnormal retention of lipids within a cell). Despite having multiple causes, fatty liver can be considered a single disease that occurs worldwide in those with excessive alcohol intake and the obese (with or without effects of insulin resistance insulin). When this process of fat metabolism is disrupted, the fat can accumulate in the liver in excessive amounts, thus resulting in a fatty liver. Accumulation of fat may also be accompanied by a progressive inflammation of the liver (hepatitis), called steatohepatitis. By considering the contribution by alcohol, fatty liver may be termed alcoholic steatosis or nonalcoholic fatty liver disease nonalcoholic fatty liver disease (NAFLD), and the more severe forms as alcoholic steatohepatitis and non-alcoholic steatohepatitis (NASH).

The term "steatohepatitis" is a type of liver disease, characterized by fatty change of hepatocytes, accompanied by intralobular inflammation and fibrosis. When not associated with excessive alcohol intake, it is referred to as Nonalcoholic steatohepatitis (NASH).

The term "progressive liver disease" is a liver disease caused by a wide range of liver pathologies that progress from a relatively benign state like hepatic steatosis to more severe states including hepatitis, fibrosis, cirrhosis, and hepatocellular carcinoma. PNPLA3 has been specifically associated with the progressive liver diseases such as NAFLD/NASH, AFLD/ASH, viral hepatitis, Wilson's disease, hereditary hemochromatosis and primary sclerosing cholangitis (Paola Dongiovanni et al. World Journal of Gastroenterology, 2013, 19(41), 6969-6978)

The term "Obesity," in terms of the human subject, can be defined as an adult with a Body Mass Index (BMI) of 30 or greater (Centers for Disease Control and Prevention). "Metabolic syndrome" can be defined as a cluster of risk factors that raises the risk for heart disease and other diseases like diabetes and stroke. These risk factors include: high blood sugar—at least 110 milligrams per deciliter (mg/dl) after fasting; high triglycerides—at least 150 mg/dL in the bloodstream; low HDL—less than 40 mg/dl; and, blood pressure of 130/85 mmHg or higher (World Health Organization).

The term "Cardiovascular diseases" are diseases related to the heart or blood vessels.

The term "Atherosclerosis" is a vascular disease characterized by irregularly distributed lipid deposits in the intima of large and medium-sized arteries, sometimes causing narrowing of arterial lumens and proceeding eventually to fibrosis and calcification. Lesions are usually focal and progress slowly and intermittently. Limitation of blood flow accounts for most clinical manifestations, which vary with the distribution and severity of lesions.

The term "Coronary heart disease", also called coronary artery disease, is a narrowing of the small blood vessels that supply blood and oxygen to the heart.

"Diabetic complications" are problems caused by high blood glucose levels, with other body functions such as kidneys, nerves (neuropathies), feet (foot ulcers and poor circulation) and eyes (e.g. retinopathies). Diabetes also increases the risk for heart disease and bone and joint disorders. Other long-term complications of diabetes include skin problems, digestive problems, sexual dysfunction and problems with teeth and gums.

As used herein, the phrase "body weight disorder" refers to conditions associated with excessive body weight and/or enhanced appetite. Various parameters are used to determine whether a subject is overweight compared to a reference healthy individual, including the subject's age, height, sex and health status. For example, a subject may be considered overweight or obese by assessment of the subject's Body Mass Index (BMI), which is calculated by dividing a subject's weight in kilograms by the subject's height in meters squared. An adult having a BMI in the range of −18.5 to −24.9 kg/m is considered to have a normal weight; an adult having a BMI between −25 and −29.9 kg/m may be considered overweight (pre-obese); an adult having a BMI of −30 kg/m or higher may be considered obese. Enhanced appetite frequently contributes to excessive body weight.

There are several conditions associated with enhanced appetite, including, for example, night eating syndrome, which is characterized by morning anorexia and evening polyphagia often associated with insomnia, but which may be related to injury to the hypothalamus.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The activity and plasma stability of a conjugate according to the present invention can be assessed by the following methods described below.

Assays and Data

The activity and plasma stability of the GDF15 conjugates of Examples 1 and 19B according to the present invention can be assessed by the following in vitro and in vivo methods described below.

Methods for Animal Studies

All animal studies described in this document were approved by the Novartis Institutes for Biomedical Research Animal Care and Use Committee in accordance with local and federal regulations and guidelines. Diet-induced obese male mice (C57BL/6NTac) were purchased from Taconic and fed a 60% fat diet (Research Diets D12492i) from 6-weeks of age onward. Upon arrival, mice were housed one animal per cage under a 12 h:12 h reverse light-dark cycle. Animals all received a minimum of 1 week acclimation prior to any use. Mice were typically studied between 3-4 months of age. One day prior to being studied, mice were randomized based on body weight such that each group had a similar average body weight. On the day of study, mice were placed in fresh cages, and the old food removed. Approximately 1 h later and just prior to the dark cycle, mice received a single subcutaneous dose of either vehicle (30 mM sodium acetate, pH 4) or a lipid conjugated GDF15 analog (0.5 mg/kg). After all injections are completed, the mice were reweighed and a defined amount of food returned (~50 g per mouse). Food intake and body weight were measured over the course of ~2 weeks at the times indicated in the figures. In surrogate animals treated as described above, plasma was collected at the indicated times, and GDF15 levels were measured by ELISA as per the manufacturer's instructions (R&D Systems Quantikine Human GDF15 Immunoassay; DGD150). DIO mice single 0.5 mg/kg sc dose.

The activity and half-life of the conjugates of the invention were tested in the assay described supra.

TABLE 1

| Conjugate (example) | PK (½ life) (hrs) | Duration of action | |
|---|---|---|---|
| | | Food Intake (FI) reduction (days) | Body weight (BW) reduction (days) |
| 1 | 36 | 6 | 8 |
| 2 | | 8 | 8 |
| 4 | 15.1 | 3 | 3 |
| 5 | 33.1 | 8 | 8 |
| 6 | | 3 | 3 |
| 7 | 21.8 | 6 | 6 |
| 12 | | 6-8 | 6-8 |
| 13 | 45.8 | 8-10 | 10 |
| 15* | | 2 | 6 |
| 16 | | 6 | 6 |
| 18 | 55 | 8-10 | 10 |
| 19A | | 8 | 10 |
| 19B crude | 86.4 | 8 | 14 |
| 19B1 | 56.9 (exp 1) | 14 (exp 1) | 14 (exp 1) |
| | 50.9 (exp 2) | 14 (exp 2) | 14 (exp 2) |
| 19B2 | 97.68 (exp 1) | 8 (exp 1) | 10 (exp 1) |
| | 74.2 (exp 2) | 14 (exp 2) | 14 (exp 2) |
| 19B3 | 98.9 | 8 | 10 |
| 19Bm | 65.04 | 14 | 17 |
| Ref ex. 2 | | 3 | 3 |
| Ref ex. 1 | | 1 | 1 |
| hGDF15 | 1 | 1 | 1 |

*Lean mice
Exp 1: in vivo experiment 1; Exp 2: in vivo experiment 2.

The data in table 1 demonstrate that the conjugates of the invention possess a significant longer duration of action as compared to non-conjugated hGDF15 and/or as compared to pegylated hGDF15.

GDF15-Conjugate Efficacy in Chow Fed Dogs: GDF15-fatty Acid Conjugate

Study Goal: To assess the effects of subcutaneous administration of 0.05 mg/kg of a GDF15-fatty acid moiety conjugate according to the invention or vehicle control on food intake in an acute setting (6 hour) and over a 96 hour period in the Beagle dog. Plasma samples were collected at various time points throughout the 14 day post-dose period in order to evaluate the PK profile of this compound. Body weight was determined throughout the study.

Animals: Baseline body weights and treatments

TABLE 2

| Dog ID | Weight (kg) | Treatment |
|---|---|---|
| 50 | 12.65 | Vehicle |
| 62 | 8.85 | Vehicle |
| 77 | 10.15 | Vehicle |
| 67 | 8.85 | GDF15 |
| 73 | 9.95 | GDF15 |
| 75 | 12.25 | GDF15 |

Dosing Procedure: Dosing of Vehicle or GDF15 was performed after baseline body weight and blood sample collection. The GDF15-fatty acid moiety conjugate was supplied as a 0.97 mg/ml solution and was dosed by subcutaneous injection without dilution at 0.05 mg/kg. An equivalent volume of 30 mmol/l Sodium Acetate pH 4 Vehicle (52 µl/kg) was given to the vehicle animals by subcutaneous injection.

Blood Collection: Blood samples were collected from the cephalic or jugular vein (3 ml, in tubes containing EDTA and the protease inhibitors Diprotin A and Aprotinin) and were placed on ice until centrifugation at 3,000 rpm for 20 min at 4° C. Plasma was distributed in aliquots and stored at −70° C. until analysis. The following time points were collected: 0, 6.75, 24.75, 48.75, 72.75 and 96.75 hours. Additional samples were collected on days 7, 10 and 14.

Food Intake Measurements: Measurement of ad libitum food intake was begun 45 minutes after dosing. This food intake measurement consists of two phases: an acute measurement (0-6 hours) and a sub-chronic measurement (0-96 hours).

From 0-2 hours, the dogs were given 500 g regular chow (Hill's J/D diet). At 2 hours, the remaining food was removed, weighed and another 500 g chow was offered for the 2-4 hour period. At 4 hours, the remaining food was removed, weighed and another 300 g chow was offered for the 4-6 hour period. At 6 hours, the remaining food was removed and weighed. A blood sample was collected at this time (6.75 hours). The dogs were then offered 500 g chow overnight. On the mornings of Day 1-4, remaining food was removed, weighed and a blood sample was collected from each animal. On days 1-3 the dogs were then offered 500 g chow for a 24 hour period. On day 4, the dogs were returned to their normal allotment of chow (260 g).

Additional Food Intake Measurements: On days 7, 14 and 28 the study animals were given 6 hours to consume their daily chow (260 g). At the end of this time period, any remaining food was collected and weighed.

Body Weight Measurements: Body weights were measured at baseline and days 2, 4, 7, 10, 14, 18 and 28. Baseline body weights were collected in the fasting state. Body weights collected on days 2 and 4 were not fasted. For the vehicle treated animals, all other body weights were collected in the fasted state. For the GDF15 treated animals, the body weights determined on days 7-28 were not fasted since the animals were given food continuously in order to stimulate appetite and regain weight.

Efficacy of GDF15-fatty Acid Assay Conjugate of the Invention in Chow Fed Dogs

Study Goal: To assess the effects of subcutaneous administration of vehicle control and 0.015 mg/kg or 0.005 mg/kg GDF15-fatty acid moiety conjugate of the invention on food intake in an acute setting (6 hour) and over a 96 hour period in the Beagle dog (In this study the vehicle arm will be performed prior to the treatment arm in all dogs). Plasma samples will be collected at various time points throughout the 14 day post-dose period in order to evaluate the PK profile of this compound. Body weight was determined throughout the study. Animals: Baseline body weights and treatments.

TABLE 3

| Dog ID | Weight (kg) | Treatment | Weight (kg) | Treatment |
|---|---|---|---|---|
| 29 | 12.75 | Vehicle | 12.85 | 5 µg/kg hGDF15 |
| 57 | 13.35 | Vehicle | 13.80 | 5 µg/kg hGDF15 |
| 61 | 9.30 | Vehicle | 9.45 | 5 µg/kg hGDF15 |
| 77 | 10.70 | Vehicle | 11.15 | 5 µg/kg hGDF15 |
| 45 | 11.90 | Vehicle | 12.20 | 15 µg/kg hGDF15 |
| 50 | 13.00 | Vehicle | 13.05 | 15 µg/kg hGDF15 |
| 59 | 14.20 | Vehicle | 14.65 | 15 µg/kg hGDF15 |
| 72 | 8.80 | Vehicle | 9.05 | 15 µg/kg hGDF15 |

Dosing Procedure: Dosing of Vehicle was performed after baseline body weight and blood sample collection. 52 µl/kg of 30 mmol/l Sodium Acetate pH 4 Vehicle (52 µl/kg) was given to the vehicle animals by subcutaneous injection. Dosing of GDF15 was performed after baseline body weight and blood sample collection. The GDF15-fatty acid moiety conjugate was supplied as a 1.20 mg/ml solution and was dosed by subcutaneous injection after dilution at 0.015 mg/kg and 0.005 mg/kg. The GDF15 stock was diluted in order to maintain the 52 µl/kg delivered in a prior study.

Blood Collection: Blood samples were collected for the vehicle and treatment arms of the study. Samples were collected from the cephalic or jugular vein (3 ml, in tubes containing EDTA and the protease inhibitors Diprotin A and Aprotinin) and were placed on ice until centrifugation at 3,000 rpm for 20 min at 4° C. Plasma was distributed in aliquots and stored at −70° C. until analysis. The following time points were collected: 0, 6.75, 24.75, 48.75, 72.75 and 96.75 hours. Additional samples were collected on days 7, 10 and 14.

Food Intake Measurements: Food Intake was measured during both the vehicle and treatment arms of the study. Measurement of ad libitum food intake was begun 45 minutes after dosing. This food intake measurement consists of two phases: an acute measurement (0-6 hours) and a sub-chronic measurement (0-96 hours).

From 0-2 hours, the dogs were given 500 g regular chow (Hill's J/D diet). At 2 hours, the remaining food was removed, weighed and another 500 g chow was offered for the 2-4 hour period. At 4 hours, the remaining food was removed, weighed and another 300 g chow was offered for the 4-6 hour period. At 6 hours, the remaining food was removed and weighed. A blood sample was collected at this time (6.75 hours). The dogs were then offered 500 g chow overnight. On the mornings of Day 1-4, remaining food was removed, weighed and a blood sample was collected from each animal. On days 1-3 the dogs were then offered 500 g chow for a 24 hour period. On day 4, the dogs were returned to their normal allotment of chow (260 g).

Additional Food Intake Measurements: On various days between days 7 and 14 in the vehicle arm and between days 7 and 28 in the treatment arm, the study animals were given 6 hours to consume their daily chow (225 g). At the end of this time period, any remaining food was collected and weighed. Once a week, a timed measurement of food consumption was taken. Consumption of 225 g chow was measured at 1, 2, 4 and 6 hours after feeding to determine whether each dog's feeding pattern had returned to normal.

Body Weight Measurements: Body Weight was measured during both the vehicle and treatment arms of the study. During the vehicle arm, body weights were measured at baseline and days 2, 4, 7, 10 and 14. During the treatment arm, body weights were measured at baseline and days 2, 4, 7, 10, 14, 17, 21, 24 and 28. Body weights collected on days 2 and 4 were not fasted. All other body weights were determined in the fasting state.

Conjugate of Example 2 was tested in above assay
Dog Single sc Dose

TABLE 4

| Dose (ug/kg) | Body weight change (%) (at 14 days) | Food intake change (% of vehicle) (0-6 hrs) | Duration of action | | |
|---|---|---|---|---|---|
| | | | (0-96 hrs) | Food Intake (FI) reduction (days) | Body weight (BW) reduction (days) |
| 5 | −5 | 55 | 45 | 7 | 14 |
| 15 | −5 | 60 | 38 | 9 | 14 |
| 50 | −13 | 50 | 26 | 7 | 18 |
| dGDF15 (50 ug/kg) | — | 31 | | | |

GDF15-Conjugate Improves Measures of Metabolic Disease Including Diabetes and Fatty Liver Disease in Obese Mice Diet-induced obese mice were dosed once weekly with vehicle or Example 19Bm (0.5 mg/kg/ s.c.) for 4 weeks. Non-fasted glucose and insulin were measured 2 weeks after the first dose, and overnight fasted blood glucose and insulin were measured 4 weeks after the first dose. Example 19Bm reduced non-fasted glucose by 23% (207.1 mg/dl vehicle treated vs. 160.4 mg/dl Example 19Bm; p<0.05). Example 19Bm reduced non-fasted insulin levels by 75% compared to vehicle treated mice (2.1 vs 8.7 ng/ml; p<0.05). Four weeks after the initial dose, Example 19Bm reduced fasting blood glucose by 28% (142.7 vs. 199.5 mg/dl; p<0.05) and fasting insulin by 78% (0.77 vs. 3.5 ng/ml; p<0.05). Markers of fatty liver disease were also improved by four, once-weekly doses of Example 19Bm. Example 19Bm reduced hepatic steatosis by 57.5% (11.36 vs. 26.73% liver fat; p<0.05) and serum levels of a marker of hepatocyte damage, alanine aminotransferase (ALT), by 58% (46.2 vs. 110.5 U/L; p<0.05). In addition, Example 19Bm decreases the hepatic expression of PNPLA3, a causative gene in progressive liver diseases, by 77% (p<0.05).

The activity and plasma stability of the APJ-agonist conjugates of Examples 20 and 21 according to the present invention can be assessed by the following in vitro and in vivo methods described below.

hAPJ Calcium Flux Assay:

Chem-5 APJ stable cells (Millipore # HTS068C) were plated in 384-well format with 10,000 cells/well in 25 ul growth media, then grown 24 hours in a 37° C. tissue culture incubator. One hour before the assay, 25 ul/well FLIPR Calcium 4 dye (Molecular Devices R8142) with 2.5 mM probenecid was added, and cells were incubated one hour in a 37° C. tissue culture incubator. Peptides were solubilized in HBSS, HEPES & 0.1% BSA buffer, and serially-diluted 10-fold, from 50 μM to 5 μM, in triplicate. FLIPR Tetra was used to add peptide to the cells with dye (1:5, for final peptide concentrations ranging from 10 uM to 1 pM). FLIPR dye inside the cells emitted fluorescence after binding to calcium, while fluorescence from outside the cells was masked. Fluorescence was measured using 470-495 excitation and 515-575 emission wavelengths on the FLIPR Tetra. Readings were done for 3 minutes total, beginning 10 seconds before the peptide addition. Maximum-minimum values were calculated and plotted for each peptide concentration, and Graph Pad prism software was used to calculate $EC_{50}$ values at the curve inflection points, for calcium flux stimulation by peptides.

In Vivo Assay:

Conjugate was dissolved in PBS (Phosphate buffered saline) to a concentration of 1 mg/ml to form Dosing solution. Dosing solution was administered intravenously to male Sprague-Dawley rats via lateral tail vein at a volume of 1 ml/kg body weight, corresponding to a dose of 1 mg/kg. Venous blood samples were acquired from a jugular vein catheter at prescribed times after dosing and immediately placed on wet ice. These samples were centrifuged at 4C, with supernatant plasma transferred to a fresh tube for analysis.

Bioanalysis:

Standard curve preparation: Stock solution was prepared by dissolving peptide conjugate in water to 1 mg/ml. 10 uL of Stock was mixed with 990 uL rat plasma to form a working stock of 10,000 ng/ml in plasma. This was serially diluted in plasma to form standards of 5000, 1000, 500, 100, 50, 10, 5 and 1 ng/ml.

Sample and standard preparation: 25 uL plasma sample or standard was transferred to a clean plate. 150 uL acetonitrile:MeOH (1:1) containing 100 ng/ml glyburide as internal standard was added to each vial and the plate vortexed to mix the contents. The plate was centrifuged at 4000 rpm at 4C. 125 uL supernatant was transferred to a clean plate, mixed with 50 uL water and analyzed by LC/MS.

LC/MS analysis:

HPLC: Agilent 1290 HPLC with autosampler
Column: MAC-MOD ACE C18, 3 μm, 30 mm×2.1 mm i.d.
Mobile phase A: 0.1% Formic acid in acetonitrile
Mobile phase B: 0.1% Formic acid in water
Gradient Program:

| Time (min) | Flow (mL) | Mobile Phase A(%) | Mobile Phase B(%) |
|---|---|---|---|
| 0 | 0.7 | 98 | 2 |
| 0.5 | 0.7 | 98 | 2 |
| 1.5 | 0.7 | 5 | 95 |
| 2.5 | 0.7 | 5 | 95 |
| 2.6 | 0.7 | 98 | 2 |
| 3.1 | 0.7 | 98 | 2 |

Mass spectrometer: AB Sciex 6500
MS conditions: Q1 (m/z+) 809.3; Q3 (m/z+) 923.7; DP: 60; CE: 25
Data analysis: MS data were captured and analyzed using WatsonLIMS v7.4 software.

Activity and Stability of APJ Agonist-conjugate of the Invention Using Assays Described Supra

TABLE 5

| Peptide | hAPJ $Ca^{2+}$ Flux $EC_{50}$ [nM] | In vivo Plasma stability $t^1/_2$ [h] |
|---|---|---|
| pE-R-P-C*-L-S-C*-K-G-P-(D-Nle)-NH(Phenethyl) (disulfide $C^4$-$C^7$) (SEQ ID NO: 28) | 3 | 0.9 |

TABLE 5-continued

| Peptide | hAPJ Ca$^{2+}$ Flux EC$_{50}$ [nM] | In vivo Plasma stability t$^{1/2}$ [h] |
|---|---|---|
| pE-R-P-R-L-C*-H-K-G-P-Nle-C*-F-OH(Disulfide C$^6$-C$^{12}$) (SEQ ID NO: 29) | 1.04 | 0.7 |
| Example 20A | 2479 | – |
| Example 21A | 65 | 7.4 |
| Example 21B | 839 | – |

The activity and plasma stability of the oxytocin conjugates of Example 26A and 26B according to the present invention can be assessed by the following in vitro and in vivo methods described below.

In vitro Assay Description:
Materials & Methods
Compound Plate Preparation

Supplied compounds were prepared in DMSO and ultimately prepared in the Eurofins Discovery Services GPCR-Profiler® Assay Buffer to concentrations that were threefold higher than the final assay concentration. Similarly, vehicle controls and positive controls were prepared to ensure all assays were properly controlled.

Reference Controls

| GPCR Target | Reference Agonist | Emax |
|---|---|---|
| OT | Oxytocin | 1.25 µM |

All wells were prepared using the Eurofins Discovery Services GPCRProfiler® Assay Buffer. The GPCRProfiler® Assay Buffer was a modified Hanks Balanced Salt Solution (HBSS) where HBSS was supplemented to contain 20 mM HEPES and 2.5 mM Probenecid at pH7.4.

Calcium Flux Assay
Agonist Assay

Compound(s) supplied were plated in duplicate for each concentration assayed. Reference agonist, oxytocin, was prepared in a similar manner to serve as assay control. The reference agonist, oxytocin, was included at Emax (the concentration where the reference agonist elicited a maximal response).

The agonist assay was conducted on a FLIPRTETRA instrument where the test compound(s), vehicle controls, and reference agonist were added to the assay plate after a fluorescence/luminescence baseline was established. The agonist assay was a total of 180 seconds and was used to assess each compound's ability to activate each GPCR assayed.

Upon completion of the three minute agonist assay, the assay plate was incubated at 25° C. for a further seven (7) minutes.

Data Processing

All plates were subjected to appropriate baseline corrections. Once baseline corrections were processed, maximum fluorescence/luminescence values were exported and data manipulated to calculate percentage activation and percentage inhibition. Negative values of 0 to −30% may be the result of biological variance. Data manipulation calculation is as followed: ((Max RLU)−(Baseline Avg.))/((Positive Avg.)−(Baseline Avg.))

In vivo Assay Description:

Conjugate was dissolved in PBS (Phosphate buffered saline) to a concentration of 3 mg/ml to form Dosing solution. Dosing solution was administered intravenously to male Sprague-Dawley rats via lateral tail vein at a volume of 1 ml/kg body weight, corresponding to a dose of 3 mg/kg. Venous blood samples were acquired from a jugular vein catheter at prescribed times after dosing and immediately placed on wet ice. These samples were centrifuged at 4C, with supernatant plasma transferred to a fresh tube for analysis.

Bioanalysis:

Standard curve preparation: Stock solution was prepared by dissolving peptide conjugate and peptide into two separate vials in dimethylsulfoxide to 1 mg/ml. 10 uL of each stock was mixed with 980 uL rat plasma to form a working stock of 10,000 ng/ml in plasma. This was serially diluted in plasma to form standards of 5000, 1000, 500, 100, 50, 10, 5, 1, 0.5, and 0.1 ng/ml.

Sample and standard preparation: 25 uL plasma sample or standard was transferred to a clean plate. 150 uL acetonitrile containing 100 ng/ml glyburide as internal standard was added to each vial and the plate vortexed to mix the contents. The plate was centrifuged at 4000 rpm at 4C. 125 uL supernatant was transferred to a clean plate, mixed with 150 uL water and analyzed by LC/MS.

LC/MS analysis:

HPLC: Agilent 1290 HPLC with autosampler

Column: MAC-MOD ACE C18, 3 µm, 30 mm×2.1 mm i.d.

Mobile phase A: 0.1% Formic acid in acetonitrile

Mobile phase B: 0.1% Formic acid in water

Gradient Program:

| Time (min) | Flow (mL) | Mobile Phase A(%) | Mobile Phase B(%) |
|---|---|---|---|
| 0 | 0.7 | 98 | 2 |
| 0.5 | 0.7 | 98 | 2 |
| 2.0 | 0.7 | 2 | 98 |
| 2.5 | 0.7 | 2 | 98 |
| 2.6 | 0.7 | 98 | 2 |
| 3.0 | 0.7 | 98 | 2 |

Mass spectrometer: AB Sciex 6500

Peptide MS conditions: Q1 (m/z+) 945.20; Q3 (m/z+) 687.27; DP: 140; CE: 39

Peptide Conjugate MS Conditions: Q1 (m/z+) 1270.85; Q3 (m/z+) 468.30; DP: 140; CE: 77

Data analysis: MS data were captured and analyzed using WatsonLIMS v7.4 software.

Activity and Stability of Oxytocin Fatty Acid Conjugate of the Invention According to Assays Described Supra

TABLE 6

| Peptide | OT Ca$^{2+}$ Flux EC$_{50}$ [nM] | In vivo Plasma stability t$_{1/2+12}$ [h] |
|---|---|---|
| Example 26A | 8.4 | 46 |
| Unconjugated oxytocin analog Example 13 of WO2014/095773 | 7.8 | 0.6 |

Example 13 of WO2014/095773 is represented below:

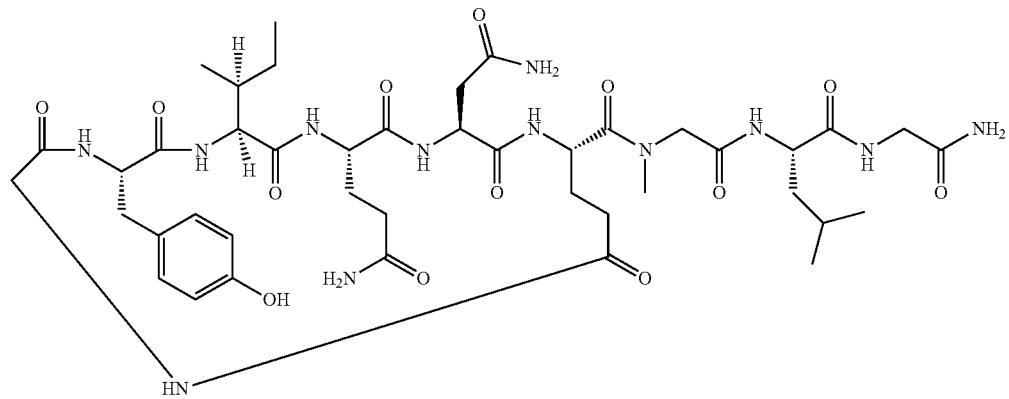 [SMILES: CC[C@H](C)[C@@H]1NC(=O)[C@H](Cc2ccc(O)cc2)NC(=O)CNC(=O)CC[C@@H](C(=O)N(C)CC(=O)N[C@@H](CC(C)C)C(=O)NCC(N)=O)NC(=O)[C@H](CC(N)=O)NC(=O)[C@H](CCC(N)=O)NC1=O]

The oxytocin-fatty acid conjugate of the invention demonstrates a 75 fold increase in half-life compared to unconjugated oxytocin analog.

The activity and plasma stability of the AgRPconjugates of Example 27A and 27B according to the present invention can be assessed by the following in vitro and in vivo methods described below.

A) HTRF cAMP Assay Protocol:
Passage of HEK293/MC4R Cells
Cell: HEK293/MC4R stable cell line
Complete medium: DMEM/F12 1:1 (Gibco, Cat. No. 11039, For assay, no-phenol red medium Cat. No. 21041)
10% FBS (Heat inactivated, Gibco, Cat. No. 10082)
200 μg/mL Geneticin (Gibco, Cat. No. 10131)
15 mM Hepes (GIBCO, Cat No. 15630)
2 mM L-glutamine (GIBCO, Cat No. 25030)
Flask: 150 cm² tissue culture treated flask (Corning, Cat. No. 430825).
  Aspirate conditioned medium
  Wash with 25 mL of DPBS (Gibco, Cat. No. 14190), then aspirate it
  FBS inhibits Trypsin-EDTA treatment.
  Add 2.5 mL of 0.05% Trypsin-EDTA (Gibco, Cat. No. 25300)
  Leave a few minutes, then tap the flask a few time to detach cells
  Add 25 mL of the complete medium to stop Trypsin-EDTA treatment
    Cell preparation for assays, no-phenol red complete medium have to be used.
Pipetting softly a few times to resuspend clumping cells
Transfer the suspension into a 50 mL centrifuge tube
Spin down at 1200 rpm for 3 min
Aspirate supernatant
Disperse the cells by softly tapping the bottom
Add 5-10 mL of the complete medium, then resuspend by softly pipetting
  Cell preparation for assays, no-phenol red complete medium have to be used.
Transfer 0.5 mL of the suspension into a sample vial for Vi-cell
Count cell number by using a Vi-cell*Record cell density and viability every time
Transfer 1-3×10⁶ cells into a new 150 cm flask
  For 3 days: 3×10⁶ cells/flask
  For 4 days: 1×10⁶ cells/flask
Incubate at 37C with 5% $CO_2$ Cell Seeding for HTRF cAMP Assay (One Day Before Assay)
  Prepare cell suspension as in the passage section
  Dilute the suspension to 2.34×10⁵ cells/mL
    13 mL is enough for one 384 well plate.
  Dispense 30 μL of the cell suspension into each well of a
    Poly-D-Lysine BIOCOAT 384-well clear plate (Becton Dickinson, Cat. No. 354660): 7000cells/well
    Poly-D-lysine coated plate is essential in this assay.
    No cell for wells of cAMP standard
  Incubate at 37C with 5% $CO_2$ over night
HTRF cAMP Assay
1. Preparation of Reagents
  1M IBMX

| | |
|---|---|
| IBMX (MW 222.25 g/mol, ACROS Cat. No. 228420010) | 111 mg |
| DMSO (Sigma Aldrich, Cat. No. D2650) | 500 uL |

Store at 4° C.

40 mg/mL BSA solution

| | |
|---|---|
| Bovine serum albumin (Sigma A7030-50G) | 200 mg |
| dH₂O | 5 mL |

Store at 4° C.

1 mg/mL (176 uM) AgRP master solution (in HBSS/ 2 mg/mL BSA)

| | |
|---|---|
| R&D human AgRP C-terminal (Cat. No. 3726-AG-100) | 100 ug/vial |
| 1x Hanks Buffered Salt Solution (HBSS) (Gibco, Cat. No. 14065, w/Ca and Mg) | 95 uL |
| 40 mg/mL BSA solution | 5 uL |

Store at 4° C.

2 mM NDP-aMSH master Solution

| | |
|---|---|
| NDP-aMSH (MW 1646.9, Bachem, Cat. No. H1100) | 1 mg/vial |
| dH₂O | 304 uL |

*Once dissolved, dispense 10 uL aliquots into 200 uL tubes, then store at −20 C.

Assay Buffer 1

| | |
|---|---|
| HBSS | 10 mL |
| 1M Hepes (Gibco, Cat. No. 15630) | 0.2 mL |
| 1M IBMX | 20 uL |

*To avoid precipitation of IBMX, please vortex the buffer until fully dissolved.

Assay buffer 2

| | |
|---|---|
| HBSS | 20 mL |
| 1M Hepes (Gibco, Cat. No.15630) | 0.4 mL |
| 1M IBMX | 40 uL |
| 40 mg/mL BSA solution | 0.25 mL |

*To avoid precipitation of IBMX, please vortex the buffer until fully dissolved.

6 nM NDP-aMSH for IgG titration and AgRP titration

| | |
|---|---|
| 2 uM NDP-aMSH (1000-fold dilution of the master solution) | 10.8 uL |
| Assay buffer 1 | 3600 uL |

*Example for one 384 well assay 120 nM AgRP for IgG titration

| | |
|---|---|
| 10-fold diluted master solution (17.6 uM) | 26 uL |
| Assay buffer2 | 3800 uL |

*Example for one 384-weell plate

NDP-aMSH working solutions for titration (see reagents)
AgRP working solutions for titration (see reagents)
IgG working solutions for titration (see reagents)
cAMP standard solutions (see reagents)

2. Assay (2 Step Protocol)
Assay Kit: Cisbio cAMP HiRange HTRF Kit (Cat. No. 62AM6PEB)

Preparation of IgG/AgRP mix (1:1)
  Mix 15 uL of IgG working solutions and 15 uL of 120 nM AgRP, then incubate for 1 hr at ambient temperature
Preparation of assay plate
  Discard culture medium by inverting the 384-well assay plate containing cells on a Wipeall, then tapping in order to remove the culture media.
  Add 100 µL of DPBS to each well and discard in the same manner
    Once discard PBS, move the next as soon as possible to avoid dry-up
  Transfer 10 µL of the following reagents into each well based on your sample alignment

| | |
|---|---|
| cAMP standard | cAMP standards |
| Negative control for cAMP titration | Diluent in HTRF kit |
| Positive control | cAMP positive control in HTRF kit |
| MSH titration | Assay buffer 2 |
| AgRP titration | AgRP working solutions |
| IgG titaration | IgG/AgRP mixture |
| Negative control for cell assay | Assay buffer 2 |

Flash spindown the 384 well plate at 1200 RPM
Incubated the cells for 15 minutes at an ambient temperature
Add 10 µL of the following reagents into each well based on your sample alignment

| | |
|---|---|
| cAMP standard | Assay buffer 1 |
| Negative control for cAMP titration | Assay buffer 1 |
| Positive control | Assay buffer 1 |
| MSH titration | MSH working solutions |
| AgRP titration | 6 nM MSH solution |
| IgG titaration | 6 nM MSH solution |
| Negative control for cell assay | Assay buffer 1 |

Flash spindown the 384 well plate at 1200 RPM
Incubate the cells for an additional 30 minutes at an ambient temperature
  This incubation time is not so strict. +/− 5 min should be OK according to assay development data.
Add 10 µL of cAMP-d2 (diluted 1:4 in the lysis buffer provided in the kit)
  Important!! For Negative control, not cAMP-d2, but just the lysis buffer
Add 10 µL of anti-cAMP Cryptate (diluted 1:4 in the lysis buffer provided in the kit)
Flash spindown at 1200 RPM.
Incubate the assay plate for 45-60 min at an ambient temperature.
Transfer 30 µL of each sample to a tissue culture treated white polystyrene 384-well assay plate (Corning, Cat. No. 3572)
Flash spindown at 1200RPM.
Measure the fluorescence with a Molecular device M5 or M5e with the following setting.

Molecular Device M5/M5e Setting

| | |
|---|---|
| Assay type | Time-resolved fluorescence |
| Integ delay | 50 us |
| Integration | 400 us |
| Read | Top read |
| Wave length | Ex 314 nm/Em668 nm Cutoff 630 nm |
| | Ex318 nm/Em570 nm Cutoff 570 nm |
| Auto mix | Off |
| Auto calibration | On |
| Sensitivity | Reading 75 |
| PMT | On |
| Plate | 384 well standard oparque |
| Setting time | off |
| Column wavelength priority | Column priority |
| Carriage speed | Normal |
| Auto read | Off |

B) MC3 cAMP Assay
Materials:
Cells: HEK293/MC3R stable cell line
Complete medium: DMEM/F12 1:1 (Gibco, Cat. No. 11039)
  10% FBS (Heat inactivated, Gibco, Cat. No. 10082)×
  200 µg/mL Geneticin (Gibco, Cat. No. 10131)
  2 mM L-glutamine (GIBCO, Cat No. 25030)
Flask: 150 $cm^2$ tissue culture treated flask (Corning, Cat. No. 430825).

Assay Buffer

| | |
|---|---|
| HBSS (Gibco - 14175-095) | 10 mL |
| 1M Hepes (Fisher, Cat. No. BP299-1) | 0.2 mL |
| 500 mM IBMX (MW 222.25 g/mol, ACROS Cat. No. 228420010) | 40 ul |
| BSA | 0.25% |

Plates 384 well solid bottom, Greiner bio-one (Cat no.-781080)

Assay Protocol (Antagonist Protocol):

I. Aspirate conditioned medium
II. Wash with 2.5 mL of DPBS (Gibco, Cat. No. 14190)
III. Add 2 mL of 0.25% Trypsin-EDTA (Gibco, Cat. No. 25200-056)
IV. Leave the flask for few minutes in incubator, tap the flask a few time to detach cells.
V. Add 10 mL of the complete medium to stop Trypsin-EDTA treatment and mix it well by pipetting softly a few times to re-suspend clumping cells
VI. Transfer 1.5 ml of cells into a new 150 cm flask containing 20 ml of complete media
VII. Transfer the remaining suspension into a 50 mL centrifuge tube
VIII. Spin down at 1200 rpm for 4 mins. Aspirate supernatant
IX. Add 6 mL of the assay buffer to the tube and re-suspend the cells by softly pipetting
X. Transfer 0.5 mL of the suspension into a sample vial for Vi-cell and add another 0.5 ml of PBS.
XI. Count cell number by using a Vi-cell*Record cell density and viability every time
   i. Plate cells at 4K/well in 10 ul/well of assay buffer containing IBMX.
   ii. Leave the plate in incubator for ~30 mins before assay is started on suspension cells.

Two step cAMP protocol is followed for cAMP determination.

Procedure

I. To 10 ul/well of cells add 5 ul of AgRP prepared at 3× in assay buffer only to antagonist wells.
II. Add 5 ul of buffer to positive control wells (wells that will have NDP-α-MSH).
III. Incubate the plate at 37° C. for ~20 mins.
IV. Add 5 ul/well of agonist EC80 (NDP-α-MSH) prepared at 4× to wells containing AgRP DRC.
V. Add 5 ul/well of agonist (NDP-α-MSH) DRC prepared at 4× (final highest concentration in plate is 100 nM) for NDP-α-MSH EC50 calculation
VI. Add buffer only to negative control.
VII. Pulse spin the 384 well plate and incubate the cells for 30 minutes in incubator.
VIII. Add 10 μL of the following reagents into each well:
   a. 10 μL of cAMP-d2
   b. *Important!! For Negative control, do not add cAMP-d2, but just the lysis buffer and 10 ul/well of Tb-cryptate
   c. 10 μL of anti-cAMP Cryptate
   d. Pulse spin the plate and incubate for 60 mins at room temperature.

C. In vivo Assay Description:

10 nanomoles of conjugate was dissolved in 300μ of PBS (Phosphate buffered saline) to form Dosing solution. Dosing solution (300 μM) was administered intravenously to male Sprague-Dawley rats via lateral tail vein (corresponding to a dose 10 nanomoles per rat). Blood was collected via tail snip at prescribed times after dosing and immediately placed on wet ice. These samples were centrifuged at 4C, with supernatant plasma transferred to a fresh tube for analysis.

Bioanalysis:

Standard Curve Preparation: The two fatty acid conjugates of examples 27A and 27B and one mature human AgRP peptide were used to make standards. Intermediate stock solutions of each AgRP were prepared by diluting the stock labeled peptides in ELISA sample diluent with casein to 100 ug/ml. For assay, intermediates were diluted to a top standard concentration of 2500 μg/mL and then diluted 2-fold serially to 16 points including a zero dose standard in ELISA sample diluent with bovine serum albumin (BSA).

Sample Dilution: Plasma samples were diluted 10-fold and then 5-fold serially out to 31,250-fold in ELISA sample diluent with BSA.

5B1 Human AgRP ELISA Method: 384 well microplates were coated with anti-human AgRP clone 5B1 overnight at 30 uL/well in 1× PBS at room temperature (RT). Plates were aspirated and blocked with a milk-based blocker at 90 uL/well for 2 hours at RT. All further incubations were carried out at 30 uL/well. Plates were aspirated again and samples and standards were added to the wells for 2 hours at RT. Then the plates were washed three times with a phosphate based wash buffer with tween-20 and a biotinylated goat anti-human AgRP polyclonal antibody was added to the wells to detect the bound AgRP for 2 hours at RT. The plates were washed again and a HRP-labeled streptavidin reagent was added to the wells for 30 minutes at RT. Plates were washed a final time and a chemiluminescent substrate was added to all wells and plates were read immediately on a Spectramx M5 for light output.

Data Analysis: Raw data was organized and analyzed for basic PK parameters.

Activity and Stability of AgRP Fatty Acid Conjugates of the Invention According to Assays Described Supra:

TABLE 7

| Peptide | MC4R EC50 [nM] | MC3R EC50 [nM] | In vivo Plasma stability t½ [h] |
|---|---|---|---|
| Example 27A (mono fatty acid conjugate) | 18 | 7 | 20 |
| Example 27B (di fatty acid conjugate) | 167 | 65 | 52 |
| AgRP | 1.7 | 12 | 4.4 |

The activity and plasma stability of the FGF23 conjugate of example 28A, 28B and 28C can be assessed by the following in vitro methods described below.

In Vitro Activity Assay:

Egr-1-luciferase: The biological activity of the purified h FGF23-FA conjugate was tested in Egr-1-luciferase reporter assays. Binding of the hFGF23-FA conjugate to the FGF23 receptor resulted in the downstream activation of Egr-1 and the expression of a luciferase reporter regulated by the Egr-1 promoter. The Egr-1-luciferase reporter gene was constructed based on that reported by Urakawa et al. (Nature, 2006, Vol 444, 770-774). HEK293T cells seeded in 48-well poly-D-lysine plate were transfected with the Egr-1-luciferase reporter gene, the full-length transmembrane form of Klotho and a transfection normalization reporter gene (Renilla luciferase). Five hours after the transfections, the transfection mix was replaced with 3 ml DMEM plus 1% FBS containing graded concentrations of the test protein. Cells were lysed 20 hours later in passive lysis buffer (Promega, Cat #E194A) and luciferase activity was determined using Dual-Glo Luciferase Assay System (Promega, Cat #E2940).

Results

TABLE 8

| Example | EC50 (nM) |
|---|---|
| Example 28B | 1.195 |
| Example 28C | 0.258 |

The activity and plasma stability of the serelaxin fatty acid conjugates of Examples 29A and 29B according to the present invention can be assessed by the following in vitro and in vivo methods described below.

In vitro Activity Assays #1:
Materials:
DMEM: F12 media (Gibco, cat#11320)
IBMX (Sigma, cat#15879)
384 solid bottom white plates (Greiner bio-one, cat #781945)
20,000 dynamic-2 cAMP kit (Cisbio, cat#62AM4PEC)
Adenosine 3',5'-cyclic monophosphate (Sigma, cat#A9501)
Matrix-plate mate plus (used for adding 5 µl of assays reagents)
PBS-Gibco (cat#10010-023)

| Abbreviation | Definition or Explanation |
| --- | --- |
| cAMP | cyclic adenosine monophosphate |
| RXFP1 | Relaxin/Insulin related receptor |
| DMSO | dimethyl sulfoxide |
| HTRF | Homogeneous Time Resolved Fluorescence |
| 8k | Eight thousand |
| cAMP-d2 | cAMP labeled with the dye d2 |
| PDL | Poly-d-lysine |
| ul | Microliter |
| @ | at |
| o/N | Overnight |
| uM | Micromolar |
| Min | Minutes |
| 37c | 37 centigrade |
| 3x | Three times |
| hr | Hour |
| DMEM: F12 | Dulbecco's Modified Eagle Medium: Nutrient Mixture F-12 (DMEM/F-12) |
| rhRLX | Recombinant human relaxin |
| RPMI | Roswell Park Memorial Institute (RPMI) 1640 Medium |
| FRET | Fluorescence resonance energy transfer |
| HEK293 | Human embryonic kidney 293 cells |
| IBMX | 3-Isobutyl-1-methylxanthine |
| nM | nano molar |
| std | Standard |
| con | Concentration |
| PBS | Phosphate buffer saline |
| cpd | compound |
| HS | Human serum |
| HBSS | Hanks buffered saline solution |

Protocol:
Day1: Seeded RXFP1-HEK293/parental HEK293 cells 8 k in 10 µl of DMEM: F12 media in solid bottom PDL coated white plates
Day2: Ran assay with the compound
Agonist Mode (Overview):
  Cells in 10 µl of DMEM:F12 media @37° c. 0/N
  5 µl of 2000 µM (4×) of IBMX to the cells for 30 min at 37° c.
  5 µl of 4× compound/Serelaxin to the above for 30 min at 37° c. (from step 3 of cpd dilution, 400 nM-final is 100 nM top)
  10 µl of cAMP-d2 conjugate
  10 µl of Anti-cAMP cryptate conjugate
  Incubate for 1 hr at RT
  Read FRET signal—Envision 665 nm/620 nm
Compound Preparation
Serelaxin:
  1) Diluted the stock 683.3 µM, i.e. 11.7 µl in 188.3 PBS pH7.4 diluted 3× times in PBS by transferring 15 µl of cpd to 30 µl (final is 40 µM)—by Hand
  2) Diluted 1:10, i.e 6 µl of above in 54 µl of DMEM:F12 (final is 4 µM)—by Hand
  3) Diluted 1:10, i.e 10 µl of above in 90 µl of DMEM:F12 (final is 400 nM)—by Hand
Serelaxin-FA Conjugate
  1) Diluted the stock to 40 µM in PBS pH7.4 diluted 3× times in PBS by transferring 15 µl of compound to 30 µl
  2) Diluted 1:10, i.e 6 µl of above in 54 µl of DMEM: F12—by Hand
  3) Diluted 1:10, i.e 10 µl of above in 90 µl of DMEM:F12 (1:100 dilution)-by Hand
Fatty Acid
  1) Diluted the stock to 40 µM in PBS pH7.4 diluted 3× times in PBS by transferring 15 µl of cpd to 30 µl
  2) Diluted 1:10, i.e 6 µl of above in 54 µl of DMEM: F12—by Hand
  3) Diluted 1:10, i.e 10 µl of above in 90 µl of DMEM:F12 (1:100 dilution)—by Hand
cAMP Standard Curve Dilutions:
  1. 150 µl of the cAMP std diluted in DMEM:F12 media to first column (2800 nM)
  2. 100 µl of the DMEM:F12 media to the subsequent columns till 10 (1-11)
  3. 3× dilutions, by transferring 50 µl to 100 µl
  4. 20 µl from the step 3 to appropriate wells of the std curve plate
  5. 10 µl of Anti-d2 & Anti-cAMP cryptate conjugate
  6. Incubate 1 h at room temperature
  7. Read FRET signal—Envision 665 nm/620 nm
Analysis:
The cAMP nM concentration was Log (x) transformed using Graph pad prism
The cAMP amount was interpolated from the standard curve using 4 parameter nonlinear regression.
The interpolated values were converted to nM using 10^Y transformation
The computed cAMP amounts were plotted against the compound concentration, using 4 parameter nonlinear regression
Results:

TABLE 9

| Compound | EC50 (nM) |
| --- | --- |
| Serelaxin | 1.12 |
| Serelaxin-FA conjugate Example 29B | 4.51 |

In vitro Activity in Presence of Bovine Serum Albumin and Human Serum #2:
Materials:
DMEM: F12 media (Gibco, cat#11320)
IBMX (Sigma, cat#15879)
384 solid bottom white plates (Greiner bio-one, cat #781945)
20,000 dynamic-2 cAMP kit (Cisbio, cat#62AM4PEC)
Adenosine 3',5'-cyclic monophosphate (Sigma, cat#A9501)
Matrix-plate mate plus (used for adding 5 µl of assays reagents)
PBS-Gibco (cat#10010-023)
1M HEPES Gibco (cat-15630-080)
1× HBSS Gibco (cat-14175-095)
Assay buffer—1×HBSS+10 mM HEPES
Bovine serum albumin cat# A2153 (Sigma-Aldrich)
Sigma Aldrich—H4522 (Human serum)
Conditions:
  600 µM of BSA
  4% Human Serum
  10% Human Serum (Sigma aldrich H4522)
  Assay buffer Compounds tested:
  Serelaxin
  Serelaxin-FA (Example 29A)
Compound Handling:
Serelaxin—: Stock is (796.57 uM) i.e 4.75 mg/ml MW is 5963 Daltons
  Serelaxin 10 ul stock dissolved in 190 ul of PBS, final concentration is 40 µM, which are diluted 3× fold by transferring 30 ul to 60 ul of the assay buffer 11 point curve, (A2-A12) $12^{th}$ is zero.
Serelaxin-FA conjugate: Stock is (287.79 uM) i.e 2.61 mg/ml MW is 9069 Daltons
  Serelaxin 27.798 ul stock dissolved in 172.2 ul of PBS, final concentration is 40 µM, which are diluted 3× fold by transferring 30 ul to 60 ul of the assay buffer 11 point curve, (A2-A12) $12^{th}$ is zero.
BSA Stock Solution Preparation:
For 666.66 uM BSA: Made assay buffer 30mls by dissolving 1.32gms of BSA
For 600 uM BSA: Made assay buffer 30mls by dissolving 1.18gms of BSA
No BSA, has only assay buffer
Human Serum
For 4.44% HS: 1.34 mls in 28.66 mls of assay buffer
For 4% HS: 1.2 mls in 28.8 mls of assay buffer
For 11.11% HS: 3.33 mls in 26.67 mls of assay buffer
For 10% HS: 3 mls in 27 mls of assay buffer
Procedure:
Day 1: Seed 8,000 cells/well of RXFP1-HEK293 and HEK293 (parental) cells in 10 µl/well volume in basal DMEM:F12 media-on solid bottom plate. Incubate cells overnight at 37° C./5% $CO_2$.
Day2:
  1. Wash cells 2× times with 50 ul of assay buffer and were tapped gently on paper towel to get rid of assay buffer after first and second wash
  2. Cells were pretreated with 15 ul of media with IBMX (666.66 uM) containing respective media (600 uM of BSA, 4% BSA, 10% Human serum and assay buffer alone) for 30 minutes at 37° c.
  3. Serially dilute cpds 3× times, 11 point curve—transferring 15 ul of cpds from previous well to subsequent well with 30 ul of PBS, well 11 is PBS only
  4. Dilute (1:10) in assay buffer from step 3 (i.e is 10 ul to 90 ul of assay buffer)
  5. Dilute again from step 4 (1:10) in respective media (666.66 µM of BSA &4.44% & 11.11% Human serum and assay buffer) final con of the BSA is 600 µM and Human serum is 4 & 10%
  6. (*Incubate the cpds for 1 hr at RT in their respective media, before adding to cells)
  7. 5 ul of from step 6 i.e is 4× Serelaxin/Serelaxin-FA to 15 ul of cells for 30 more minutes at 37° c. (top concentration of Serelaxin is 100 nM)
  8. Add 10 ul cAMP d2 conjugate
  9. Add 10 ul anti-cAMP-Cryptate
  10. Incubate for 1 hr at room temperature
  11. Read FRET on Envision
  12. cAMP std curves were made in their respective media.
cAMP Standard Curve Dilutions:
The initial stock of cAMP standard is 1120000 nM
  1. Dilute the initial stock (1:4) by dissolving 20 ul of the cAMP stock in 60 ul of assay buffer
  2. (1:10) dilution of step 1 in assay buffer (i.e is 20 ul in 180 ul of assay buffer)
  3. (1:10) dilution of step 2 in respective concentration of 4.44% & 11.11% HS, 666.66 uM BSA or No BSA—The final concentration would end up to be 4%, 10% of HS and 600 µM of BSA.
cAMP Standard Curve
  1. Add 150 µl of the respective cAMP standards to first column (2800 nM)
  2. Add 100 µl of the assay buffer with respective concentrations 600 uM BSA, 4% &10% HS and 0%) to the subsequent 11 columns i.e is (2-12)
  3. 3× dilutions, by transferring 50 µl to 100 µl of subsequent wells $12^{th}$ well is Zero no cAMP
  4. 20 µl from the step 3 to appropriate wells of the std curve plate
  5. Add 10 µl of d2 conjugate
  6. Incubate 1 hr at room temperature
  7. Read on HTRF-Envision
Analysis:
The cAMP nM concentration is Log (x) transformed using Graph pad prism
The cAMP amount was interpolated from the standard curve using 4 parameter nonlinear regression.
The interpolated values were converted to nM using $10^Y$ transformation
The computed cAMP amounts were plotted against the compound concentration, using 4 parameter nonlinear regression
Result:

TABLE 10

| | $Ec_{50}$ (nM) | | | |
| --- | --- | --- | --- | --- |
| | 0% Plasma | 4% Plasma | 10% Plasma | 600 uL BSA |
| SeRelaxin | 8 | 0.3 | 0.4 | 0.7 |
| FA-SeRelaxin (Ex 29a) | 100 | 11 | 15 | 15 |

In vivo Assay:
Compounds (serelaxin and serelaxin conjugates) can be tested in various rodent models to evaluate short- and long-term cardiovascular responses.
Short-Term Models—Mice (any strain, but DBA/2 preferred) or rats (any strain, but Sprague-Dawley preferred) are anesthetized with inhaled isoflurane, maintained at a stable surgical plane of anesthesia with ~2% isoflurane in 100% oxygen, and rectal temperature maintained at a normal level. A carotid artery and jugular vein (mice) or a femoral artery and vein (rat) are exposed through overlying skin incisions, and the vessels catheterized. The arterial catheter is connected to a pressure transducer and the signal is directed to a digital data acquisition system (e.g., Ponemah) for continuous measurement of arterial pressure and triggering of heart rate. Alternatively, heart rate is triggered by an electrocardiogram signal recorded via subcutaneously inserted needle electrodes. After allowing the arterial pressure and heart rate to stabilize, a cocktail of autonomic blocking agents (e.g., atropine and propranolol at 2 mg/kg each) are administered intravenously over ~3-4 minutes. When cardiovascular parameters re-stabilize, serelaxin or serelaxin conjugates are injected as an intravenous bolus over ~3 sec. Relaxin elicits an increase in heart rate with a characteristic slow onset (peak response in ~6 minutes) and sustained duration of action (hours). In the same animal preparation, ventricular cardiac function (e.g., ejection fraction, fractional shortening, cardiac output) is measured by collecting serial echocardiographic images, which are analyzed offline.

Long-Term Models—Mice (any strain, but DBA/2 preferred) or rats (any strain, but Sprague-Dawley preferred) are anesthetized with inhaled isoflurane and maintained at a stable surgical plane of anesthesia with ~2% isoflurane in 100% oxygen. Analgesics are administered peri- and post-operatively. An artery and vein are cannulated as described above, but the catheters are exteriorized through the dorsal skin region, flushed with heparinize saline, and plugged with a stainless-steel pin. A subcutaneous catheter might also be implanted subcutaneously in mice and exteriorized in a similar fashion. In rats, the catheters are directed through a spring-tether/swivel system. On the day of the study, arterial catheters are connected to pressure transducers, autonomic blockade is achieved as described above except that the blocking agents can also be administered via the subcutaneous catheter in mice, and the blockade in both species is maintained thereafter by continuous intravenous or subcutaneous infusions of the autonomic agents. Arterial pressure and heart rate are monitored continuously with a digital data acquisition system. After allowing the arterial pressure and heart rate to stabilize, the autonomic blocking agents are administered intravenously or subcutaneously over ~3-4 minutes. When cardiovascular parameters re-stabilize, serelaxin or serelaxin conjugates are injected as an intravenous bolus over ~3 sec. For assessing ventricular cardiac function and heart rate over a period of weeks in mice or rats, serelaxin conjugates are injected subcutaneously 1-3 times per week and serial echocardiographic images collected at baseline and weekly thereafter.

Serelaxin Source:
Serelaxin (Recombinant 1-chain human relaxin)
Connetics corporation, lot #00L605
1.0 mg/mL (5 mL vial) in 20 nM Na acetate buffer (pH 5.0)
Dilution of stock solution in vehicle to the desired concentration of serelaxin for each dose.

The activity and plasma stability of the PIP conjugate of example 30 can be assessed by the following in vitro and in vivo methods described below.

Glucose-Stimulated Insulin Secretion (GSIS) Assay:
GSIS test was performed as a measurement of in vivo pancreatic beta cell function following recombinant human Prolactin-inducible Protein (hPIP) in high fat diet-induced obese (DIO) mice. Briefly, mice (m=5-7/group) were fasted overnight (5:00 PM-8:00 AM) and on the test day body weight and blood glucose (BG; determined with Embrace glucose meters) which was designated as baseline timepoint. Next, mice were administered with hPIP (native and FA-conjugated PIP; solution in PBS; administered at 4 ml/kg body weight) or a vehicle-control (PBS) once intravenously (IV). Forty-five min following the hPIP administration, all mice were dosed with oral glucose (3 g/kg dextrose; solution in PBS; administered at 4 ml/kg body weight). Blood glucose was measured immediately before the glucose load (designated as 0 min time point) and at 15 and 30 min post-glucose. Blood samples were collected for plasma isolation and measurement of plasma insulin were carried out at 0, 15 and 30 min post-glucose.

Pharmacokinetics (PK) Assay:
Plasma exposure of hPIP were measured in DIO mice following a single IV administration. Briefly, freely-fed DIO mice (n=2) were administered with hPIP (native and FA-conjugated PIP; solution in PBS; administered at 4 ml/kg body weight) once intravenously (IV). Blood samples were collected and plasma isolated at 0.25, 0.5, 1, 3, 7, 24 and 48 hrs post-dose by and in-house ELISA assay (protocol shown below).

Assay were measured by the following steps:
Plates were coated overnight at room temperature with 30 ul hPIP antibody (designated as PIP-8-AB; produced in-house; NBC clone#87.19G9A11, at 8 ug/ml in PBS).
Aspirated before blocking 2 hr with 100 ul blocking reagent.
Aspirated and 30 ul samples added to incubate for 2 hrs, samples and standards are diluted in Casein buffer (1% Casein, 1.7 mM Sodium Phosphate Monobasic, 8.1 mM Sodium Phosphate Dibasic Heptahydrate, 0.15M Sodium Chloride, 0.7% Triton X-100, and 0.1% Sodium Azide.)
Plates were washed 3×100 ul with Teknova wash buffer (0.05% Tween in PBS)
30 ul biotinylated PIP antibody (designated as PIP-6 Ab; produced in-house, MBC clone#87.8C6B3, at 10 ug/ml in casein buffer) and incubates for 1 hr
Washed as above
Added 30 ul Streptavidine-HRP (Pierce cat #21140, at 0.4 ug/ml in HRP buffer) HRP buffer (0.4% Casein, 1.7 mM Sodium Phosphate Monobasic, 8.1 mM Sodium Phosphate Dibasic Heptahydrate, 0.15M Sodium Chloride, and 0.1% Chloroacetamide) incubate 30 min.
Washed as above
Added 30 Femto Chemiluminescent Substrate (Thermo cat #34096) and read immediately Activity and Stability of PIP Fatty Acid Conjugate of the Invention According to Assays Described Supra

TABLE 11

| Peptide | Plasma Insulin AUCB (ng/mL*min)** | In vivo Plasma stability t½ [h] | Cmax (nM) | MRT (hr) |
| --- | --- | --- | --- | --- |
| Example 30 | +75% | ---13.8- | 497.1 | 18.1 |
| Unconjugated PIP | +29% | --18.0- | 219.8 | 12.0 |

**compared to the vehicle

The PIP fatty acid conjugate of the invention has an extended exposure resulting in an improved efficacy.

The activity and plasma stability of the NPFF conjugate of example 31 can be assessed by the following in vitro methods described below.

cAMP Assay Protocol with Cisbio cAMP Kit
The NPFF-FA conjugate of the invention was tested in presence of Forskolin in the assay described below.

Reagents/Materials

| | Vendor | Cat# | Location (Stock) |
| --- | --- | --- | --- |
| Greiner 384 clear bottom plate precoated with Poly-Lysine | Greiner Bio-One | 781944 | |
| cAMP kit | Cisbio | 62AM4PEJ | 4° C./−20° C. |
| DMSO | Sigma | D2650 | |
| cAMP standard (1.12 mM in assay buffer + IBMX) | Sigma | A9501 | −80° C. |
| Forskolin 5 mM Stock solution (DMSO) | Sigma | F6886 | −20° C. |
| IBMX 250 mM stock solution (DMSO) | Sigma | I5879 | −20° C. |
| HBSS | Invitrogen | 14175-095 | R.T |
| HEPES | invitrogen | 15630-080 | R.T |
| PTX (Pertussis Toxin) | Sigma | P2880 | −20° C. |
| BSA Free Fatty Acid (30%) | Sigma | A9205 | 4° C. |

Day 1: Plate Cells into 384-Well Plate.
Following "Subculturing Protocol".
1. Make growth media without antibiotics (if necessary).
2. Equilibrate Growth medium without antibiotics bottle in 37° C. water bath after spraying with 70% ethanol.
3. Detach cells with Versene (3 ml per T.75 flask).

4. Transfer into 50 ml Falcon tube containing 17 ml of growth media.
5. Centrifuge 4 min at 150 g.
6. Resuspend cell pellet in 10 ml Stimulation Buffer. Count cells.
7. Prepare cell suspension in growth media with antibiotics at 5'000 cells/50 ul.
8. Plate 50 ul of cell suspension using the Viaflow 384-125 ul pipet.
9. Let plates sit under the TC hood for 15 min.
10. Incubate at 37° C., 5% $CO_2$ and 90% humidity.

Day 2:
Preparation of Reagents Solutions:
1. Assay Buffer:
   500 ml HBSS+10 ml HEPES. Store at R.T
   Assay Buffer: 250 ml HBSS/HEPES+250 ul IBMX 1000× solution+0.1% BSA (825 ul).
   Make fresh daily.
2. Forskolin 2× Solution: 1 uM Final in Assay:
   For cpds dilutions: 40 ul FSK/100 ml Assay buffer.
   For NPFF dilution: 10 ul DMSO/ 10 ml 2× FSK.
3. NPFF dilutions: stock solution 1 mM in $dH_2O$— Final in assay 1 uM
   a. 5 ul stock/625 ul FSK 2×/DMSO.
   b. 100 ul sol. a +300 ul FSK 2×/DMSO. Final in assay 1 uM.
   c. Make 10 dilution steps 1/4: 100 ul+300 ul in FSK 2×/DMSO.
4. Cpds dilutions: stock solution 10 mM in DMSO-Final in assay 40 uM
   a. 5 ul stock/625 ul FSK 2×.
   b. Make 11 dilution steps 1/4: 100 ul+300 ul FSK 2×.
5. cAMP standard:
   a. 10 ul cAMP standard stock (1.12 mM)+90 ul Assay buffer.
   b. 10 ul dilution a +90 ul stimulation buffer.
   c. 20 ul dilution b+428 ul stimulation buffer: 500 nM.
   d. Make 11 dilutions 1/2 starting from dilution c: 100 ul dilution c+100 ul stimulation buffer.
6. cAMP Detection Reagents:
   a. d2-cAMP: 1000 ul/ 20 ml Lysis buffer. (250 ul/ 5 ml for one 384-well plate).
   b. Cryptate conjugate: 1000 ul/ 20 ml Lysis Buffer. (250 ul/ 5 ml for one 384-well plate).

Assay Procedure
Step One:
1. Prepare Stimulation buffer.
2. Put Cisbio Lysis buffer at R.T.
3. Prepare the WellMate (wash with 70% alcohol followed by $dH_2O$ and HBSS/HEPES).
4. Prepare Forskolin and cpds dilutions.

Step Two: Stimulation with Forskolin
1. Wash cells with 50 ul of stimulation buffer:
   a. Gently tap plates to remove 0/N media.
   b. Put white paper towel on top of plate and centrifuge plate upside down for 20 sec at 300RPM using the VWR Symphony 4417 centrifuge.
   c. Add 50 ul of stimulation buffer using the WellMate.
   d. Gently tap plates to remove 0/N media.
   e. Put white paper towel on top of plate and centrifuge plate upside down for 20 sec at 300RPM using the VWR Symphony 4417 centrifuge.
   f. Check at cells under the microscope.
2. Add 10 ul of Stimulation buffer containing IBMX using Viaflow 384
3. Add 10 ul of 2× Forskolin solution containing the cpds using the Viaflow 384 (on the $7^{th}$ floor). Mix solution before adding to cells.
4. Incubate 30 min at R.T. (put plate in a drawer to avoid temperatures changes).
5. Prepare cAMP standard curve and cAMP detection reagents.
6. Add 20 ul/well of cAMP standard curve to the standard curve plate (same plate than assay plate).

Step Three: LANCE cAMP assay
1. Add 10 ul d2 cAMP/well to assay plate using Combi 384.
2. Add 10 ul/well Cryptate conjugate to assay plate manually.
3. Seal plate.
4. Incubate 1 hour minimum at R.T (plate can read within 24 hour).
5. Put Tape on the bottom of the plate.
6. Read on Envision program "Cisbio 384 full plate"
7. See raw data into accessories files.
8. Data analyzed with GraphPad (see file in accessories files).

Results:

TABLE 12

|  | 0.1% BSA (FFA) | 3% BSA (FFA) | 0.1% HSA | 3% HSA |
| --- | --- | --- | --- | --- |
| Human R2 | | | | |
| compound | IC50(nM) n = 4 | IC50(nM) n = 4 | IC50(nM) n = 2 | IC50(nM) n = 2 |
| NPFF | 0.43 (+/−0.11) | 0.36 (+/−0.17) | 0.63 (+/−0.25) | 1.9 (+/−1.7) |
| Example 31 | 53.9 (+/−26) | 133 (+/−47) | 33.5 (+/−3.11) | 98.5 (+/−19) |
| Human R1 | | | | |
| compound | IC50(nM) n = 4 | IC50(nM) n = 4 | IC50(nM) n = 2 | IC50(nM) n = 2 |
| NPFF | 6.23 (+/− 3.3) | 7.2 (+/− 6.0) | 8.4 (+/−0.6) | 33.4 (+/−29) |
| Example 31 | >1000 | >4000 | 620 (+/−142) | >4 uM |

The activity and plasma stability of the conjugate of the invention wherein the biomolecule is a siRNA can be assessed by the following in vivo methods described below.

Methods

Conjugate of Example 24 is a compound of the APOC3 siRNA conjugated with GalNAc (Reference Example 3) and the fatty acid. Human APOC3 transgenic mice (B6; CBA-Tg(APOC3)3707Bres/J) were purchased from the Jackson Laboratory (Bar Harbor, Me.). Mice were fed standard rodent chow and water ad libitum with a 12 h light/dark cycle. Under this condition, APOC3 transgenic mice spontaneously develop hypertriglyceridemia with markedly increased plasma TG content (Aalto-Setala K, J Clin Invest 1992). Four mice in each group were injected subcutaneously with either reference example 3 (APOC3 siRNA- GalNAc) or conjugate of Example 24 at a dose of 25 mg/Kg of body weight. Blood was collected at baseline immediately before injection, and 2, 4, 7 and 14 days after the injection. Plasma was used to measure human APOC3 protein levels with an HTRF assay from Cisbio. One-way ANOVA was used to compare the statistical difference between groups.

Results

Baseline plasma APOC3 levels were 176±21 mg/dL and 178±9 mg/dL in the reference example 3 and the conjugate 24 groups, respectively. Reference example 3 time-dependently decreased plasma APOC3 levels, by 56% five days after dosing versus baseline levels. By comparison, conjugate of example 24 decreased plasma APOC3 more effectively, with an 80% decrease five days after dosing (FIG. 1). The duration of action is similar for both reference example 3 and example 24 as shown in FIG. 1.

The conjugate of the present invention have plasma stability of at least 5 h, at least 10 h, at least 20 h, at least 30 h, at least 40 h or at least 50 h. In one embodiment, the plasma stability improvement compared to the non-conjugated biomolecule is at least 2 fold, 5 fold, 10 fold, 20 fold, 30 fold, 40 fold or 50 fold or 75 fold.

Combination Therapy

The conjugate of the present invention may be administered either simultaneously with, or before or after, one or more other therapeutic agent. The conjugate of the present invention may be administered separately, by the same or different route of administration, or together in the same pharmaceutical composition as the other agents.

In one embodiment, the invention provides a product comprising a conjugate of any one of preceeding embodiments or a mixture of conjugates as described in embodiments 10 and 13, and at least one other therapeutic agent as a combined preparation for simultaneous, separate or sequential use in therapy. In one embodiment, the therapy is the treatment of a metabolic disorders or diseases, type 2 diabetes mellitus, obesity, dyslipidemia, elevated glucose levels, elevated insulin levels and diabetic nephropathy in a subject in need thereof, comprising: administering to the subject a therapeutically effective amount of a conjugate of the invention, or an amide, ester or salt thereof, wherein the biomolecule is human Growth Differentiation Factor 15 (GDF15), homologs, variants, mutants, fragments and other modified forms thereof.

Products provided as a combined preparation include a composition comprising a conjugate of any one of the preceeding embodiments, and the other therapeutic agent(s) together in the same pharmaceutical composition, or a conjugate of any one of the preceeding embodiments, and the other therapeutic agent(s) in separate form, e.g. in the form of a kit.

In one embodiment, the invention provides a pharmaceutical composition comprising a conjugate of any one of the preceeding embodiments or a mixture of conjugates according to embodiment 10 or 13, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a conjugate according to any one of the preceeding embodiments. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral, subcutaneous and parenteral, for administering the separate compositions at different dosage intervals, or for titrating the separate compositions against one another. To assist compliance, the kit of the invention typically comprises directions for administration.

In the combination therapies of the invention, the conjugate of the invention and the other therapeutic agent may be manufactured and/or formulated by the same or different manufacturers. Moreover, the conjugate of the invention and the other therapeutic may be brought together into a combination therapy: (i) prior to release of the combination product to physicians (e.g. in the case of a kit comprising the conjugate of the invention and the other therapeutic agent); (ii) by the physician themselves (or under the guidance of the physician) shortly before administration; (iii) in the patient themselves, e.g. during sequential administration of a conjugate of the invention and the other therapeutic agent.

The invention also provides the use of a conjugate according to any one of preceeding embodiments, for treating a disease or condition set forth herein, wherein the patient has previously (e.g. within 24 hours) been treated with another therapeutic agent. The invention also provides the use of another therapeutic agent for treating a disease or condition set forth herein, wherein the patient has previously (e.g. within 24 hours) been treated with a conjugate according to any one of preceeding embodiments.

The term "in combination with" a second agent or treatment includes co-administration of the conjugate of the invention (e.g., a conjugate according to any one of the preceeding embodiments or a conjugate otherwise described herein) with the second agent or treatment, administration of the compound of the invention first, followed by the second agent or treatment and administration of the second agent or treatment first, followed by the conjugate of the invention.

The terms "second agent" and "co-agent" are used interchangeably and include any agent which is known in the art to treat, prevent, or reduce the symptoms of a disease or disorder described herein, e.g.a disorder or disease selected from a metabolic disorders or diseases, type 2 diabetes mellitus, obesity, pancreatitis, dyslipidemia, alcoholic and nonalcoholic fatty liver disease/steatohepatitis and other progressive liver diseases, insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, diabetic complications (including but not limited to chronic kidney disease), neuropathy, gastroparesis and other metabolic disorders.

In one embodiment, the therapy is the treatment of metabolic disorders or diseases, type 2 diabetes mellitus, obesity, pancreatitis, dyslipidemia, alcoholic and nonalcoholic fatty liver disease/steatohepatitis and other progressive liver diseases, insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, diabetic complications (including but not limited to chronic kidney disease), neuropathy, gastroparesis and other metabolic disorders, in a subject in need thereof, comprising: administering to the subject a therapeutically effective amount of a conjugate of the invention, or an amide, ester or salt thereof, wherein the biomolecule is human Growth Differentiation Factor 15 (GDF15), homologs, variants, mutants, fragments and other modified forms thereof.

Examples of second agents to combine with a conjugate of the instant invention, wherein the biomolecule is human Growth Differentiation Factor 15 (GDF15), homologs, variants, mutants, fragments and other modified forms thereof; include:

1. Antidiabetic agents, such as insulin, insulin derivatives and mimetics; insulin secretagogues such as the sulfonylureas (e.g., chlorpropamide, tolazamide, acetohexamide, tolbutamide, glyburide, glimepiride, glipizide); glyburide and Amaryl; insulinotropic sulfonylurea receptor ligands such as meglitinides, e.g. nateglinide and repaglinide; thiazolidinediones (e.g., rosiglitazone (AVANDIA), troglitazone (REZULIN), pioglitazone (ACTOS), balaglitazone, rivoglitazone, netoglitazone, troglitazone, englitazone, ciglitazone, adaglitazone, darglitazone that enhance insulin action (e.g., by insulin sensitization), thus promoting glucose utilization in peripheral tissues; protein tyrosine phosphatase-1B (PTP-1B) inhibitors such as PTP-112; Cholesteryl ester transfer protein (CETP) inhibitors such as torcetrapib, GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin and other agents that act by promoting glucose utilization, reducing hepatic glucose production and/or diminishing intestinal glucose output; alpha-glucosidase inhibitors such as acarbose and migiitoi) and other agents that slow down carbohydrate digestion and consequently absorption from the gut and reduce postprandial hyperglycemia; GLP-1 (glucagon like peptide-1), GLP-1 analogs such as Exendin-4 and GLP-1 mimetics; and DPPIV (dipeptidyl peptidase IV) inhibitors such as vildagliptin;

2. Hypolipidemic agents such as 3-hydroxy-3-methyl-glutaryl coenzyme A (HMG-CoA) reductase inhibitors, e.g. lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; bile acid sequestrants, such as cholestyramine and colesevelam; fibrates; nicotinic acid and aspirin;

3. Anti-obesity agents such as orlistat or rimonabant, phentermine, topiramate, qunexa, and locaserin;

4. Anti-hypertensive agents, e.g. loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;

5. Agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof; and 6. The specific anti-diabetic compounds described in *Expert Opin Investig Drugs* 2003, 12(4): 623-633, FIGS. 1 to 7.

Furthermore, the present disclosure contemplates combination therapy with agents and methods for promoting weight loss, such as agents that stimulate metabolism or decrease appetite, and modified diets and/or exercise regimens to promote weight loss.

EXAMPLE OF THE INVENTION

Abbreviation
ACN Acetonitrile
BEH Ethylene Bridged Hybrid
BOC tert-Butyloxycarbonyl
BSA Bovine serum albumin
DCM dicloromethane
DCC N,N'-dicyclohexylcarbodiimide
DIC N,N'-Diisopropylcarbodiimide
DIPEA N,N'-Diisopropylethylamine
DMAP Dimethylaminopyridine
DMF N,N'-Dimethylformamide
DTT Dithiothreitol
DOT 3,6-Dioxa-1,8-octanedithiol
EDC 1-Ethyl-3-(3-dimethylaminopropyl)carbodiimide
EDTA ethylenediaminetretraacetic acid
ESI electrospray ionization
FFA fluorescent focus assay
Fmoc fluorenylmethyloxycarbonyl chloride
HCTU: O-(6-Chlorobenzotriazol-1-yl)-N,N,N',N'-tetramethyluronium hexafluorophosphate
HEP Heptane
HFIP Hexafluoroisopropanol
HPLC High performance liquid chromatography
HRMS High resolution mass spectrometry
HOBT Hydroxybenzotriazole
HS Human serum
LC/MS liquid chromatography/mass spectrometry
MS Mass spectrometry
MW molecular weight
MRT mean residence time
NHS N-hydroxysuccinimide
NMM N-methylmorpholine
NMR Nuclear magnetic resonance
PEG polyethylene glycol
pE Pyroglutamate
pbf 2,2,4,6,7-Pentamethyldihydrobenzofuran-5-sulfonyl
PG: protective group
PK pharmacokinetic
Pol Polymer support
QTOF: Quadrupole time-of-flight mass spectrometer
Rt: retention time Rt or RT: room temperature
Rpm: round per minute
Sc subcutaneous
SFC super critical fluid
SPPS Solid phase peptide synthesis
TBME methyl tert-butyl ether
Trt trityl
THF Tetrahydrofuran
TEA trimethylamine
TIS triethylsilane
t, s, quin, br, m, d (triplet, singlet, quintet, broad, multiplet)
UPLC Ultra performance liquid chromatography
Syntheses:
LCMS Methods Described

| Method A | Column | Acquity BEH 1.7 μm 2.1 × 50 mm |
| --- | --- | --- |
| | Column Temperature | 50 C. |
| | Eluents | A: Water (0.1% formic acid); B: ACN (0.1% formic acid) |
| | Flow Rate | 1 mL/min |
| | Gradient | 0 min 2% B; 2% to 98% B in 1.7 min; 2.06 min 98% B; 2.16 min 2% B |
| | Mass Spectrometer | Single Quadrupole ESI scan range 120-1600 |
| | UPLC | Waters Acquity |
| Method B | Column | Acquity BEH 1.7 μm 2.1 × 50 mm |
| | Column Temperature | 50 C. |
| | Eluents | A: Water (0.1% formic acid); B: ACN (0.1% formic acid) |
| | Flow Rate | 1 mL/min |
| | Gradient | 0 min 40% B; 40% to 98% B in 1.40 min; 2.05 min 98% B; 2.1 min 40% B |
| | Mass Spectrometer | Single Quadrupole ESI scan range 120-1600 |
| | UPLC | Waters Acquity |
| Method C | Column | XBridge C18 Column, 3.5 μm, 3.0 × 30 mm |
| | Column Temperature | 40 C. |
| | Eluents | A: Water (0.1% formic acid); B: ACN |
| | Flow Rate | 2 mL/min |
| | Gradient | 0 min 40% B; 40% to 95% B in 1.70 min; 2.0 min 95% B; 2.1 min 40%B |
| | Mass Spectrometer | Single Quadrupole ESI scan range 150-1600 |
| | HPLC | Agilent 1100 series |
| Method D | Column | Hilic 2.1 × 100 mm |
| | Column Temperature | 55 C. |
| | Eluents | A: $CO_2$ B: MeOH |
| | Flow Rate | 2 mL/min |
| | Gradient | 0.15 min 2% B; 2% to 50% B in 1.5 min; 2.1 min 50% B; 2.25 min 2% B; 2.5 min 2% B |
| | Mass Spectrometer | Single Quadrupole ESI |
| | SCF | Waters Acquity |
| Method E | Column | Proswift Monolith 4.6 × 50 mm |
| | Column Temperature | 50 C. |
| | Eluents | A: Water (0.1% formic acid); B: ACN (0.1% formic acid) |
| | Flow Rate | 1 mL/min |
| | Gradient | 0.7 min 2% B; 2% to 60% B in 12.8 min; 14 min 60% B; 14.2 min 2% B |
| | Mass Spectrometer | Qtof ESI scan range 600-3500; deconvoluted by Max Ent 1 in Mass Lynx software package |
| | UPLC | Waters Acquity |

HPLC—Analytical Method F
  Column: XBridge BEH300 C18 (100×4.6 mm), 3 μm; Part n°: 186003612
  Eluent A: 0.1% TFA in water/Eluent B: 0.1% TFA in ACN
  Flow: 1.0 ml/min
  Temperature: 40° C.

Gradient:

| Time [min] | A [%] | B [%] |
| --- | --- | --- |
| 0.0 | 98 | 2 |
| 18 | 2 | 98 |
| 20 | 2 | 98 |
| 22 | 98 | 2 |

UPLC-HRMS—Analytic Method G
  Waters Acquity UPLC® BEH C18, 1.7 μm, 2.1×50 mm; Part n°: 186002350
  Eluent A: 0.05% FA+3.75 mM ammonium acetate in water; Eluent B: 0.04% FA in ACN
  Flow: 1.0 ml/min
  Temperature: 50° C.
  Gradient: 2 to 98% in 4.4 min
Method H: LC-MS method
  HPLC: Mobile phase A: 2% HFIP+0.1% TEA; Mobile phase B: Methanol;
  Gradient: 0 min 95% A, 4 min:75% A, 8 min 10% A, 8.1 min 95% A, 10 min 95% A;
  Flow rate: 250 μl/min;
  Column: Acquity UPLC BEH C18, 1.7 um, 2.1×50 mm (waters);
  Column temp: 75° C.
  MS: QTOF (waters) negative mode;
  ESI: 2.9 kv; Capillary temp 350° C.; Spray gas: 600 ml/min; Source temp: 150° C.
Method I: LC-MS method:
  Mobile phase A: WATER+0.1% FORMIC ACID;
  Mobile phase B: ACETONITRILE+0.1% FORMIC ACID;
  Gradient: 0 min. 98% A, 0.06 min. 98% A, 1.76 min. 2% A, 2.06 min. 2% A, 2.16 min. 98%; Flow rate: 1 ml/min.;
  Column: ACQUITY UPLC BEH C18, 130Å, 1.7 μm, 2.1 mm×50 mm;
  Column Temperature: 50° C.;
  Detector: UV/Vis/CAD (charged Aerosol Detector)
UPLC HRMS Method J:
  Column: Acquity BEH300 C4 1.7 μm, 2.1×50 mm
  Eluent A: Water (0.1% TFA)
  Eluent B: ACN (0.1% TFA)
  Flow: 0.5 mL/min
  Temperature: 40° C.
  Gradient: 20% hold 0.5 min, ramp to 80% ACN in 10 min
Method K:
  Column: Waters Protein BEH C4 Column, 300 Angstrom, 3.5 um, 4.6×100 mm
  Mobile phase: A: Water (0.05% TFA) B: ACN (0.05% TFA)
  Flow: 2 mL/min
  Temperature: 40° C.
  Gradient: Hold 25% B for 1 min, ramp from 25-60% ACN at 10 min, ramp to 95% B at 10.50 min and hold for 2 mins, then equilibrate at 25% for 2 min. Total runtime is 15 mins.
  Mass Spectrometer: Waters ZQ mass spec
  UPLC: Column: BEH C4, 300 Angstrom, 1.7 um, 2.1×50 mm
Method L:
  Column: Proswift Monolith 4.6×50 mm
  Mobile phase: A: Water (0.1% formic acid) B: ACN (0.1% formic acid)
  Flow: 1 mL/min Temperature: 50° C.

Gradient: 0 min 3% B; 3% to 80% B in 2 min; 2.1 min 10% B; 2.8 min 95% B; 2.9 min 3% B Mass Spectrometer: Qtof ESI scan range 100-1900; deconvoluted by Max Ent 1 in Mass Lynx software package UPLC: Waters Acquity

| Method M | Column | Acquity BEH 1.7 μm 2.1 × 50 mm |
| --- | --- | --- |
| | Column Temperature | 50 C. |
| | Eluents | A: Water (0.1% formic acid); B: ACN (0.1% formic acid) |
| | Flow Rate | 1 mL/min |
| | Gradient | 0 min 2% B; 2% to 98% B in 4.40 min; 5.15 min 98% B; 5.19 min 2% B |
| | Mass Spectrometer | Single Quadrupole ESI scan range 120-1600 |
| | UPLC | Waters Acquity |
| Method N | Column | Sunfire 30 × 50 mm 5 um |
| | Eluents | A: Water (0.1% TFA); B: ACN (0.1% TFA) |
| | Flow Rate | 75 mL/min |
| | Gradient | 5-20% ACN over 3.2 min |
| Method O | Column | Acquity BEH 1.7 μm 2.1 × 50 mm |
| | Column Temperature | 50 C. |
| | Eluents | A: Water (0.1% formic acid); B: ACN (0.1% formic acid) |
| | Flow Rate | 1 mL/min |
| | Gradient | 0 min 40% B; 40% to 98% B in 3.40 min; 5.15 min 98% B; 5.19 min 40% B |
| | Mass Spectrometer | Single Quadrupole ESI scan range 120-1600 |
| | UPLC | Waters Acquity |
| Method P | Column | Proswift Monolith 4.6 × 50 mm |
| | Column Temperature | 50 C. |
| | Eluents | A: Water (0.1% formic acid) B: ACN (0.1% formic acid) |
| | Flow Rate | 1 mL/min |
| | Gradient | 0 min 2% B; 2% to 98% B in 2 min; 2.1 min 98% B; 2.3 min 2% B; 3.3 min 2% B |
| | Mass Spectrometer | Qtof ESI scan range 100-1900; deconvoluted by Max Ent 1 in Mass Lynx software package |
| | UPLC | Waters Acquity |
| Method Q | Column | Proswift Monolith 4.6 × 50 mm |
| | Column Temperature | 50 C. |
| | Eluents | A: Water (0.1% formic acid); B: ACN (0.1% formic acid) |
| | Flow Rate | 1 mL/min |
| | Gradient | 0.7 min 2% B; 2% to 60% B in 12.8 min; 14 min 60% B; 14.2 min 2% B |
| | Mass Spectrometer | Qtof ESI scan range 600-3500; deconvoluted by Max Ent 1 in Mass Lynx software package |
| | UPLC | Waters Acquity |
| Method R | Column | Proswift Monolith 4.6 × 50 mm |
| | Column Temperature | 50 C. |
| | Eluents | A: Water (0.1% formic acid) B: ACN (0.1% formic acid) |
| | Flow Rate | 1 mL/min |
| | Gradient | 0 min 3% B; 3% to 90% B in 7 min; 7.1 min 15% B; 7.70 min 95% B; 7.8 min 3% B |
| | Mass Spectrometer | Qtof ESI scan range 100-1900; deconvoluted by Max Ent 1 in Mass Lynx software package |
| | UPLC | Waters Acquity |

Analytical Method S:

Xbridge C18 Column, 3.5 μM, 3.0×3.0 mm

Eluent: A: Water+5 mM Ammonium Hydroxide B: ACN

Flow rate: 2 mL/min

Gradient: 0.0 min 2% B; 2% to 95% B in 1.70 min; 2.00 min 95% B; 2.10 min 5% B;

Mass Spectrometer: Single Quadrupole ESI

HPLC: Agilent 1100 series

Temperature: 40C

Analytical Method T:

| Column | Acquity BEH 1.7 μm 2.1 × 50 mm |
| --- | --- |
| Column Temperature | 50 C. |
| Eluents | A: Water (0.1% formic acid) B: ACN (0.1% formic acid) |
| Flow Rate | 1 mL/min |
| Gradient | 0 min 5% B; 5% to 60% B in 4 min; 7.2 min 98% B; 4.5 min 95% B; 4.6 min 5% B |
| Mass Spectrometer | Acquity G2 Xevo QTof - Rs(FWHM) >20000 Accuracy <5 ppm |
| UPLC | Waters Acquity |

Intermediate 1

Benzyl 11-bromoundecanoate

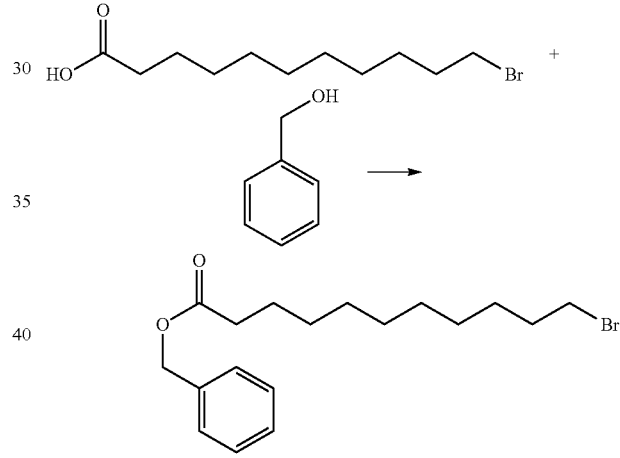

11-bromoundecanoic acid (4 g, 15.08 mmol), benzyl alcohol (1.875 mL, 18.10 mmol), and DMAP (92 mg, 0.754 mmol) were dissolved in DCM under $N_2$ at room temperature. EDC-HCl (4.34 g, 22.63 mmol) was added and the reaction stirred for 17 hr. The reaction was concentrated, followed by dilution with $Et_2O$ (150 mL). The mixture was extracted with water (30 mL), and the aqueous phase extracted with $Et_2O$ (150 mL). The combined organics were washed with brine (20 mL) and dried over Na2SO4. The solvent was removed and the residue purified by flash column (silica 120 g, 0-10% $Et_2O$/petroleum ether) to yield intermediate 1 as a colorless liquid (6.75 g, quantitative): LCMS method Method A Rt=1.79 min, M+H 355.2; $^1$H NMR (400 MHz, CHLOROFORM-d) δ ppm 1.18-1.36 (m, 10 H) 1.37-1.47 (m, 2 H) 1.64 (quin, J=7.33 Hz, 2 H) 1.85 (dt, J=14.56, 7.06 Hz, 2 H) 2.35 (t, J=7.58 Hz, 2 H) 3.40 (t, J=6.88 Hz, 2 H) 5.11 (s, 2 H) 7.28-7.45 (m, 5 H).

Intermediate 2

Tribenzyl undecane-1,1,11-tricarboxylate

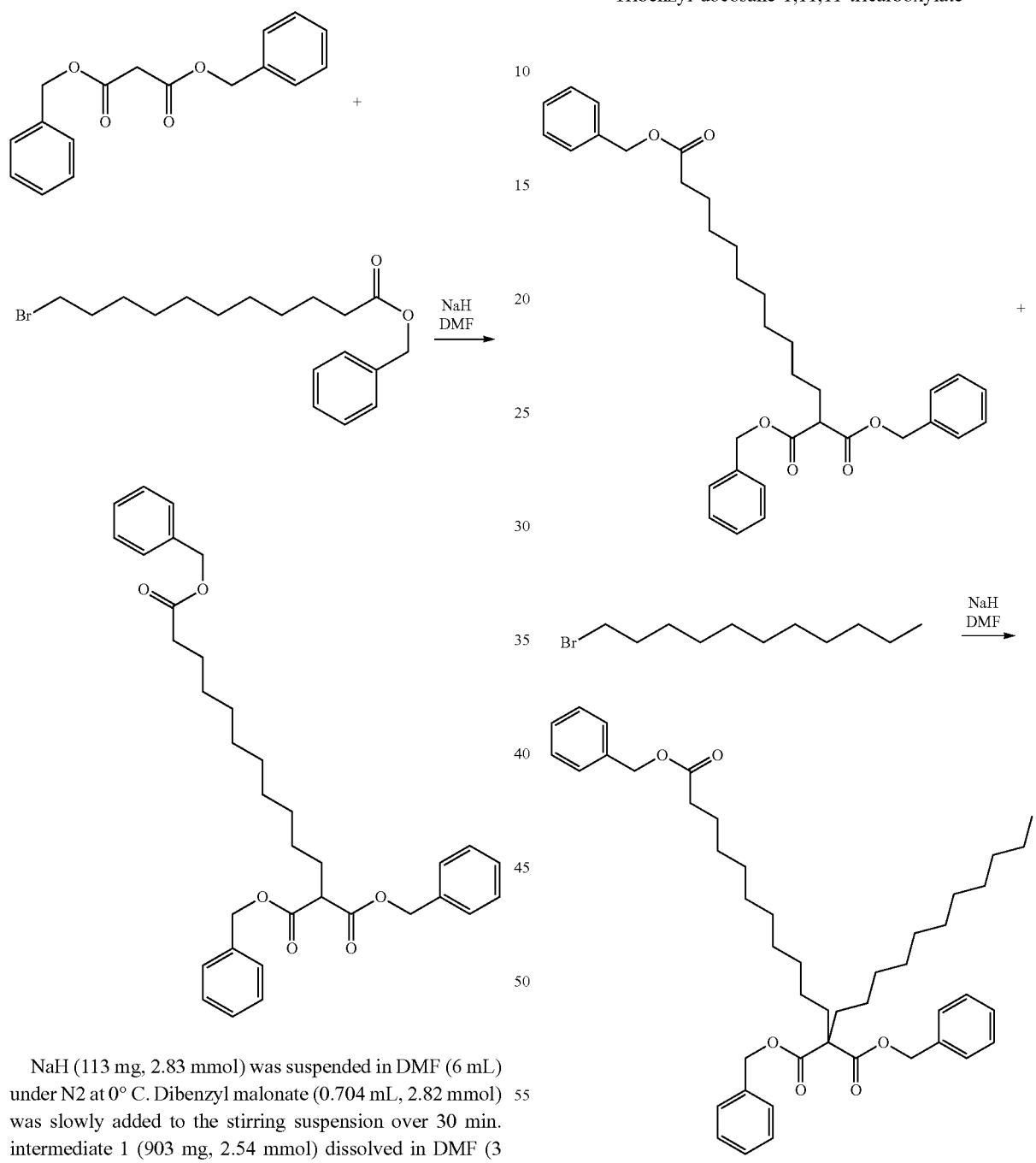

NaH (113 mg, 2.83 mmol) was suspended in DMF (6 mL) under N2 at 0° C. Dibenzyl malonate (0.704 mL, 2.82 mmol) was slowly added to the stirring suspension over 30 min. intermediate 1 (903 mg, 2.54 mmol) dissolved in DMF (3 mL) was added and the reaction allowed to stir at 0° C. for 2.75 hr before being allowed to warm to room temperature and stir overnight. The reaction was diluted with Et$_2$O (75 mL) and extracted with water (20 mL). The aqueous phase was extracted with Et$_2$O (75 mL) and the combined organics washed with brine (30 mL). The organics were dried over Na2SO4 and concentrated. The concentrate was purified by flash column (silica 80 g, 0-10% EtOAc/HEP) to yield a colorless oil (770 mg, 1.38 mmol, 34%) of 70% purity: LCMS Method B Rt=1.41 min, M+H 559.6.

Intermediate 3

Tribenzyl docosane-1,11,11-tricarboxylate

To a suspension of NaH (66.1 mg, 1.65 mmol) in DMF (2 mL) at 0° C. under N2, was added Intermediate 2 (770 mg, 1.38 mmol) in DMF (4 mL). After 35 min a solution of 1-bromoundecane (0.338 mL, 1.52 mmol) in DMF (2 mL) was added to the reaction, which was allowed to warm to room temperature after stirring for 25 min. The reaction was stirred for 2 days. The reaction was diluted with Et$_2$O (75 mL) and extracted with 10% LiCl (25 mL). The aqueous phase was extracted with Et$_2$O (75 mL). The combined organics were washed with brine, dried over Na2SO4, and the solvent evaporated. Purification of the residue by flash column (silica 80 g, 0-10% EtOAc/HEP) yielded intermediate 3 as a colorless oil (590 mg, 0.827 mmol, 33%): LCMS method Method B Rt=1.89 min, M+Na 735.5; $^1$H NMR (400 MHz, CHLOROFORM-d) δ ppm 0.87-0.95 (m, 3 H) 1.07 (br. s., 4 H) 1.14-1.36 (m, 28 H) 1.66 (quin, J=7.43 Hz, 2 H) 1.85-1.95 (m, 4 H) 2.37 (t, J=7.58 Hz, 2 H) 5.12 (s, 4 H) 5.14 (s, 2 H) 7.27 (d, J=2.32 Hz, 1 H) 7.28-7.43 (m, 14 H).

Intermediate 4

Docosane-1,11,11-tricarboxylic acid

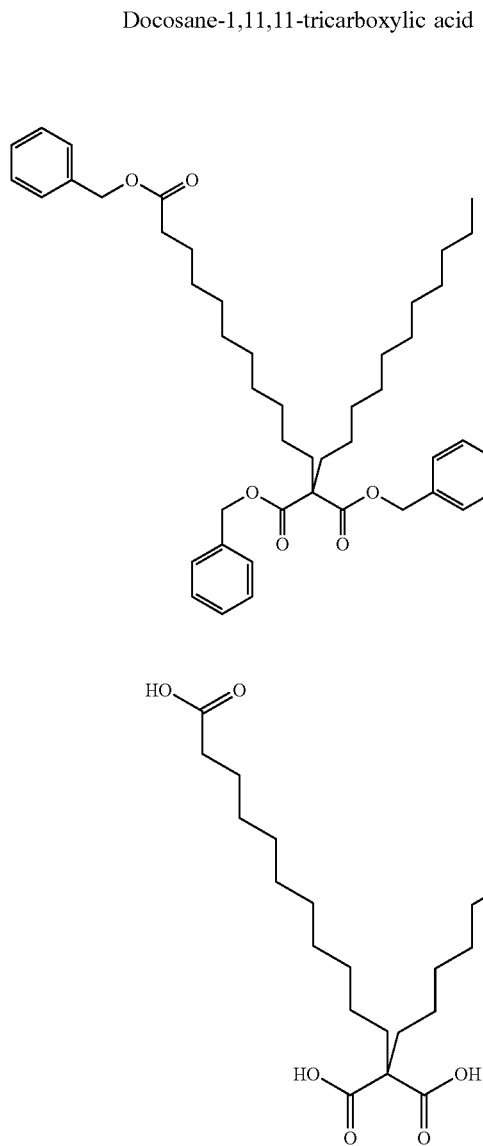

Intermediate 3 (590 mg, 0.827 mmol) dissolved in THF (12 mL) was combined with a suspension of 10% Pd on carbon in THF (8 mL). The suspension was stirred and placed under a hydrogen atmosphere via balloon. After 1 hr the reaction was passed through a membrane filter and the solids rinsed with EtOAc. The filtrate was evaporated, yielding the title compound as a colorless oil (353 mg, 0.798 mmol, 96%): LCMS method Method B Rt=1.16 min, M+H 443.5; $^1$H NMR (400 MHz, CHLOROFORM-d) δ ppm 0.77-0.84 (m, 3 H) 1.06-1.33 (m, 32 H) 1.59 (quin, J=7.18 Hz, 2 H) 1.83-1.92 (m, 4 H) 2.32 (t, J=7.03 Hz, 2 H).

Intermediate 5

2-(((2,5-Dioxopyrrolidin-1-yl)oxy)carbonyl)-2-undecyltridecanedioic acid

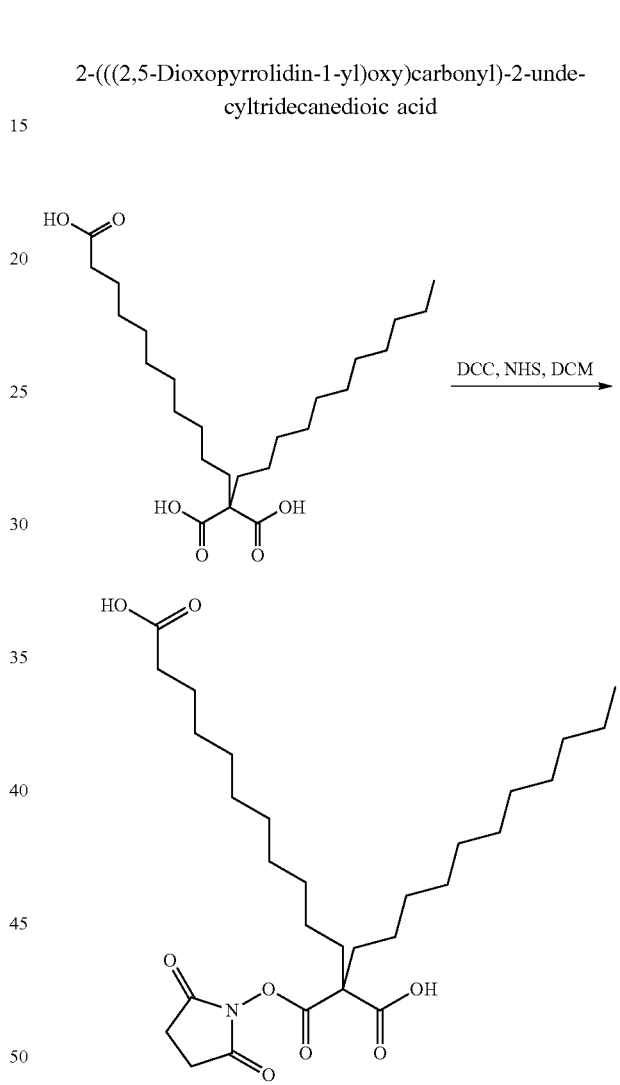

A solution of DCC (126 mg, 0.610 mmol) in DCM (1.57 mL) was added to a solution of intermediate 4 and N-hydroxysuccinimide in DCM (5 mL) and THF (5 mL) under N$_2$. After 3.5 hrs the solvent was evaporated and the residue purified by supercritical fluid chromatography (SFC; Princeton 2-ethyl-pyridine, 20×150 mm, 20-30% MeOH/CO$_2$), yielding the title compound as a colorless oil (138 mg, 0.256 mmol, 50%): LCMS method B Rt=1.21 min, M+H 540.5; $^1$H NMR (600 MHz, ACETONITRILE-d3) δ ppm 0.91 (t, J=7.20 Hz, 3 H) 1.22-1.42 (m, 34 H) 1.57 (quin, J=7.34 Hz, 2 H) 1.93-1.96 (m, 2 H) 2.28 (t, J=7.47 Hz, 2 H) 2.79 (br. d, J=6.30 Hz, 4 H).

Intermediate 6 and 6A 2-(Azido-PEG23-carbamoyl)-2-undecyltridecane-dioic acid construct (6) and 12-(Azido-PEG23-cabamoyl)tricosanoic acid construct (6A)

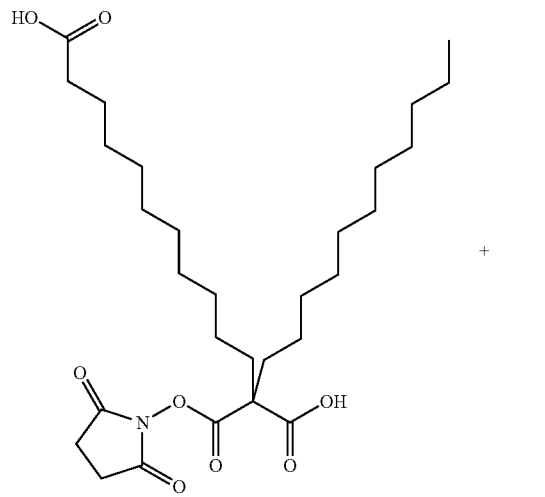

+

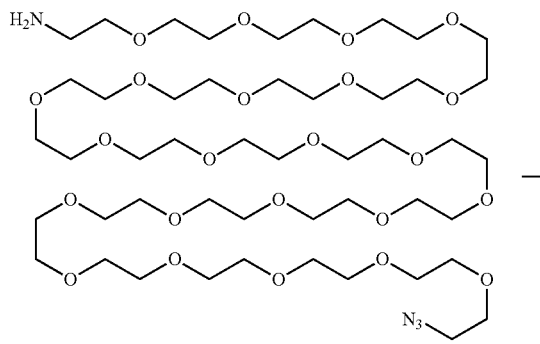

→

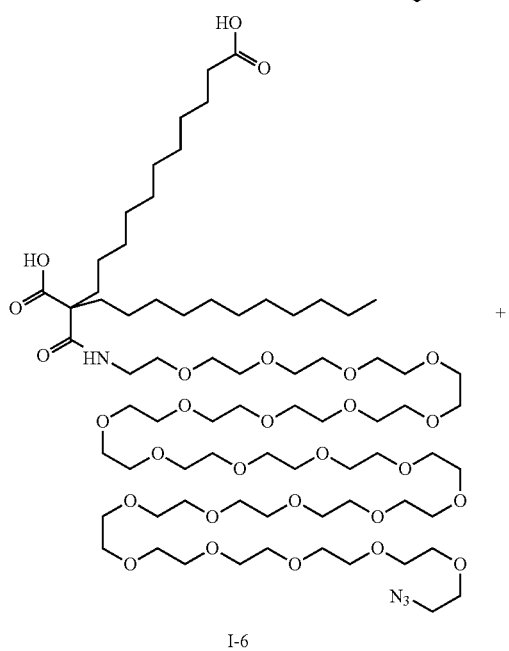

I-6

+

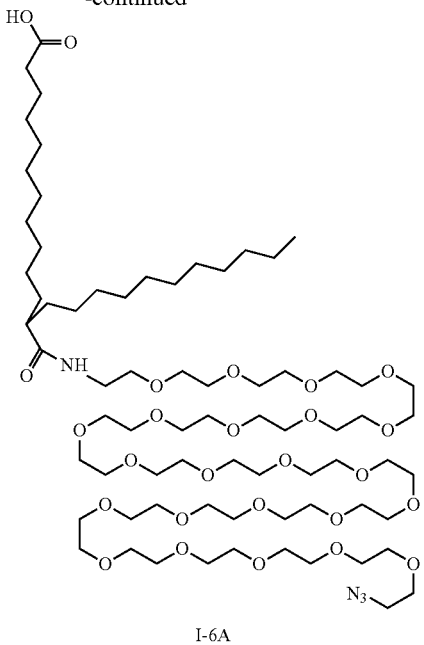

I-6A

Intermediate 5 (36 mg, 0.066 mmol) and azido-dPEG23-NH$_2$ (Quanta Biodesign: 73 mg, 0.066 mmol) were combined in THF (1.5 mL) and mixed on a shaker plate for 15 min before addition of DIPEA (17 μL, 0.10 mmol). The reaction was left on the shaker plate overnight. The solvent was evaporated and the residue purified by HPLC (Sunfire C18 30×50 mm, 55-80% ACN/water+0.1% TFA) to yield Intermediate 6 (39 mg, 0.025 mmol, 38%) and intermediate 6a (20 mg, 0.013 mmol, 20%): LCMS Method B Rt=1.11 min, [M+2H]$^{+2}$ 763.4; $^1$H NMR (400 MHz, CHLOROFORM-d) δ ppm 0.86-0.93 (m, 3 H) 1.10-1.19 (m, 2 H) 1.20-1.29 (m, 23 H) 1.32 (br. s., 7 H) 1.58-1.69 (m, 2 H) 1.69-1.79 (m, 2 H) 1.96-2.10 (m, 2 H) 2.35 (t, J=7.15 Hz, 2 H) 3.41 (t, J=5.07 Hz, 2 H) 3.51-3.57 (m, 2 H) 3.58-3.62 (m, 2 H) 3.62-3.73 (m, 90 H) 7.46 (br. s., 1 H); LCMS Method B Rt=1.23 min, [M+2]$^{+2}$ 740.9; $^1$H NMR (400 MHz, CHLOROFORM-d) δ ppm 0.83-0.96 (m, 3 H) 1.27 (br. s., 25 H) 1.29-1.37 (m, 7 H) 1.37-1.46 (m, 2 H) 1.53-1.73 (m, 4 H) 2.34 (t, J=7.21 Hz, 2 H) 3.41 (t, J=5.07 Hz, 2 H) 3.44-3.52 (m, 2 H) 3.55-3.60 (m, 2 H) 3.60-3.74 (m, 90 H) 6.19-6.30 (m, 1 H).

Alternatively construct 6 A is obtained according to the following procedure: A solution of intermediate 5 (48 mg, 0.042 mmol) in THF (1 mL) was added to a vial charged with azido-PEG23-amine (Quanta Biodesign cat #10525) (46 mg, 0.042 mmol). The reaction was agitated for 20 min before the addition of DIPEA (11 μL, 0.063 mmol) and then maintained overnight. Azido-PEG23-amine (23 mg, 0.021 mmol) and DIPEA (5 μL, 0.029 mmol) were added and the reaction agitated another day. The solvent was evaporated and the residue purified by HPLC (Xbridge C18 30×50 mm, 10-30% ACN/5 mM NH4OH). Lyophilization of the fractions resulted in a mixture of products. The material was purified by HPLC (Sunfire C18 30×50 mm, 45-70% ACN/water+0.1% TFA) to yield the title intermediate 6A (30 mg, 0.020 mmol, 48%): LCMS method B Rt=0.81 min, [M+H+H$_3$O]$^{+2}$ 764.5; $^1$H NMR (400 MHz, ACETONITRILE-d3) δ ppm 1.30 (br. s., 28 H) 1.40-1.50 (m, 2 H) 1.50-1.62 (m, 6 H) 2.14 (t, J=7.52 Hz, 2 H) 2.23-2.35 (m, 3 H) 3.32 (q, J=5.58 Hz, 2 H) 3.37-3.43 (m, 2 H) 3.47-3.52 (m, 2 H) 3.53-3.68 (m, 90 H) 6.54 (br. s., 1 H).

Intermediate 7

(((11-Bromoundecyl)oxy)methanetriyl)tribenzene

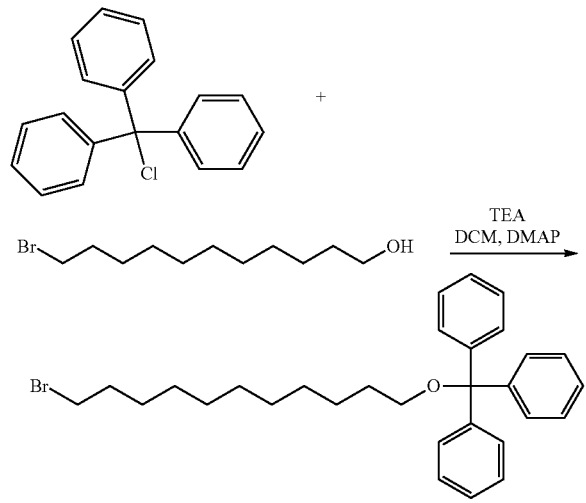

Trityl chloride (2.49 g, 8.92 mmol), 11-bromoundecan-1-ol (2.00 g, 7.96 mmol), and DMAP (10 mg, 0.080 mmol) were dissolved in DCM (16 mL) under $N_2$. With stirring DIPEA (1.39 mL, 7.96 mmol) was added and the reaction was maintained for 7 days. The reaction was partitioned between DCM (20 mL) and water (10 mL). The organic phase was extracted with water (20 mL), dried over $MgSO_4$, and concentrated. The concentrate was purified by flash column (silica 120 g, 0-6% EtOAc/HEP) to yield Intermediate 7 (2.50 g, 5.07 mmol, 64%) as a colorless oil: 1H NMR (400 MHz, CHLOROFORM-d) δ ppm 1.19-1.49 (m, 14 H) 1.58-1.69 (m, 2 H) 1.79 (dt, J=14.50, 7.00 Hz, 1 H) 1.87 (dt, J=14.55, 7.03 Hz, 1 H) 3.07 (t, J=6.66 Hz, 2 H) 3.43 (t, J=6.85 Hz, 1 H) 3.55 (t, J=6.79 Hz, 1 H) 7.18-7.36 (m, 10 H) 7.42-7.52 (m, 5 H).

Intermediate 8

Dibenzyl 2-(11-(trityloxy)undecyl)malonate

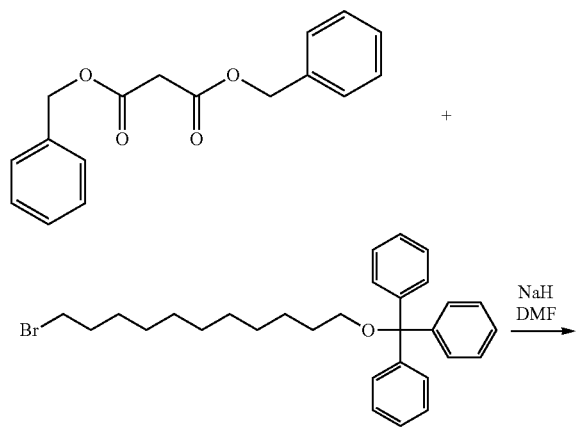

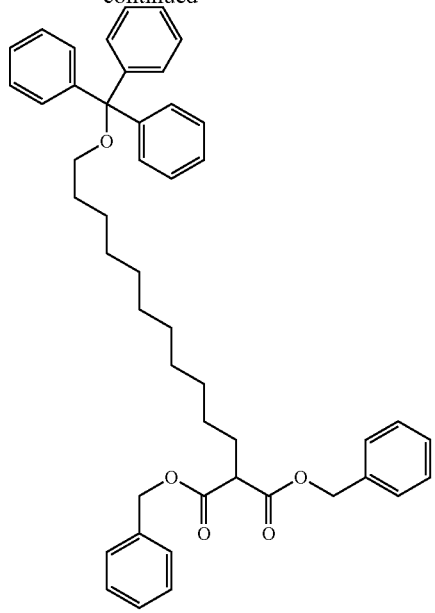

NaH (113 mg, 2.83 mmol) was suspended in DMF (6 mL) at 0° C. under N2. Dibenzyl malonate was slowly added to the stirred suspension. After 30 min a solution of Intermediate 7 (1.26 g, 2.54 mmol) in DMF (3 mL) was added. After 15 min of stirring, the resulting mixture was allowed to warm to room temperature. After 3 days the reaction was diluted with $Et_2O$ (75 mL) and extracted with water (40 mL). The aqueous phase was extracted with $Et_2O$ (75 mL). The combined organics were dried over $Na_2SO_4$ and concentrated. The concentrate was purified by flash column (silica 80 g, 0-10% EtOAc/HEP) to yield the title compound as a colorless oil (815 mg, 1.17 mmol, 41%): HPLC Method B Rt=1.68 min; $^1$H NMR (400 MHz, CHLOROFORM-d) δ ppm 1.16-1.40 (m, 16 H) 1.58-1.69 (m, 2 H) 1.94 (q, J=7.38 Hz, 2 H) 3.06 (t, J=6.66 Hz, 2 H) 3.45 (t, J=7.52 Hz, 1 H) 5.16 (s, 4 H) 7.21-7.28 (m, 3 H) 7.28-7.39 (m, 16 H) 7.42-7.51 (m, 6 H).

Intermediate 9

Tribenzyl 22-(trityloxy)docosane-1,11,11-tricarboxylate

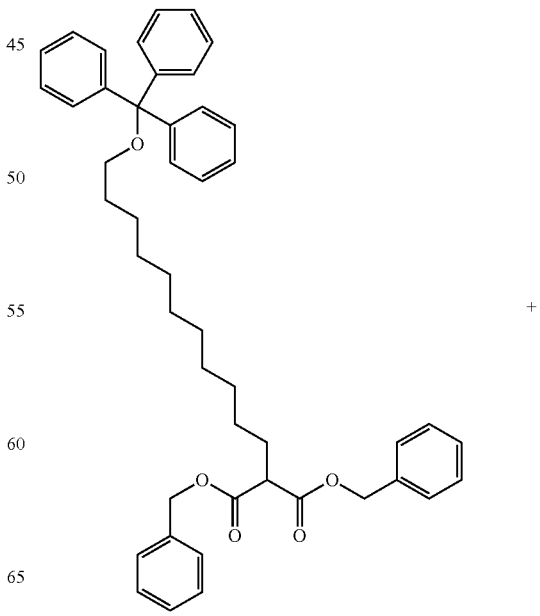

98

Intermediate 10

22-(Trityloxy)docosane-1,11,11-tricarboxylic acid

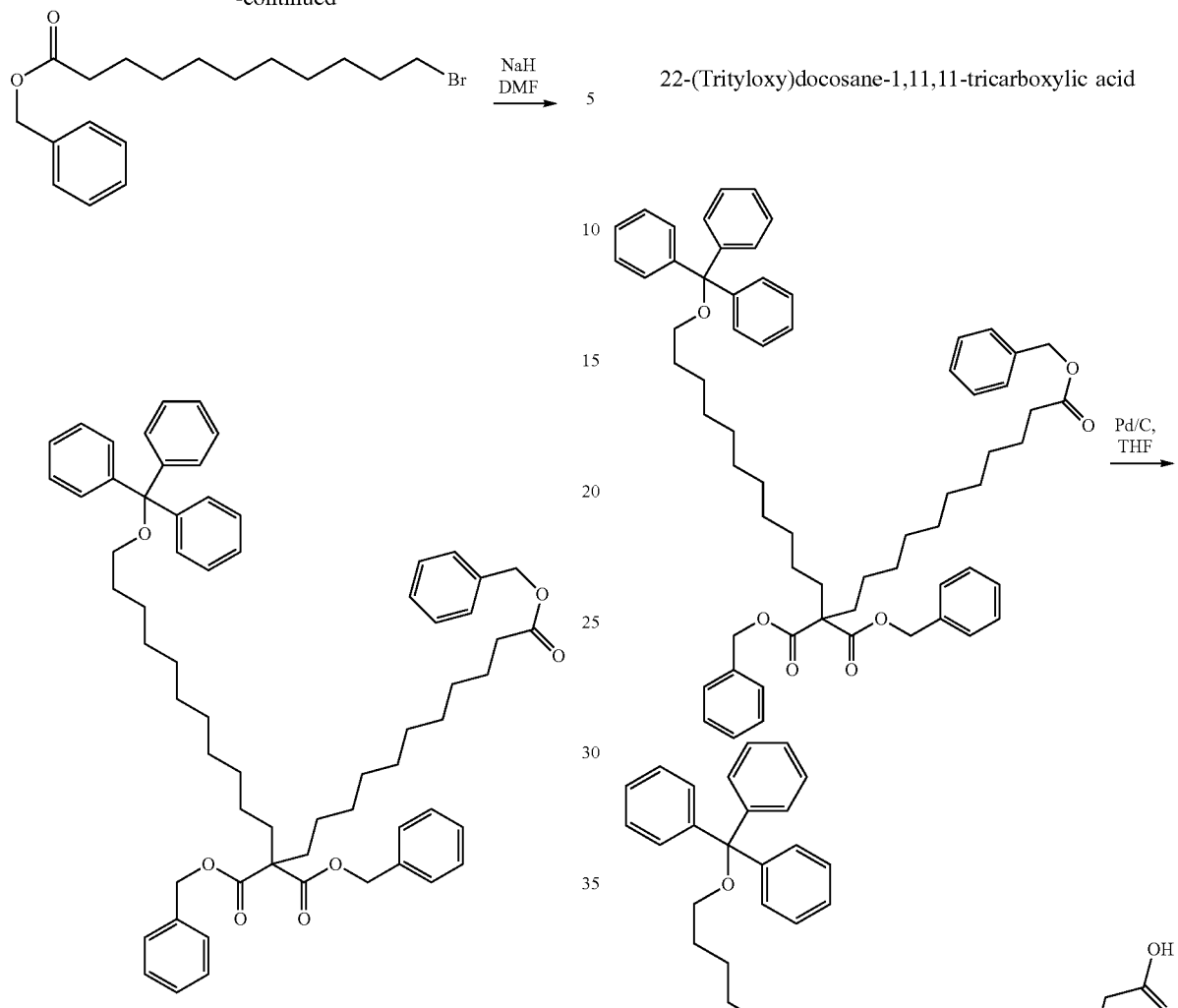

A solution of intermediate 8 (815 mg, 1.17 mmol) in DMF (2 mL) was added to a suspension of NaH (56 mg, 1.40 mmol) in DMF (2 mL) under $N_2$ at 0° C. The mixture was stirred for 1 hr. Benzyl 11-bromoundecanoate (457 mg, 1.29 mmol) in DMF (2 mL) was added to the reaction. The reaction was allowed to warm to room temperature 20 min after the addition and stirred overnight. The reaction was diluted with $Et_2O$ (75 mL) and extracted with water (25 mL). The aqueous phase was extracted with $Et_2O$ (75 mL) and the organics combined. The combined organics were dried over $Na_2SO_4$ and evaporated. The residue was purified by flash column (silica 40 g, 0-10% EtOAc/HEP) to yield the title compound as a colorless oil (780 mg, 0.803 mmol, 69%): $^1$H NMR (400 MHz, CHLOROFORM-d) δ ppm 0.99-1.14 (m, 4 H) 1.15-1.41 (m, 26 H) 1.58-1.71 (m, 4 H) 1.82-1.96 (m, 4 H) 2.37 (t, J=7.52 Hz, 2 H) 3.06 (t, J=6.66 Hz, 2 H) 5.12 (s, 4 H) 5.14 (s, 2 H) 7.28 (s, 24 H) 7.42-7.52 (m, 6 H).

A suspension of 10% Pd on carbon (11 mg, 0.010 mmol) in THF (2.5 mL) was added to a solution of intermediate 9 (200 mg, 0.206 mmol) in THF (2.5 mL). The stirred suspension was placed under hydrogen via balloon. After 2.25 hrs the reaction was passed through a membrane filter and the solids rinsed with EtOAc. The filtrate was evaporated to yield intermediate 10 (150 mg, quantitative): $^1$H NMR (400 MHz, CHLOROFORM-d) δ ppm 1.04-1.33 (m, 30 H) 1.45-1.62 (m, 4 H) 1.76-1.91 (m, 4 H) 2.21-2.36 (m, 2 H) 2.97 (t, J=6.60 Hz, 2 H) 7.06-7.18 (m, 4 H) 7.19-7.24 (m, 5 H) 7.33-7.50 (m, 6 H).

Intermediate 11: 2-(((2,5-Dioxopyrrolidin-1-yl)oxy)carbonyl)-2-(11-(trityloxy)undecyl)tridecanedioic acid (11)

Intermediate 12

2-((Azido-PEG23)carbamoyl)-2-(11-hydroxyundecyl)tridecanedioic acid construct

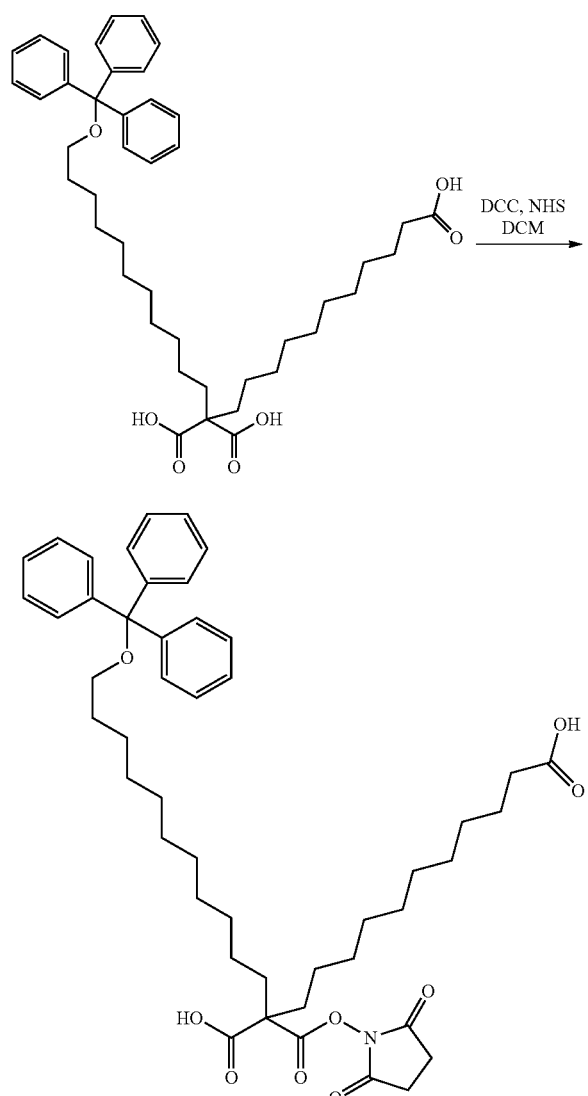 [SMILES: O=C(O)CCCCCCCCCCC(CCCCCCCCCCCOC(c1ccccc1)(c1ccccc1)c1ccccc1)(C(=O)O)C(=O)O ; O=C(O)CCCCCCCCCCC(CCCCCCCCCCCOC(c1ccccc1)(c1ccccc1)c1ccccc1)(C(=O)O)C(=O)ON1C(=O)CCC1=O]

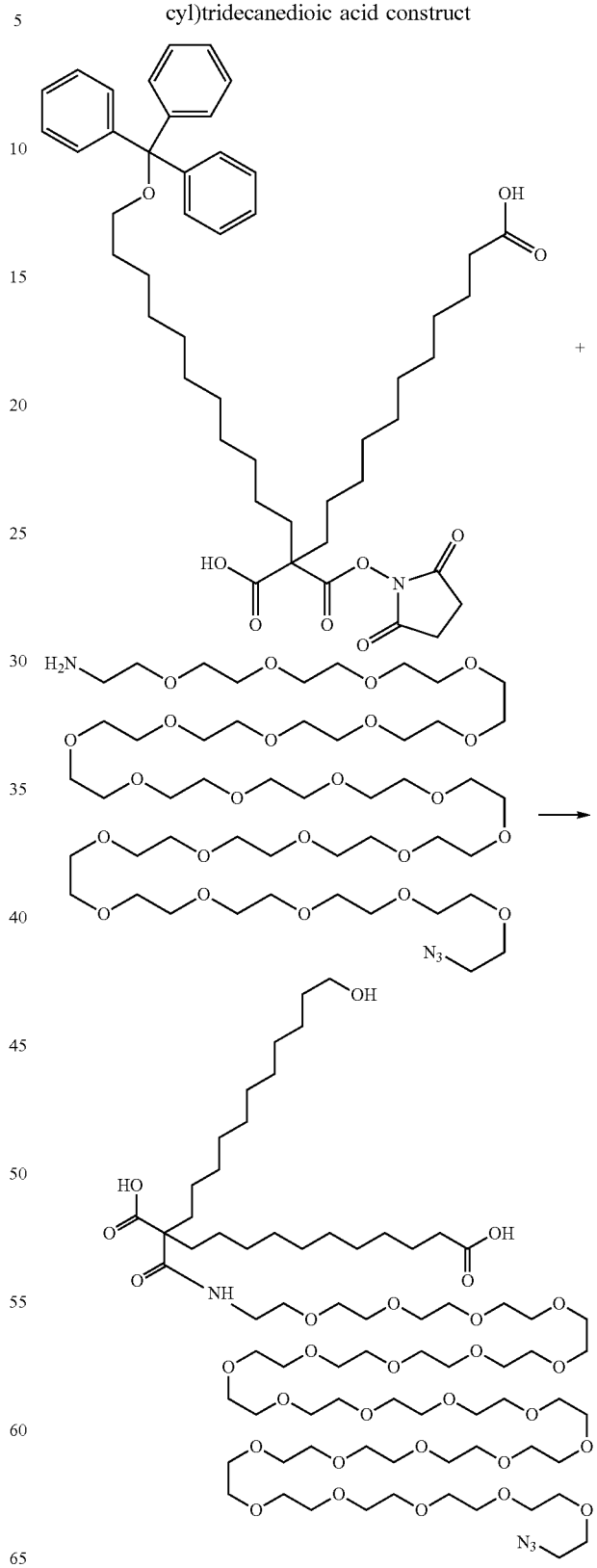

Intermediate 10 (150 mg, 0.214 mmol) and N-hydroxysuccinimide (25 mg, 0.214 mmol) were combined in DCM (4 mL). DCC (49 mg, 0.235 mmol) dissolved in DCM (0.61 mL) was added, and the reaction stirred at room temperature for 7 hrs. The solvent was evaporated and the residue purified by HPLC (Sunfire C18 30×50 mm; 65-95% ACN/water+0.1% TFA) followed by SFC (Princeton 2-ethylpyridine column 20×100 mm, 25-35% MeOH/CO2) to yield Intermediate 11 (34 mg, 0.043 mmol, 20%) as a colorless oil: LCMS Method B Rt=1.47 min, M-CO$_2$H 752.7; $^1$H NMR (400 MHz, CHLOROFORM-d) δ ppm 1.13-1.42 (m, 30 H) 1.56-1.73 (m, 4 H) 1.94-2.14 (m, 4 H) 2.37 (t, J=7.21 Hz, 2 H) 2.83 (br. s., 4 H) 3.06 (t, J=6.66 Hz, 2 H) 7.15-7.28 (m, 3 H) 7.29-7.36 (m, 6 H) 7.41-7.50 (m, 6 H).

Azido-dPEG23-amine (Quanta Biodesign) 42 mg, 0.038 mmol) in THF (1.5 mL) was combined with intermediate 11 (34 mg, 0.043 mmol) under $N_2$. The reaction was placed on a shaker plate and agitated for 20 min. DIPEA (7.44 µL, 0.043 mmol) was added and the reaction agitated for 2 hrs. DIPEA (4 µL, 0.023 mmol) was added and the reaction maintained overnight. The solvent was evaporated and the residue taken up in DCM (3 mL) and TFA (0.5 mL). The solution was agitated for 1 hr at which point the solvent was stripped. The residue was purified by HPLC (sunfire C18 30×50 mm, 45-70% ACN/water+0.1% TFA) to yield intermediate 12 (4 mg, 1.8 µmol, 4.2%): LCMS Method B Rt=0.75 min, $[M+2H]^{+2}$ 771.4; $^1$H NMR (400 MHz, CHLOROFORM-d) δ ppm 1.05-1.39 (m, 30 H) 1.52-1.82 (m, 6 H) 1.97-2.09 (m, 2 H) 2.35 (t, J=7.21 Hz, 2 H) 3.41 (t, J=5.07 Hz, 2 H) 3.51-3.63 (m, 6 H) 3.63-3.75 (m, 90 H) 4.36 (t, J=6.72 Hz, 1 H) 7.49-7.65 (m, 1 H).

Intermediate 13

13-(Benzyloxy)-12-((benzyloxy)carbonyl)-13-oxotridecanoic acid

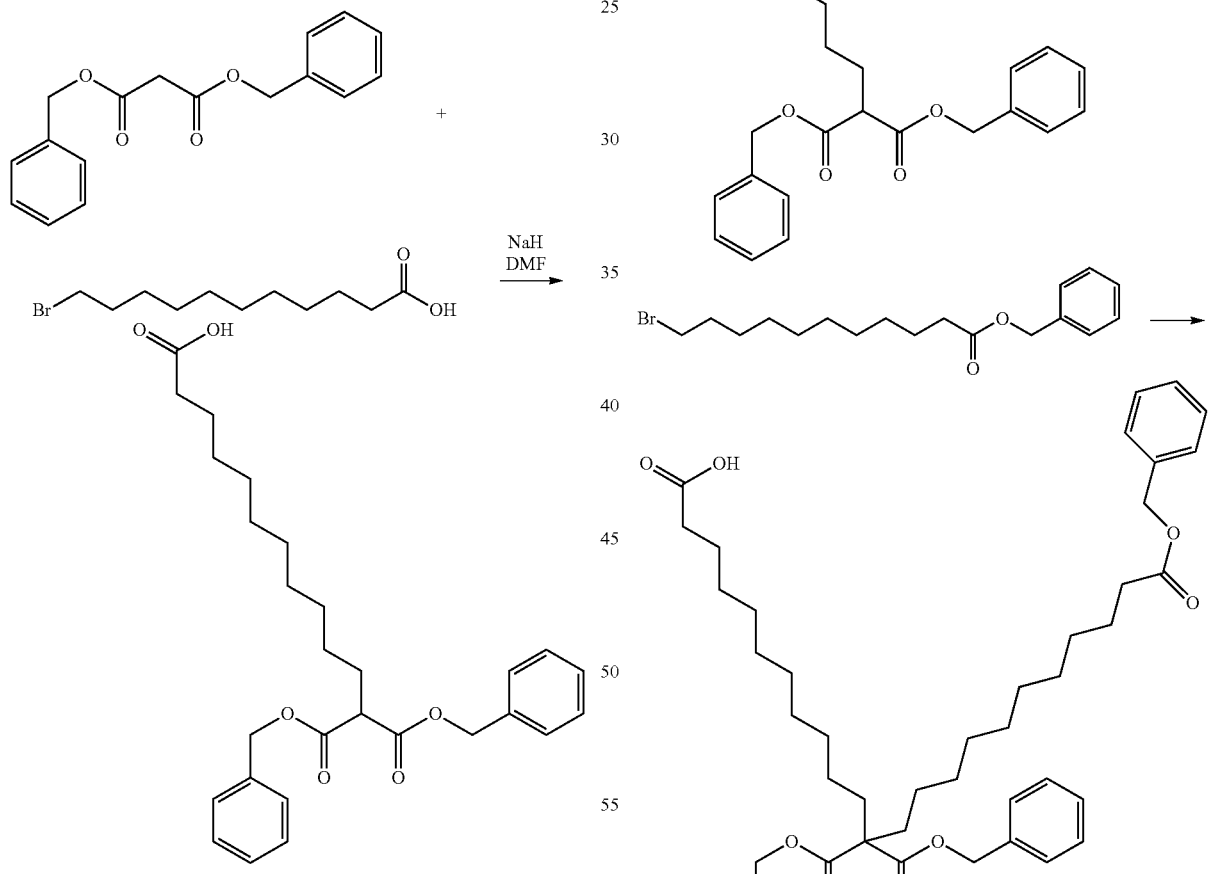

Dibenzyl malonate (0.88 mL, 3.52 mmol) in DMF (3 mL) was slowly added to a suspension of NaH (274 mg, 6.86 mmol) under $N_2$ at 0° C. The mixture was stirred for 1.5 hrs before being allowed to warm to room temperate. 11-bromoundecanoic acid (933 mg, 3.52 mmol) in DMF (3 mL) was added and the reaction allowed to go overnight. The reaction was heated to 80° C. for 3 hrs before being allowed to cool. The reaction was diluted with EtOAc (50 mL) and $Et_2O$ (50 mL) and extracted with 1M HCl (25 mL). The aqueous phase was extracted with $EtOAc/Et_2O$ (100 mL). The combined organics were dried over $Na_2SO_4$ and the solvent evaporated. The residue was purified by flash column (C18 50 g 30-100% ACN/water+0.1 TFA) to yield intermediate 13 (315 mg, 0.672 mmol, 19%) as white powder: LCMS Method B Rt=1.05 min, M+H 469.5.

Intermediate 14

23-(Benzyloxy)-12,12-bis((benzyloxy)carbonyl)-23-oxotricosanoic acid

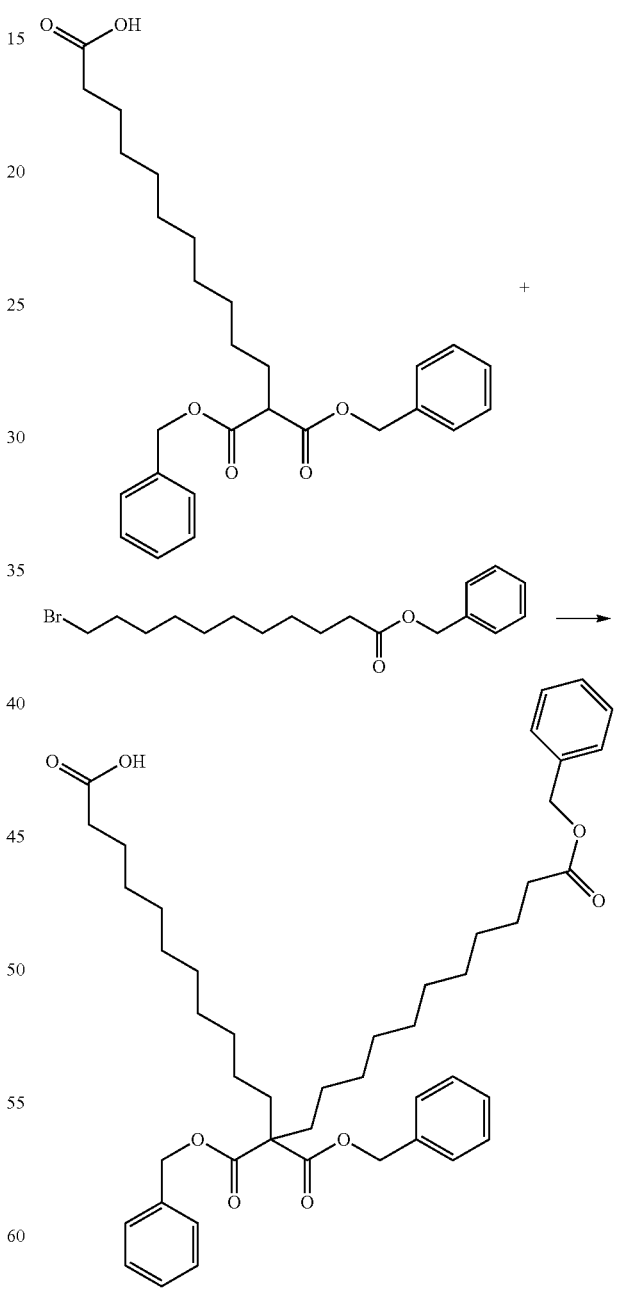

NaH (54 mg, 1.34 mmol) was suspended in DMF (1 mL) at 0° C. under $N_2$. To the mixture was added intermediate 13 (315 mg, 0.672 mmol) in DMF (3 mL) in a drop wise fashion. The reaction was stirred for 1 hr before intermediate 1 (239 mg, 0.672 mmol) in DMF (1 mL) was added. The reaction was maintained at 0° C. for an additional 45 min before being allowed to warm to room temperature. The reaction was stirred a overnight. The reaction was diluted with 1:1 Et₂O and EtOAc (75 mL) and extracted with 1M HCl (20 mL). The aqueous phase was extracted with 1:1 Et₂O and EtOAc (75 mL). The combined organics were dried over Na₂SO₄ and evaporated. Purification of the resulting residue by HPLC (Xbridge C18 30×50 mm, 45-70% ACN/water+5 mM NH4OH) yielded the title compound (132 mg, 0.178 mmol, 26%): LCMS method B; Rt=1.53 min, M−H 741.8.

Intermediate 15

1,11,11-Tribenzyl 21-(2,5-dioxopyrrolidin-1-yl) henicosane-1,11,11,21-tetracarboxylate DCC (44 mg, 0.213 mmol) in DCM (1 mL) was added to a solution of intermediate 14 (132 mg, 0.178 mmol) and of N-hydroxysuccinimide (20 mg, 0.178 mmol) in DCM (2.5 mL). The reaction was agitated on a shaker plate for 17 hrs. The reaction was filtered and the solids rinsed with DCM. The filtrate was concentrated and purified by flash column (silica 12 g, 0-40% EtOAc/HEP) to yield intermediate 15 (107 mg, 0.127 mmol, 72%): LCMS Method B Rt=1.53 min, M+Na 862.8.

Intermediate 16

22-((2,5-Dioxopyrrolidin-1-yl)oxy)-22-oxodo-cosane-1,11,11-tricarboxylic acid

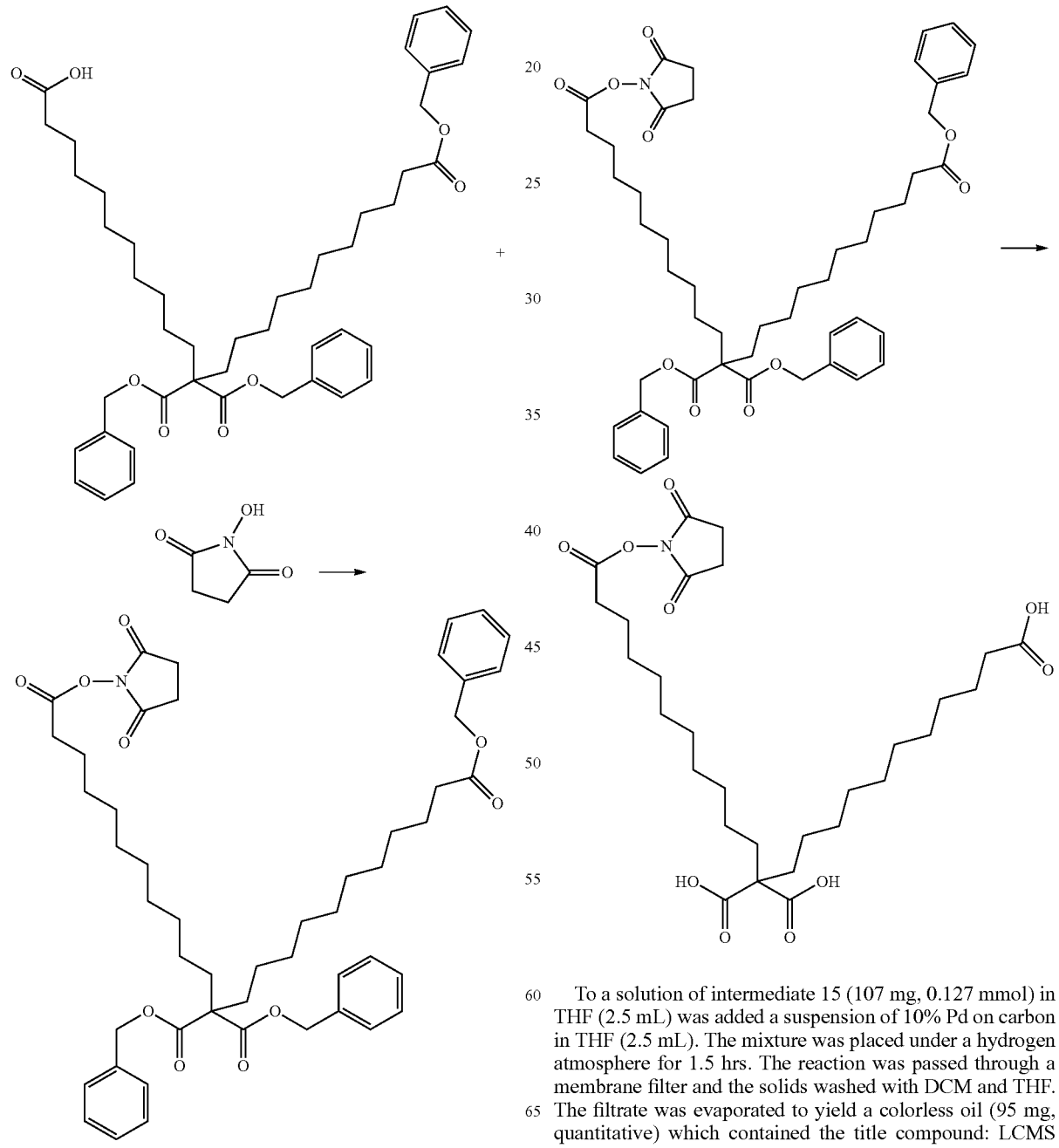

To a solution of intermediate 15 (107 mg, 0.127 mmol) in THF (2.5 mL) was added a suspension of 10% Pd on carbon in THF (2.5 mL). The mixture was placed under a hydrogen atmosphere for 1.5 hrs. The reaction was passed through a membrane filter and the solids washed with DCM and THF. The filtrate was evaporated to yield a colorless oil (95 mg, quantitative) which contained the title compound: LCMS Method B Rt=0.65 min, M+H 570.5.

Intermediate 17

2-(11-(azido-PEG23-amino)-11-oxoundecyl)tridecanedioic acid construct

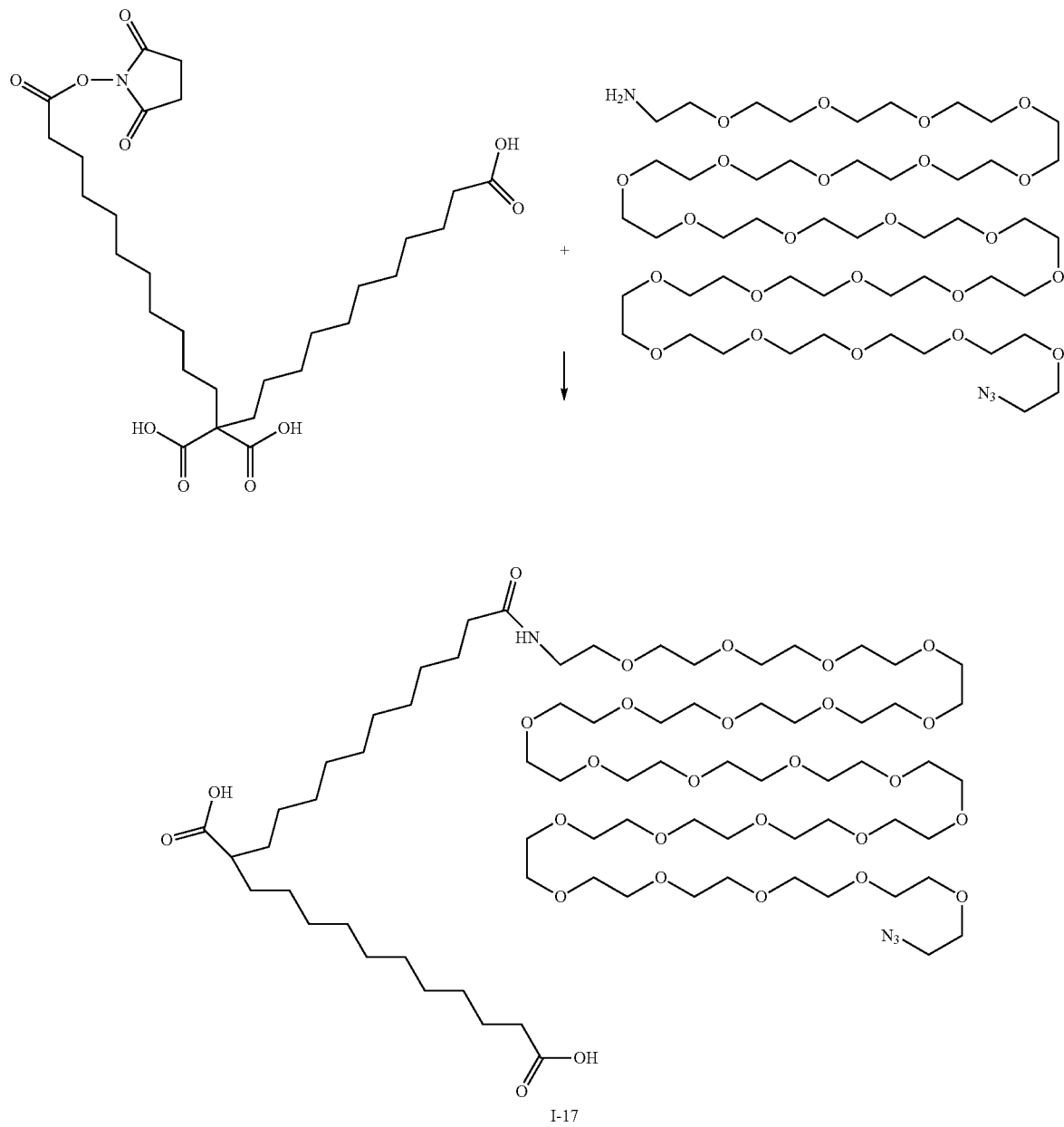

I-17

A solution of intermediate 16 (48 mg, 0.042 mmol) in THF (1 mL) was added to a vial charged with azido-dPEG23-amine (Quanta Biodesign: 46 mg, 0.042 mmol). The reaction was agitated for 20 min before the addition of DIPEA (11 µL, 0.063 mmol) and then maintained overnight. Azido-PEG23-amine (23 mg, 0.021 mmol) and DIPEA (5 µL, 0.029 mmol) were added and the reaction agitated another day. The solvent was evaporated and the residue purified by HPLC (Xbridge C18 30×50 mm, 10-30% ACN/5 mM NH4OH). Lyophilization of the fractions resulted in a mixture of products. The material was purified by HPLC (Sunfire C18 30×50 mm, 45-70% ACN/water+0.1% TFA) to yield the title intermediate 17 (30 mg, 0.020 mmol, 48%): LCMS SQ4 Rt=0.81 min, [M+H+H$_3$O]$^{+2}$ 764.5; $^1$H NMR (400 MHz, ACETONITRILE-d3) δ ppm 1.30 (br. s., 28 H) 1.40-1.50 (m, 2 H) 1.50-1.62 (m, 6 H) 2.14 (t, J=7.52 Hz, 2 H) 2.23-2.35 (m, 3 H) 3.32 (q, J=5.58 Hz, 2 H) 3.37-3.43 (m, 2 H) 3.47-3.52 (m, 2 H) 3.53-3.68 (m, 90 H) 6.54 (br. s., 1 H).

Intermediate 18

Tetrabenzyl henicosane-1,11,11,21-tetracarboxylate

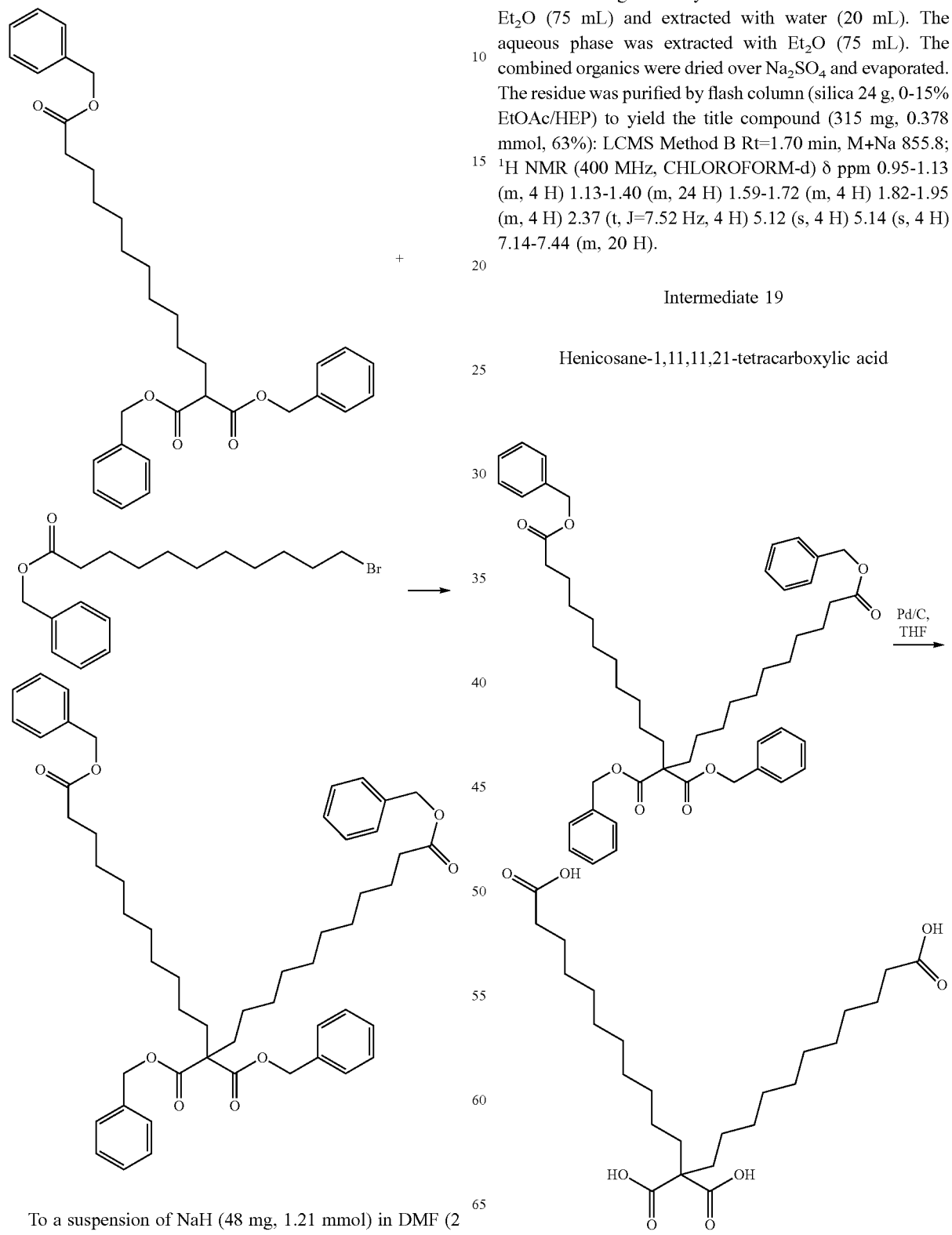

To a suspension of NaH (48 mg, 1.21 mmol) in DMF (2 mL) at 0° C. under $N_2$, was slowly added intermediate 2 (337 mg, 0.603 mmol) in DMF (2 mL). The mixture was stirred for 15 min before the addition of intermediate 1 (429 mg, 1.21 mmol) in DMF (2 mL). The reaction was stirred at 0° C. for 20 min before being allowed to warm to room temperature. The reaction was maintained at room temperature with stirring for 3 days. The reaction was diluted with $Et_2O$ (75 mL) and extracted with water (20 mL). The aqueous phase was extracted with $Et_2O$ (75 mL). The combined organics were dried over $Na_2SO_4$ and evaporated. The residue was purified by flash column (silica 24 g, 0-15% EtOAc/HEP) to yield the title compound (315 mg, 0.378 mmol, 63%): LCMS Method B Rt=1.70 min, M+Na 855.8; $^1$H NMR (400 MHz, CHLOROFORM-d) δ ppm 0.95-1.13 (m, 4 H) 1.13-1.40 (m, 24 H) 1.59-1.72 (m, 4 H) 1.82-1.95 (m, 4 H) 2.37 (t, J=7.52 Hz, 4 H) 5.12 (s, 4 H) 5.14 (s, 4 H) 7.14-7.44 (m, 20 H).

Intermediate 19

Henicosane-1,11,11,21-tetracarboxylic acid

A suspension of 10% Pd on carbon (20 mg, 0.019 mmol) in THF (4 mL) was added to a solution of intermediate 18 (315 mg, 0.378 mmol) in THF (6 mL), and the reaction was placed under a hydrogen atmosphere for 2 hr. A membrane filter was used to remove the solids which were washed with EtOAc. Evaporation of the filtrate yielded intermediate 19 (179 mg, quantitative) as a white solid: LCMS Method A Rt=1.24 min, M+H 473.4; $^1$H NMR (400 MHz, DMSO-d6) δ ppm 0.99-1.15 (m, 4 H) 1.24 (br. s., 24 H) 1.48 (quin, J=6.94 Hz, 4 H) 1.62-1.76 (m, 4 H) 2.18 (t, J=7.34 Hz, 4 H) 12.23 (br. s, 4 H).

Intermediate 20

11-(((2,5-Dioxopyrrolidin-1-yl)oxy)carbonyl)henicosane-1,11,21-tricarboxylic acid

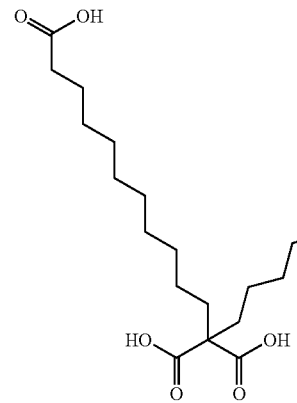

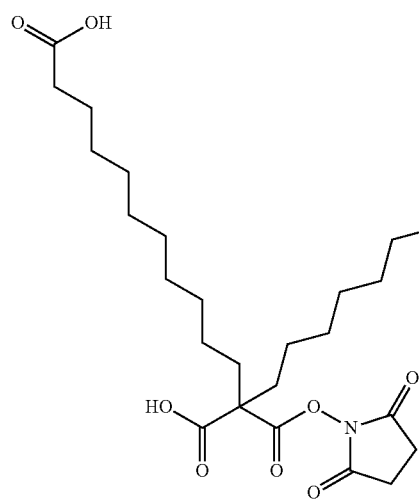

N-hydroxysuccinimide (20 mg, 0.170 mmol) and intermediate 19 (90 mg, 0.190 mmol) were dissolved in DCM (3 mL) and THF (0.3 mL). A solution of DCC (39 mg, 0.190 mmol) in DCM (0.5 mL) was added and the reaction agitated overnight. The solvent was evaporated and the residue purified by HPLC (Sunfire C18 30×50 mm; 35-60% ACN/water+0.1% TFA) to yield the title compound as a white powder (21 mg, 0.037 mmol, 19%): LCMS (Method C Rt=1.01 min, M+H 570.3.

Intermediate 21 and 21a 11-((Azido-PEG23)carbamoyl) henicosane-1,11,21-tricarboxylic acid (21) and 12-((Azido-PEG23)carbamoyl) tricosanedioic acid (21a)

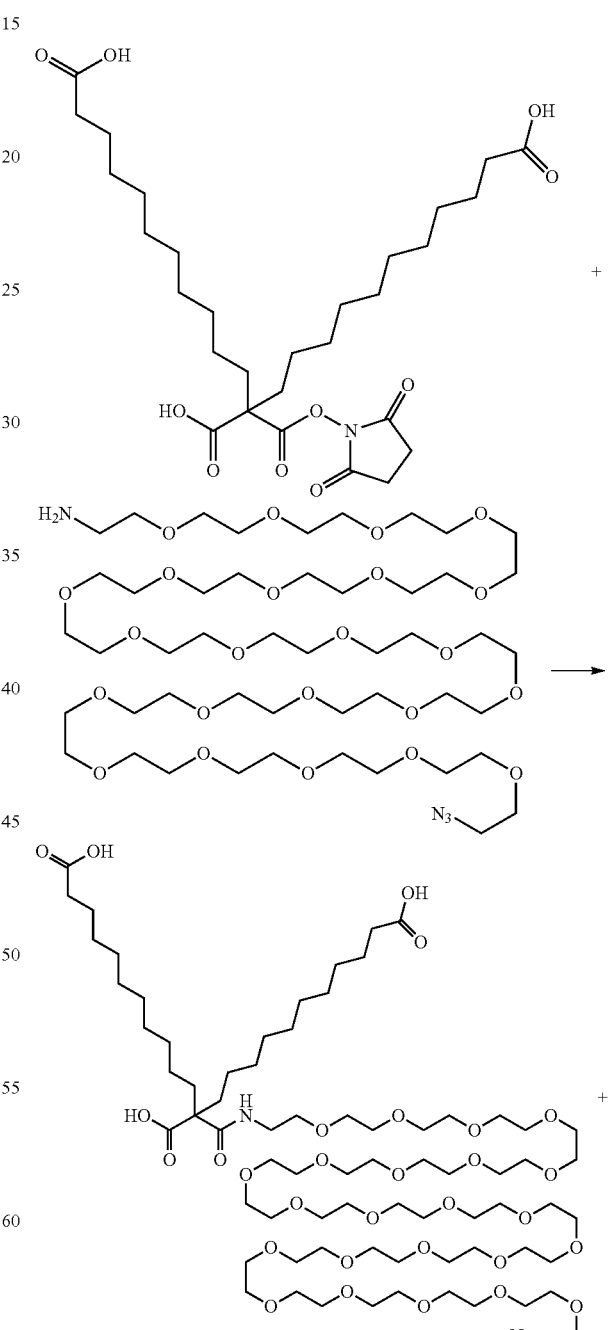

I-21

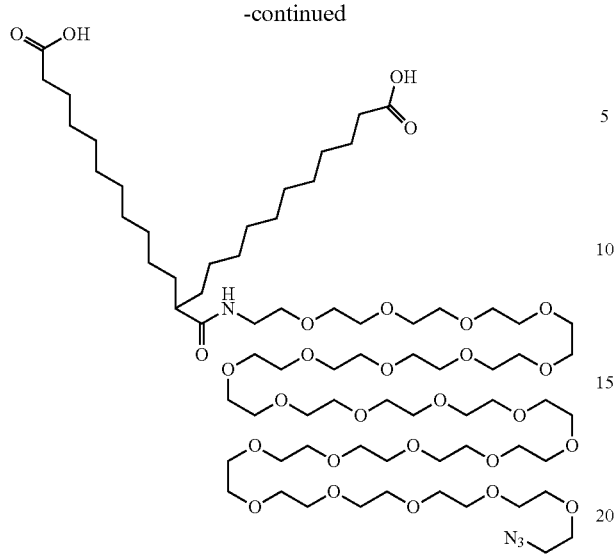

I-21A

Azido-PEG23-amine (41 mg, 0.037 mmol) and intermediate 20 (21 mg, 0.037 mmol) were combined in THF (1 mL) and agitated for 10 min. DIPEA (9.66 µL, 0.055 mmol) was added, and the reaction was agitated overnight. The solvent was evaporated, and the residue purified by HPLC (Sunfire C18 30×50 mm, 35-60% ACN/water+0.1% TFA) to yield intermediate 21 (22 mg, 0.014 mmol, 38%) and 21a (4 mg, 2.6 µmol, 7%): LCMS Method B Rt=0.69 min, M+H 1555.3; $^1$H NMR (400 MHz, CHLOROFORM-d) δ ppm 1.27 (br. s., 19 H) 1.29-1.41 (m, 9 H) 1.65 (quin, J=7.12 Hz, 4 H) 1.78 (td, J=12.13, 4.22 Hz, 2 H) 1.95-2.08 (m, 2 H) 2.35 (t, J=7.21 Hz, 4 H) 3.41 (t, J=5.07 Hz, 2 H) 3.54 (q, J=5.05 Hz, 2 H) 3.58-3.77 (m, 92 H) 7.60 (t, J=4.95 Hz, 1 H); LCMS Method B Rt=0.78 min, M−H 1509.3; $^1$H NMR (400 MHz, CHLOROFORM-d) δ ppm 1.18 (br. s., 19 H) 1.21-1.38 (m, 11 H) 1.43-1.63 (m, 6 H) 1.91-2.04 (m, 1 H) 2.26 (t, J=7.15 Hz, 4 H) 3.31 (t, J=5.07 Hz, 2 H) 3.40 (q, J=5.14 Hz, 2 H) 3.46-3.50 (m, 2 H) 3.51-3.69 (m, 90 H) 6.23 (t, J=5.01 Hz, 1 H).

Intermediate 22

Dibenzyl 2-undecylmalonate

Dibenzyl malonate (0.88 mL, 3.52 mmol) in DMF (1.5 mL) was added drop wise to a suspension of NaH (155 mg, 3.87 mmol) in DMF (6 mL) under N2 at 0° C. The mixture was stirred for 30 min before the addition of 1-bromoundecane (0.785 mL, 3.52 mmol) in DMF (1.5 mL) to the reaction. The reaction was allowed to warm to room temperature and stirred for 5 days. The reaction was diluted with Et$_2$O (75 mL) and extracted with water (20 mL). The aqueous phase was extracted with Et$_2$O (75 mL). The combined organics were dried over Na$_2$SO$_4$ and evaporated. The residue was purified by flash column (silica 80 g, 0-10% EtOAc/HEP) to yield the title compound (974 mg, 2.22 mmol, 63%) as a colorless oil: LCMS Method B Rt=1.55 min, M+H 439.5.

Intermediate 23

2-(((2,5-Dioxopyrrolidin-1-yl)oxy)carbonyl)-2-undecyltridecanoic acid

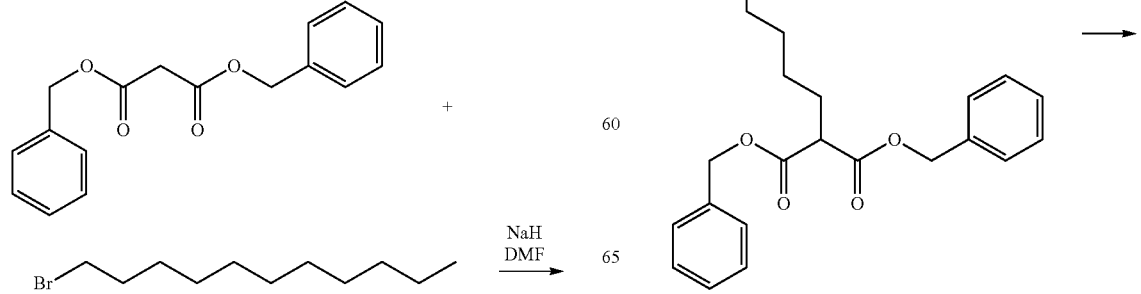

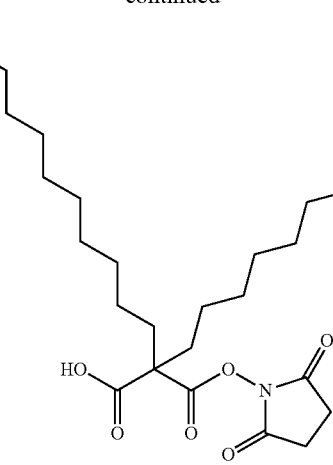

Dibenzyl 2-undecylmalonate (Intermediate 22: 400 mg, 0.912 mmol) in DMF (1 mL) was added drop wise to a suspension of NaH (44 mg, 1.09 mmol) in DMF (2 mL) under N2 at 0° C. The mixture was stirred for 45 min before the addition of 1-bromoundecane (0.285 mL, 1.28 mmol) in DMF (1 mL) to the reaction. The reaction was allowed to warm to room temperature and stirred for 1 day. The reaction was diluted with Et$_2$O (75 mL) and extracted with water (20 mL). The aqueous phase was extracted with Et$_2$O (75 mL). The combined organics were dried over Na$_2$SO$_4$ and evaporated. The residue was purified by flash column (silica 40 g, 0-5% EtOAc/HEP) to yield a colorless oil (412 mg). The oil was dissolved in THF/MeOH and passed through a Thales Nano H-Cube (1 mL/min, 2 bar H2, 22C) with a 10% Pd/C cartridge. The effluent was collected and evaporated to yield a waxy solid (272 mg). The waxy solid was dissolved in 3:1 DCM/THF and concentrated to an oil. The oil was redissolved in DCM (6 mL) under N$_2$, and N-hydroxysuccinimide (68 mg), followed by DCC (136 mg) in DCM (3 mL), was added. The reaction was stirred for day. The reaction was filtered and the filtrate concentrated. The concentrate was purified by flash column (C18 12 g, 25-100% ACN/water+0.1% formic acid). The resulting material was purified further by supercritical fluid chromatography (Princeton 2-ethylpyridine 20×150 mm; 5-15% MeOH/CO2) to yield intermediate 23 (37 mg, 0.073 mmol, 8%): LCMS Method B Rt=1.67 min, M+NH$_4$ 527.6; $^1$H NMR (400 MHz, CHLOROFORM-d) δ ppm 0.80-0.94 (m, 6 H) 1.18-1.42 (m, 36 H) 1.97-2.14 (m, 4 H) 2.87 (br. s., 4 H).

Intermediate 24

2-((azido-PEG23)carbamoyl)-2-undecyltridecanoic acid

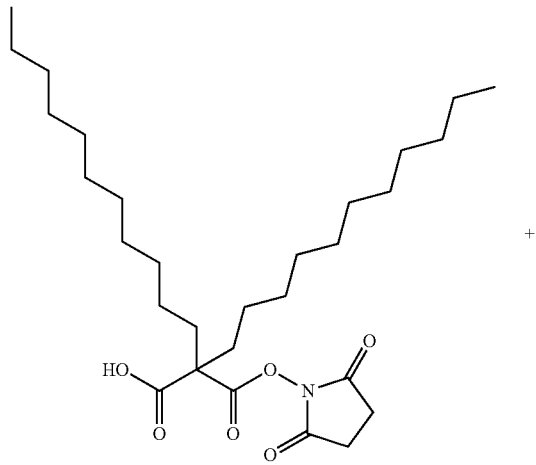

+

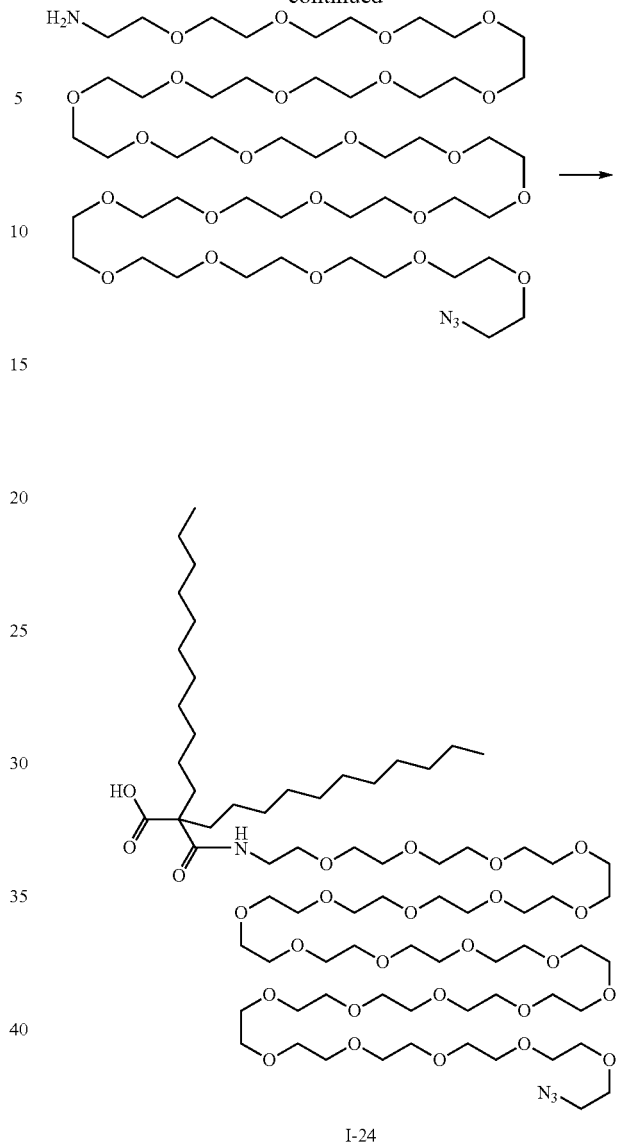

I-24

A solution of intermediate 23 (37 mg, 0.073 mmol) in THF (1 mL) was added to a vial charged with azido-dPEG23-amine (Quanta Biodesign: 80 mg, 0.073 mmol). The solution was agitated on a shaker plate and DIPEA (11 mL, 0.065 mmol) added. The reaction was agitated overnight before an additional portion of DIPEA (12 µL, 0.071 mmol) was added, and the reaction allowed to go overnight. The solvent was evaporated and the residue purified by supercritical fluid chromatography (Princeton Amino 21×150 mm; 20-30% MeOH/CO2) to yield the title compound (45 mg, 0.030 mmol, 41%): LCMS Method B Rt=1.50 min, [M+2H]$^{+2}$ 748.1; $^1$H NMR (400 MHz, CHLOROFORM-d) σ ppm 0.90 (t, J=6.85 Hz, 6 H) 1.09-1.38 (m, 30 H) 1.58 (br. s., 12 H) 1.64-1.76 (m, 2 H) 1.98-2.16 (m, 2 H) 3.41 (t, J=5.14 Hz, 2 H) 3.46-3.64 (m, 5 H) 3.64-3.91 (m, 83 H).

Intermediate 25

Di-tert-butyl 2-undecylmalonate

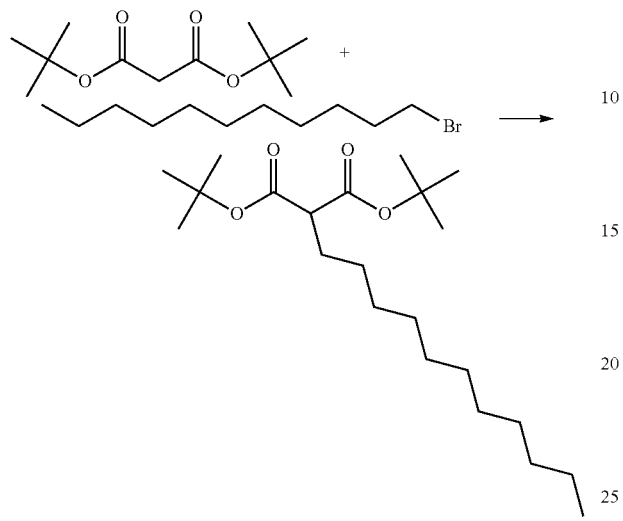

Di-tert-butyl malonate (1.0 g, 4.62 mmol) in DMF (2 mL) was added to a suspension of NaH (213 mg, 5.32 mmol) in DMF (5 mL) under $N_2$ at 0° C. The reaction was stirred for 30 min before the addition of 1-bromoundecane in DMF (2 mL). Upon addition the reaction was allowed to warm to room temperature and stirred for 2 days. The reaction was diluted with $Et_2O$ (75 mL) and extracted with water (25 mL). The aqueous phase was extracted with $Et_2O$ (75 mL). The combined organics were dried over $Na_2SO_4$ and the solvent evaporated. The concentrate was purified by flash column (silica 120 g, 0-40% $Et_2O$/ petroleum ether) to yield intermediate 25 (0.998 g, 2.69 mmol, 58%): LCMS Method B Rt=1.64 min, M+Na 393.5; $^1$H NMR (400 MHz, CHLOROFORM-d) δ ppm 0.85-0.94 (m, 3 H) 1.24-1.36 (m, 18 H) 1.41-1.52 (m, 18 H) 1.74-1.86 (m, 2 H) 3.13 (t, J=7.58 Hz, 1 H).

Intermediate 26

1-Benzyl 11,11-di-tert-butyl docosane-1,11,11-tricarboxylate

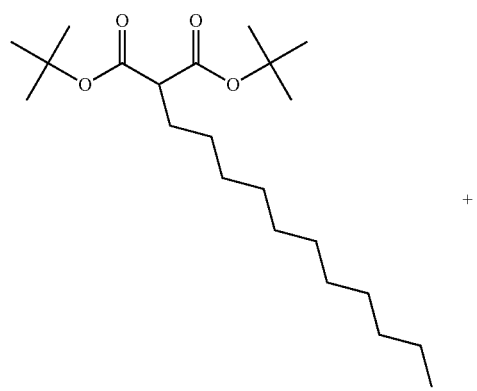

+

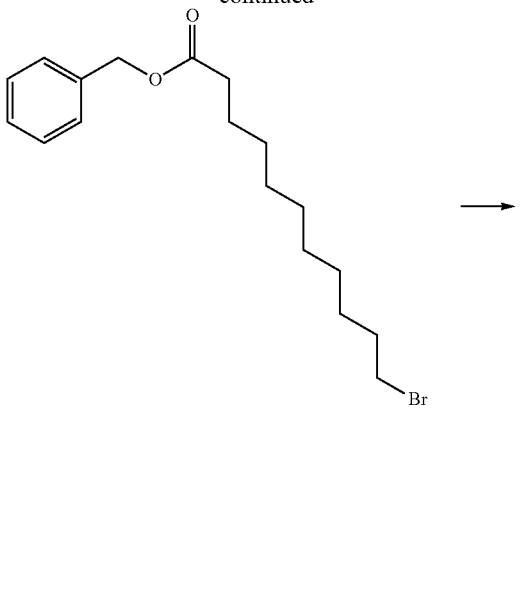

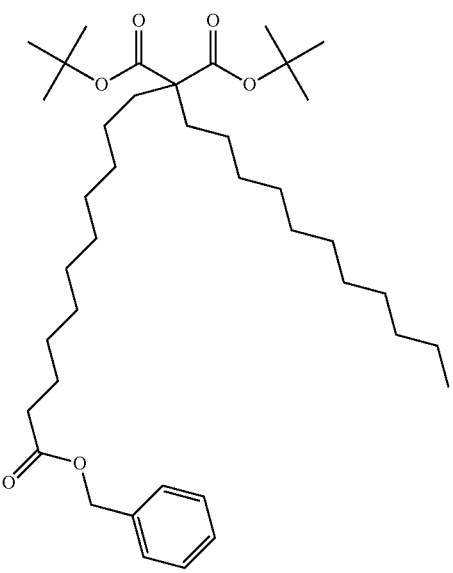

The title compound was synthesized in a similar fashion as intermediate 9 using intermediate 25 as a starting material to yield a colorless oil (980 mg, 1.52 mmol, 66%): $^1$H NMR (400 MHz, CHLOROFORM-d) δ ppm 0.89 (t, J=6.91 Hz, 3 H) 1.06-1.20 (m, 4 H) 1.20-1.35 (m, 28 H) 1.45 (s, 18 H) 1.58-1.70 (m, 2 H) 1.72-1.83 (m, 4 H) 2.36 (t, J=7.52 Hz, 2 H) 5.12 (s, 2 H) 7.30-7.45 (m, 5 H).

117

Intermediate 27

12,12-Bis(tert-butoxycarbonyl)tricosanoic acid

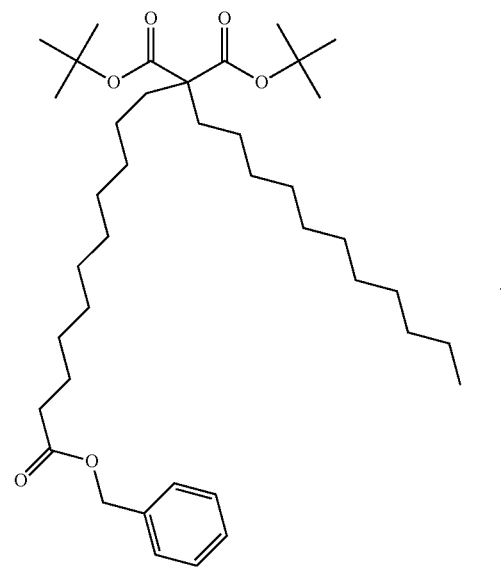

Using intermediate 26, the title compound (472 mg, 0.851 mmol, 100%) was synthesized in a similar fashion as intermediate 19: LCMS Method B Rt=1.76 min, M–H 553.6; $^1$H NMR (400 MHz, CHLOROFORM-d) δ ppm 0.84-0.95 (m, 3 H) 1.07-1.21 (m, 4 H) 1.21-1.40 (m, 28 H) 1.46 (s, 18 H) 1.58-1.70 (m, 2 H) 1.72-1.84 (m, 4 H) 2.37 (t, J=7.46 Hz, 2 H).

118

Intermediate 28

11,11-Di-tert-butyl 1-(2,5-dioxopyrrolidin-1-yl) docosane-1,11,11-tricarboxylate

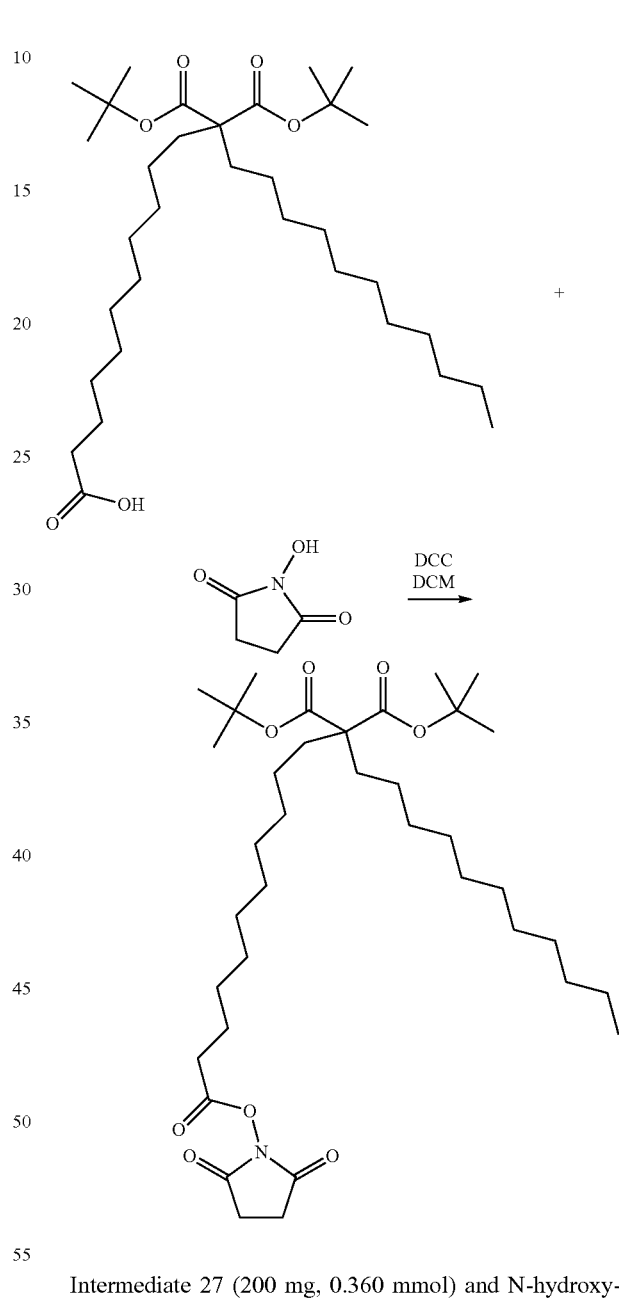

Intermediate 27 (200 mg, 0.360 mmol) and N-hydroxysuccinimide (42 mg, 0.360 mmol) were dissolved in DCM (3 mL). A solution of DCC (89 mg, 0.433 mmol) in DCM (1.6 mL) was added and the reaction stirred for 4.5 hrs. The reaction was filtered and the filtrate concentrated. The concentrate was purified by flash column (silica 24 g, 0-40% EtOAc/HEP) to yield the title compound as a colorless oil (70 mg, 0.107 mmol, 30%): LCMS Method B Rt=1.74 min, M+Na 674.7.

Intermediates 29 and 29A
2-(11-((azido-PEG23)-amino)-11-oxoundecyl)-2-undecylmalonic acid (29) and 13-((azido-PEG23)-amino)-13-oxo-2-undecyltridecanoic acid (29A)
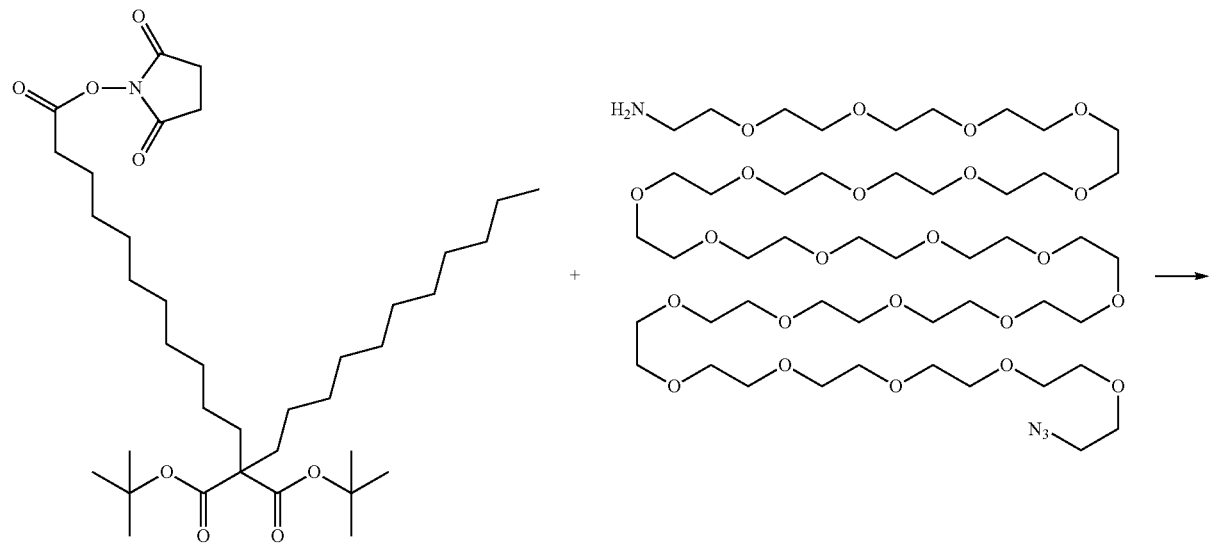
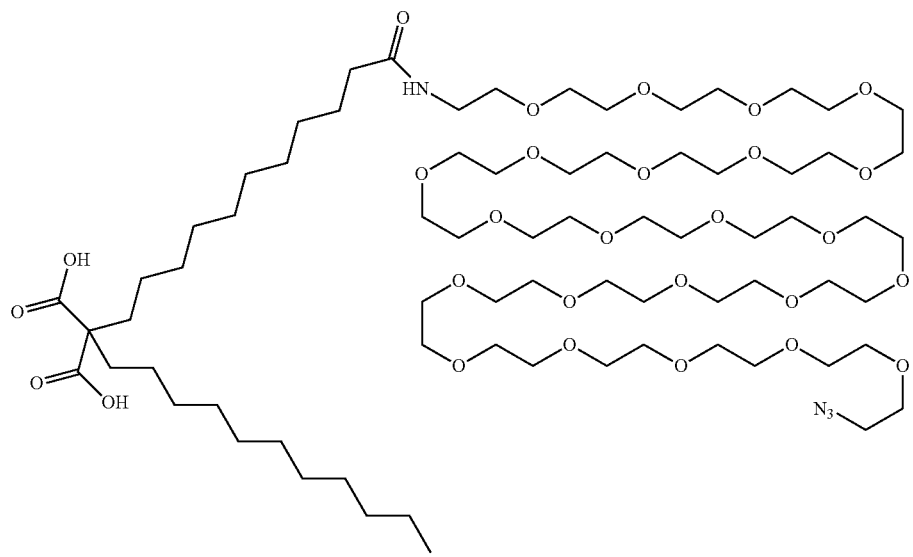
I-29

-continued

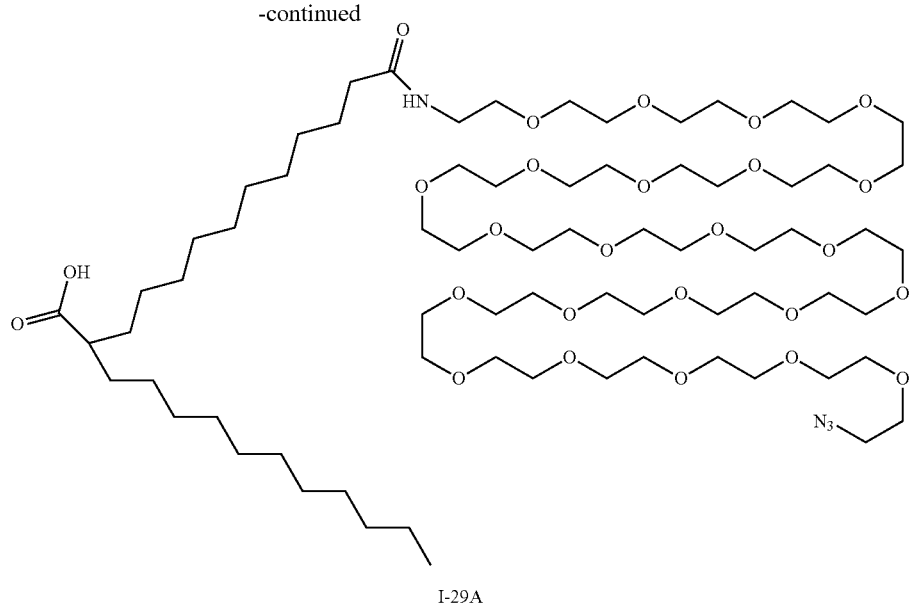

I-29A

A solution of Intermediate 28 (35 mg, 0.054 mmol) in THF (1 mL) was added to a vial charged with azido-PEG23-amine (59 mg, 0.054 mmol). DIPEA (14 µL, 0.081 mmol) was added and the reaction was agitated overnight. The solvent was evaporated and the residue redissolved in DCM (1 mL) and TFA (0.2 mL). The reaction was agitated for 1.25 hr before the solvent was evaporated. The residue was purified by HPLC (Sunfire 30×50 mm C18, 55-80% ACN/water+0.1% TFA) and the resulting material was redissolved in DCM (4 mL) and TFA (2 mL) and agitated for a 1.5 hrs. The solvent was evaporated and the residue purified by HPLC (Sunfire 30×50 mm C18, 55-80% ACN/water+0.1% TFA) to yield intermediate 29 (28 mg, 0.016 mmol, 29%) and intermediate 29A (1 mg, 0.6mmol, 1%): LCMS Method B Rt=1.08 min, [M+H+H$_3$O]$^{+2}$771.5; $^1$H NMR (400 MHz, CHLOROFORM-d) σ ppm 0.90 (t, J=6.72 Hz, 3 H) 1.26 (br. s., 24 H) 1.32-1.41 (m, 8H) 1.62 (quin, J=7.64 Hz, 2 H) 1.88-2.01 (m, 4 H) 2.31 (t, J=7.70 Hz, 2 H) 3.41 (t, J=5.07 Hz, 2 H) 3.46-3.56 (m, 3 H) 3.57-3.90 (m, 91 H); LCMS Method B Rt=1.29 min, [M+2H]$^{+2}$ 741.1.

Intermediate 30

22-((azido-PEG23)amino)-22-oxodocosane-1,11,11-tricarboxylic acid

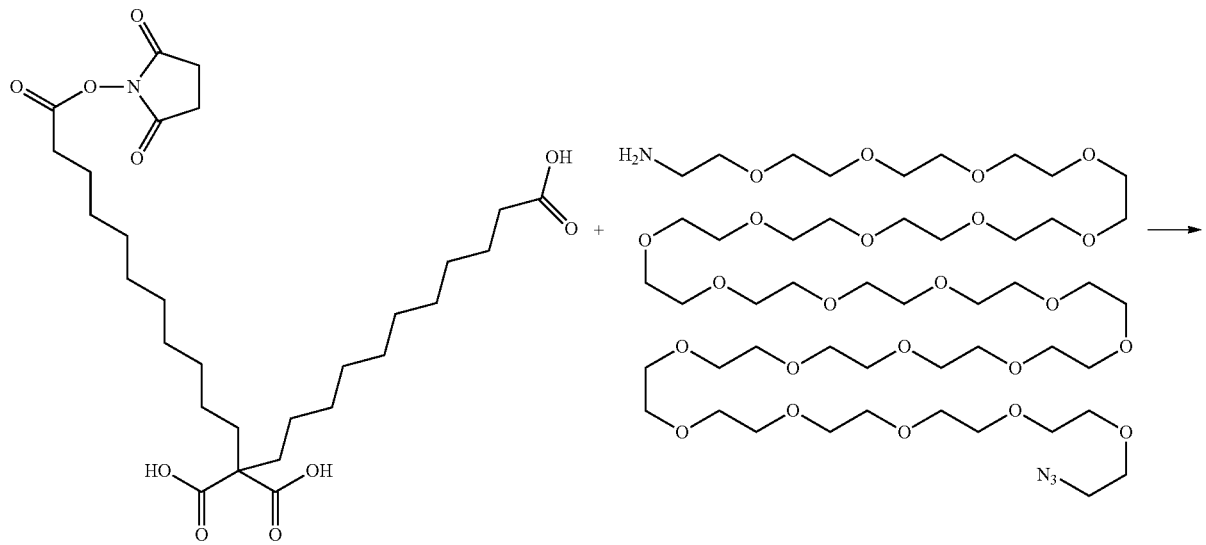

-continued

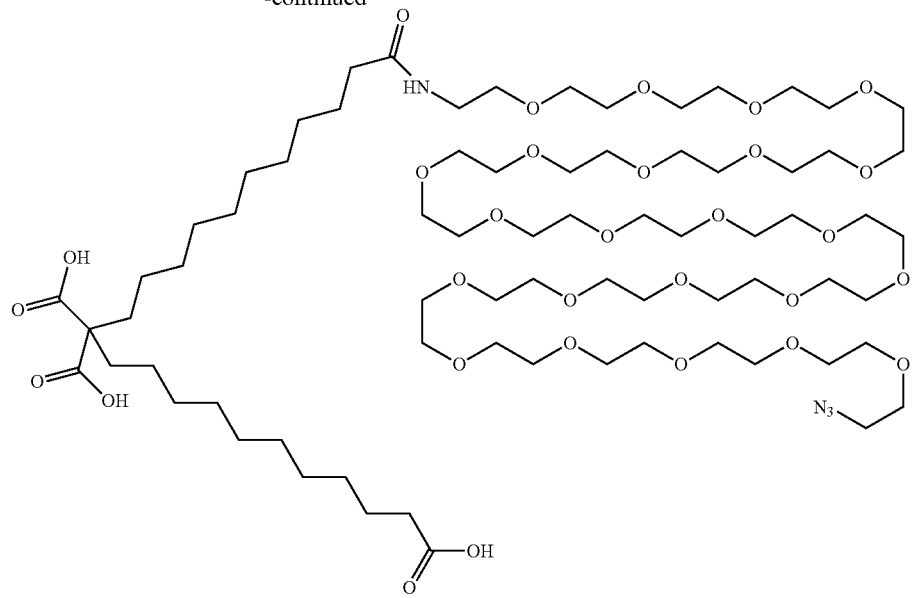

A solution of intermediate 16 (58 mg, 0.063 mmol) in THF (1 mL) was added to a vial charged with azido-PEG23-amine (70 mg, 0.063 mmol). DIPEA (17 µL, 0.095 mmol) was added and the reaction agitated on a shaker plate overnight. The reaction was concentrated and purified by HPLC (Sunfire C18 30×50 mm, 35-60% ACN/water+0.1% TFA) to yield intermediate 30 (57 mg, 0.036 mmol, 57%) as waxy white solid: LCMS Method B Rt=0.62 min, M+H 1555.4; $^1$H NMR (400 MHz, CHLOROFORM-d) δ ppm 1.28 (br. s., 18 H) 1.30-1.40 (m, 10 H) 1.63 (m, J=7.10, 7.10, 7.10, 7.10, 7.10 Hz, 4 H) 1.88-2.02 (m, 4 H) 2.28 (t, J=8.10 Hz, 2 H) 2.35 (t, J=7.40 Hz, 2 H) 3.41 (t, J=5.07 Hz, 2H) 3.50 (dt, J=9.20, 4.39 Hz, 2 H) 3.57-3.63 (m, 2 H) 3.63-3.73 (m, 90 H)

Intermediate 31

1-Benzyl 3-tert-butyl 2-undecylmalonate

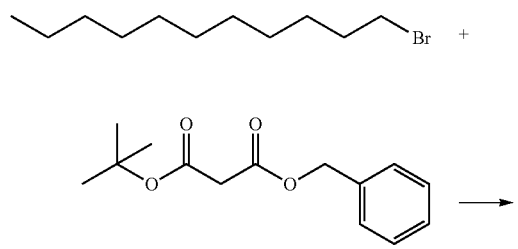

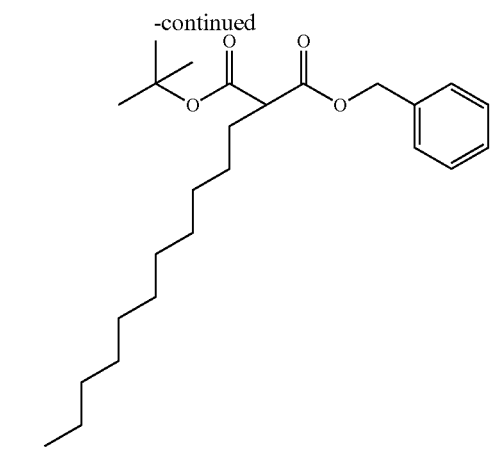

To a suspension of NaH (160 mg, 4.0 mmol) in DMF (8 mL) at 0° C. under $N_2$, was added benzyl tert-butyl malonate (1.0 g, 4.0 mmol) in DMF (2 mL). The mixture was stirred for 50 min after which 1-bromoundecane in DMF (2 mL) was added. After an additional hour of stirring the reaction was allowed to warm to room temperature. The reaction was maintained overnight. $Et_2O$ (100 mL) and water (20 mL) were added to partition the reaction. The aqueous phase was extracted with $Et_2O$ (100 mL), and the combined organics dried over $Na_2SO_4$. The solvent was evaporated and the residue purified by flash column (C18 12 g, 40-100% ACN/water+0.1% TFA) to yield the title compound as a colorless oil (1.14 g, 2.82 mmol, 71%): LCMS Method A Rt=1.58 min, M+Na 427.4; $^1$H NMR (400 MHz, CHLOROFORM-d) δ ppm 0.84-0.96 (m, 3 H) 1.28 (br. s, 12 H) 1.31 (m, J=3.90 Hz, 6 H) 1.41 (s, 9 H) 1.88 (q, J=7.38 Hz, 2 H) 3.29 (t, J=7.58 Hz, 1 H) 5.19 (q, J=12.27 Hz, 2 H) 7.30-7.42 (m, 5 H).

Alternatively, alkylation of tert-butyl malonate can be carried out using 1-iodoundecane (1.2 eq) in the presence of potassium carbonate (2 eq) in DMF.

Intermediate 32
1,11-Dibenzyl 11-tert-butyl docosane-1,11,11-tricarboxylate
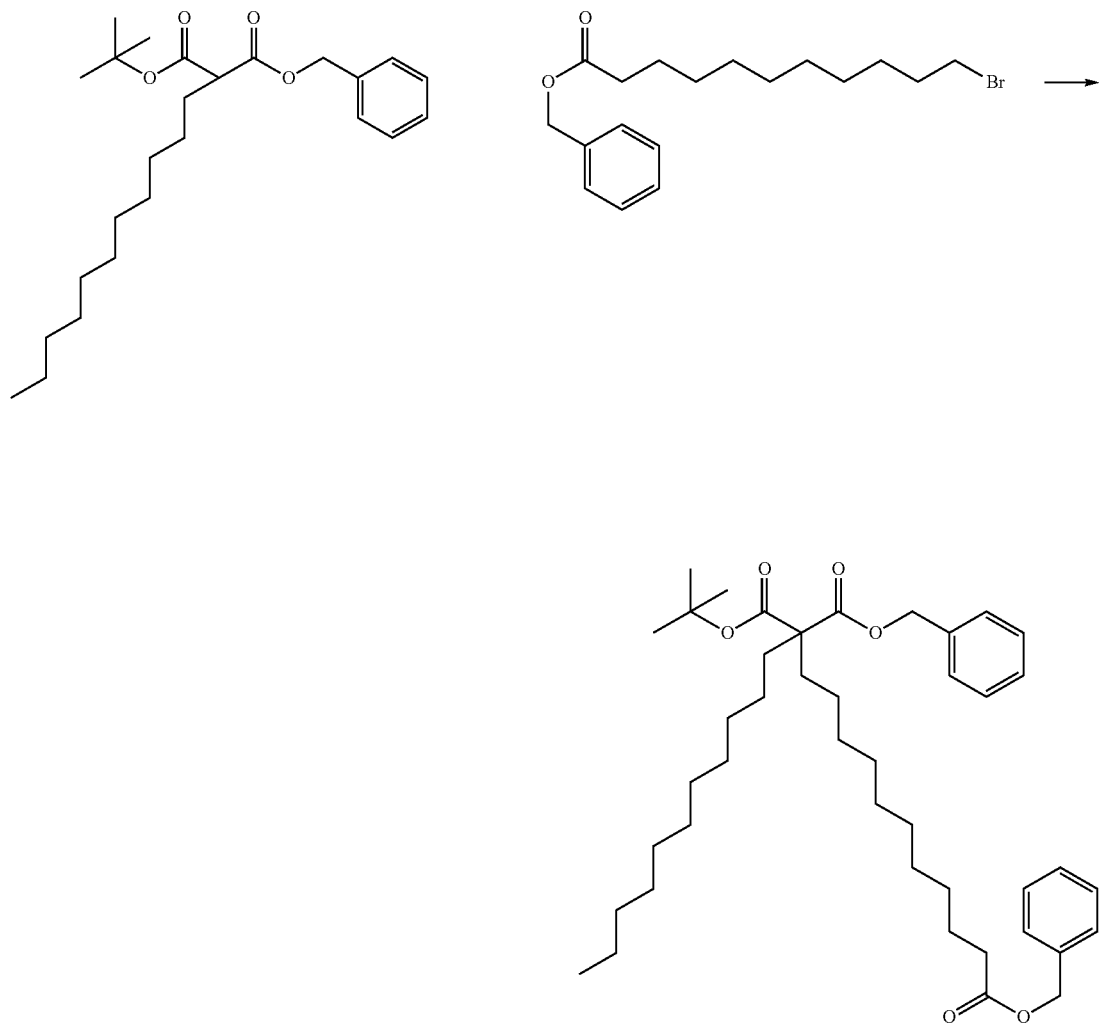
The title compound was synthesized in a similar fashion as intermediate 9 using intermediate 31 (650 mg, 1.61 mmol) as a starting material to yield a colorless oil (823 mg, 1.21 mmol, 75%): $^1$H NMR (400 MHz, CHLOROFORM-d) δ ppm 0.84-0.94 (m, 3 H) 1.12 (m, J=6.60 Hz, 4 H) 1.19-1.33 (m, 28 H) 1.35 (s, 9 H) 1.66 (quin, J=7.40 Hz, 2 H) 1.85 (t, J=8.44 Hz, 4 H) 2.37 (t, J=7.52 Hz, 2 H) 5.14 (s, 2 H) 5.16 (s, 2 H) 7.30-7.42 (m, 10 H).

127
Intermediate 33

13-(Benzyloxy)-2-((benzyloxy)carbonyl)-13-oxo-2-undecyltridecanoic acid

128
Intermediate 34

1,11-Dibenzyl 11-(2,5-dioxocyclopentyl) docosane-1,11,11-tricarboxylate

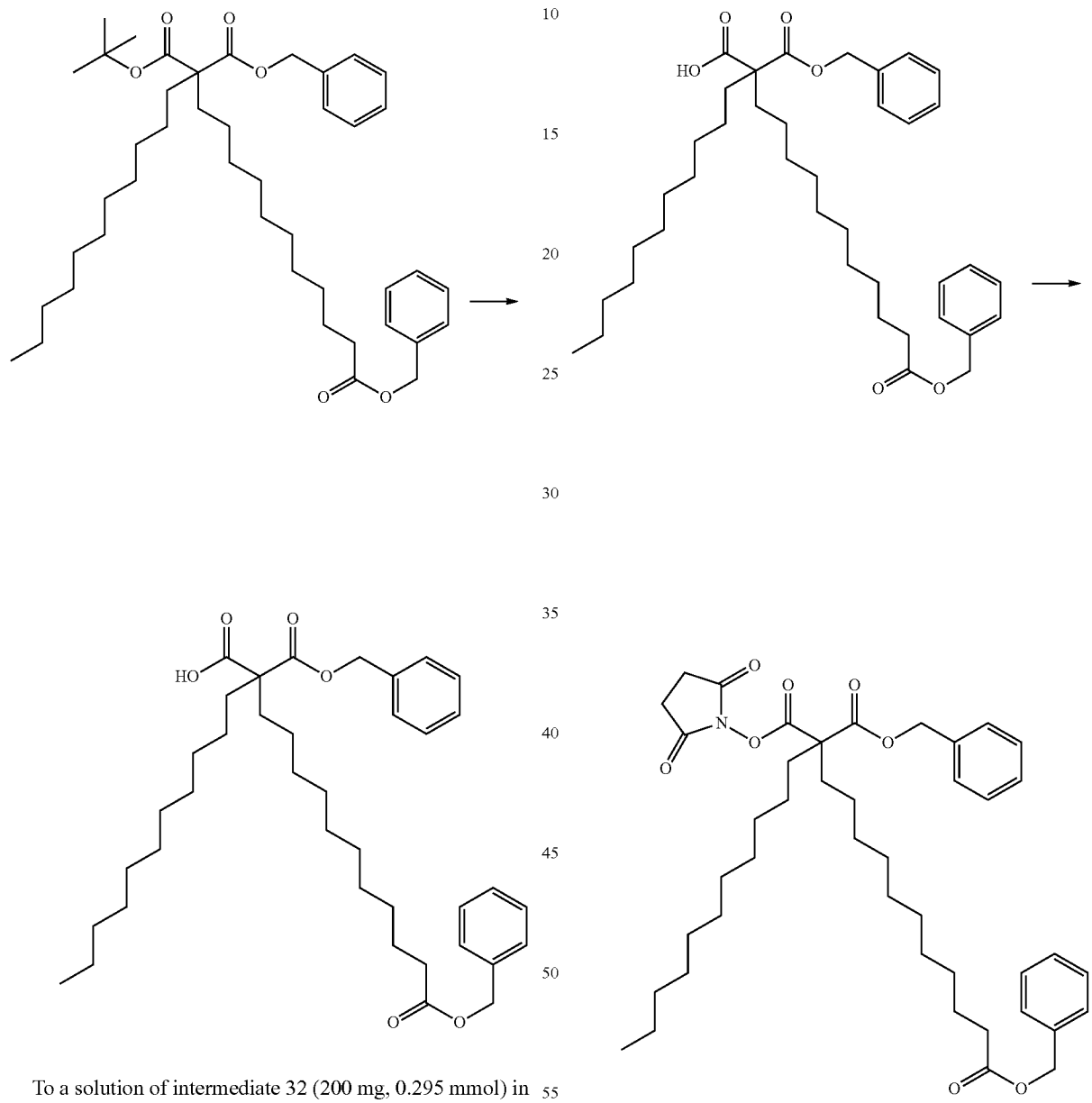

To a solution of intermediate 32 (200 mg, 0.295 mmol) in DCM (3 mL) was added TFA (0.6 mL), and the reaction stirred at room temperature for 3 hrs. The solvent was evaporated and the residue purified by flash column (silica 12 g, 0-15% EtOAc/HEP) to yield the title compound (177 mg, 0.284 mmol, 96%): $^1$H NMR (400 MHz, CHLOROFORM-d) δ ppm 0.87-0.94 (m, 3 H) 0.94-1.05 (m, 2 H) 1.19 (br. s., 14 H) 1.23-1.37 (m, 16 H) 1.65 (quin, J=7.40 Hz, 2 H) 1.78-1.91 (m, 2 H) 1.93-2.05 (m, 2 H) 2.37 (t, J=7.52 Hz, 2 H) 5.14 (s, 2 H) 5.27 (s, 2 H) 7.31-7.44 (m, 10 H).

The title compound was synthesized in a fashion similar to intermediate 15 using intermediate 33 (177 mg, 0.284 mmol) as a starting material to yield a colorless oil (153 mg, 0.213 mmol, 75%): $^1$H NMR (400 MHz, CHLOROFORM-d) δ ppm 0.86-0.93 (m, 3 H) 1.12-1.21 (m, 2 H) 1.21-1.37 (m, 30 H) 1.66 (quin, J=7.40 Hz, 2 H) 1.89-2.07 (m, 4 H) 2.37 (t, J=7.58 Hz, 2 H) 2.84 (br. s., 4 H) 5.13 (s, 2 H) 5.25 (s, 2 H) 7.30-7.47 (m, 10 H).

Intermediate 35

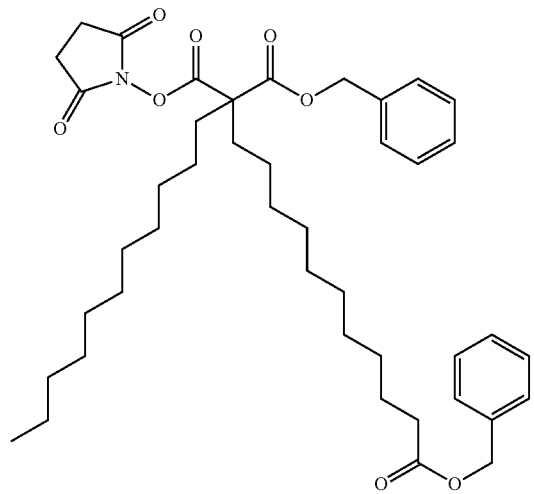
+
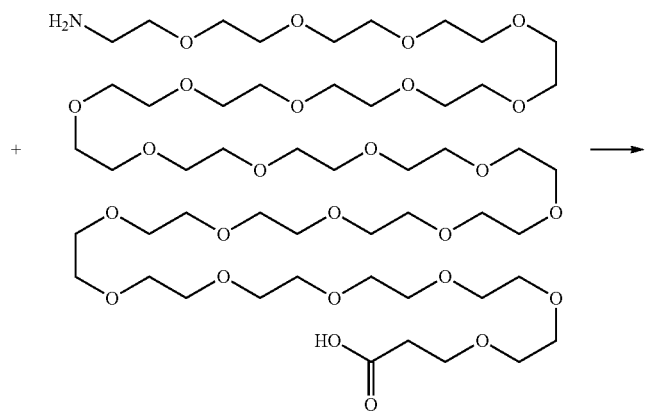
→

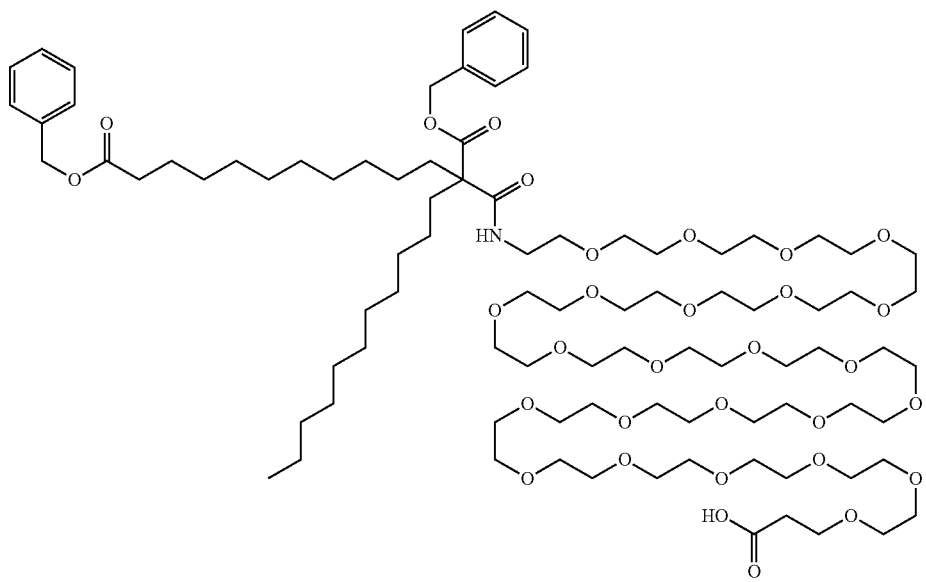

I-35

A solution of intermediate 34 (145 mg, 0.201 mmol) in THF (1.5 mL) and DCM (1.5 mL) was added to a vial charged with amino-PEG24-acid. DIPEA (88 L, 0.504 mmol) was added and the reaction agitated on a shaker plate for 15 hrs. The solvent was evaporated and the residue purified by supercritical fluid chromatography (Waters HILIC 20×150 mm; 15-25% MeOH/CO2) to yield intermediate 35 (151 mg, 0.086 mmol, 43%): LCMS Method D Rt=1.30 min, [M+2H]+2 876.4; $^1$H NMR (400 MHz, CHLOROFORM-d) δ ppm 0.86-0.93 (m, 3 H) 0.93-1.04 (m, 2 H) 1.19 (br. s., 15 H) 1.23-1.37 (m, 15 H) 1.61-1.68 (m, 2 H) 1.78 (td, J=12.44, 4.34 Hz, 2 H) 1.92-2.05 (m, 2 H) 2.37 (t, J=7.58 Hz, 2 H) 2.62 (t, J=6.05 Hz, 2 H) 3.49 (dd, J=6.72, 2.32 Hz, 2 H) 3.52-3.59 (m, 2 H) 3.59-3.73 (m, 92 H) 3.80 (t, J=6.05 Hz, 2 H) 5.13 (s, 2 H) 5.18 (s, 2 H) 7.31-7.42 (m, 10 H) 8.09 (t, J=5.26 Hz, 1 H).

Intermediate 36

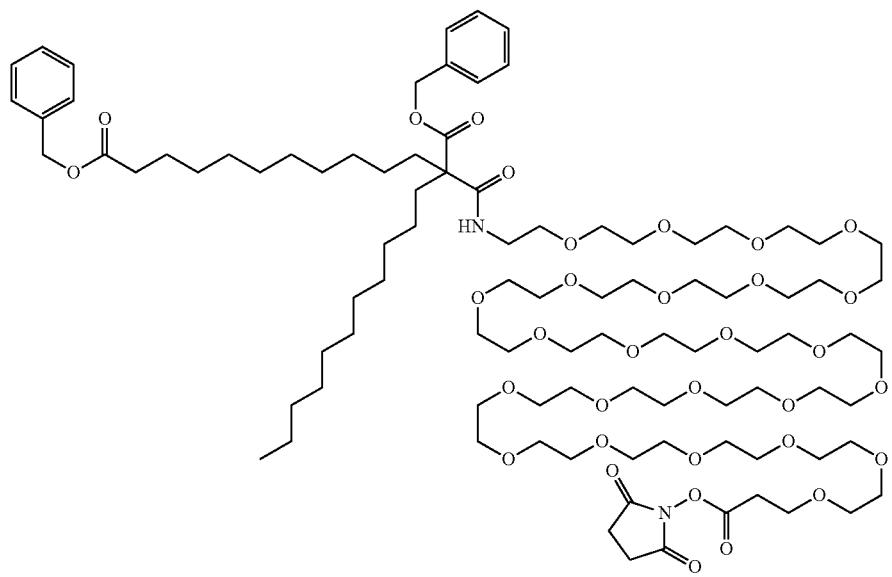

I-36

DCC (22 mg, 0.103 mmol) in DCM (0.265 mL) was added to a solution of intermediate 35 (150 mg, 0.086 mmol) and N-hydroxysuccinimide in DCM (1.5 mL). The reaction was stirred for 1.5 hrs. Additional N-hydroxysuccinimide (10 mg) in THF (0.5 mL) and DCC (22 mg) in DCM (0.265 mL) was added and the reaction stirred overnight. The solvent was evaporated and the residue purified by flash column (silica 12, 0-5% MeOH/DCM) to yield intermediate 36 (159 mg, quantitative) as a white solid: LCMS Method B Rt=1.55 min, $[M+H_3O+H]^{+2}$ 933.9.

Intermediate 37

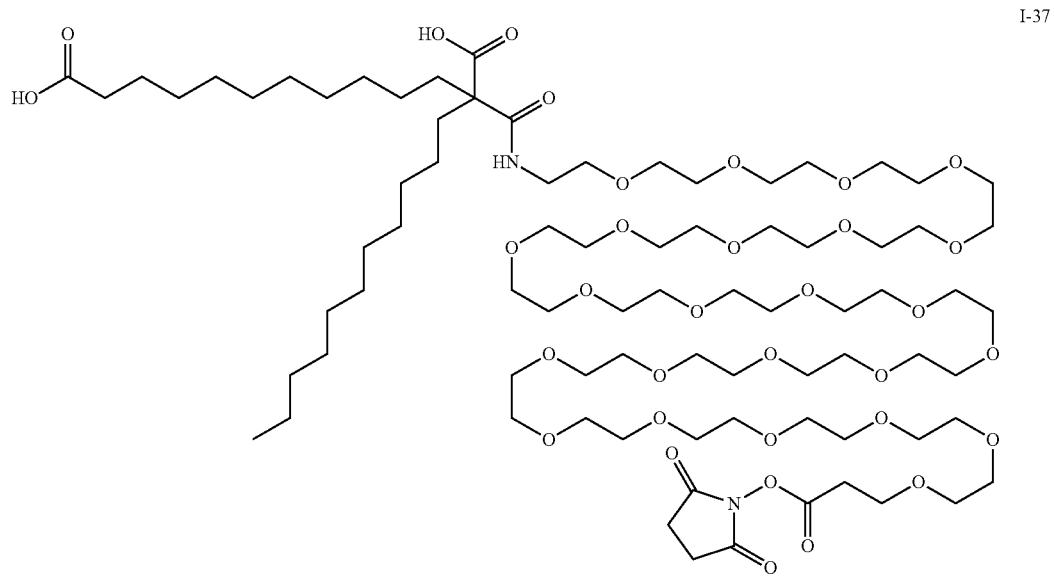 [SMILES: CCCCCCCCCCCC(CCCCCCCCCCC(=O)O)(C(=O)O)C(=O)NCCOCCOCCOCCOCCOCCOCCOCCOCCOCCOCCOCCOCCOCCOCCOCCOCCOCCOCCOCCOCCOCCOCCOCCOCCC(=O)ON1C(=O)CCC1=O]

I-37

To a solution of intermediate 36 (159 mg, 0.086 mmol) in THF (5 mL) was added a suspension of 10% Pd on carbon (4.6 mg, 4.3 µmol) in THF (1 mL). The reaction was placed under hydrogen and stirred for 40 min. More Pd on carbon (7 mg, 6.5 µmol) was added and the stirred another 1 hr under hydrogen. The reaction was passed through a membrane filter and the filtrate evaporated. The residue was purified by HPLC (Sunfire C18 30×50 mm, 45-70% ACN/water+0.1% TFA) to yield the title compound (83 mg, 0.047 mmol, 54%): LCMS Method B Rt=1.03 min, [M+2H]+2 835.2; $^1$H NMR (400 MHz, CHLOROFORM-d) δ ppm 0.84-0.94 (m, 3 H) 1.17 (br. s., 2 H) 1.21-1.39 (m, 30 H) 1.57-1.68 (m, 2 H) 1.69-1.80 (m, 2 H) 1.97-2.10 (m, 2 H) 2.34 (t, J=7.21 Hz, 2 H) 2.86 (s, 4 H) 2.92 (t, J=6.48 Hz, 2 H) 3.51-3.73 (m, 96 H) 3.87 (t, J=6.48 Hz, 2 H) 7.45 (t, J=4.46 Hz, 1 H)

Intermediate 38

11-Bromoundec-1-yne

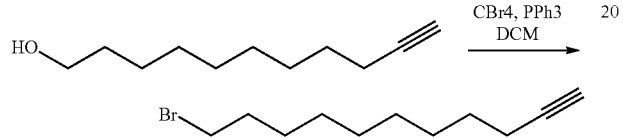

To a solution of 10-undecyn-1-ol (2.29 mL, 11.9 mmol) and carbon tetrabromide (4.34 g, 13.1 mmol) in DCM (10 mL) under N2 at 0° C. was added triphenylphosphine (3.43 g, 13.1 mmol) portion-wise over 30 min. Upon completion of the addition the reaction was allowed to warm to room temperature. After 1.5 hr the reaction was poured into stirring cyclohexane (75 mL) and the precipitate collected. The solid was washed with cyclohexane and the combined filtrates evaporated. The residue was purified by flash column (silica 80 g, 0-10% EtOAc/HEP) to yield the title compound (1.75 g, 7.57 mmol, 64%): 1H NMR (400 MHz, CHLOROFORM-d) δ ppm 1.21-1.35 (m, 6 H) 1.35-1.48 (m, 4 H) 1.48-1.59 (m, 2 H) 1.80-1.91 (m, 2 H) 1.94 (t, J=2.63 Hz, 1 H) 2.19 (td, J=7.09, 2.69 Hz, 2 H) 3.41 (t, J=6.85 Hz, 2 H).

Intermediate 39

Di-tert-butyl 2-(undec-10-yn-1-yl)malonate

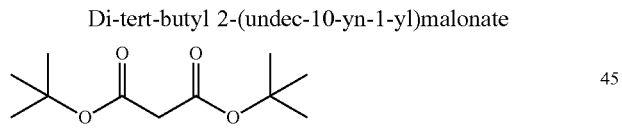

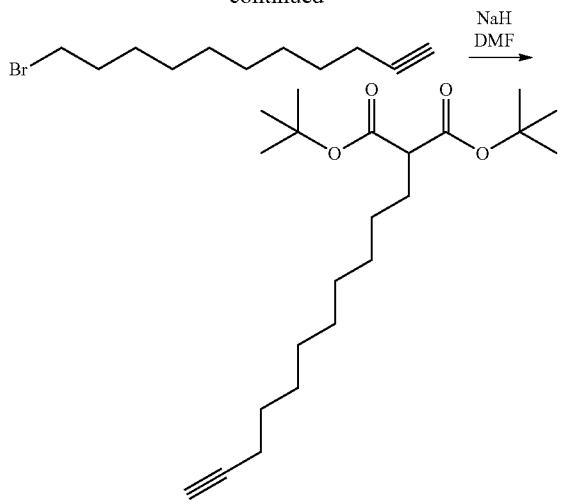

Di-tert-butyl malonate (800 mg, 3.70 mmol) was dissolved in DMF (9 mL) at 0° C. under N$_2$ and NaH (148 mg, 3.70 mmol) was added. The reaction was stirred 30 minutes at 0° C. and intermediate 38 (770 mg, 3.33 mmol) was added slowly dropwise, resulting in a yellow solution. The reaction was stirred at 0° C. for 2 hours then warmed to r.t. and stirred for 16 hours. The mixture was taken up in EtOAc (75 mL) and washed with H$_2$O (25 mL). The aqueous layer was extracted with EtOAc (75 mL) and the combined organic layers were dried over Na$_2$SO$_4$, filtered and concentrated. The mixture was purified twice via flash column (12 g silica cartridge, 0-20% EtOAc/heptanes) and fractions were concentrated to yield 162.1 mg of the desired product as a colorless oil (12%). LCMS (Waters Acquity UPLC BEH C18, 130 Å, 1.7 µm, 2.1 mm×50 mm, 50° C., Solvent Name A: Water+0.1% Formic Acid, Solvent Name B: Acetonitrile+0.1% Formic Acid, 98% B over 2.20 min): R$_f$=1.37 min, MS [M+H] observed: 366.0, calculated: 366.535. $^1$H NMR (400 MHz, Chloroform-d) δ ppm 1.29 (s, 10 H) 1.47 (s, 18 H) 1.52 (dd, J=14.78, 7.20 Hz, 3 H) 1.48 (d, J=1.26 Hz, 1 H) 1.75-1.83 (m, 2 H) 1.94 (t, J=2.65 Hz, 1 H) 2.18 (td, J=7.14, 2.65 Hz, 2 H) 3.11 (t, J=7.58 Hz, 1 H).

Intermediate 40

11,11-di-tert-butyl 1-ethyl docos-21-yne-1,11,11-tricarboxylate

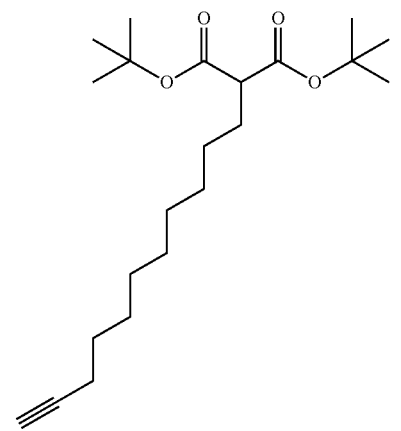

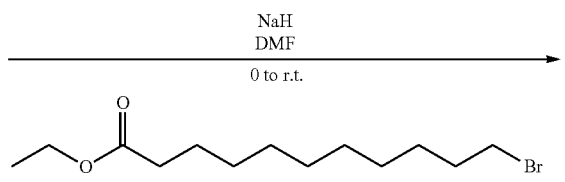

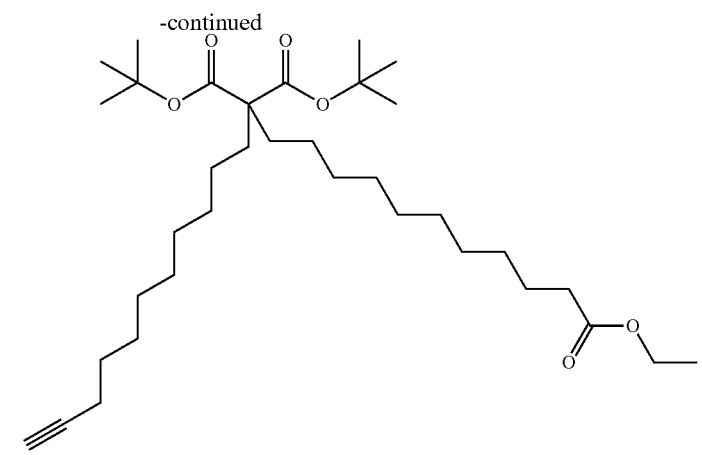

Intermediate 39 (162.1 mg, 0.442 mmol) was dissolved in DMF (2 mL) at 0° C. and NaH (21.23 mg, 0.531 mmol) was added. The reaction stirred at 0° C. for 15 minutes and ethyl 11-bromoundecanoate (143 mg, 0.486 mmol) was added slowly dropwise. The reaction was warmed to r.t. and stirred for 16 hours. The mixture was diluted with EtOAc (40 mL) and washed once with $H_2O$ (20 mL). The aqueous layer was extracted once with EtOAc (40 mL) and the organic layers were combined, dried over $Na_2SO_4$, filtered and concentrated to give a clear, yellow oil. The sample was dissolved in 1 mL DCM and purified via flash column (12 g silica column, 0-20% EtOAc/heptane, 15 min). The fractions were combined and concentrated to give 90.1 mg of the desired product (35%). $^1$H NMR (400 MHz, Chloroform-d) δ ppm 1.28 (br. s., 24 H) 1.45 (s, 18 H) 1.48 (s, 3 H) 1.53 (d, J=7.58 Hz, 3 H) 1.51 (s, 1 H) 1.64 (br. s., 1 H) 1.61 (d, J=7.33 Hz, 1 H) 1.77 (d, J=16.93 Hz, 2 H) 1.74-1.80 (m, 2 H) 1.94 (t, J=2.65 Hz, 1 H) 2.18 (td, J=7.07, 2.53 Hz, 2 H) 2.29 (t, J=7.58 Hz, 2 H) 4.13 (q, J=7.24 Hz, 2 H).

Intermediate 41

12,12-bis(tert-butoxycarbonyl)tricos-22-ynoic acid

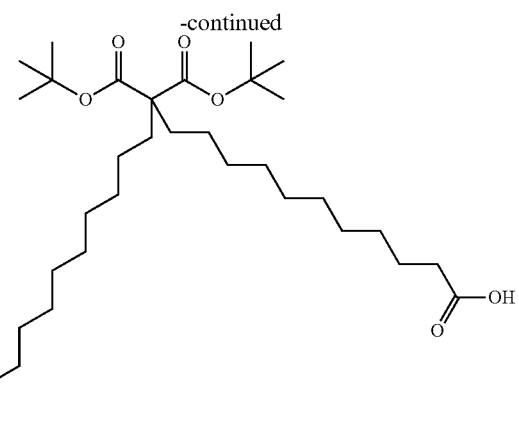

To a solution of intermediate 40 (21.7 mg, 0.037 mmol) in $^t$BuOH (1 mL) was added a solution of KOtBu (114 mg, 1.012 mmol) in $^t$BuOH (2 mL) at 30° C. under $N_2$. The mixture was stirred at r.t. and monitored by TLC (1:1 EtOAc/hexanes, $KMnO_4$, reflux). The starting material was consumed after 3 hours and the reaction mixture was quenched with 1 M HCl (20 mL) and extracted twice with EtOAc (25 mL). The organic layers were combined, dried over $Na_2SO_4$, filtered and concentrated to a clear, colorless oil (18 mg, 87%). The material was carried on to the next step without further purification. $^1$H NMR (400 MHz, Chloroform-d) δ ppm 1.27 (br. s., 22H) 1.44 (br. s., 18 H) 1.48 (s, 3 H) 1.52 (s, 3 H) 1.62 (br. s., 2 H) 1.77 (br. s., 4 H) 1.94 (br. s., 1 H) 2.18 (s, 2 H) 2.35 (s, 2 H).

Intermediate 42

Docos-21-yne-1,11,11-tricarboxylic acid

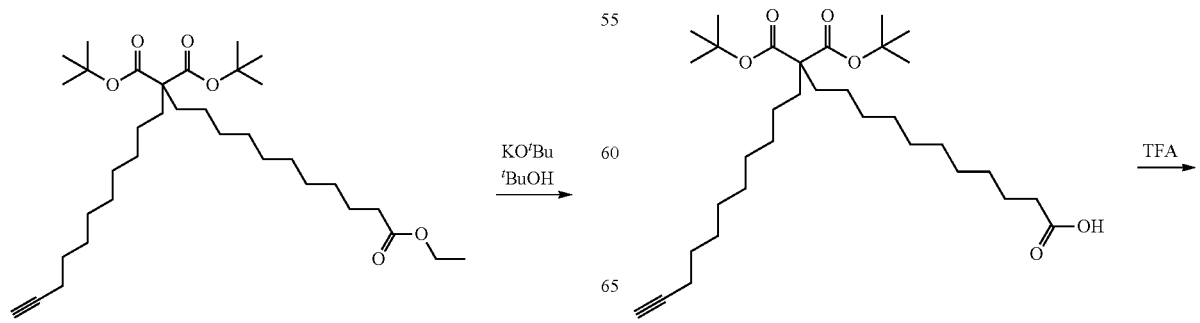

-continued

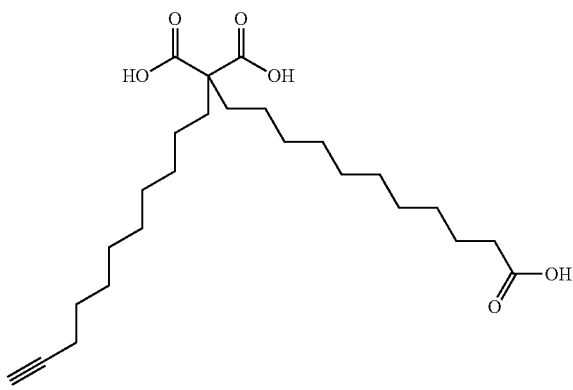

TFA (2 mL) was added to intermediate 41 (12 mg, 0.022 mmol) and the reaction stirred at r.t. for 1 hour. The mixture was diluted with DCM (10 mL) and concentrated twice to give a brown oil. The material was taken up in EtOAc (10 mL) and washed with $H_2O$ (20 mL). The organic layer was dried over $Na_2SO_4$, filtered and concentrated to a brown oil. The crude material was dissolved in 1 mL MeOH and purified via MS-triggered HPLC (Sunfire 30×50 mm 5 um column ACN/H2O w/ 0.1% TFA 75 ml/min, 1.5 ml injection, 45-70% ACN over 3.5 min): $R_t$=3.42 min; MS [M+H+Na] observed: 461.00, calculated: 461.597. Fractions were pooled and lyophilized to give 5.3 mg of title compound in 56% yield.

Intermediate 43

2-(((2,5-dioxopyrrolidin-1-yl)oxy)carbonyl)-2-(undec-10-yn-1-yl)tridecanedioic acid

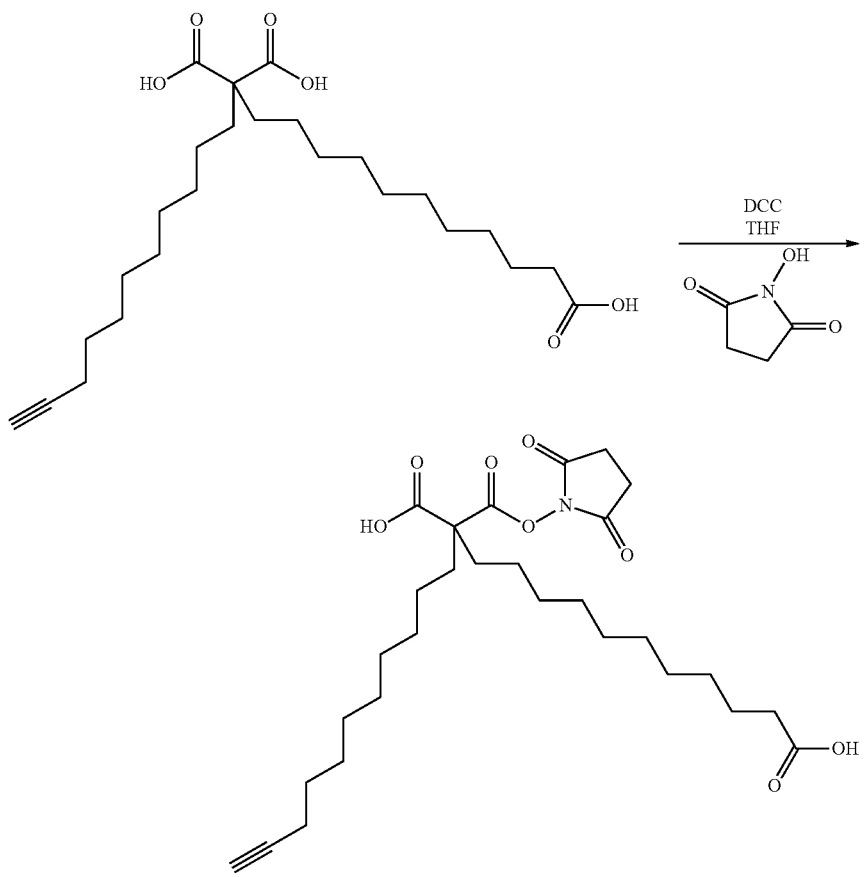

To a solution of intermediate 42 (5.3 mg, 0.012 mmol) in THF (0.5 mL) was added N-hydroxy succinimide (1.53 mg, 0.013 mmol). A solution of DCC (2.493 mg, 0.012 mmol) in THF (0.5 mL) was added and the mixture was stirred at r.t. under $N_2$ for 4 hours. Complete conversion of starting material was observed by LCMS. The mixture was concentrated and taken on to the next step without further purification. LCMS (Sunfire C18 3.5 μm 3.0×30 mm, 40° C., Acidic Eluent A: Water+0.05% Trifluoroacetic Acid, Basic Eluent A: Water+5 mM Ammonium Hydroxide, Eluent B: ACN, 5-95% over 2 min): $R_t$=1.72 min; MS [M+H+Na] observed: 558.0, calculated: 558.67.

Intermediate 44

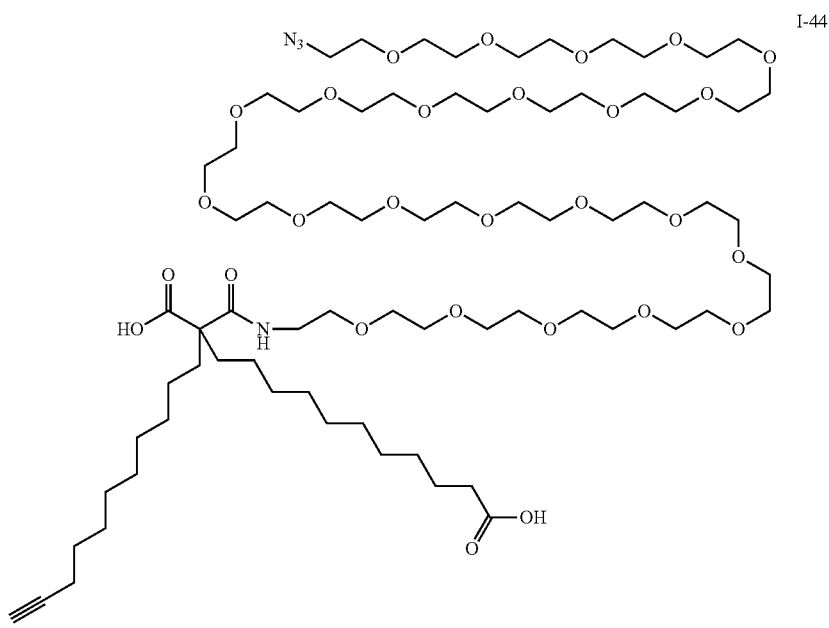 [SMILES: C#CCCCCCCCCCC(CCCCCCCCCCC(=O)O)(C(=O)O)C(=O)NCCOCCOCCOCCOCCOCCOCCOCCOCCOCCOCCOCCOCCOCCOCCOCCOCCOCCOCCOCCOCCOCCOCCOCCN=[N+]=[N-]]

To a solution of intermediate 43 (3.2 mg, 5.97 μmol) in DCM (0.5 mL) was added a solution of azido-dPEG23-amine (Quanta Biodesign, 7.88 mg, 7.17 μmol) in DCM (0.5 mL) and DIPEA (2.09 μL, 0.012 mmol) and the mixture was stirred at r.t. for 16 hours at which point conversion of starting material was observed by LCMS. The reaction mixture was concentrated and dissolved in 1 mL MeOH and purified by MS-triggered HPLC (Sunfire 30×50 mm 5 um column ACN/H2O w/ 0.1% TFA 75 ml/min, 1.5 ml injection, 55-80% ACN 5 min gradient, $R_t$=1.92 min) and the fractions were pooled and lyophilized to give 1.7 mg of the title compound in 19% yield. LCMS (Acquity BEH 1.7 μm 2.1×50 mm–50° C., Solvent Name A: Water+0.1% Formic Acid, Solvent Name B: Acetonitrile+0.1% Formic Acid, 98% B over 2.20 min): $R_t$=1.89 min; MS [M+H/2] observed: 760.0, calculated: 759.5.

Intermediate 45 docos-21-ene-1,11,11-tricarboxylic acid

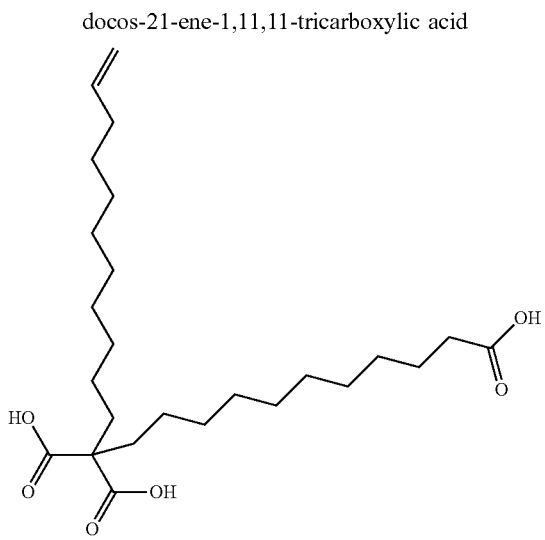

Intermediate 45 is prepared following the procedure for intermediate 39-42 substituting 11-bromo-dec-1-ene for 11-bromo-dec-1-yne.

Intermediate 46

2-(((2,5-Dioxopyrrolidin-1-yl)oxy)carbonyl)-2-(undec-10-en-1-yl)tridecanedioic acid

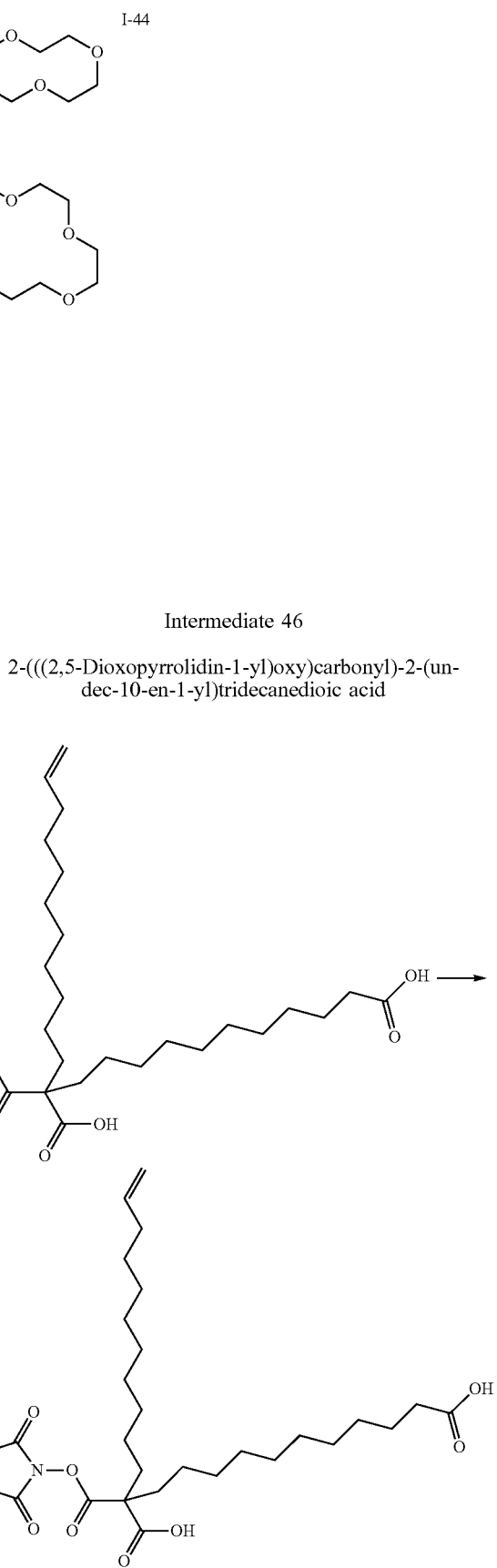

DCC (187 mg, 0.908 mmol) in DCM (2 mL) was added to a solution of N-hydroxysuccinimide (99 mg, 0.862 mmol) and docos-21-ene-1,11,11-tricarboxylic acid (Intermediate 45: 400 mg, 0.908 mmol) in DCM (7 mL) and THF (0.7 mL). The reaction was stirred overnight before the solvent was evaporated. The residue was purified by HPLC (Sunfire C18 30×50 mm; 55-80% ACN/water+0.1% TFA) to yield the title compound (155 mg, 0.288 mmol, 32%): by LCMS Method C Rt=1.51 min, M+H 538.3; $^1$H NMR (400 MHz, CHLOROFORM-d) δ ppm 1.16-1.46 (m, 28 H) 1.60-1.87 (m, 3 H) 1.91-2.17 (m, 5 H) 2.38 (t, J=7.03 Hz, 2 H) 2.86 (br. s., 4 H) 3.68 (dd, J=11.25, 7.34 Hz, 1 H) 3.78 (dd, J=11.31, 5.20 Hz, 1 H) 3.99-4.10 (m, 1 H).

Intermediates 47 and 47A

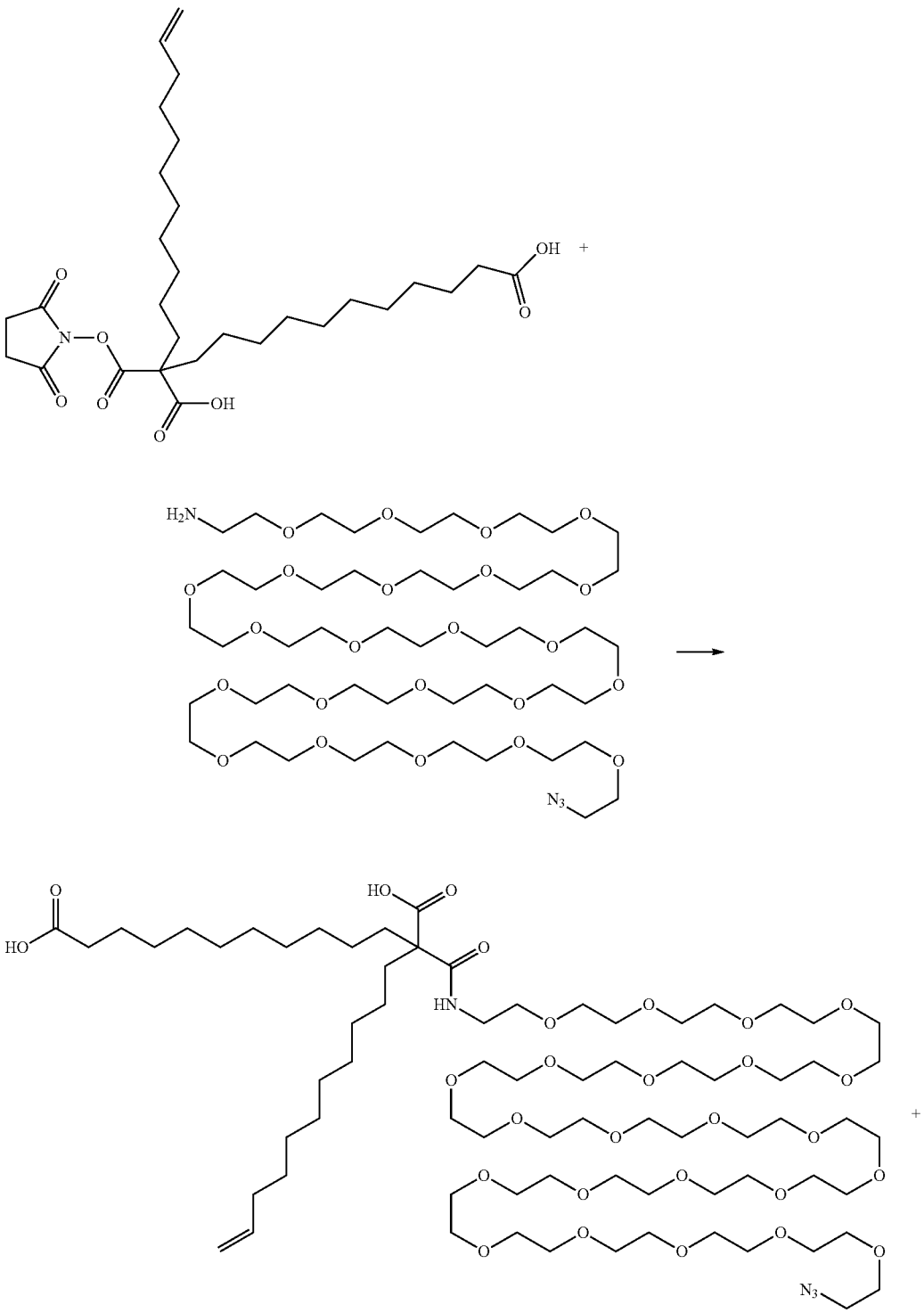

I-47

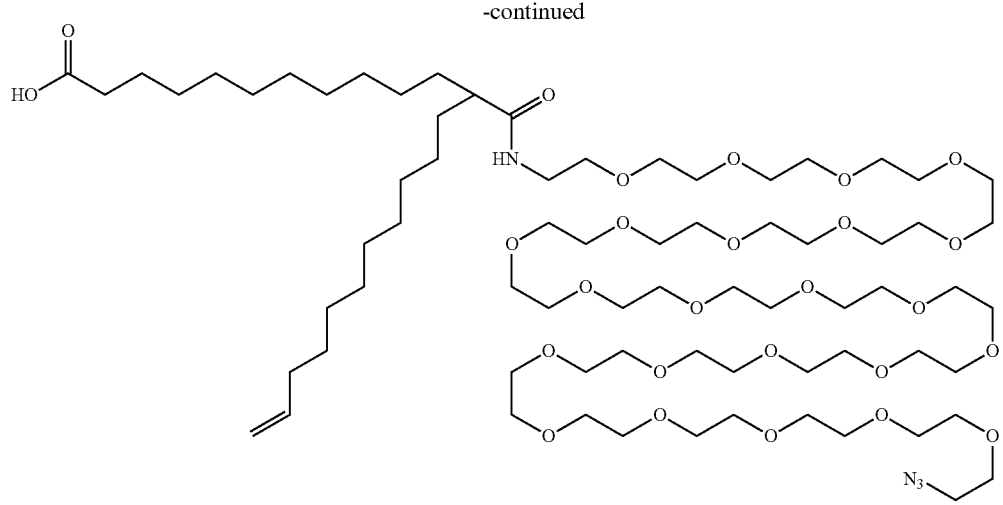

I-47A

Azido-dPEG23-amine (Quanta Biodesign: 164 mg, 0.149 mmol) and intermediate 46 (80 mg, 0.149 mmol) were dissolved in THF (2.5 mL). DIPEA (39μL, 0.233 mmol) was added and the reaction agitated overnight. The solvent was evaporated and the residue purified by HPLC (Sunfire C18 30×50 mm; 45-70% ACN/water+0.1% TFA) to yield compounds 47 (97 mg, 0.061 mmol, 41%) and 47A (32 mg, 0.021 mmol, 14%): LCMS Method C Rt=1.35 min, [M+2H]$^{+2}$ 761.9; $^1$H NMR (400 MHz, ACETONITRILE-d3) δ ppm 1.05-1.18 (m, 3 H) 1.19-1.32 (m, 20 H) 1.36 (t, J=7.15 Hz, 1 H) 1.48-1.59 (m, 2 H) 1.65-1.75 (m, 2 H) 2.01-2.06 (m, 2 H) 2.25 (t, J=7.46 Hz, 2 H) 3.33-3.39 (m, 2 H) 3.39-3.44 (m, 2 H) 3.50-3.67 (m, 98 H) 4.84-4.95 (m, 1 H) 4.95-5.06 (m, 1 H) 5.83 (ddt, J=17.07, 10.29, 6.68, 6.68 Hz, 1 H) 7.31 (t, J=5.44 Hz, 1 H); LCMS method C Rt=1.50 min, [M−2H]$^{+2}$ 739.9; $^1$H NMR (400 MHz, ACETONITRILE-d3) δ ppm 1.16-1.42 (m, 30 H) 1.42-1.63 (m, 5 H) 2.00-2.07 (m, 2 H) 2.22-2.28 (m, 2 H) 2.40-2.52 (m, 2 H) 3.25-3.33 (m, 2 H) 3.33-3.42 (m, 2 H) 3.42-3.50 (m, 2 H) 3.50-3.68 (m, 88 H) 4.86-5.06 (m, 2 H) 5.83 (ddt, J=17.04, 10.26, 6.71, 6.71 Hz, 1 H) 6.40-6.74 (m, 1 H).

Intermediate 48

2-Undecylmalonic acid

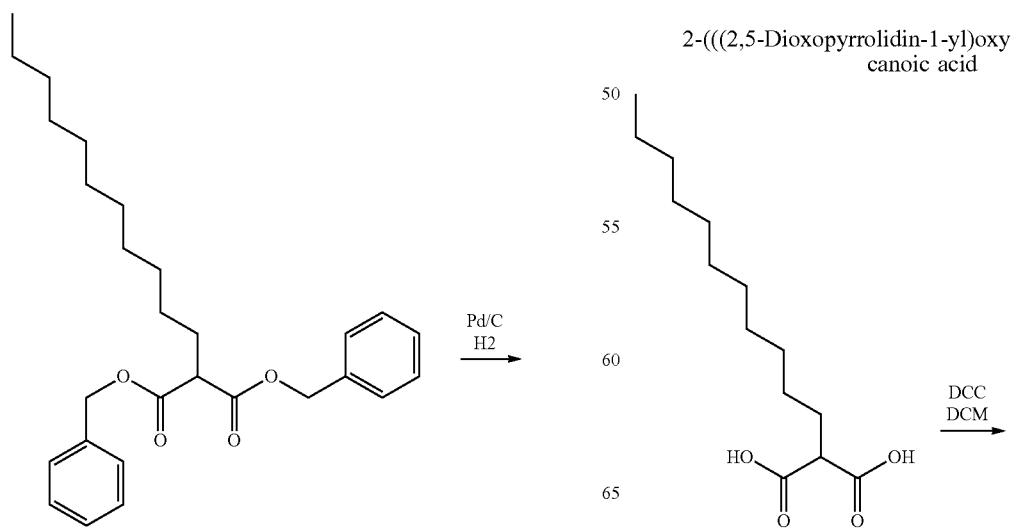

-continued

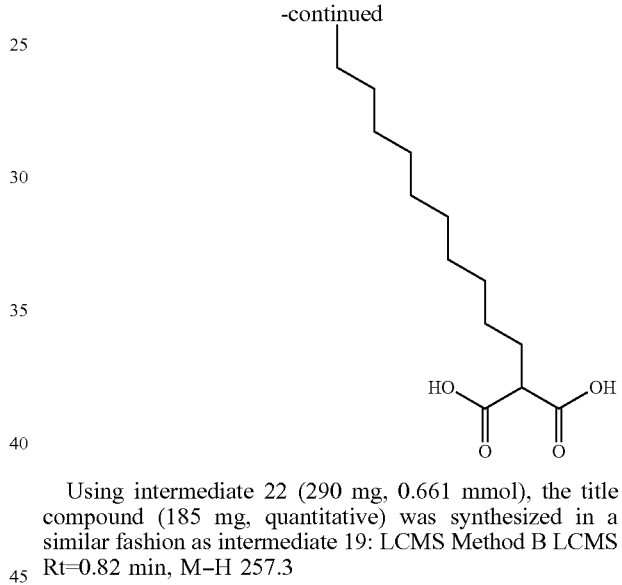

Using intermediate 22 (290 mg, 0.661 mmol), the title compound (185 mg, quantitative) was synthesized in a similar fashion as intermediate 19: LCMS Method B LCMS Rt=0.82 min, M−H 257.3

Intermediate 49

2-(((2,5-Dioxopyrrolidin-1-yl)oxy)carbonyl)tridecanoic acid

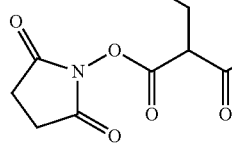

DCC (122 mg, 0.592 mmol) was added to a solution of intermediate 48 (170 mg, 0.658 mmol) and N-hydroxysuccinimide (68 mg, 0.592 mmol) in DCM (6 mL) and THF (0.5 mL). The reaction was stirred for 16 hrs before more DCC (30 mg, 0.145 mmol) in DCM (0.5 mL) was added. The reaction was stirred for a further 2 days. The solvent was evaporated and the residue purified by HPLC (Sunfire C18 30×50 mm, 45-70% ACN/water+0.1% TFA) to yield the title compound as a white powder (46 mg, 0.129 mg, 20%): LCMS Method B Rt=0.94 min, M+H 356.3; $^1$H NMR (400 MHz, CHLOROFORM-d) δ ppm 0.89 (t, J=7.00 Hz, 3 H) 1.20-1.40 (m, 16 H) 1.43-1.55 (m, 2 H) 1.99-2.14 (m, 2 H) 2.86 (s, 4 H) 3.71 (t, J=7.46 Hz, 1 H).

Intermediate 50 and 50A

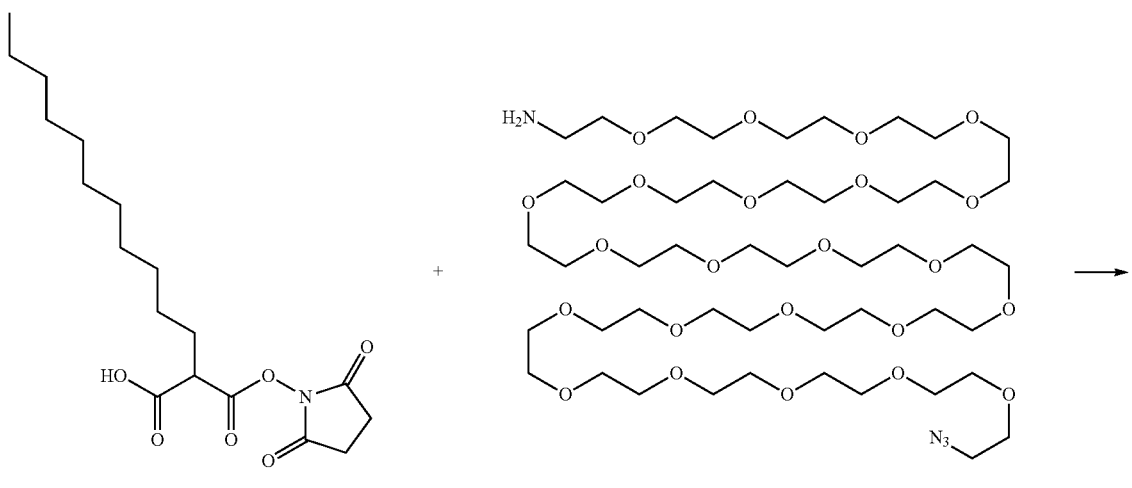

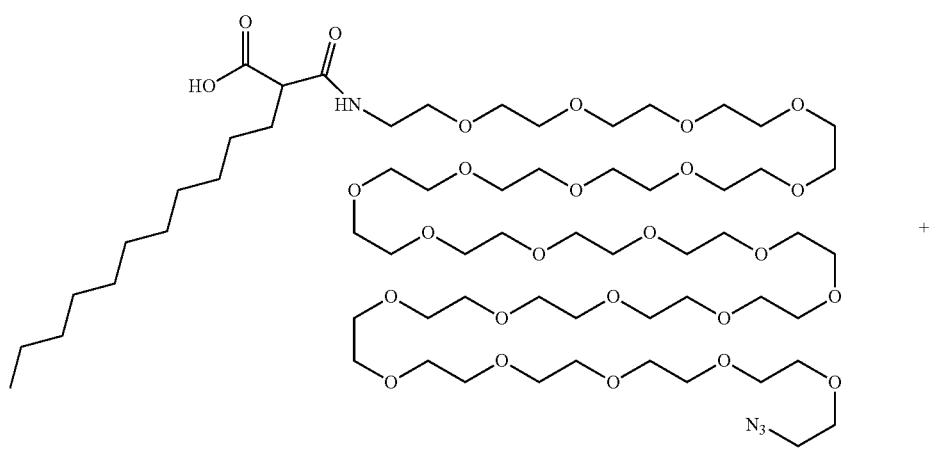

I-50

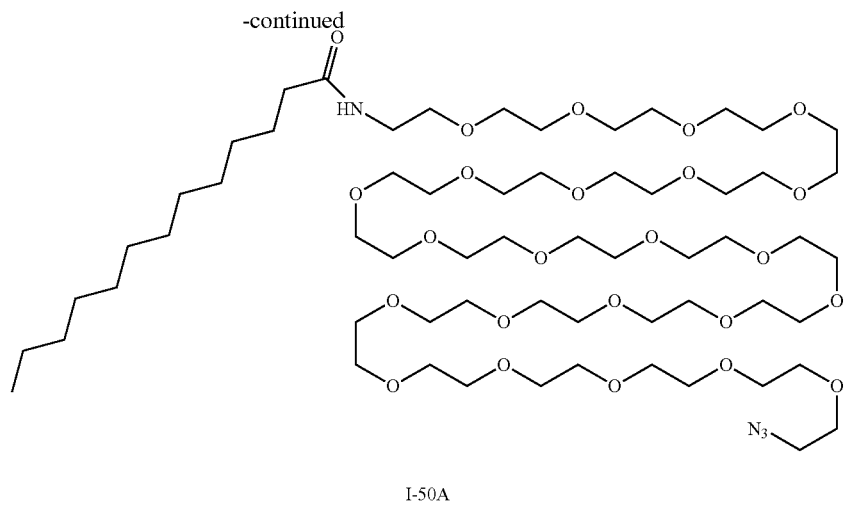

I-50A

The title compounds were synthesized in a fashion similar to 50 and 50A from intermediate 49 (30 mg, 0.084 mmol) yielding intermediate 50 (18 mg, 0.013 mmol, 16%) and intermediate 50A (5 mg, 4 μmol, 5%): LCMS Method B Rt=0.85 min, M+H 1340.3; $^1$H NMR (400 MHz, CHLOROFORM-d) δ ppm 0.82-0.98 (m, 3 H) 1.20-1.36 (m, 16 H) 1.36-1.51 (m, 2 H) 1.83-2.02 (m, 1 H) 2.11-2.27 (m, 1 H) 2.33 (dd, J=11.80, 4.22 Hz, 1 H) 3.41 (t, J=5.14 Hz, 3 H) 3.49 (d, J=5.01 Hz, 1 H) 3.56-3.79 (m, 92 H); LCMS Method B Rt=0.96 min, M+H 1296.3.

Intermediates 51-57

Mutant of GDF15 Protein

Expression of Human GDF-15 Proteins in E. coli Cells

E. coli strains BL21 (DE3) Gold (Stratagene) and Rosetta (DE3) pLysS cells (Novagen) were transformed with constructs 51 to 56 and construct MAHA-(200-308)-hGDF15 respectively, cloned into pET26b vectors. Transformed cells were grown under antibiotic selection first in 3 ml and then in 50 ml Luria Broth (Bacto-Tryptone 10 g/L, yeast extract 5 g/L, NaCl 5/L, glucose 6 g/L) until an OD600 of 1.5 was reached. The pre-cultures were used to inoculate two 1-L fermenters filled with Terrific Broth medium (NH4SO4 1.2 g/L, H2PO4 0.041 g/L, K2HPO4 0.052 g/L, Bacto-Tryptone 12 g/L, Yeast Extract 24 g/L). The cultures were induced by automatic addition of 1 mM isopropyl-beta-D-thiogalactopyranoside (IPTG) when pH increased above 7.1. Other fermentation parameters were: temp=37° C.; pH 7.0+/−0.2 adjusted by addition of 2N NaOH/H2SO4; pO2>30% with cascades of stirrer speed, air flow and oxygen addition. Five hours post induction the cultures were cooled to 10° C. and cells were harvested by centrifugation.

Purification and Refolding of GDF15 Variants a) Inclusion Bodies

Recombinant coli pellets expressing the protein of interest were resuspended (5% w/v) in 50 mM NaH$_2$PO$_4$/150 mM NaCl/5 mM benzamidine.HCl/5 mM DTT, pH 8.0 at 4° C., homogenized and lysed by 2 passages through a French press (800 and 80 bar). Inclusion bodies (IBs) were isolated by centrifugation at 12'000 rpm for 60 min at 4° C.

b) Purification of Crude Unfolded Protein

IBs were solubilized (5% w/v) in 6M guanidine/100 mM NaH$_2$PO$_4$/10 mM Tris/20 mM beta-mercaptoethanol, pH 8.0 and stirred for 2 hours at room temperature. Debris was removed by centrifugation at 12'000 rpm. The solubilized IBs were further purified on Ni-NTA-Superflow (the construct without His tag binds as well to this resin due to the high histidine content). After base-line washing with 6M guanidine/100 mM NaH$_2$PO$_4$/10 mM Tris/5 mM beta-mercaptoethanol, pH 8.0, bound material was eluted with the same buffer adjusted to pH 4.5. The eluate was adjusted to pH 8.0, 100 mM DTT was added and the solution stirred over night at 4° C. The pH was then adjusted to 2 by addition of trifluoroacetic acid (TFA, 10% stock in water) and the solution further diluted 1:1 with 0.1% TFA in water. The crude protein solution was further purified by RP-HPLC (Poros) using a gradient of 0-50% acetonitrile in 50 min. The GDF-15 containing fractions were pooled and lyophilized.

c) Protein Folding

Method 1: Lyophilized material was dissolved at 2 mg/ml in 100 mM acetic acid, diluted 15-20 folds in folding buffer (100 mM CHES/1M NaCl/30 mM CHAPS/5 mM GSH/0.5 mM GSSG/20% DMSO, pH 9.5, 4° C.) and the solution gently stirred during 3 days at 4° C. After 3 days 3 volumes of 100 mM acetic acid was added and the solution concentrated by ultrafiltration (5 kDa cut-off) to about 100-200 ml, diluted 10 fold with 100 mM acetic acid and re-concentrated. The refolded material was further purified by preparative RP-HPLC on a Vydac C4 column run at 50° C. (buffer A: 0.1% TFA in water; buffer B: 0.05% TFA in acetonitrile). After loading the column was washed with 15% buffer B and eluted with a gradient of 15% B to 65% B in 50 min. Collected fractions containing the protein of interest were diluted with an equal volume of buffer A and lyophilized. Refolding yields were about 25% for both proteins.

Method 2: Protocol followed as in method 1 with folding buffer: 100 mM CHES, pH 9.4, 0.9M arginine, 0.5M NaCl, 1 mM EDTA, 2.5 mM GSH, 1 mM GSSG (final concentration).

The following GDF15 mutants were prepared according to above procedure:

Intermediate 51

M-(His)$_6$-hGDF15

MHHHH HHAR NGDHC PLGPG RCCRL HTCRA
SLEDL GWADW VLSPR EVQVT MCIGA CPSQF

RAANM HAQIK TSLHR LKPDT VPAPC CVPAS YNPMV LIQKT DTGVS LQTYD DLLAK DCHCI (SEQ ID NO: 1)

LCMS: Calculated mass: 26462 Observed Mass: 26464

Intermediate 52

M-(His)₆-M-hGDF15

(SEQ ID NO: 2)
MHHHHHHMARNGDHCPLGPGRCCRLHTVRASLEDLGWADWVLSPREVQVT
MCIGACPSQFRAANMHAQIKTSLHRLKPDTVPAPCCVPASYNPMVLIQKT
DTGVSLQTYDDLLAKDCHCI

LCMS: Calculated mass: 26724 Observed Mass: 26725

Intermediate 53

His-dGDF15

(SEQ ID NO: 3)
MHHHHHHAHARDGCPLGEGRCCRLQSLRASLQDLGWANVVVVAPRELDV
RMCVGACPSQFRSANTHAQMQARLHGLNPDAAPAPCCVPASYEPVVLMH
QDSDGRVSLTPFDDLVAKDCHCV

LCMS: Calculated mass (dimer): 26368 Observed Mass: 26363

Intermediate 54

MH-(199-308)-hGDF15

(SEQ ID NO: 4)
MHNGDHCPLGPGRCCRLHTVRASLEDLGWADWVLSPREVQVTMCIGACP
SQFRAANMHAQIKTSLHRLKPDTVPAPCCVPASYNPMVLIQKTDTGVSL
QTYDDLLAKDCHCI

LCMS: Calculated mass: 24636 Observed Mass: 24638

Intermediate 55

AH-(199-308)-hGDF15

(SEQ ID NO: 5)
AHNGDHCPLGPGRCCRLHTVRASLEDLGWADWVLSPREVQVTMCIGACP
SQFRAANMHAQIKTSLHRLKPDTVPAPCCVPASYNPMVLIQKTDTGVSL
QTYDDLLAKDCHCI

Step 1: preparation of construct M-His₆-TEV(ENLYFQ/A)-H-hsGDF15 aa199-308 The construct M-His6-TEV(ENLYFQ/A)-H-hsGDF15 aa199-308 was prepared according to the above procedure (steps a, b and c).

Step 2: TEV cleavage of the protein from step 1

The lyophilized protein was solubilized in water to a final concentration of 1.75 mg/ml. The protein was unfolded again by diluting 1:1 in 6M Guan/50 mM Tris, pH 8.0+50 mM DTT, and stirred at RT for 1 h. The material was re-purified by preparative RP-HPLC on a Vydac C4 column and lyophilized. 26 mg of lyophilisate were solubilized in 26 ml 50 mM Tris/3M UREA, pH 7.5+3000 Units AcTEV Protease (Invitrogen, 12575-023) and incubated for 4 days. The pH was then adjusted to pH 2.0 by addition of trifluoroacetic acid (TFA, 10% stock in water) and the solution further diluted to 150 ml with 0.1% TFA in water. After filtration through a 0.22 um membrane the material was again purified by preparative RP-HPLC on a Vydac C4 column to isolate successfully cleaved protein. Fractions were collected manually; target protein-containing fractions were isolated and lyophilized. The cleaved GDF15 protein was then refolded and refolded protein purified as described above.

LCMS: Calculated mass (dimer): 24516 Observed Mass: 24518

The following GDF15 mutant can be prepared according to the above procedure:

Intermediate 56

MHA-(200-308)-hGDF15

(SEQ ID NO: 6)
MHAGDHCPLGPGRCCRLHTVRASLEDLGWADWVLSPREVQVTMCIGACP
SQFRAANMHAQIKTSLHRLKPDTVPAPCCVPASYNPMVLIQKTDTGVSL
QTYDDLLAKDCHCI

LCMS: Calculated mass (dimer): 24752

The following GDF15 mutant was prepared according to the above procedure:

Intermediate 57

AHA-(200-308)-hGDF15

(SEQ ID NO: 7)
AHAGDHCPLGPGRCCRLHTVRASLEDLGWADWVLSPREVQVTMCIGACP
SQFRAANMHAQIKTSLHRLKPDTVPAPCCVPASYNPMVLIQKTDTGVSL
QTYDDLLAKDCHCI

LCMS: Calculated mass (dimer): 24430: Observed mass (dimer): 24432

Intermediate 58

His-hGDF15 BCN Conjugate

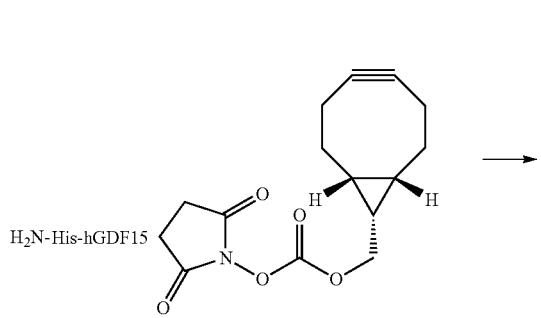

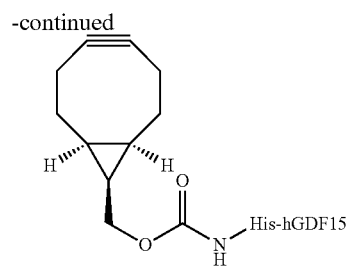

His-hGDF15

Seq: MHHHHHHMARNGDHCPLGPGRCCRLHTVRASLEDLGWADWVLSP
REVQVTMCIGACPSQFRAANMHAQIKTSLHRLKPDTVPAPCCVPASYNP
MVLIQKTDTGVSLQTYDDLLAKDCHCI
(SEQ ID NO: 2)

A stock solution of His-hGDF15 (Intermediate 52: 0.6 mL, 4.8 mg/mL) was diluted to 0.5 mg/mL with 30 mM NaOAc pH 4.5 buffer (5.2 mL). A 10 mg/mL stock solution of (1R,8S,9s)-bicyclo[6.1.0]non-4-yn-9-ylmethyl (2,5-dioxopyrrolidin-1-yl) carbonate (NHS-BCN) in DMSO (251 µL) was slowly added and the reaction placed on a shaker plate at 24° C. for 21 hrs. The reaction was diluted to 30 mL with 30 mM NaOAc pH 4.5 buffer and concentrated to 2 mL using a 10 kDa MWCO ultrafiltration cartridge (repeat 4×) to yield 2.5 mL of concentrate. Based on $A_{280}$ ($\varepsilon=29090M^{-1}$ $cm^{-1}$, 26730 g/mol) the concentrate was 0.93 mg/mL (2.33 mg, 80%): LCMS QT2_15-60 kDa_15 min_polar (method E). The resulting solution was analyzed by MALDI to indicate major conjugation to be +1 and +2 (N-terminus labeling of monomer and dimer)

| Degree of Labelling | Calculated | Observed | % TIC (MS+) Intensity |
|---|---|---|---|
| GDF15 | 26726 | 26726 | 26 |
| GDF15 + 1BCN | 26903 | 26904 | 43 |
| GDF15 + 2BCN | 27080 | 27080 | 23 |
| GDF15 + 3BCN | 27257 | 27256 | 9 |

His-hGDF15 + 1BCN (bicyclo[6.1.0]non-4-ynyl) corresponds to a reaction at the N-terminus amino functionality on the one molecule of the GDF15 homodimer.
His-hGDF15 + 2BCN corresponds to a reaction at the N-terminus amino functionality on both monomeric units of the GDF15 homodimer.
His-hGDF15 + 3BCN corresponds to a non-selective reaction at some other site of the GDF15 homodimer.

His-hGDF15 Seq:

MHHHH HHAR NGDHC PLGPG RCCRL HTVRA SLEDL GWADW
VLSPR EVQVT MCIGACPSQF RAANM HAQIK TSLHR LKPDT
VPAPC CVPAS YNPMV LIQKT DTGVS LQTYD DLLAK DCHCI.
(SEQ ID NO: 1)

A stock solution of His-hGDF15 (Intermediate 51: 7.04 mL, 1.42 mg/mL) was diluted to 0.5 mg/mL with 30 mM NaOAc pH 4.5 buffer (12.95 mL). A 10 mg/mL stock solution of (1R,8S,9s)-bicyclo[6.1.0]non-4-yn-9-ylmethyl (2,5-dioxopyrrolidin-1-yl) carbonate (NHS-BCN) in DMSO (0.88 mL) was slowly added and the reaction placed on a shaker plate at 24° C. for 24 hrs. An additional portion of the NHS-BCN stock solution (176 µL) was added, and the reaction maintained at 24° C. for 24 hrs. The reaction was diluted to 60 mL with 30 mM NaOAc pH 4.5 buffer and concentrated to 4 mL using a 10 kDa MWCO ultrafiltration cartridge (repeat 4×) to yield 4.1 mL of concentrate. Based on $A_{280}$ ($\varepsilon=29090M^{-1}$ $cm^{-1}$, 26700 g/mol) the concentrate was 2.19 mg/mL (8.98 mg, 89%): LCMS QT2_15-60 kDa_15 min_polar (Method E)

| Degree of Labelling | Calculated | Observed | % TIC (MS+) Intensity |
|---|---|---|---|
| GDF15 | 26468 | 26464 | 33 |
| GDF15 + 1BCN | 26645 | 26640 | 34 |
| GDF15 + 2BCN | 26822 | 26817 | 21 |
| GDF15 + 3BCN | 26999 | 26993 | 3 |

His-hGDF15 + 1BCN (bicyclo[6.1.0]non-4-ynyl) corresponds to a reaction at the N-terminus amino functionality on the one molecule of the GDF15 homodimer.
His-hGDF15 + 2BCN corresponds to a reaction at the N-terminus amino functionality on both monomeric units of the GDF15 homodimer.
His-hGDF15 + 3BCN corresponds to a non-selective reaction at some other site of the GDF15 homodimer.

Intermediate 59

His-hGDF15 BCN Conjugate

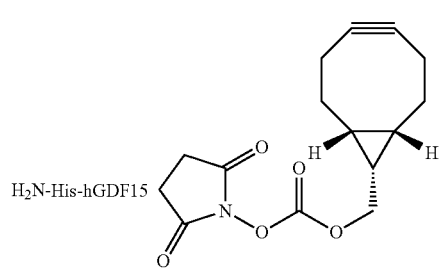

Intermediate 60

His-dog-GDF15-BCN

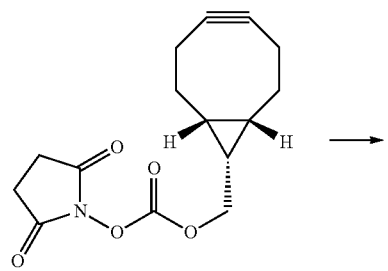

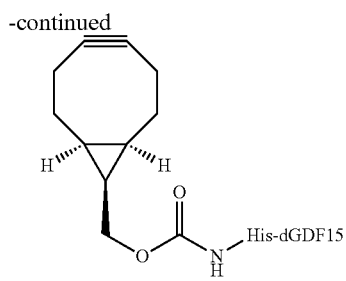

100 uL His-dGDF15 (0.68 mg/mL), 100 uL pH 4.5 buffer, 4 uL of a 10 mg/mL BCN-NHS solution was combined and incubated at rt for two days. The resulting mixture was washed with Amicon 10 k 4 times to give 200 uL solution, which was used in next step. The product was carried on as crude for further conversion to conjugate.

mM NaOAc pH 4.5 buffer while a 10 mg/mL solution of FA-PEG-$N_3$ (fatty acid-PEG23-azide) in water was prepared. To the GDF15 solution was added 10 eq of FA-PEG-$N_3$, and the reaction was placed on a shaker plate at 24° C. overnight. Reaction progress was monitored by LCMS (QTOF method 15-60 kDa_15 min_polar) and additional FA-PEG-$N_3$ was added, if necessary up to 50 eq, until no unreacted BCN labelled GDF15 was observed. The reaction was then diluted 5-10× with 30 mM NaOAc pH 4 buffer and the buffer exchanged with fresh buffer using a 10 kDa MWCO ultrafiltration cartridge (4 cycles of concentration followed by dilution). The sample was concentrated to ~1 mg/mL as measured by $A_{280}$, recoveries were quantitative to 34%. Final conjugates were analyzed by LCMS (QTOF method 15-60 kDa_15 min_polar) or Maldi.

EXAMPLES OF THE INVENTION

General procedure for His-hGDF15+fatty acid-PEG-$N_3$ click. BCN labelled GDF15 was diluted to 0.5 mg/mL in 30

Example 1

His-hGDF15 BCN (1-59) Conjugated to Intermediate 21

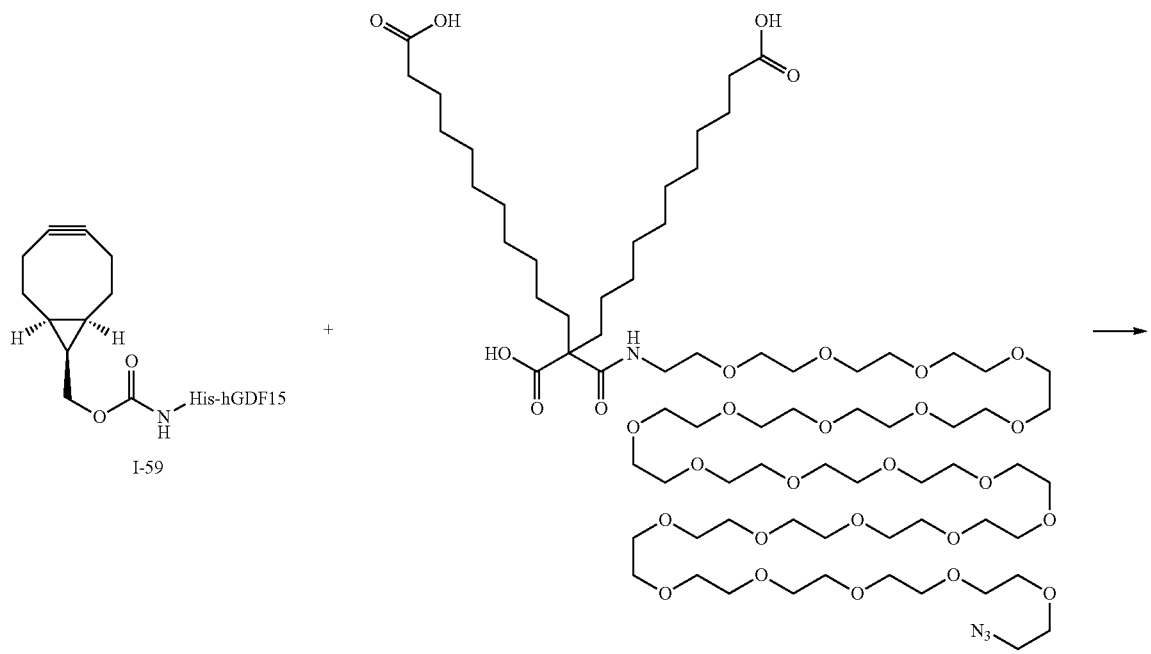

-continued

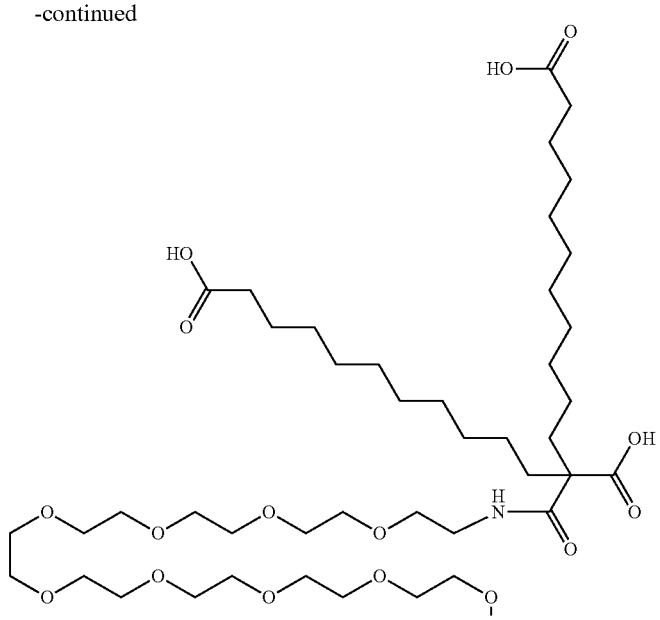

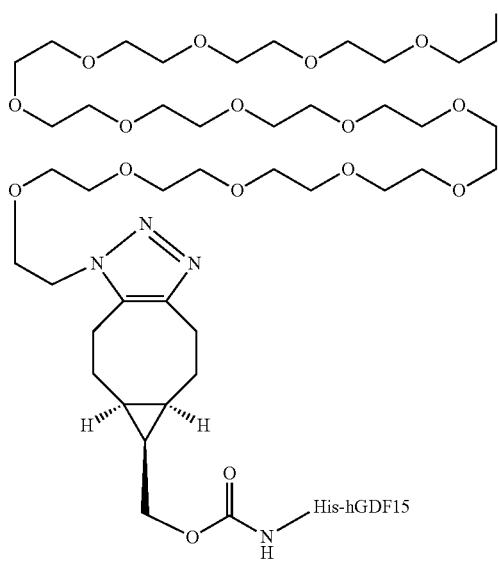

| Degree of Labelling | Calculated | Observed | % AUC @ 280 nm |
|---|---|---|---|
| His-hGDF15 | 26468 | 26466 | 18 |
| His-hGDF15 + 1FA | 28198 | 28192 | 36 |
| His-hGDF15 + 2FA | 29928 | 29926 | 35 |
| His-hGDF15 + 3FA | 31658 | 31654 | 11 |

His-hGDF15 + 1FA (Fatty acid) corresponds to a reaction at the N-terminus amino functionality on the one molecule (one monomeric unit) of the GDF15 homodimer.

His-hGDF15 + 2FA (Fatty acid) corresponds to a reaction at the N-terminus amino functionality on both monomeric units of the GDF15 homodimer.

His-hGDF15 + 3FA (Fatty acid) corresponds to a non-selective reaction at some other site of the GDF15 homodimer.

Example 2
His-hGDF15 BCN (1-59) Conjugated to Intermediate 44
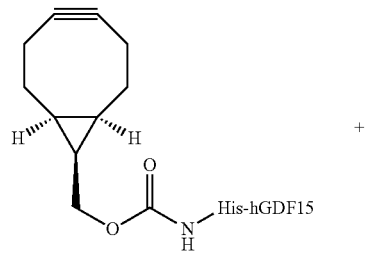
+
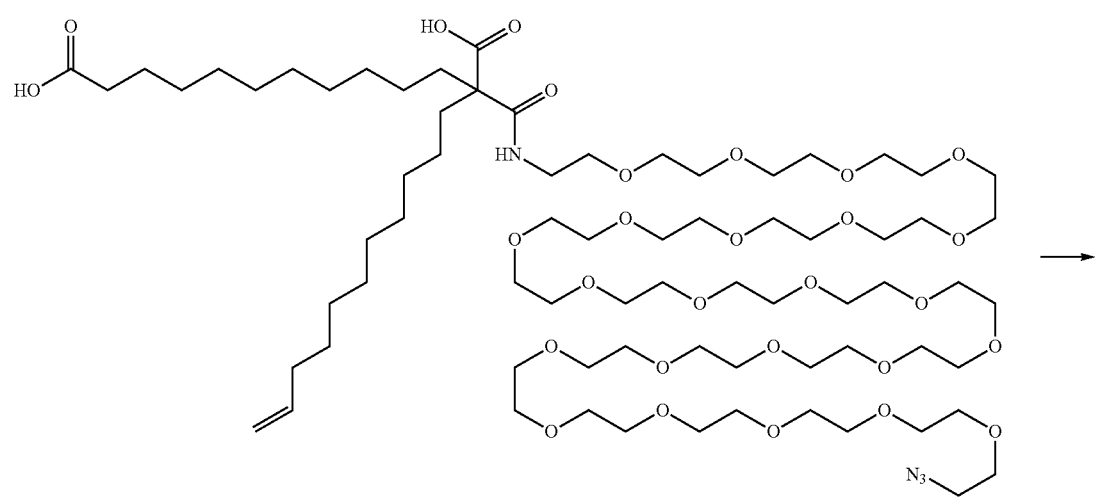
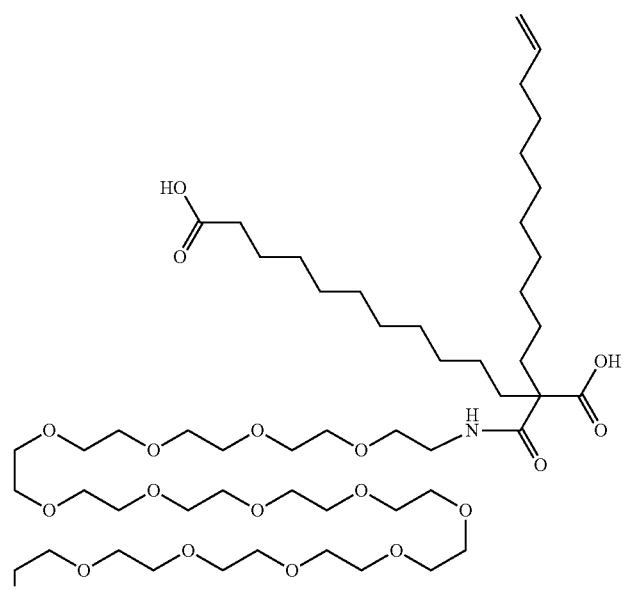

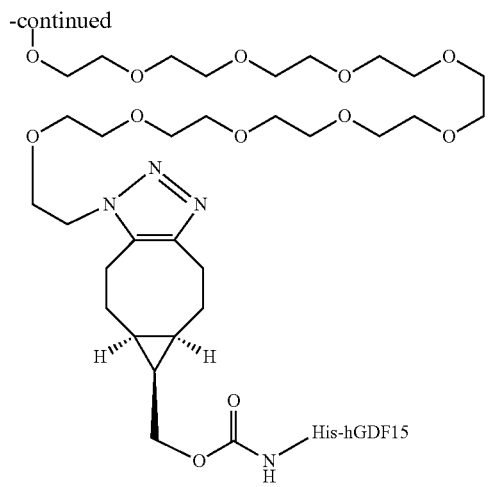

20

| Degree of Labelling | Calculated | Observed | % AUC @ 280 nm |
|---|---|---|---|
| His-hGDF15 | 26464 | 26464 | 38 |
| His-hGDF15 + 1FA | 28162 | 28162 | 33 |
| His-hGDF15 + 2FA | 29860 | 29860 | 21 |
| His-hGDF15 + 3FA | 31558 | 31558 | 9 |

His-hGDF15 + 1FA (Fatty acid) corresponds to a reaction at the N-terminus amino functionality on the one molecule (one monomeric unit) of the GDF15 homodimer.
His-hGDF15 + 2FA (Fatty acid) corresponds to a reaction at the N-terminus amino functionality on both monomeric units of the GDF15 homodimer.
His-hGDF15 + 3FA (Fatty acid) corresponds to a non-selective reaction at some other site of the GDF15 homodimer.

Example 3

His-hGDF15 BCN (1-59) Conjugated to Intermediate 29A

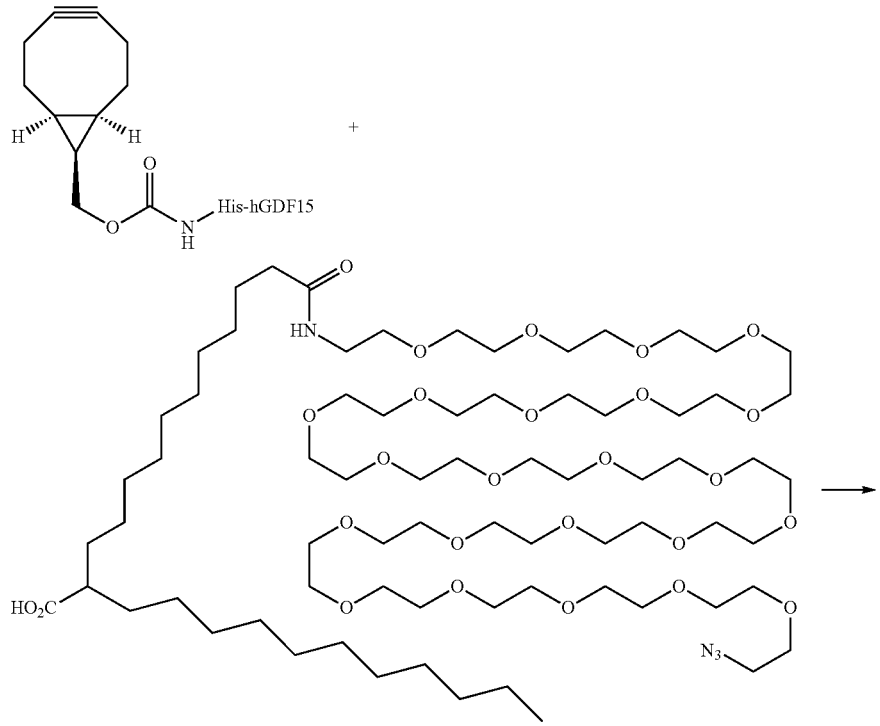

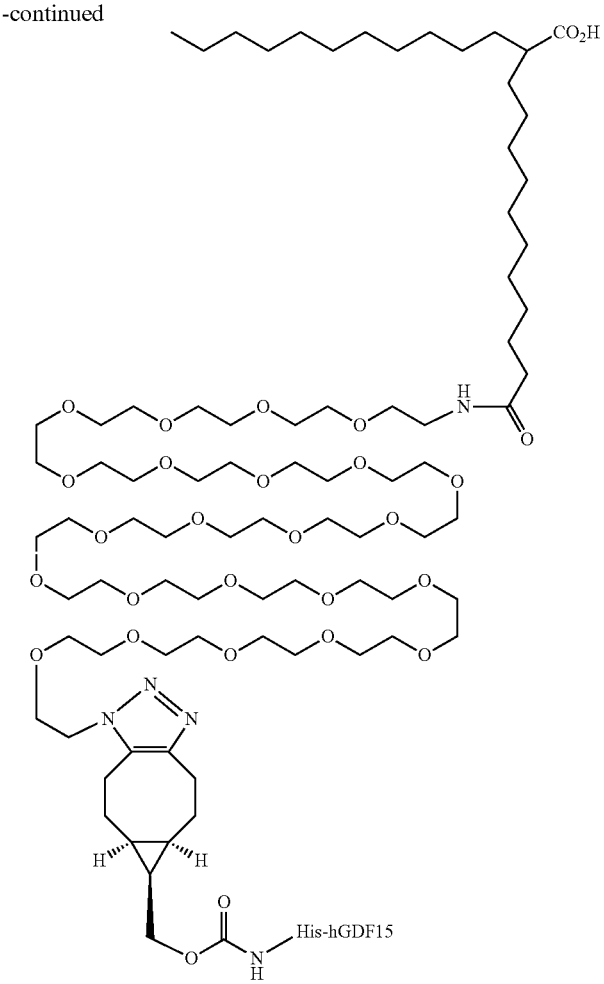

| Degree of Labelling | Calculated | Observed | % AUC @ 280 nm |
|---|---|---|---|
| His-hGDF15 | 26464 | 26466 | 50 |
| His-hGDF15 + 1FA | 28124 | 28120 | 28 |
| His-hGDF15 + 2FA | 29780 | 29776 | 16 |
| His-hGDF15 + 3FA | 31436 | 31432 | 7 |

His-hGDF15 + 1FA (Fatty acid) corresponds to a reaction at the N-terminus amino functionality on the one molecule (one monomeric unit) of the GDF15 homodimer.
His-hGDF15 + 2FA (Fatty acid) corresponds to a reaction at the N-terminus amino functionality on both monomeric units of the GDF15 homodimer.
His-hGDF15 + 3FA (Fatty acid) corresponds to a non-selective reaction at some other site of the GDF15 homodimer.

Example 4

His-hGDF15 BCN (Intermediate 58) Conjugated Intermediate 24

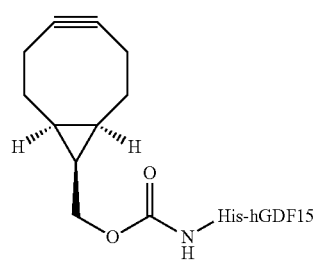

+

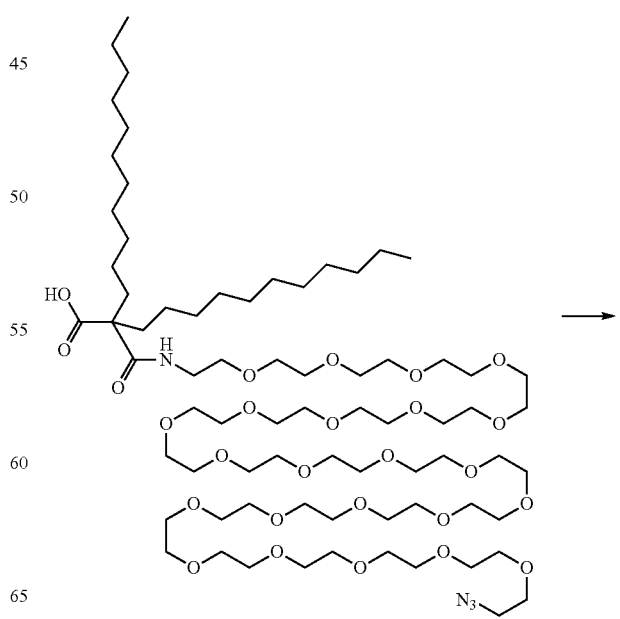

-continued

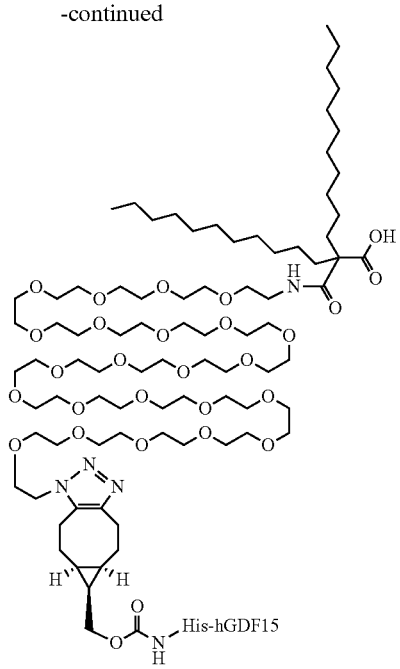

| Degree of Labelling | Calculated | Observed | % AUC @ 280 nm |
|---|---|---|---|
| His-hGDF15 | 26726 | 26728 | 27 |
| His-hGDF15 + 1FA | 28396 | 28398 | 42 |
| His-hGDF15 + 2FA | 30066 | 30068 | 24 |
| His-hGDF15 + 3FA | 31736 | 31738 | 7 |

His-hGDF15 + 1FA (Fatty acid) corresponds to a reaction at the N-terminus amino functionality on the one molecule (one monomeric unit) of the GDF15 homodimer.

His-hGDF15 + 2FA (Fatty acid) corresponds to a reaction at the N-terminus amino functionality on both monomeric units of the GDF15 homodimer.

His-hGDF15 + 3FA (Fatty acid) corresponds to a non-selective reaction at some other site of the GDF15 homodimer.

Example 5

His-hGDF15 BCN (1-58) Conjugated to Intermediate 29

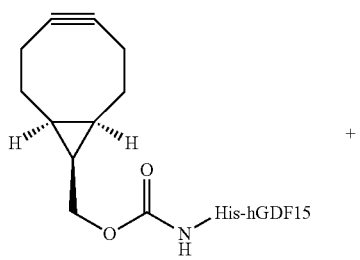

+

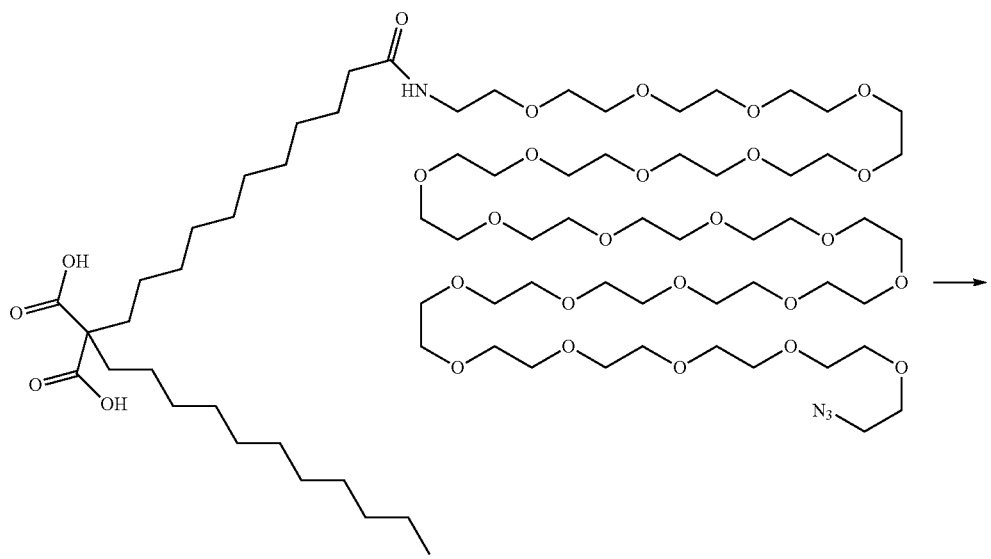

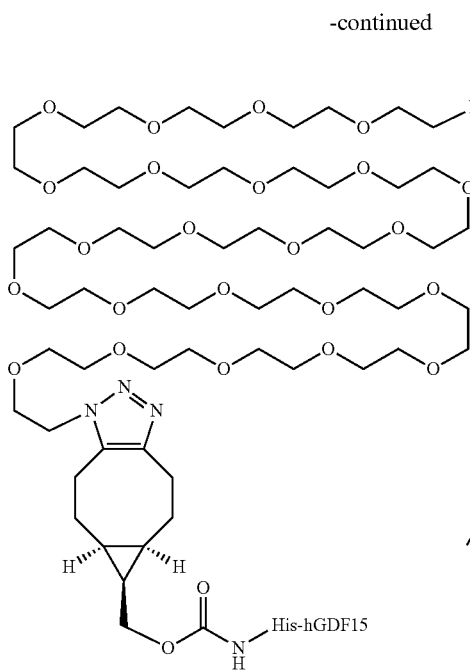

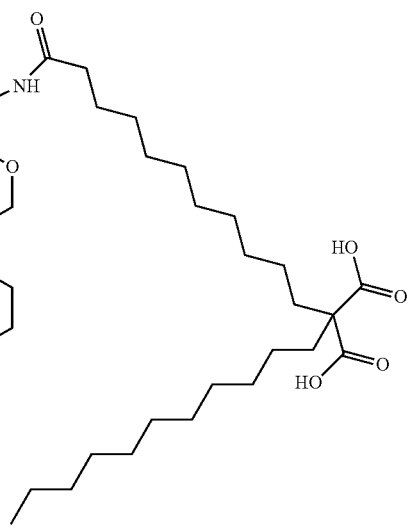

| Degree of Labelling | Calculated | Observed | % AUC @ 280 nm |
|---|---|---|---|
| His-hGDF15 | 26726 | 26728 | 30 |
| His-hGDF15 + 1FA | 28425 | 28426 | 36 |
| His-hGDF15 + 2FA | 30125 | 30126 | 23 |
| His-hGDF15 + 3FA | 31825 | 31740 | 12 |

His-hGDF15 + 1FA (Fatty acid) corresponds to a reaction at the N-terminus amino functionality on the one molecule of the GDF15 homodimer.
His-hGDF15 + 2FA (Fatty acid) corresponds to a reaction at the N-terminus amino functionality on both monomeric units of the GDF15 homodimer.
His-hGDF15 + 3FA (Fatty acid) corresponds to a non-selective reaction at some other site of the GDF15 homodimer.

Example 6

His-hGDF15 BCN (1-58) Conjugated to Intermediate 55

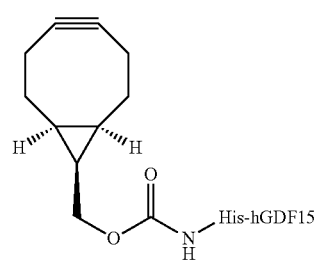

+

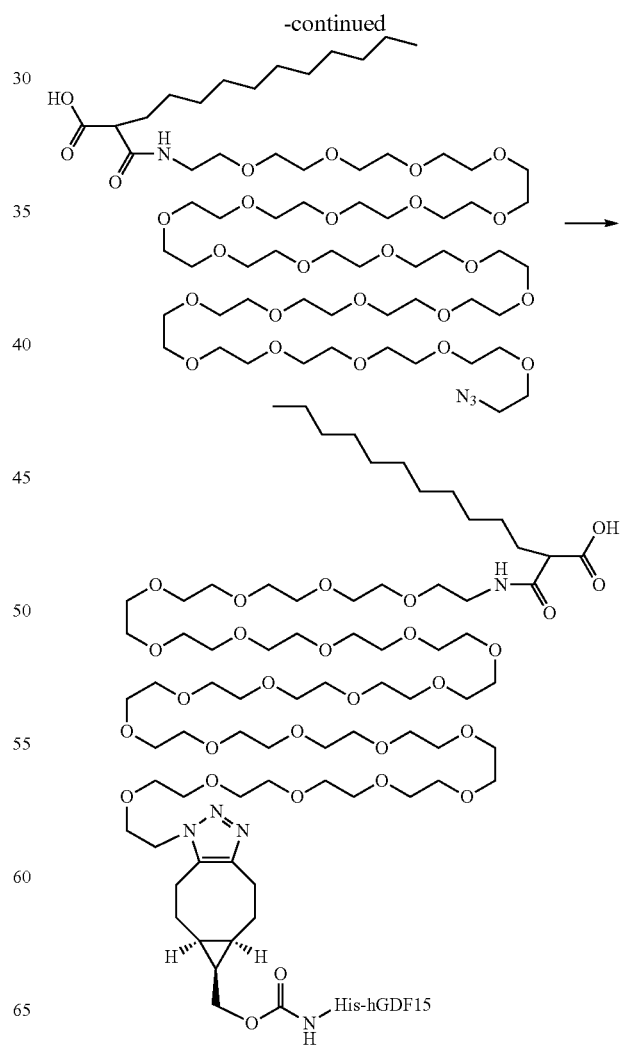

→

| Degree of Labelling | Calculated | Observed | % AUC @ 280 nm |
|---|---|---|---|
| His-hGDF15 | 26726 | 26728 | 28 |
| His-hGDF15 + 1FA | 28242 | 28243 | 36 |
| His-hGDF15 + 2FA | 29758 | 29759 | 28 |
| His-hGDF15 + 3FA | 31274 | 31275 | 11 |

His-hGDF15 + 1FA (Fatty acid) corresponds to a reaction at the N-terminus amino functionality on the one molecule of the GDF15 homodimer.

His-hGDF15 + 2FA (Fatty acid) corresponds to a reaction at the N-terminus amino functionality on both monomeric units of the GDF15 homodimer.

His-hGDF15 + 3FA (Fatty acid) corresponds to a non-selective reaction at some other site of the GDF15 homodimer.

Example 7

His-hGDF15 BCN (1-58) Conjugated to Intermediate 6A

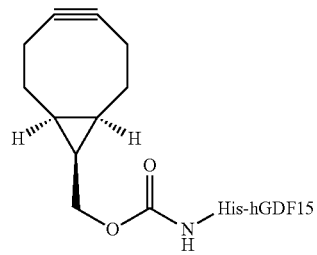

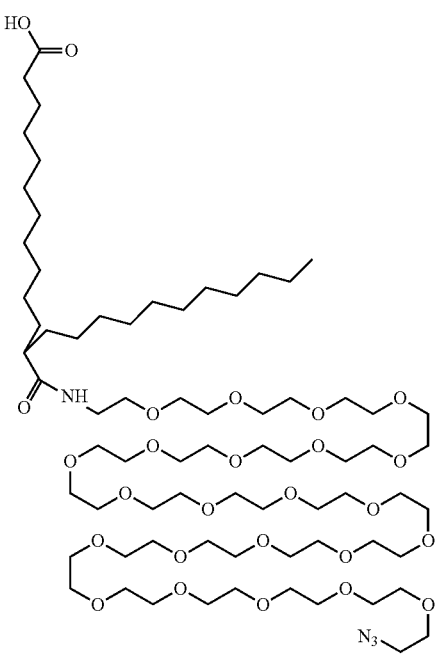

⟶

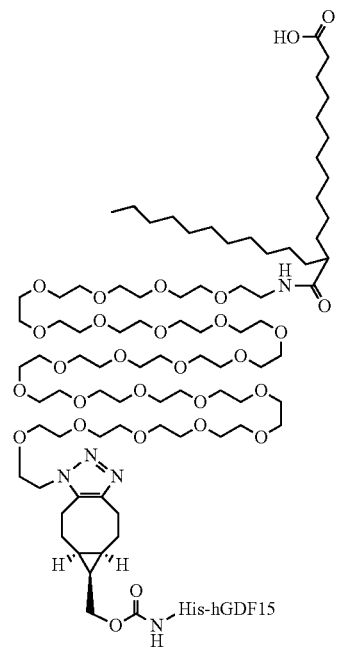

| Degree of Labelling | Calculated | Observed | % AUC @ 280 nm |
|---|---|---|---|
| His-hGDF15 | 26726 | 26728 | 28 |
| His-hGDF15 + 1FA | 28382 | 28382 | 42 |
| His-hGDF15 + 2FA | 30038 | 30040 | 29 |
| His-hGDF15 + 3FA | 31916 | n/a | n/a |

His-hGDF15 + 1FA (Fatty acid) corresponds to a reaction at the N-terminus amino functionality on the one molecule (one monomeric unit) of the GDF15 homodimer.

His-hGDF15 + 2FA (Fatty acid) corresponds to a reaction at the N-terminus amino functionality on both monomeric units of the GDF15 homodimer.

His-hGDF15 + 3FA (Fatty acid) corresponds to a non-selective reaction at some other site of the GDF15 homodimer.

Example 9

His-hGDF15 BCN (1-58) Conjugated to Intermediate 30

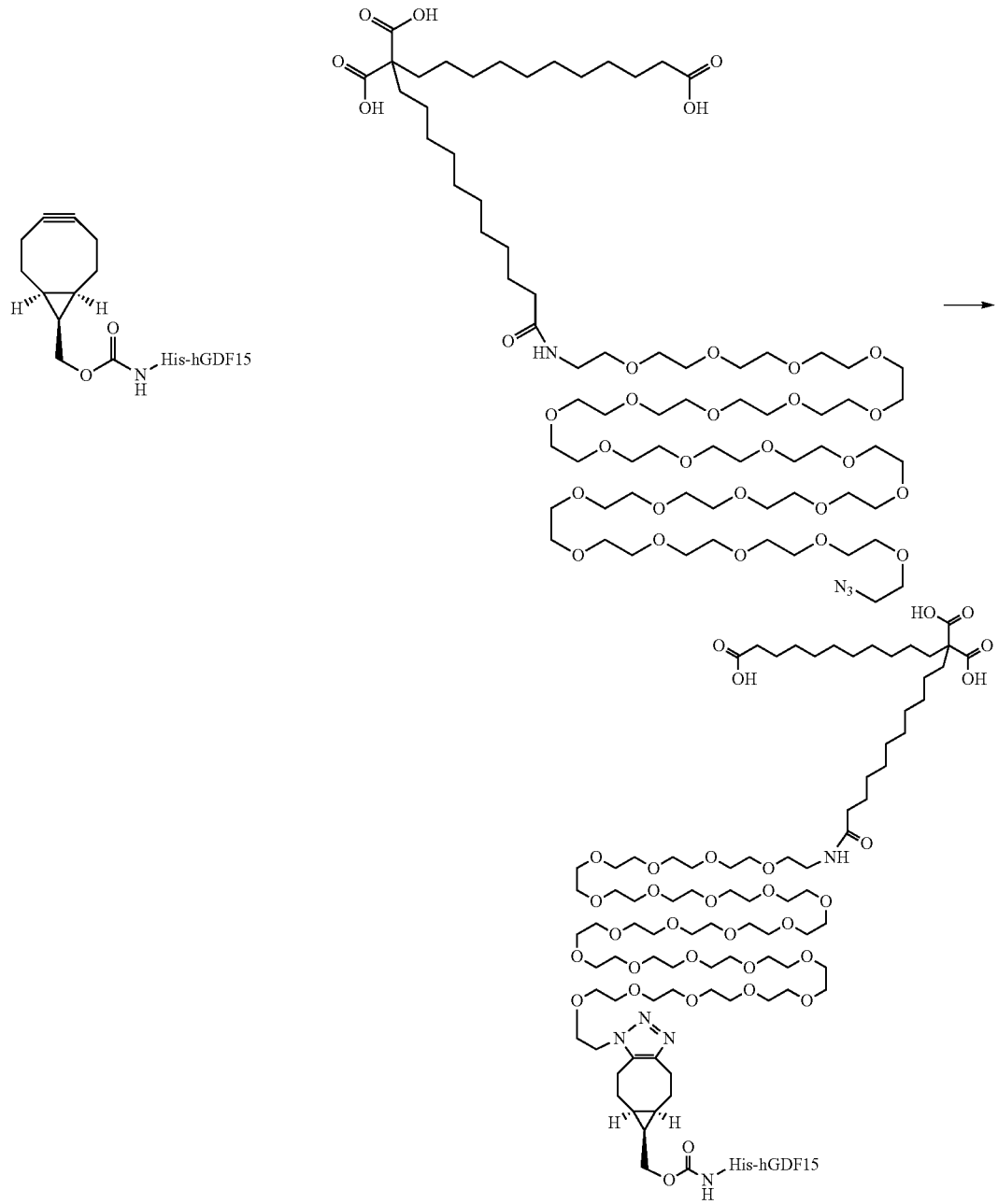

| Degree of Labelling | Calculated | Observed | % AUC @ 280 nm |
|---|---|---|---|
| His-hGDF15 | 26726 | 26728 | 21 |
| His-hGDF15 + 1FA | 28456 | 28456 | 47 |
| His-hGDF15 + 2FA | 30186 | 30188 | 32 |
| His-hGDF15 + 3FA | 31916 | n/a | n/a |

His-hGDF15 + 1FA (Fatty acid) corresponds to a reaction at the N-terminus amino functionality on the one molecule (monomeric unit) of the GDF15 homodimer.
His-hGDF15 + 2FA (Fatty acid) corresponds to a reaction at the N-terminus amino functionality on both molecules (monomeric units) of the GDF15 homodimer.
His-hGDF15 + 3FA (Fatty acid) corresponds to a non-selective reaction at some other site of the GDF15 homodimer.

Example 10

His-hGDF15 BCN (1-58) Conjugated to Intermediate 12

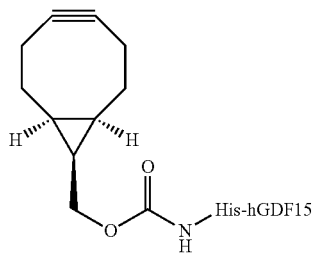

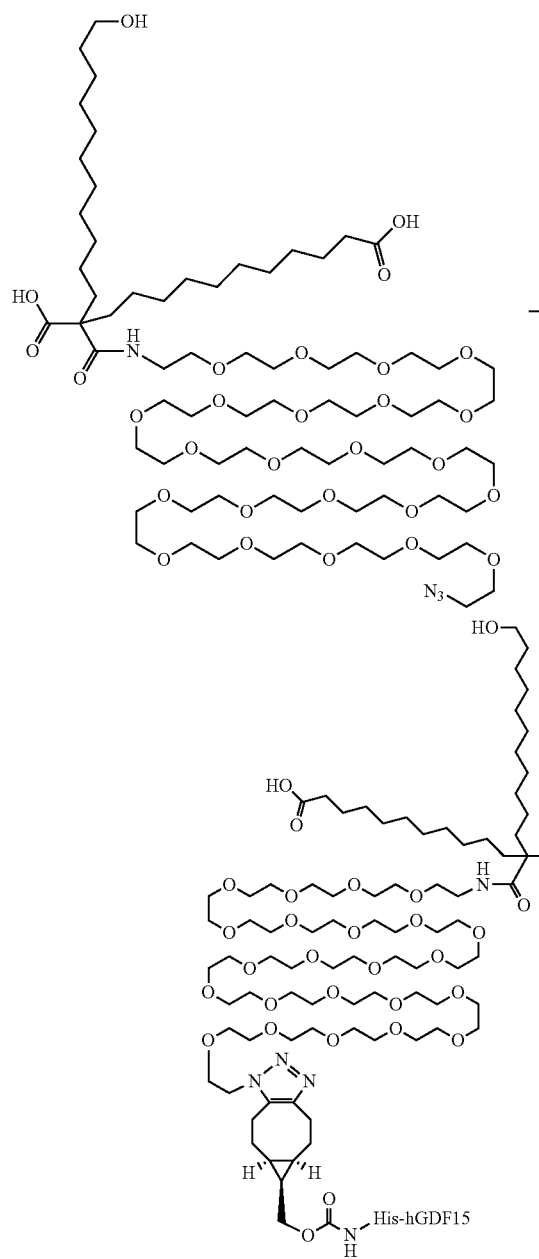

| Degree of Labelling | Calculated | Observed | % AUC @ 280 nm |
|---|---|---|---|
| His-hGDF15 | 26726 | 26729 | 17 |
| His-hGDF15 + 1FA | 28442 | 28445 | 37 |
| His-hGDF15 + 2FA | 30158 | 30158 | 32 |
| His-hGDF15 + 3FA | 31874 | 31877 | 13 |

His-hGDF15 + 1FA (Fatty acid) corresponds to a reaction at the N-terminus amino functionality on the one molecule (one monomeric unit) of the GDF15 homodimer.

His-hGDF15 + 2FA (Fatty acid) corresponds to a reaction at the N-terminus amino functionality on both molecules (monomeric units) of the GDF15 homodimer.

His-hGDF15 + 3FA (Fatty acid) corresponds to a non-selective reaction at some other site of the GDF15 homodimer.

Example 13

His-hGDF15 BCN (1-59) Conjugated to Intermediate 6

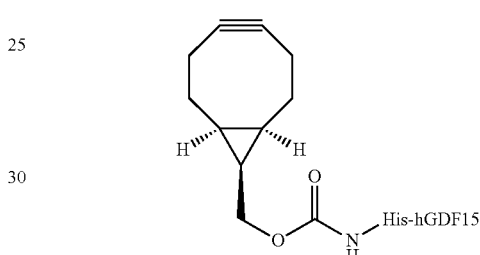

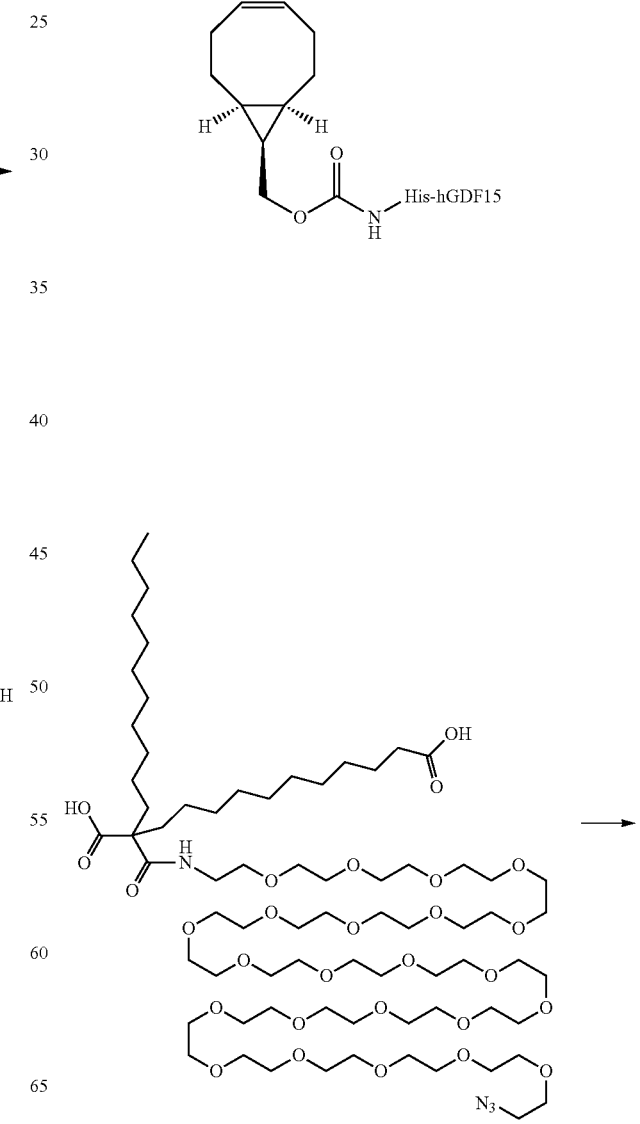

-continued

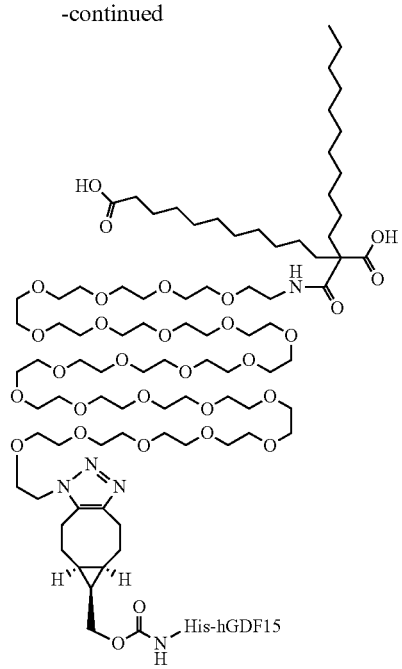

| Degree of Labelling | Calculated | Observed | % AUC @ 280 nm |
|---|---|---|---|
| His-hGDF15 | 26468 | 26464 | 28 |
| His-hGDF15 + 1FA | 28168 | 28164 | 42 |
| His-hGDF15 + 2FA | 29868 | 29864 | 21 |
| His-hGDF15 + 3FA | 31568 | 31564 | 10 |

His-hGDF15 + 1FA (Fatty acid) corresponds to a reaction at the N-terminus amino functionality on the one molecule (one monomeric unit) of the GDF15 homodimer.
His-hGDF15 + 2FA (Fatty acid) corresponds to a reaction at the N-terminus amino functionality on both molecules (both monomeric units) of the GDF15 homodimer.
His-hGDF15 + 3FA (Fatty acid) corresponds to a non-selective reaction at some other site of the GDF15 homodimer.

Example 14

His-hGDF15 BCN (1-58) Conjugated to Intermediate 17

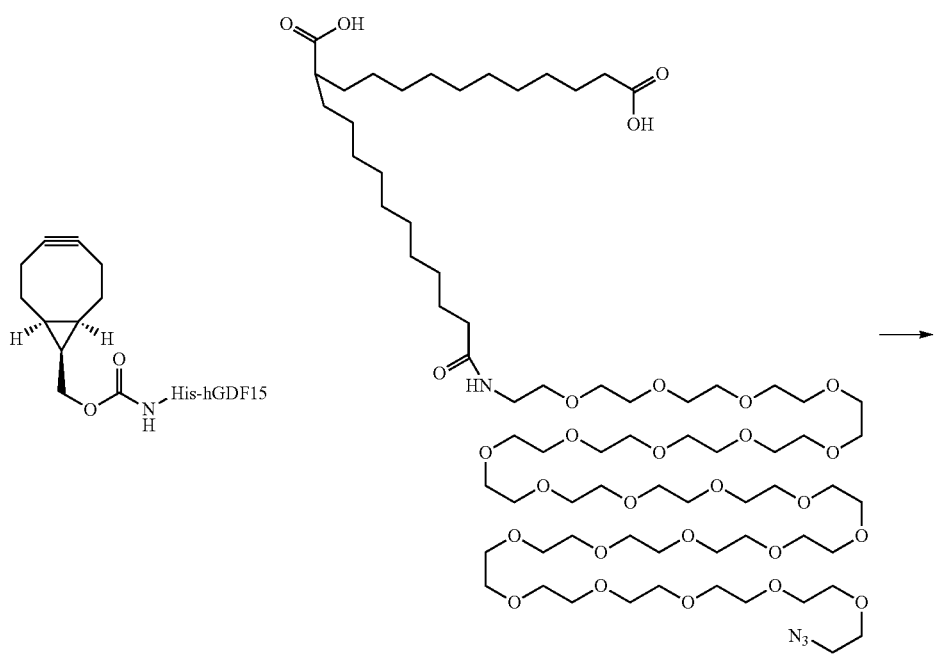

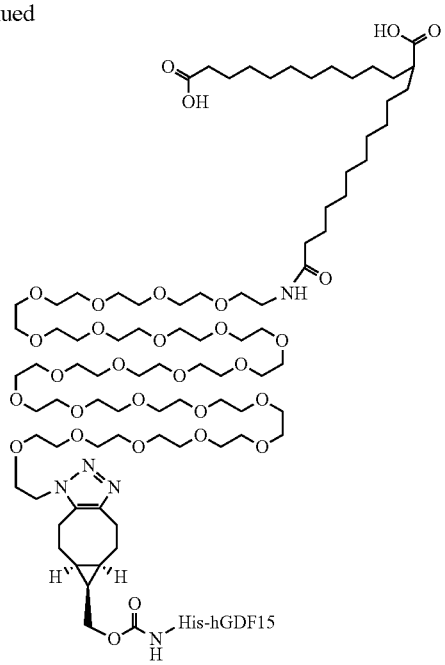

| Degree of Loading | Calculated | Observed | % AUC @ 280 nm |
|---|---|---|---|
| His-hGDF15 | 26726 | 26728 | 18 |
| His-hGDF15 + 1FA | 28413 | 28414 | 34 |
| His-hGDF15 + 2FA | 30100 | 30054 | 35 |
| His-hGDF15 + 3FA | 31787 | 31726 | 13 |

His-hGDF15 + 1FA (Fatty acid) corresponds to a reaction at the N-terminus amino functionality on the one molecule (one monomeric unit) of the GDF15 homodimer.
His-hGDF15 + 2FA (Fatty acid) corresponds to a reaction at the N-terminus amino functionality on both molecules (both monomeric units) of the GDF15 homodimer.
His-hGDF15 + 3FA (Fatty acid) corresponds to a non-selective reaction at some other site of the GDF15 homodimer.

Example 15

Step 1:

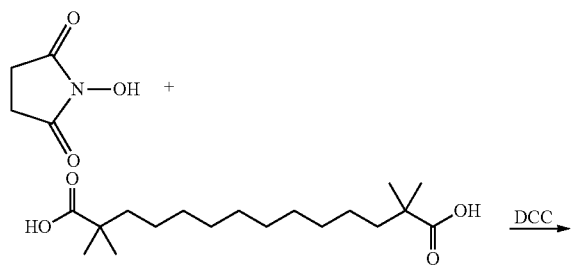

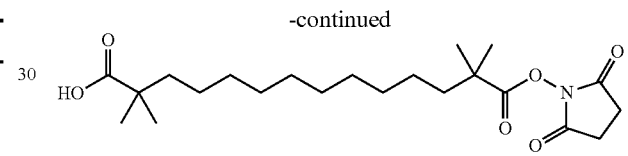

To a solution of 2,2,13,13-tetramethyltetradecanedioic acid (Aldrich CPR, order number PH002322) (100 mg, 0.318 mmol) and N-hydroxysuccinimide (40.3 mg, 0.35 mmol) in THF (5 mL) was added a solution of DCC (65.6 mg, 0.318 mmol) in THF (5 mL), and the mixture was stirred at r.t. overnight. Partial conversion to the desired product was observed by LC-MS analysis. The mixture was filtered, and the filtrate was concentrated. The residue was re-dissolved in DCM (40 mL), and washed with water, dried over Na2SO4, and purified by silica chromatography eluting with a heptane/EtOAc/DCC (10:1:1) to give a mixture. The mixture was further purified by MS triggered acid HPLC [(55-80% ACN 3.5 min gradient): rt=2.48 min, mass calculated: 314.46 mass observed: 314.00] to give to give clean product (50 mg, 38.2% yield) and to recover starting material.

Step 2:

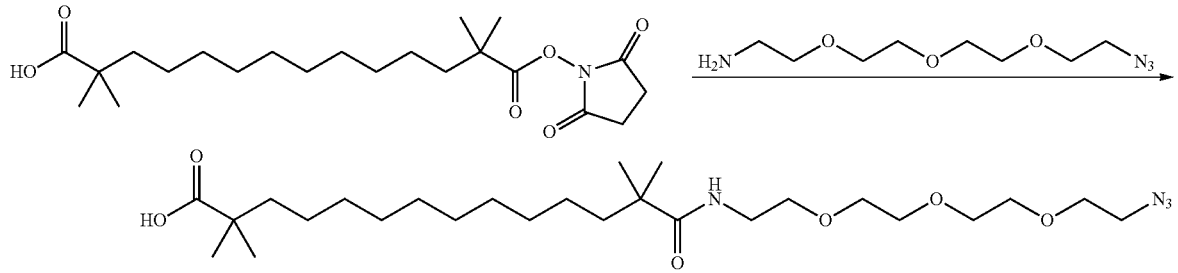

To a solution of NHS-2,2,13,13-tetramethyltetradecane-dioic acid (10 mg, 0.024 mmol) in DCM (3 mL) was added azido-dPEG3-amine (10 mg, 0.049 mmol) and DIPEA (9 uL, 0.049 mmol), and the mixture was stirred at r.t. for 1 h. The mixture was concentrated, re-dissolved in MeOH (3 mL) and purified by MS-triggered HPLC (55-80% ACN 3.5 min gradient rt=2.35, mass expected: 514.70 mass observed: 514.40) to give 7 mg clean product in 58% yield.

Step 3:

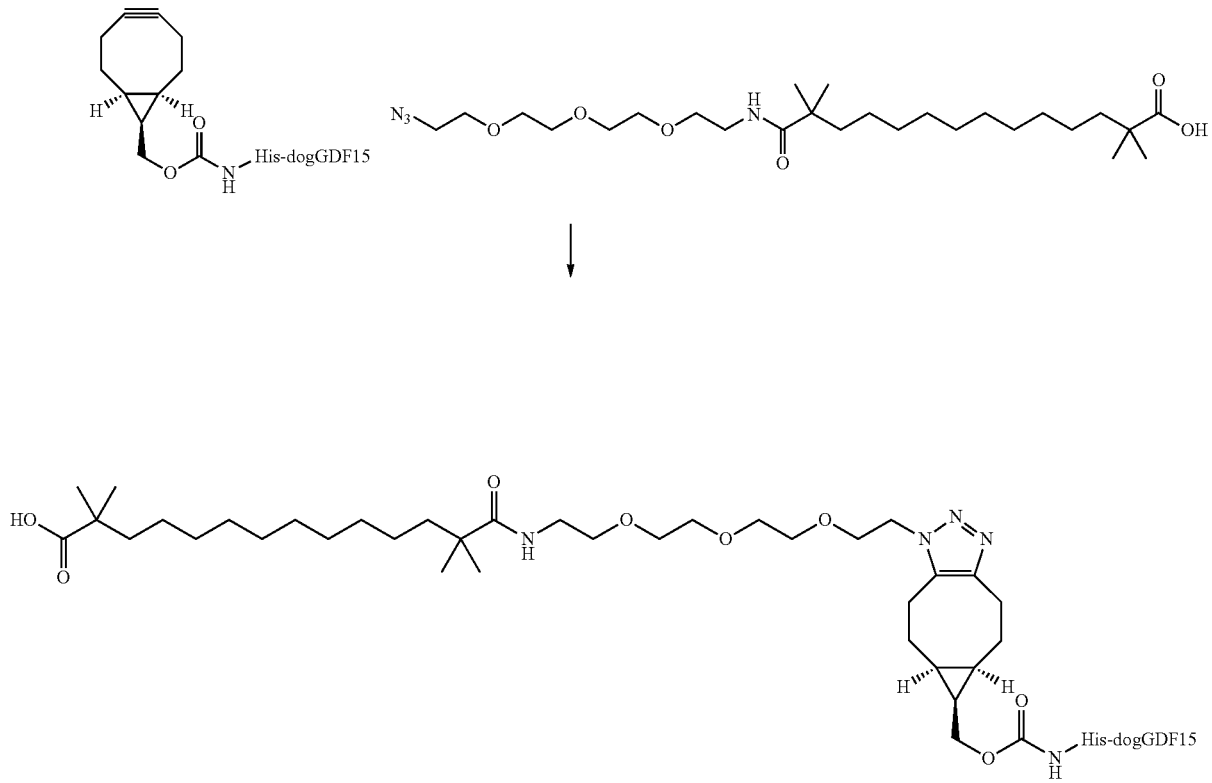

To a solution of 100 L BCN-dGDF15 (1-60: 0.68 mg/mL in pH 4.5 buffer) was added pH 4.5 buffer (100 μL) and azide (6 μL in DMSO, 10 mg/mL), and the mixture was incubated at r.t. overnight. The mixture was washed by Amicon 10k 4 times. The resulting solution was analyzed by MALDI to indicate major conjugation to +1 and +2. Maldi: Calculated mass: 26546 Observed mass: 26483; Calculated mass: 27060 Observed mass: 27128; Calculated mass: 27574 Observed mass: 27789.

Example 16

His-hGDF15 BCN (1-58) Conjugated to Intermediate 44

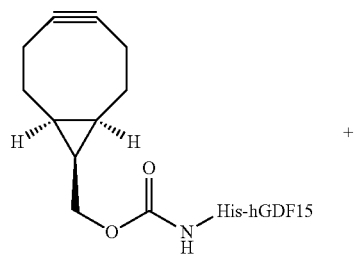

+

-continued

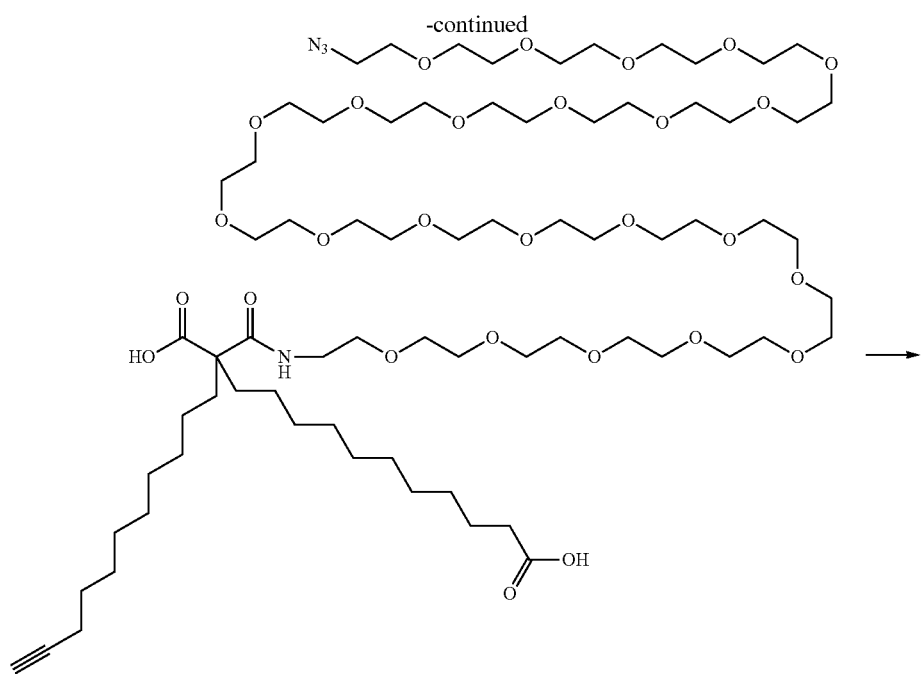

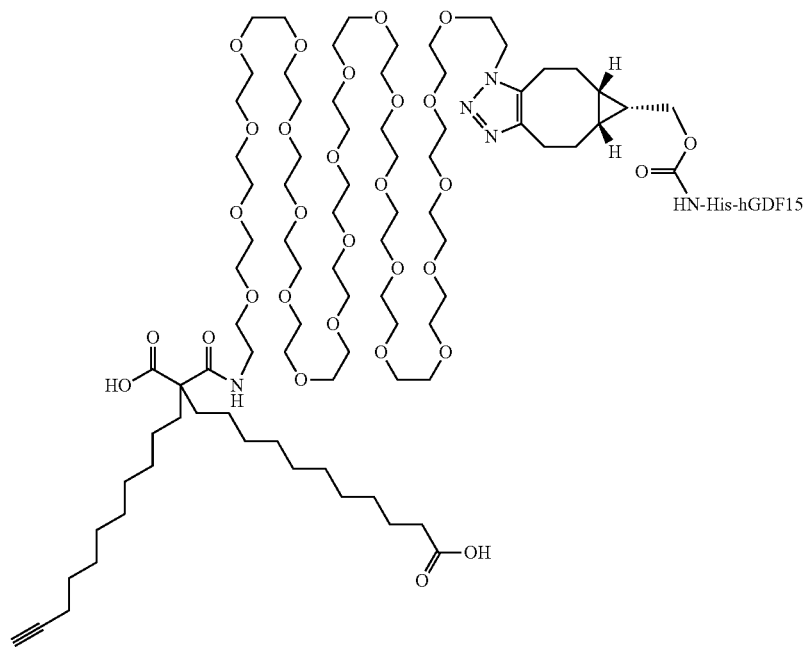

| Degree of Labelling | Calculated | Observed | % AUC @ 280 nm |
|---|---|---|---|
| His-hGDF15 | 26726 | 26728 | 45 |
| His-hGDF15-BCN | 26902 | 26904 | 21 |
| His-hGDF15 + 1FA | 28422 | 28360 | 25 |
| His-hGDF15 + 2FA | 29868 | 30012 | 9 |

His-hGDF15 + 1FA (Fatty acid) corresponds to a reaction at the N-terminus amino functionality on the one molecule (one monomeric unit) of the GDF15 homodimer.
His-hGDF15 + 2FA (Fatty acid) corresponds to a reaction at the N-terminus amino functionality on both molecules (both monomeric units) of the GDF15 homodimer.

Example 17

His-hGDF15-BCN Conjugated to Intermediate 52

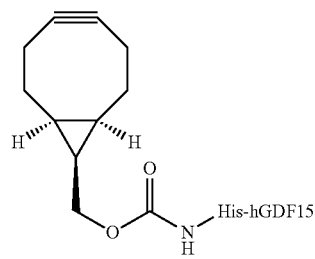

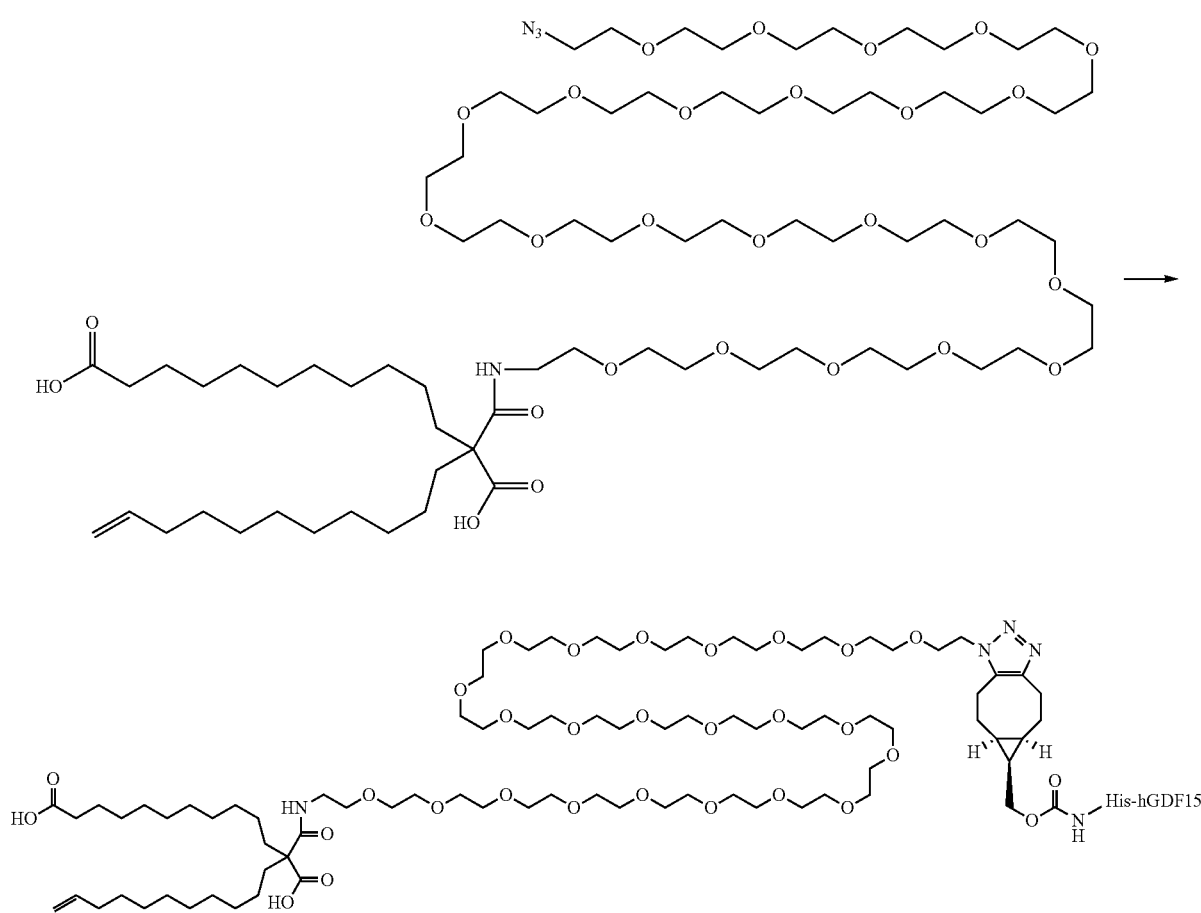

To a solution of 3 mL cyclooctyne GDF15 (1-58: 0.46 mg/mL, 0.051 umol) in 7 mL of pH 4 sodium acetate buffer was added fatty acid peg azide (15 uL in 35 mg/mL DMSO, 0.36umol), and the mixture was incubated at r.t. overnight. Complete conversion was observed by MALDI analysis. Product purified by amicon filtration 10kD washing three times to give 4.3 ml of 0.29 mg/ml desired product in 90% yield. Maldi: cyclooctyne sm ~5% expected mass: 26902 mass observed: 26997; +1 fatty acid ~40% expected mass: 28421 observed mass: 28525; +2 fatty acids ~50% expected mass: 29940 observed mass: 30191+3 fatty acids 5% expected mass: 31459 observed mass:31874.

Example 18

MH-(199-308)GDF15 (1-54) Conjugated to Intermediate 37

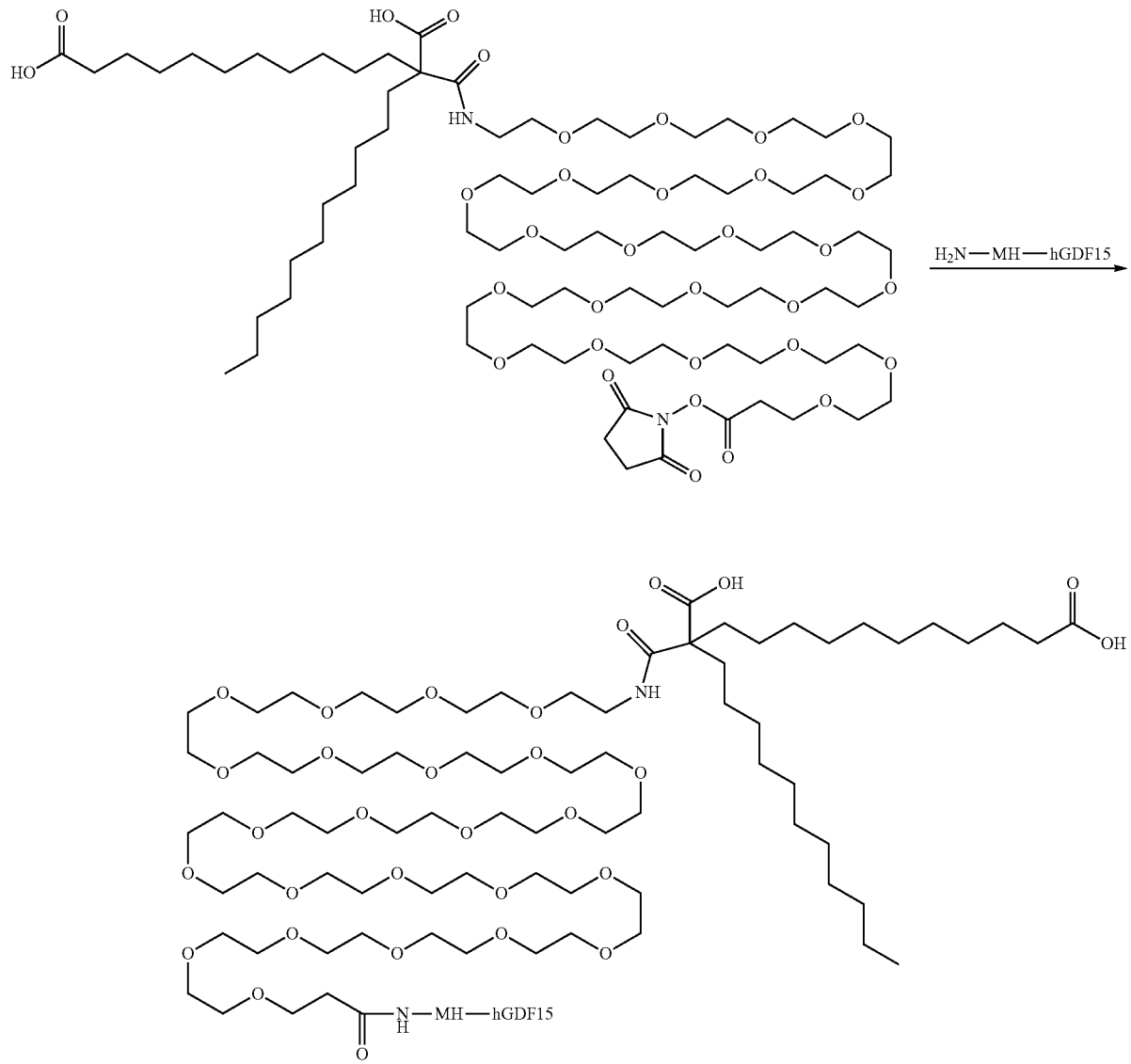

MH-(199-308)-GDF15 (Intermediate 54: 0.393 mL, 0.028 μmol, 1.78 mg/mL) was added to 1.5 ml of 30 mM sodium acetate buffer NHS fatty acid (474 ug, 0.284umol, 10 mg/ml) was added to solution. After 5 hours, reaction was complete according to MALDI. Products were purified by washing 5 times using amicon ultrafiltration 10kD to give 575 ug of conjugate in 73% yield. MALDI: sm (18%), expected mass: 24638 observed mass: 24735; +1 fatty acid (38%) expected mass: 26192 observed mass: 26268; +2 fatty acid (40%) expected mass: 27746 observed mass: 27798; +3 fatty acid (4%) expected mass: 29300 observed mass: 29333.

Example 19A

His-hGDF15 (1-59) Conjugated to Intermediate 37

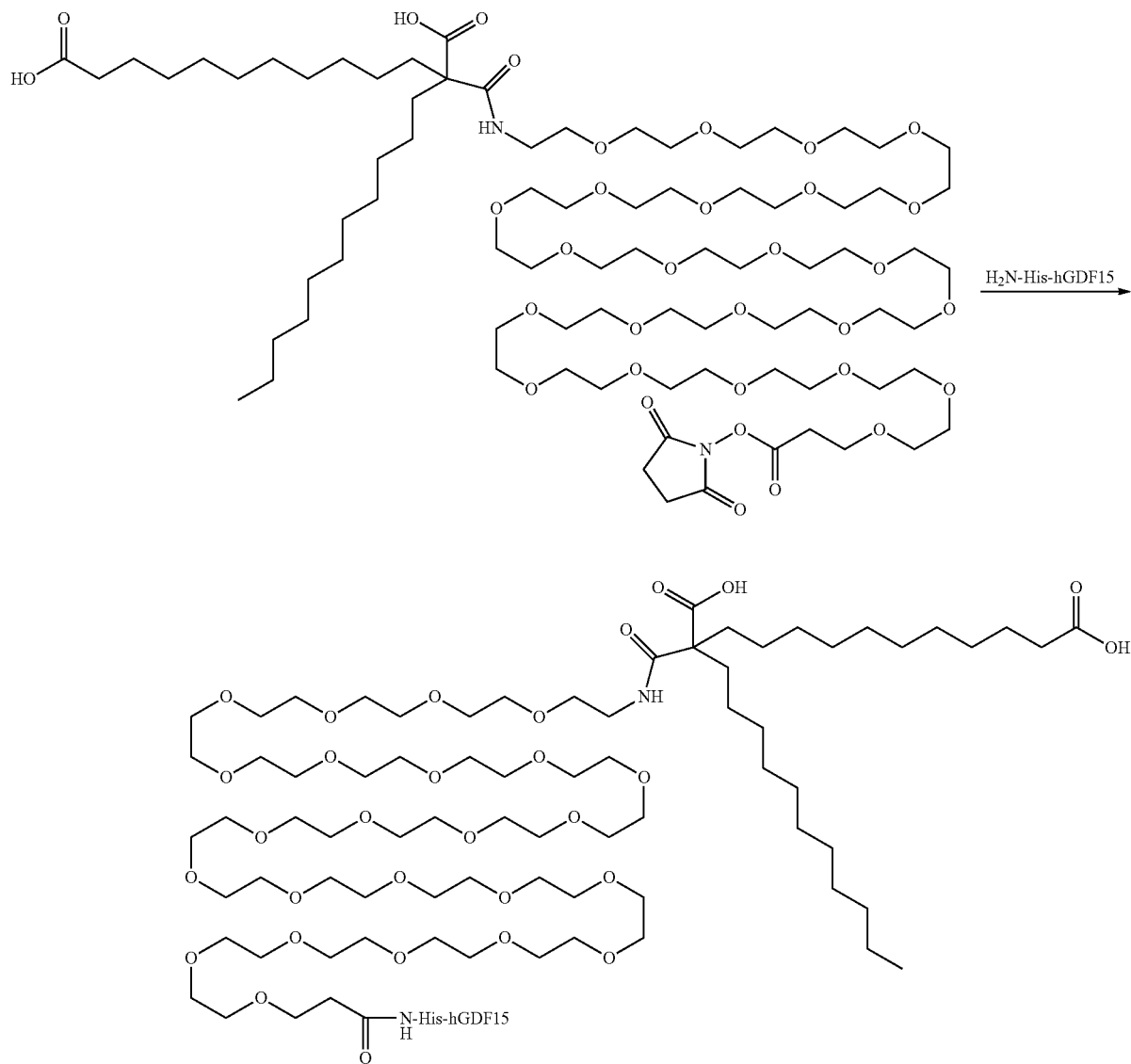

His-GDF15 (0.493 ml, 0.026 µmol, 1.42 mg/ml) was added to 1.5 ml of 30 mM sodium acetate pH=4 buffer nhs fatty acid (0.221 mg, 0.132 umol, 10 mg/mL) was added to the solution. Overnight the reaction was not complete so 2.5 more equivalents of fatty acid NHS (0.110 mg, 0.066 umol, 10 mg/mL) were added and after 5 hrs Maldi showed+2 conjugate as major product. Product was purified by washing 5 times using amicon ultrafiltration 10kD to give 565 ug of conjugate in 76% yield. MALDI: sm (18%), expected mass: 26468 observed mass: 26553; +1 fatty acid (38%) expected mass: 28022 observed mass: 28099; +2 fatty acid (40%) expected mass: 29576 observed mass: 29649; +3 fatty acid (4%) expected mass: 31130 observed mass: 31201.

Example 19B

AHA-hGDF15 Conjugated with Intermediate 37

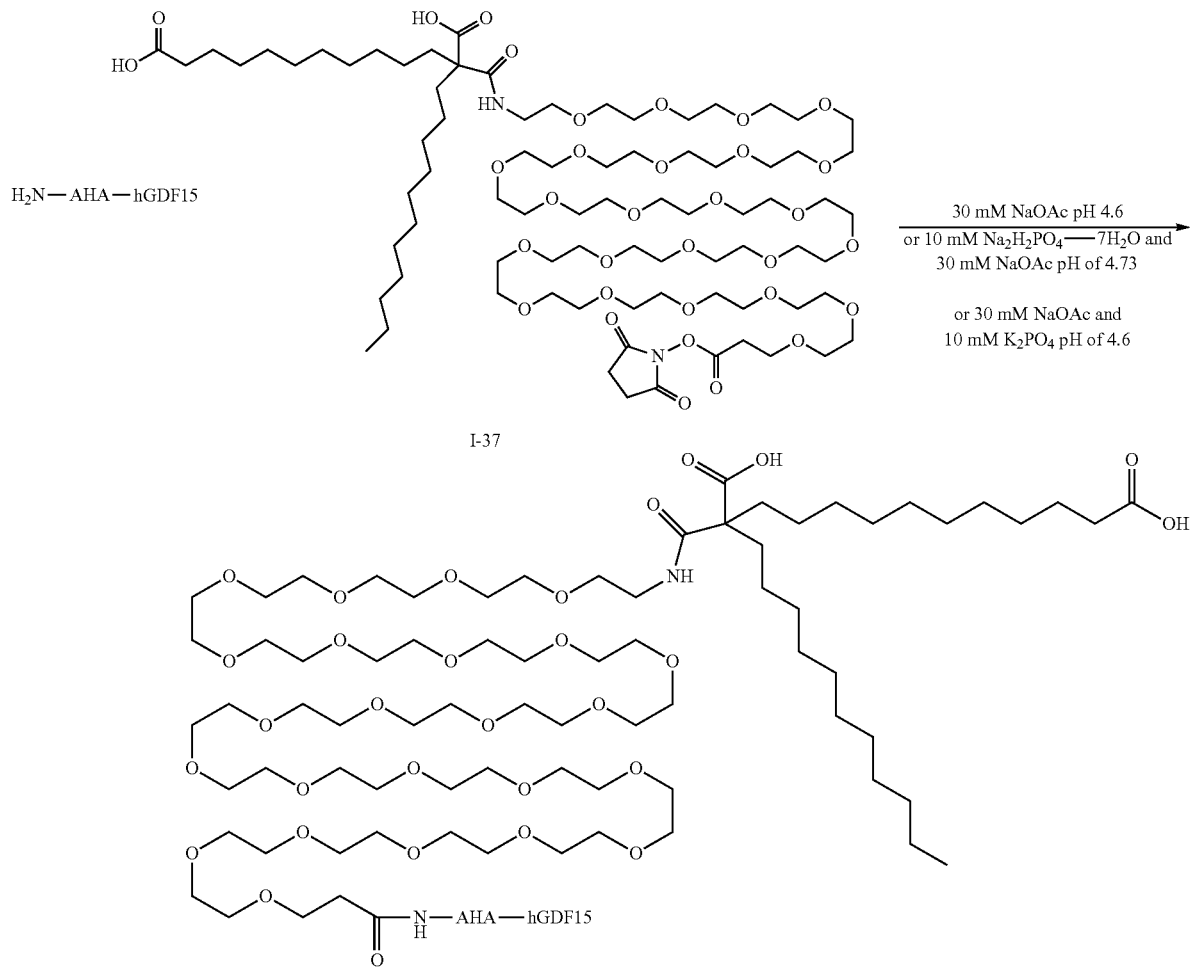

A 10 mg/mL solution of Intermediate 37 in molecular biology grade water was prepared. To AHA-hGDF15 (intermediate 57, 6.67 mg/mL in 30 mM NaOAc pH 4.0, 5.247 mL, 1.433 μmol) was added 30 mM NaOAc pH 4.6 (acceptable range 4.5-5.0) to give a final protein concentration of 0.88 mg/mL. Intermediate 37 (10 eq., 2.39 mL, 0.014 mmol) was added and the reaction was mixed at r.t. for 18 hours. Precipitate had formed in the reaction vial. The reaction mixture was split amongst 4×15 mL 10 kDa Amicon centrifugal filters and each was diluted to 15 mL with 30 mM NaOAc pH 4.0. The material was buffer exchanged 4× into 30 mM NaOAc pH 4.0 and samples were combined to a volume of 25.6 mL, agitating the precipitate in the filter with a pipette tip in between washes. Precipitate remained in solution so the mixture was let sit at 4° C. overnight. Concentration was measured by A280 (30040 $cm^{-1}M^{-1}$, 27538 g/mol) to be 1.62 mg/mL (100%). UPLC analysis showed 60% recovery of +1 FA (Retention time: 4.88 min) and +2FA products (Retention time: 5.80 min) (Method J). LCMS method T shows desired masses.

Example 19B

Crude Mixture (Ratio Represented in Table Below) was Tested In Vivo and Reported in Table 1

| Species | Calculated | Observed LCMS Method T | % observed UPLC Method J | Retention time (min) UPLC Method J |
|---|---|---|---|---|
| AHA-GDF15 | 24430 | 24432 | 29 | 3.24 |
| AHA-GDF15 + 1FA | 25984 | 25985 | 27 | 4.88 |
| AHA-GDF15 + 2FA | 27538 | 27540 | 33 | 5.80 |
| AHA-GDF15 + 3FA | 29092 | 29091 | 11 | 6.66 |

AHA-hGDF15 + 1FA (Fatty acid) corresponds to a reaction at the N-terminus amino functionality on one of the polypeptide chains (on the monomeric unit) of the GDF15 homodimer (as represented in embodiment 11B, Formula H).
AHA-hGDF15 + 2FA (Fatty acid) corresponds to a reaction at the N-terminus amino functionality on both polypeptide chains of the GDF15 homodimer (as represented in embodiment 11B, Formula G).
AHA-hGDF15 + 3FA (Fatty acid) corresponds to a non-selective reaction at some other site of the GDF15 homodimer.

Purification:

The crude product was purified by reverse phase chromatography (Buffer A 0.1% TFA in water; Buffer B 0.1M TFA in ACN gradient; 99%-80% Buffer A) on a Waters BEH300 130Å, 3.5 μm, 4.6 mm×100 mm flow rate 2.5 ml/min.

Fraction 1: Unreacted AHA-hGDF15: Rt=17.33 min
Fraction 2: (19B1): AHA-GDF15+1FA: Rt=20.2 min (approximately 15% yield) (Formula H)
Fraction 3: (19B2): AHA-GDF15+2FA: Rt=21.6 min (approximately 15% yield) (Formula G)
Fraction 4: (19B3): AHA-GDF15+3 FA: Rt=23.0 min (approximately 5% yield)

A 1:1 ratio mixture of 19B1 and 19B2 was prepared and tested (19Bm).

Alternatively the reaction may be carried out in 10 mM $Na_2HPO_4$-$7H_2O$ and 30 mM NaOAc at a pH of 4.73: A 10 mg/mL solution of Intermediate 37 in molecular biology grade water was prepared. To AHA-hGDF15 (Intermediate 57, 12.04 mg/mL in 30 mM NaOAc pH 4.0, 4.15 μL, 0.002 μmol) was added 30 mM NaOAc 10 mM $Na_2HPO_4$-$7H_2O$ pH 4.73 to give a final protein concentration of 0.88 mg/mL. Intermediate 37 (20 eq., 6.83 μL, 0.041 μmol) was added and the reaction was mixed at r.t. for 18 hours. The reaction mixture had turned cloudy with precipitate. UPLC analysis showed 58%+1 and +2 products (Method J).

| Species | Calculated | % observed |
|---|---|---|
| AHA-GDF15 | 24430 | 0 |
| AHA-GDF15 + 1 FA | 25984 | 11 |
| AHA-GDF15 + 2 FA | 27538 | 47 |
| AHA-GDF15 + 3 FA | 29092 | 34 |
| AHA-GDF15 + 4 FA | 30646 | 7 |

The reaction may also be carried out in 30 mM NaOAc and 10 mM $K_2HPO_4$ at a pH of 4.6: A 10 mg/mL solution of intermediate 37 in molecular biology grade water was prepared. To AHA-hGDF15 (intermediate 57, 6.21 mg/mL in 30 mM NaOAc pH 4.0, 5.261 mL, 1.337 μmol) was added 30 mM NaOAc 10 mM $K_2HPO_4$ pH 4.6 (acceptable range 4.5-5.0) to give a final protein concentration of 0.88 mg/mL. Intermediate 37 (10 eq., 68.3 μL, 0.409 μmol) was added and the reaction was mixed at r.t. for 7 hours. The reaction mixture had turned cloudy with precipitate. The reaction mixture was split into four 9 mL portions in 15 mL 10 kDa Amicon centrifugal filter and diluted to 15 mL with 30 mM NaOAc pH 4.0. The material was buffer exchanged 4× into 30 mM NaOAc pH 4.0, agitating the precipitate between each wash with a pipette tip. The reaction mixture was concentrated to a volume of 75 mL. Precipitate remained so the material was stored at 4° C. for two days. Concentration was measured by A280 (30040 $cm^{-1}M^{-1}$, 27538 g/mol) to be 0.4 mg/mL (97%). UPLC analysis showed 61% recovery of +1 and +2 products (Method J).

| Species | Calculated | Observed LCMS method T | % observed UPLC Method J |
|---|---|---|---|
| AHA-GDF15 | 24430 | 24434 | 34 |
| AHA-GDF15 + 1 FA | 25984 | 25987 | 34 |
| AHA-GDF15 + 2 FA | 27538 | 27540 | 27 |
| AHA-GDF15 + 3 FA | 29092 | n/a | 5 |

Reference Example 1

His-hGDF15 BCN (1-58) Conjugated to Intermediate PEG-Myristic Acid Construct

Step 1:

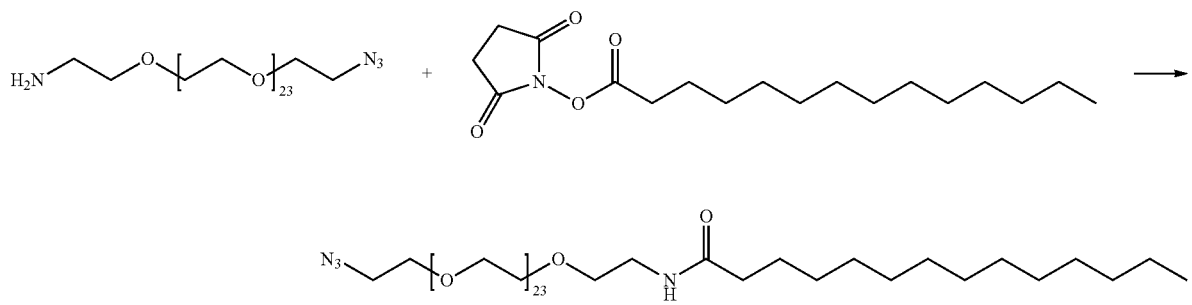

To a mixture of Azido-PEG23-Amine (30 mg, 0.027 mmol) and myristic NHS ester (Toronto Research Chemicals, cat # S69080) (12 mg, 0.037 mmol) was added DCM (1 mL) and DIPEA (13 uL), and the mixture was stirred at r.t. overnight. The mixture was purified by silica chromatography eluting with EtOAc/heptane (0-100%) then MeOH/DCM (0-10%) to give clean prduct at around 5% MeOH/DCM. LCMS: (Gradient: from 40 to 98% B in 1.4 min-flow 1 mL/min Eluent A: water+0.05% formic acid+3.75 mM ammonium acetate, Eluent B: acetonitrile+0.04% formic acid) LCMS: rt=2.20 (Method C) Mass+H calculated: 1354.71 Mass observed: 1354.4.

Step 2:
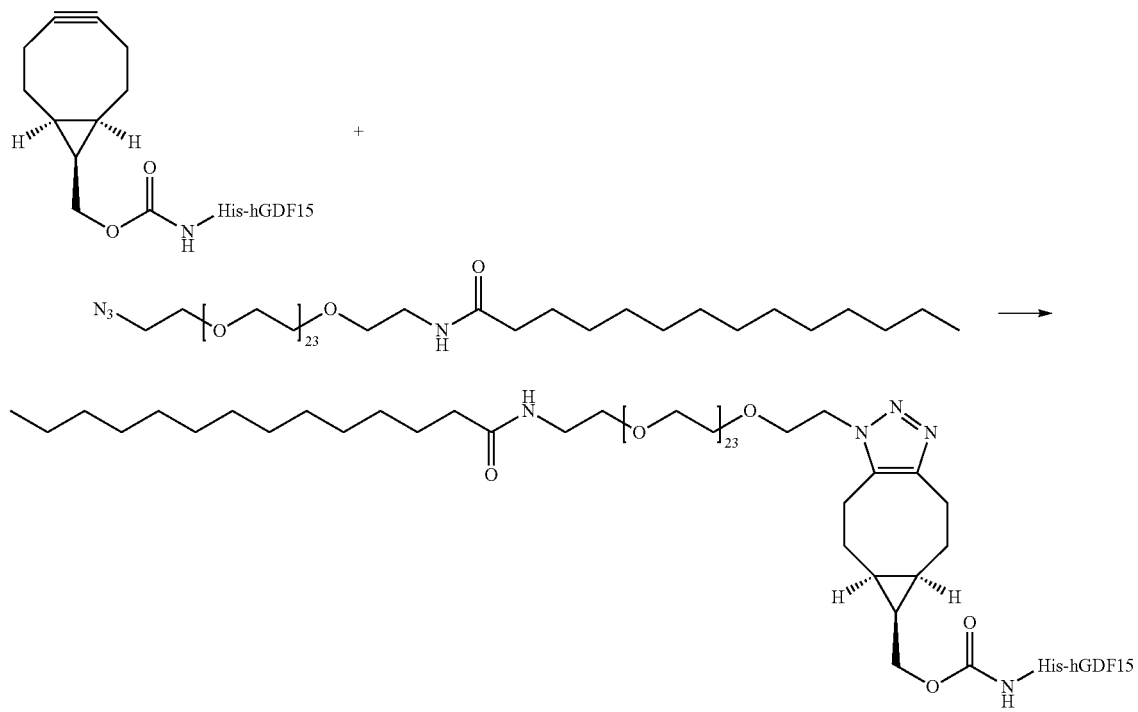
To a solution of BCN-hGDF15 (1-52: 800 uL, 0.25 mg/mL) was added a (2 mg/mL in DMSO, 6.3 uL, 10 eq), and the mixture was stirred at r.t. overnight. 1.1 mL 0.20 mg/mL in quantitative yield. (Maldi: +1 mass calculated: 28223 mass observed: 28640; +2 mass calculated: 29543; mass observed:29962, +3 mass calculated: 30863 mass observed:31426, +4 mass calculated: 32183 mass observed: 32911).
Reference Example 2
his-hGDF15-PEG23
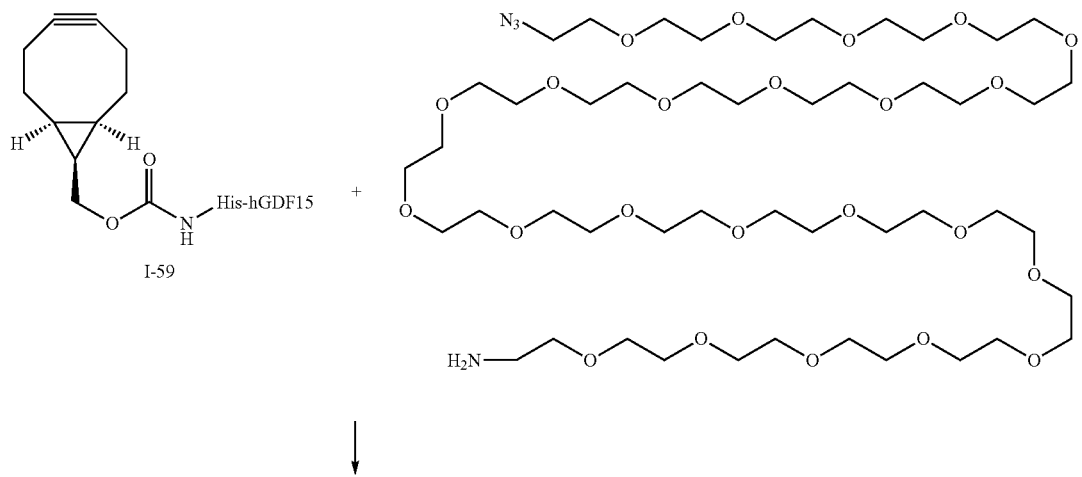

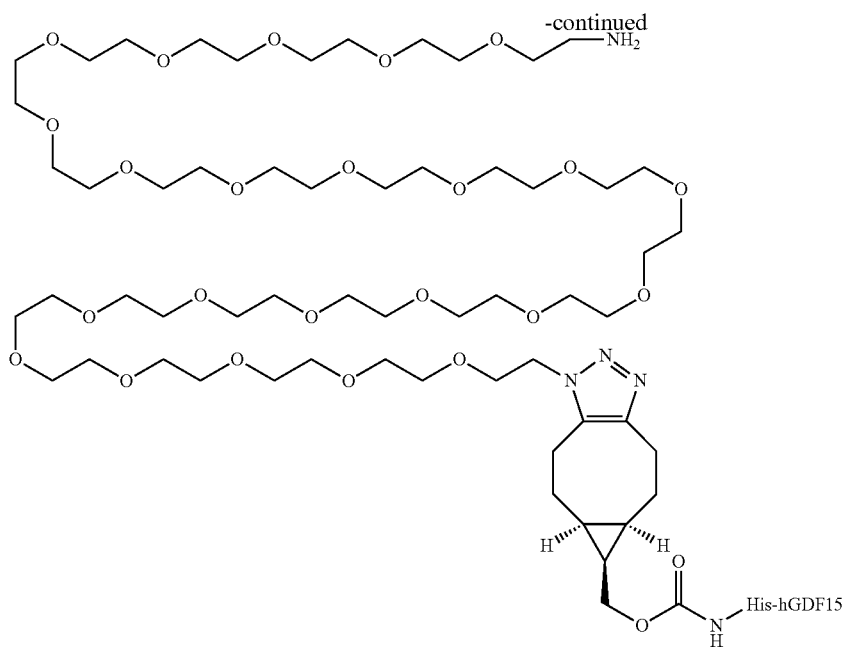

| Degree of Labelling | Calculated | Observed | % |
| --- | --- | --- | --- |
| His-hGDF15 | 26468 | 26360.3 | 5 |
| His-hGDF15-BCN | 26644 | n/a | 0 |
| His-hGDF15 + 1 PEG23 | 27567 | 28178.6 | 15 |
| His-hGDF15 + 2 PEG23 | 28666 | 29385.1 | 46 |
| His-hGDF15 + 3 PEG23 | 29765 | 30547.2 | 28 |
| His-hGDF15 + 4 PEG23 | 30864 | 31731.8 | 5 |

To a solution of His-hGDF15 BCN (159: 427 μL, 1.17 mg/mL, 0.019 μmol) in 30 mM NaOAc pH 4.0 (427 μL) was added azido-dPEG$_{23}$-amine (Quanta Biodesign, 104 μg, 0.094 μmol). The reaction was mixed at r.t. for 16 hours at which point the mixture was exchanged into 30 mM NaOAc pH 4.0 using 10 kDa MWCO Amicon centrifugal filter by diluting and concentrating the sample 5 times to a volume of 140 μL. MALDI analysis showed full conversion to +1 through +4 products. The concentration was measured by A$_{280}$ (29090M-1 cm-1, 27600 g/mol) to be 2.099 mg/mL (57%).

Example 20

Apelin Cyclic Peptide BCN Conjugated to Intermediate 47

Step 1: Synthesis of pE-R-P-C*-L-S-C*-K-G-P-(D-Nle)-NH(Phenethyl) (disulfide C$^4$-C$^7$) (SEQ ID NO: 28) Acetate

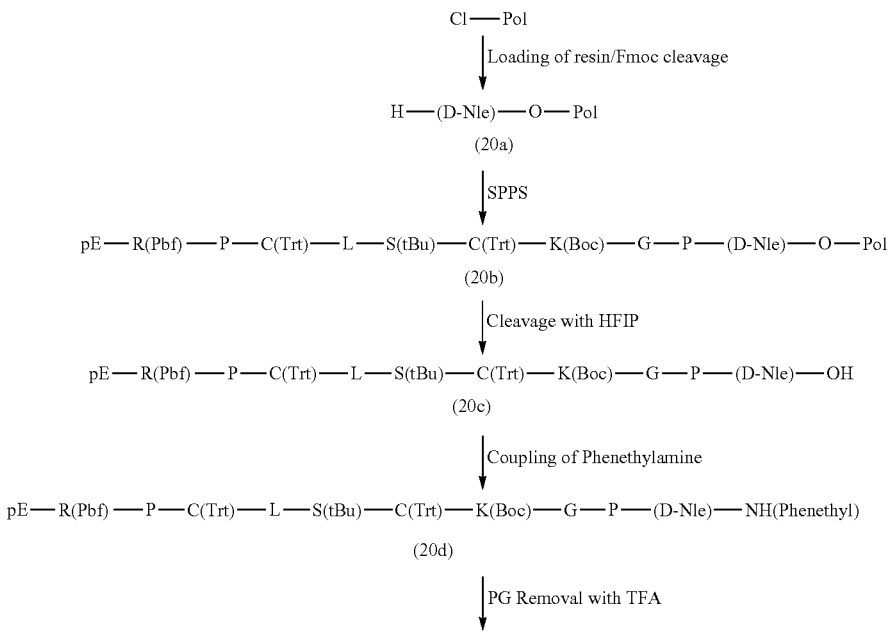

pE—R—P—C—L—S—C—K—G—P—(D-Nle)—NH(Phenethyl)

(20e)

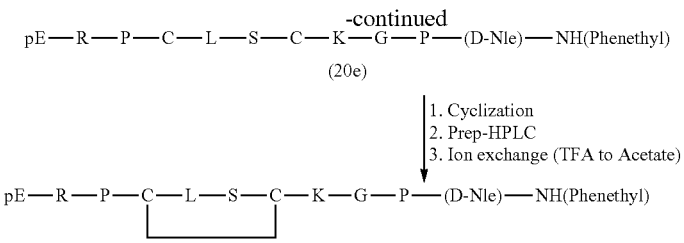

Preparation of Intermediate 20a (Loading of 2-Chlorotrityl Chloride Resin with Fmoc-D-Nle-OH, Fmoc Removal and Determination of the Loading of the Resin)

2-Chlorotrityl chloride resin (50.0 g, 85.0 mmol) was suspended in of DCM (400 mL) the suspension was stirred for 10 min and then the solvent was drained, the resin was washed with DCM (3×200 mL). Then a solution of Fmoc-D-Nle-OH (24.0 g, 68.0 mmol) and DIPEA (96.5 ml, 552.5 mmol) in DCM (120.0 mL) was added to the resin, the suspension was flushed with nitrogen and stirred at rt for 5 min. Another portion of DIPEA (22.7 ml, 127.5 mmol) was added and the reaction mixture was stirred at r.t. overnight.

The reaction mixture was drained and the resin was washed with DCM (3×250 mL) for 2 min each time. The resin was quenched with of a mixture DCM/MeOH/DIPEA (70:15:15) (2×250 mL) for 10 min each time.

The Fmoc group was cleaved by treating the resin with piperidine/DMF (1:3) (1×300 mL) for 5 min. the resin was drained then (1×300 mL) for 15 min, followed by washing steps: DMF (6×250 mL, 2 min each time), isopropanol (2×250 mL, 2 min each time) and TBME (6×250 mL, 2 min each time). The resin was dried under vacuum at 35° C. for 24 hours to afford Intermediate 20a (57.8 g, loading=1.08 mmol/g).

Preparation of Intermediate 20b (Assembly of Linear Peptide)

Intermediate 20a (18.5 g, 20.0 mmol) was subjected to solid phase peptide synthesis on an automatic peptide synthesizer (CSBI0536™). A coupling cycle was defined as follows:

Amino acid coupling: AA (3.0 eq.), DIC (3.0 eq.), HOBt (3.0 eq.), DMF (see table below)

Washing: DMF (4×150 mL, 2 min each time).

Fmoc deprotection: Piperidine/DMF (1:3) (150 mL for 5 min then 150 mL for 15 min).

Washing: DMF (6×150 mL, 2 min each time).

| Coupling | AA | Number of couplings × Reaction time | Coupling Method |
|---|---|---|---|
| 1 | Fmoc-L-Pro-OH | 1 × 120 min | DIC/HOBt |
| 2 | Fmoc-Gly-OH | 1 × 120 min | DIC/HOBt |
| 3 | Fmoc-L-Lys(Boc)-OH | 1 × 120 min | DIC/HOBt |
| 4 | Fmoc-L-Cys(Trt)-OH | 1 × 120 min | DIC/HOBt |
| 5 | Fmoc-L-Ser(tBu)-OH | 1 × 120 min | DIC/HOBt |
| 6 | Fmoc-L-Leu-OH | 1 × 120 min | DIC/HOBt |
| 7 | Fmoc-L-Cys(Trt)-OH | 1 × 120 min | DIC/HOBt |
| 8 | Fmoc-L-Pro-OH | 1 × 120 min | DIC/HOBt |
| 9 | Fmoc-L-Arg(Pbf)-OH | 1 × 120 min | DIC/HOBt |
| 10 | Boc-L-Pyr-OH | 1 × 120 min | DIC/HOBt |

After the assembly of the peptide, the resin was washed with DMF (6×150 mL, 2 min each time), isopropanol (6×150 mL, 2 min each time) and TBME (6×150 mL, 2 min each time). The peptide resin was dried overnight under high vacuum at 35° C. to give Intermediate 20b (57.6 g, 20.0 mmol).

Preparation of Intermediate 20c (HFIP Cleavage from the Resin)

A portion of Intermediate 20b (27 g, 9.37 mmol) was suspended in DCM (300 mL) and stirred for 15 min. The resin was drained then treated with HFIP/DCM (3:7) (3×270 mL, 15 min each time). The cleavage solution was filtered off and collected. The resin was washed with DCM (3×300 mL). The combined cleavage and washing solutions were concentrated to dryness in vacuo. The white powder was dried overnight under vacuum at 35° C. yielding Intermediate 20c-Batch1 (23.5 g, 9.37 mmol).

The above mentioned procedure was repeated with another portion of Intermediate 20b (28.0 g, 9.72 mmol), affording Intermediate 20c-Batch2 (26.1 g, 9.72 mmol).

Preparation of Intermediate 20d (Solution Phase Coupling of Phenethylamine)

Intermediate 20c-Batch2 (20.0 g, 7.44 mmol, 1.0 eq) and HATU (5.23 g, 13.8 mmol, 1.85 eq) were dissolved in DMF (400 mL). A solution of phenethylamine (1.67 g, 13.8 mmol, 1.85 eq) and DIPEA (3.56 g, 27.6 mmol, 3.71 eq) in DMF (60 mL) was added.

The reaction mixture was stirred at rt for 30 min then cooled down to 0° C. then brine (460 mL) was added. The suspension was stirred for 10 min then the product was isolated by filtration. The filter cake was washed with $H_2O$ (300 mL), which was then carefully removed, then dissolved in DCM (300 mL). The solution was dried over MgSO4 then concentrated to dryness in vacuo. The crude product was subjected to flash chromatography over silica gel (eluents: DCM and DCM/iPrOH (8:2)) to afford Intermediate 20d-Batch1 (14.4 g, 6.6 mmol).

The same procedure was repeated with Intermediate 20c-Batch1 (23.4 g, 9.37 mmol), excluding the flash chromatography, affording Intermediate 20d-Batch2 (28.0 g, 9.37 mmol).

Preparation of Intermediate 20e (Protecting Group Removal)

Intermediate 20d-Batch2 (28.0 g, 9.37 mmol) was dissolved in TFA/DCM/EDT/TIS (90:5:2.5:2.5) (290 mL) and the reaction stirred at rt for 2 h.

The cleavage solution was filtered off and poured onto cold TBME (3 L) (0-4° C.). The turbid suspension was stirred in an ice-water bath for 30 min then filtered through a pore 4 glass filter. The white solid thus obtained was washed with TBME (2×100 mL) then dried in vacuum at 35° C. overnight to afford Intermediate 20e-Batch1 (8.9 g, 5.9 mmol).

The same procedure was repeated with Intermediate 20d-Batch1 (14.4 g, 6.6 mmol) yielding Intermediate 20e-Batch2 (9.6 g, 6.3 mmol).

Preparation of pE-R-P-C*-L-S-C*-K-G-P-(D-Nle)-NH (Phenethyl) (disulfide $C^4$-$C^7$) Acetate 1) Cyclization Intermediate 20e (5.0 g, 3.3 mmol) was dissolved in water (500 mL). A solution of iodine (1.18 g, 4.66 mmol, 1.41 eq)

in acetic acid (93 mL) was added in one portion. The reaction mixture was stirred at rt for 10 min. A solution of ascorbic acid (1.03 g, 5.83 mmol, 1.77 eq) in water (5.8 mL) was added and the reaction mixture stirred for 10 min, filtered and stored at 4° C. until purification.

The same cyclization procedure was repeated until 18.3 g (12.1 mmol) of Intermediate 20e had been processed.

2) Purification

The solutions of cyclic peptide were subjected to preparative HPLC in portions of 0.5-5.0 g peptide per injection. The fractions having purity higher than 95% were pooled and freeze dried to yield a total amount of 4.89 g (3.2 mmol) of purified peptide (TFA salt) was produced.

3) Acetate Formation by Ion Exchange 75 g (100 mL) of a strong anion exchanger resin (Ion exchanger III, Merck) in its OH$^-$ form was placed in sintered glass filter (porosity 3) and then a solution of acetic acid/water (1:3) (300 mL) was added, the suspension was manually stirred for 2 min then the resin was drained. The process was repeated with another portion of acetic acid/water (1:3) (300 mL). The resin was washed with deionized water until a neutral drain was observed. Then the resin was transferred to a 4×20 cm column equipped with a sintered glass filter (porosity 3).

4.8 g of purified peptide was dissolved in deionized water (50 mL) and added to the column. The product was eluted with deionized water (200 mL). Control of product elution was done by TLC spotting, the rich fractions were pooled and freeze dried to give pE-R-P-C*-L-S-C*-K-G-P-(D-Nle)-NH(Phenethyl) (disulfide C$^4$-C$^7$) (SEQ ID NO: 28) Acetate (4.1 g, 2.9 mmol).

The pure product was analyzed by analytical HPLC (Analytical method F; $t_R$=8.01 min) and UPLC-HRMS (Analytical method G; measured: [M+2H]$^{2+}$=643.328; calculated: [M+2H]$^{2+}$=643.324). The acetate content was 7.99-8.27% and the water content was 1.94-1.96%.

Step 2: Preparation of pE-R-P-C*-L-S-CP-N$^6$-[[(1α,8α,9α)-bicyclo[6.1.0]non-4-yn-9-ylmethoxy]carbonyl]-K-G-P-(D-Nle)-NH(Phenethyl) [disulfide C4-C7] (SEQ ID NO: 30)

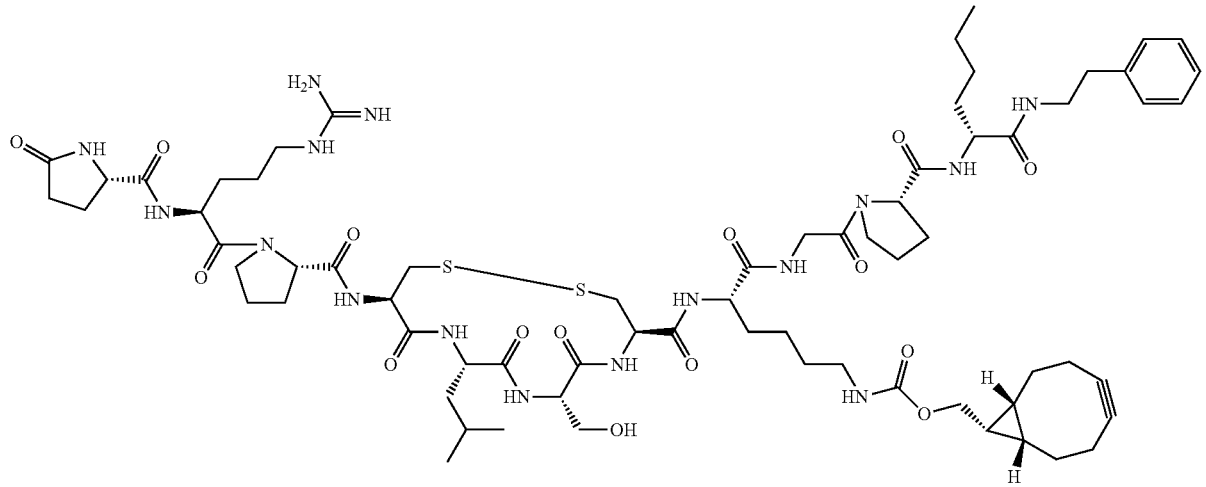 [SMILES: CCCC[C@@H](NC(=O)[C@@H]1CCCN1C(=O)CNC(=O)[C@H](CCCCNC(=O)OC[C@@H]1[C@@H]2CCC#CCC[C@@H]21)NC(=O)[C@@H]1CSSC[C@H](NC(=O)[C@@H]2CCCN2C(=O)[C@H](CCCNC(=N)N)NC(=O)[C@@H]2CCC(=O)N2)C(=O)N[C@@H](CC(C)C)C(=O)N[C@@H](CO)C(=O)N1)C(=O)NCCc1ccccc1]

A mixture of pE-R-P-C*-L-S-C*-K-G-P-(D-Nle)-NH(Phenethyl)triacetate [disulfide C4-C7] (100 mg, 0.068 mmol), sodium bicarbonate (38 mg, 0.452 mmol) and water (83 uL) in DMF (1 mL) was stirred at RT for 10 mins, then (1R,8S)-bicyclo[6.1.0]non-4-yn-9-ylmethyl succinimidyl carbonate (Berry & associates, 20 mg, 0.068 mmol) was added. The reaction mixture was stirred at RT for 90 mins. 1 mL of water was added to the mixture, and the resultant solution was lyophilized to give a powder which was used for the next step without further purification.

Step 3: Preparation of Example 20

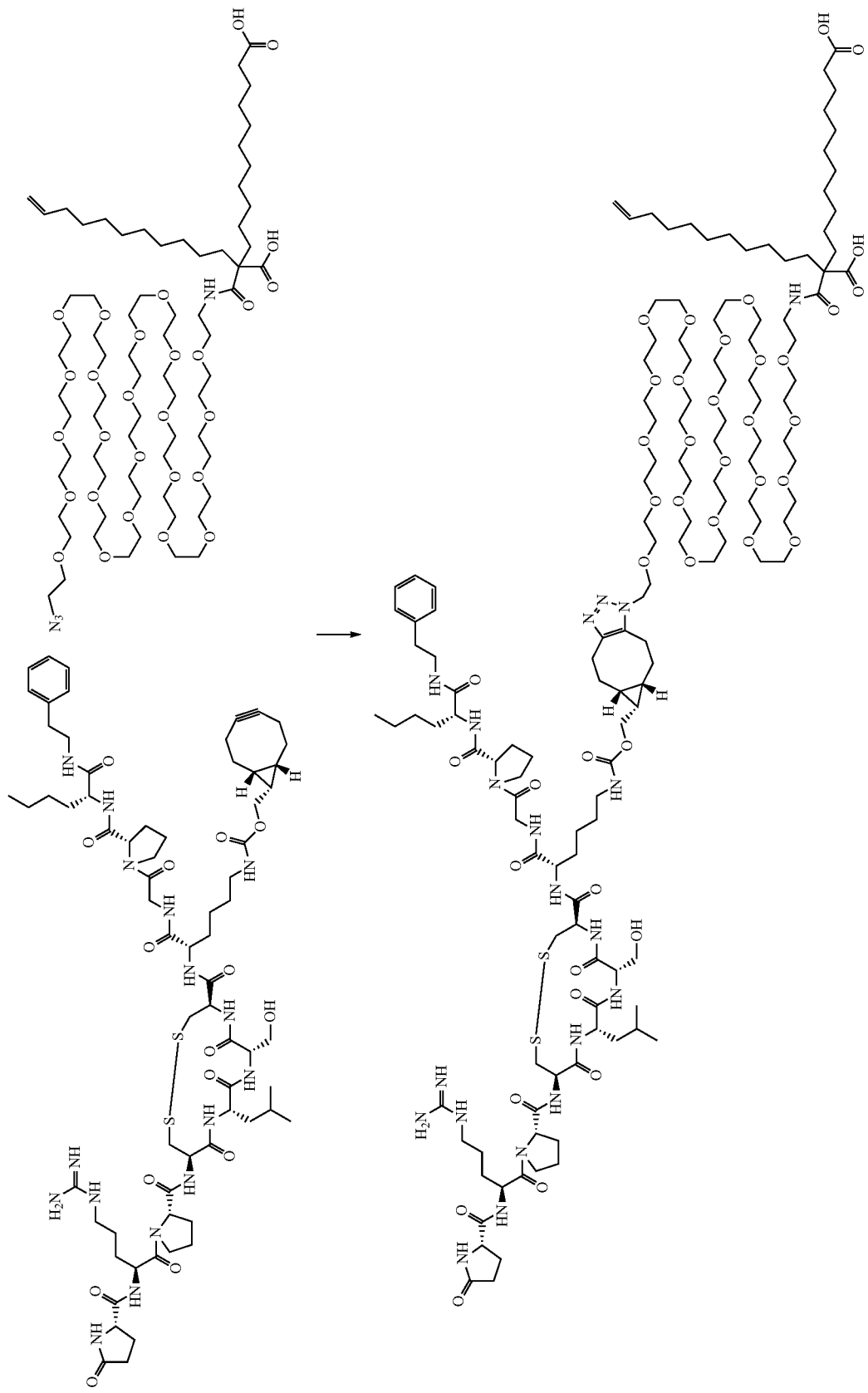
Example 20

A mixture of pE-R-P-C*-L-S-C*-N$^6$-[[(1α,8α,9α)-bicyclo[6.1.0]non-4-yn-9-ylmethoxy]carbonyl]-K-G-P-(D-Nle)-NH(Phenethyl) [disulfide C4-C7] (SEQ ID NO: 30) (50 mg of the product from Step 2 in 1 mL of water, 0.034 mmol) and Intermediate 47(52 mg, in 268 uL of water) was stirred at RT for about 3 hrs. The reaction mixture was then purified by preparative HPLC (Sunfire 30×50 mm 5 um column ACN/H2O w/ 0.1% TFA 75 ml/min, 15-40% ACN 5 min gradient). The product fraction was lyophilized to give the titled product as TFA salt (24 mg, 21%). LCMS (Waters Acquity UPLC BEH C18 1.7 um 2.1×50 mm, 50° C., Eluent A: Water+0.1% Formic Acid, Eluent B: Acetonitrile+0.1% Formic Acid, gradient 2% to 98% B/A over 5.15 mins): Retention time: 2.77 mins; MS [M+2]$^{2+}$: observed: 1491.8808, calculated: 1491.8560.

Example 21A

Apelin Cyclic Peptide BCN Conjugated to Intermediate 47

Step 1

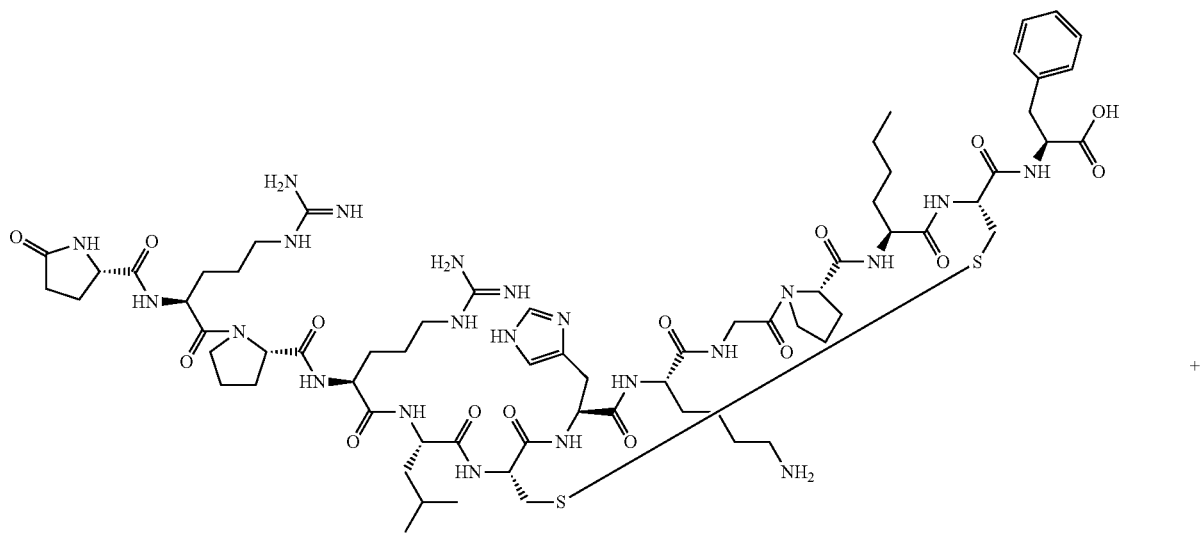

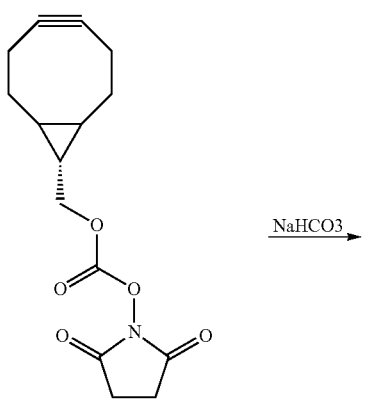

NaHCO3

203
204
-continued
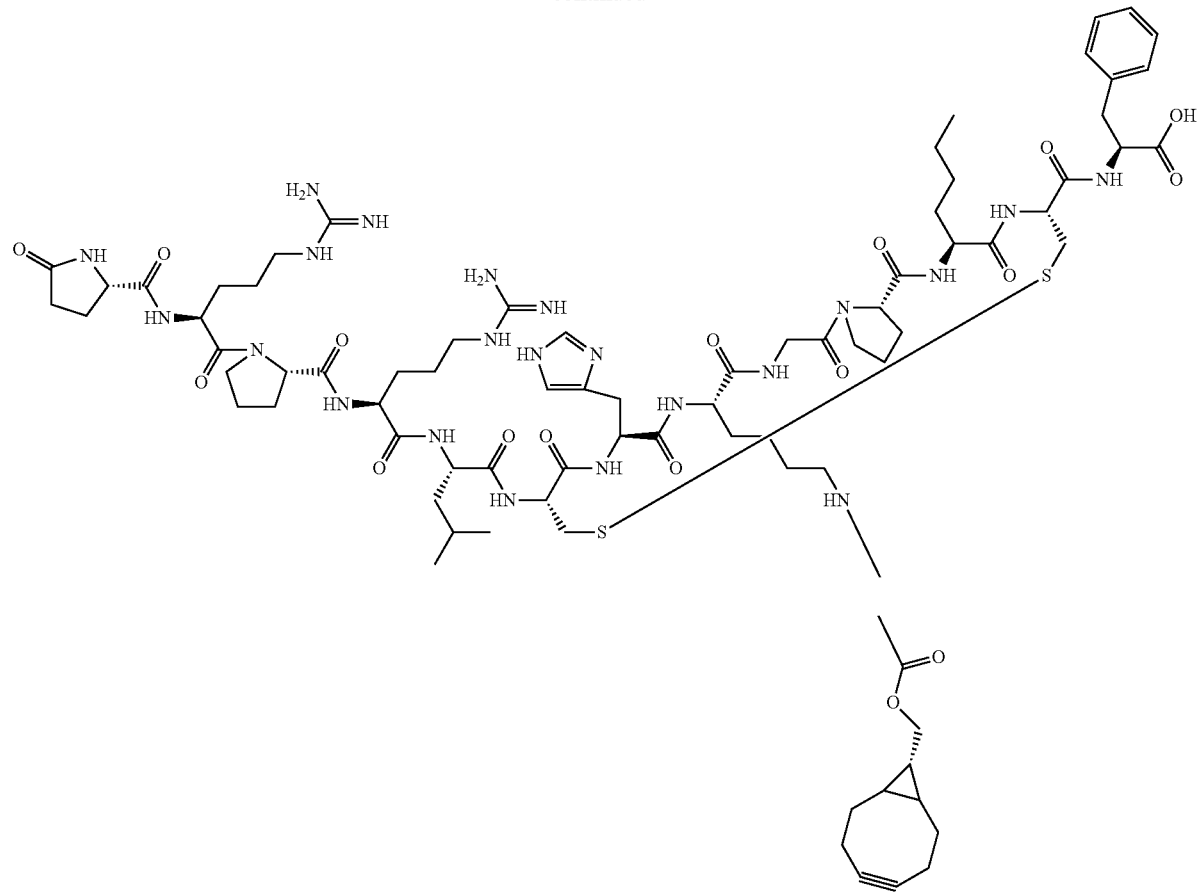
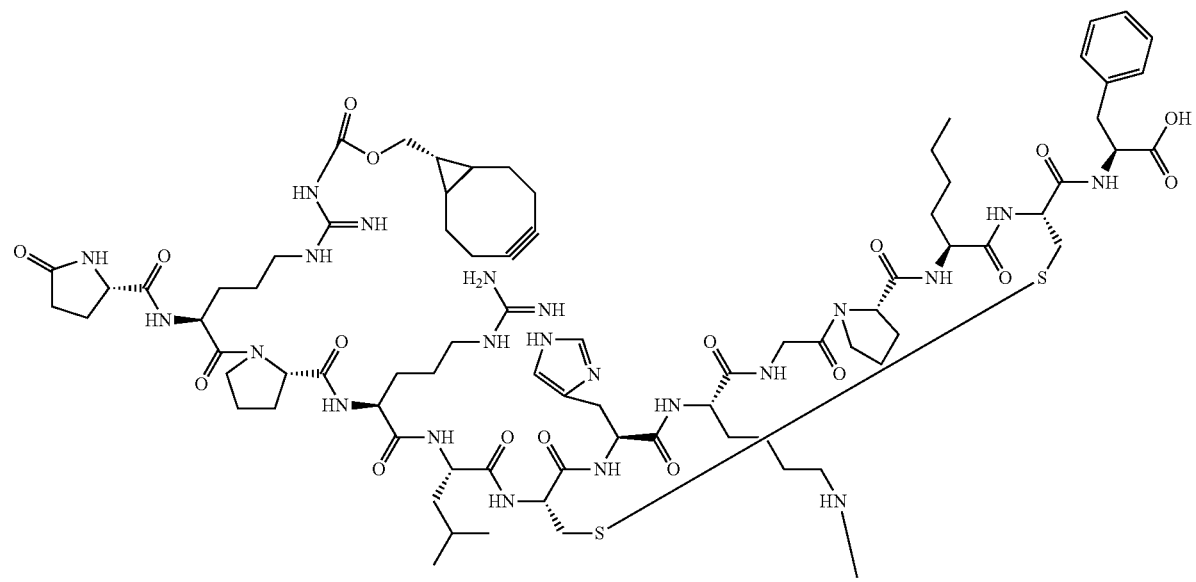

-continued

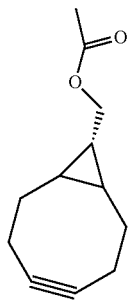

A mixture of pE-R-P-R-L-C*-H-K-G-P-Nle-C*-F-OH (Disulfide $C^6$-$C^{12}$) (SEQ ID NO: 29) 50 mg, 0.033 mmol, as prepared in U.S. Pat. No. 8,673,848), sodium bicarbonate (18 mg, 0.215 mmol) and water (40 uL) in DMF (0.5 mL) was stirred at RT for 10 mins, then (1R,8S)-bicyclo[6.1.0]non-4-yn-9-ylmethyl succinimidyl carbonate (Berry & associates, 18 mg, 0.065 mmol) was added. The reaction mixture was stirred at RT for 90 mins. A mixture of +1 and +2 additions was observed by LCMS, so mixture was purified by mass triggered HPLC (Peptide Method 5 25-50% ACN 5 min gradient: Conditions: Sunfire 30×50 mm 5 um column ACN/H2O w/0.1% TFA 75 ml/min 1.5 ml injection): rt 3.2 min (+1), rt 4.65 min, 4.9 min (+1 and +2 mixture). LCMS confirms desired+1 product in 61% yield and +1, +2 mixture in 18% yield. LCMS: (Basic Eluent A: Water+5 mM Ammonium Hydroxide Eluent B: ACN Acidic Column: Sunfire C18 3.5 μm 3.0×30 mm-40° C. Basic Column: XBridge C18 3.5 μm 3.0×30 mm-40° C.) Retention time: 0.98 mins; MS [M+2]$^{2+}$: observed: 856.0, calculated: 865.0245.

Step 2

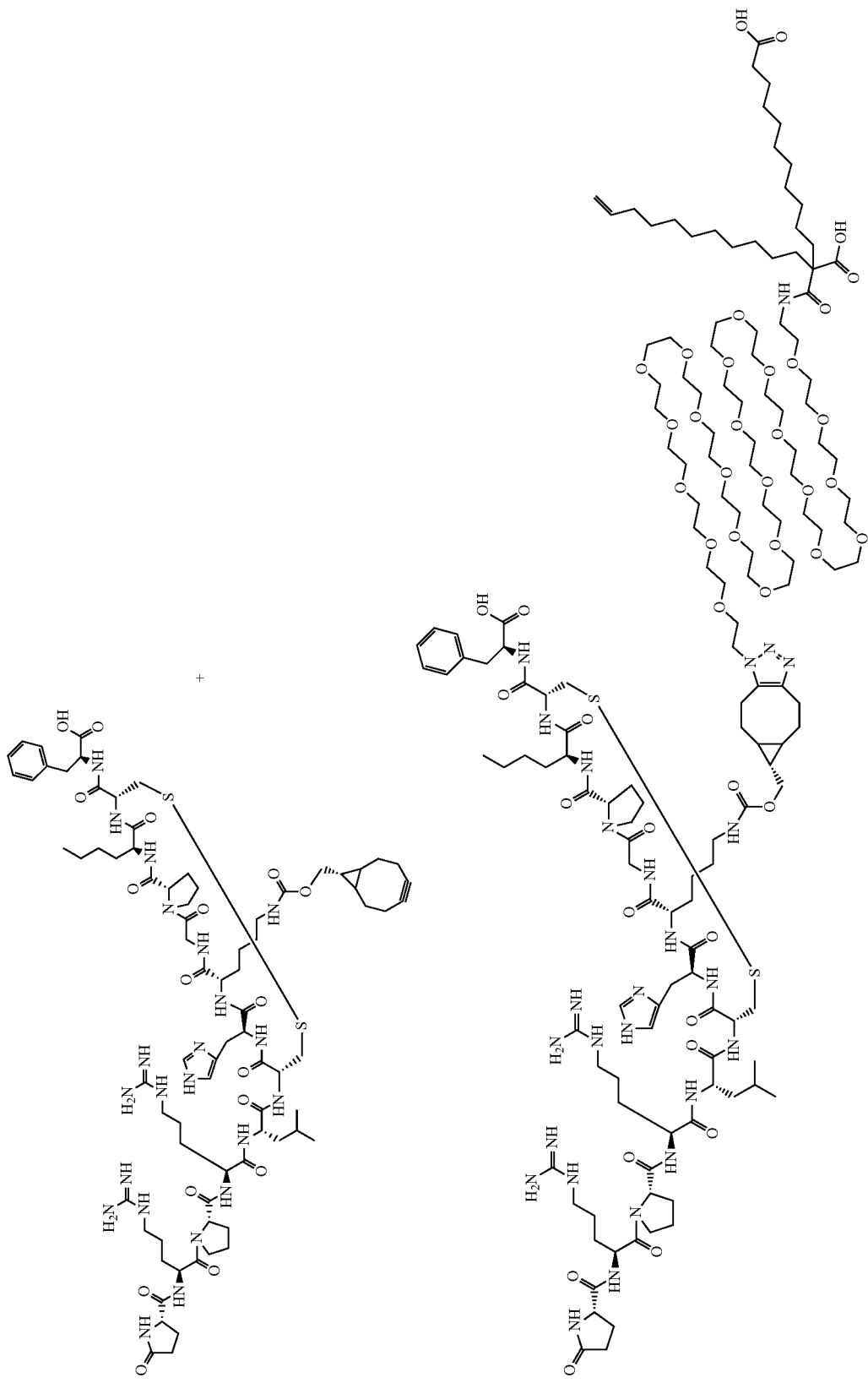
Example 21A

A mixture of pE-R-P-R-L-C*-H-N$^6$-[[(1α,8α,9α)-bicyclo[6.1.0]non-4-yn-9-ylmethoxy]carbonyl]-K-G-P-Nle-C*-F-OH(Disulfide C$^6$-C$^{12}$) (SEQ ID NO: 31) (21.33 mg, 0.014 mmol) and intermediate 47 (24 mg, 0.014 mmol) was stirred at RT for about 3 hrs. The reaction was complete by LCMS and was lyophilized to give the titled product (23 mg, 48%). LCMS (Waters Acquity UPLC BEH C18 1.7 um 2.1×50 mm, 50° C., Eluent A: Water+0.1% Formic Acid, Eluent B: Acetonitrile+0.1% Formic Acid, gradient 2% to 98% B/A over 5.15 mins): Retention time: 2.22 mins; MS [M+2]$^{2+}$: observed: 1616.9464, calculated: 1616.976.

Example 21B

Apelin Cyclic Peptide Conjugated to Fatty Acid-Linker Construct 1-37

Step 1: Synthesis of A-H-Q-R-P-C-L-S-C-K-G-P-Dnle-Phenethyl amine Intermediate 21B1 (SEQ ID NO: 32)

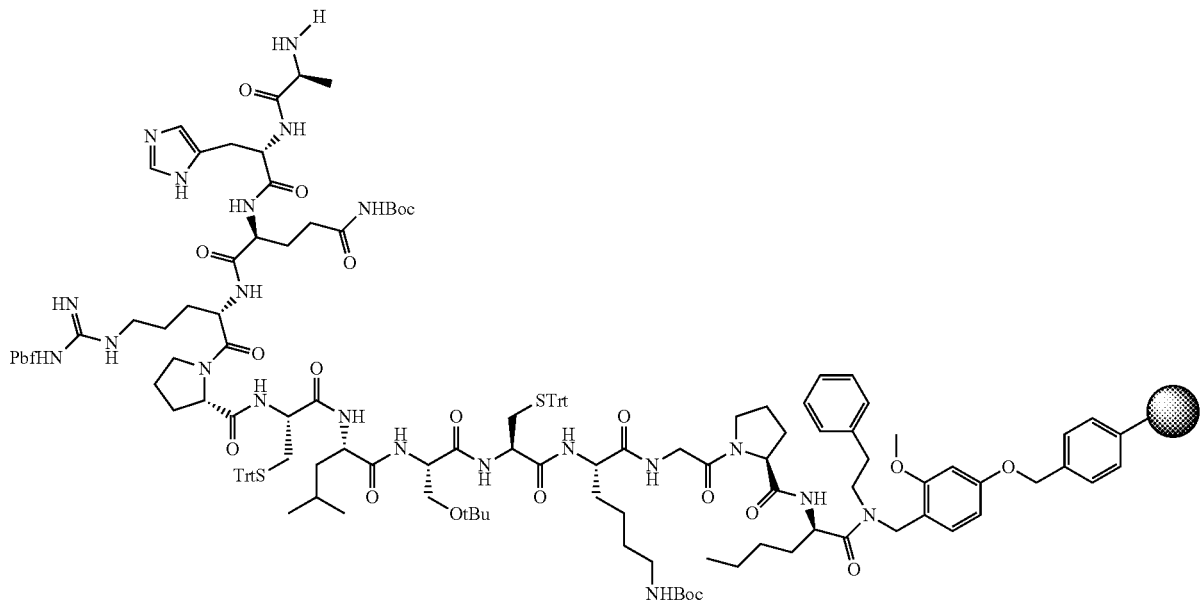

Phenethylamine-AMEBA resin (Sigma Aldrich, 0.1 mmol, 1.0 mmol/g) was subjected to solid phase peptide synthesis on an automatic peptide synthesizer (CEM Liberty Blue Microwave) with standard double Arg for the Arg residues and Dnle coupled double time. Amino acids were prepared as 0.2M solutions in DMF. A standard coupling cycle was defined as follows:

Amino acid coupling: AA (5 eq.), HATU (5 eq.), DIEA (25 eq.)
Washing: DMF (3×7 mL)
Fmoc Deprotection: 20% Piperidine/0.1M HOBt (2×7 mL)
Washing: DMF (4×7 mL then 1×5 mL)

| Coupling | AA | Number of couplings × Reaction time (Temp) | Coupling Method |
|---|---|---|---|
| 1 | Fmoc-D-Nle-OH | 1 × 10 min (70° C.) | DIEA/HATU |
| 2 | Fmoc-L-Pro-OH | 1 × 5 min (70° C.) | DIEA/HATU |
| 3 | Fmoc-L-Gly-OH | 1 × 5 min (70° C.) | DIEA/HATU |
| 4 | Fmoc-L-Lys-OH | 1 × 5 min (70° C.) | DIEA/HATU |
| 5 | Fmoc-L-Cys-OH | 1 × 5 min (70° C.) | DIEA/HATU |
| 6 | Fmoc-L-Ser-OH | 1 × 5 min (70° C.) | DIEA/HATU |
| 7 | Fmoc-L-Leu-OH | 1 × 5 min (70° C.) | DIEA/HATU |
| 8 | Fmoc-L-Cys-OH | 1 × 5 min (70° C.) | DIEA/HATU |
| 9 | Fmoc-L-Pro-OH | 1 × 5 min (70° C.) | DIEA/HATU |
| 10 | Fmoc-L-Arg-OH | 2 × 25 min (25° C.) | DIEA/HATU |
| 11 | Fmoc-L-Gln-OH | 1 × 5 min (70° C.) | DIEA/HATU |
| 12 | Fmoc-L-His-OH | 1 × 5 min (70° C.) | DIEA/HATU |
| 13 | Fmoc-L-Ala-OH | 1 × 5 min (70° C.) | DIEA/HATU |

After the assembly of the peptide, the resin was washed with DMF (2×50 mL) and DCM (2×50 mL) then dried under vacuum to give Intermediate 21B1 (276 mg, 0.1 mmol).

Step 2: Preparation of Intermediate 21B2 (Cleavage of Peptide from Resin)

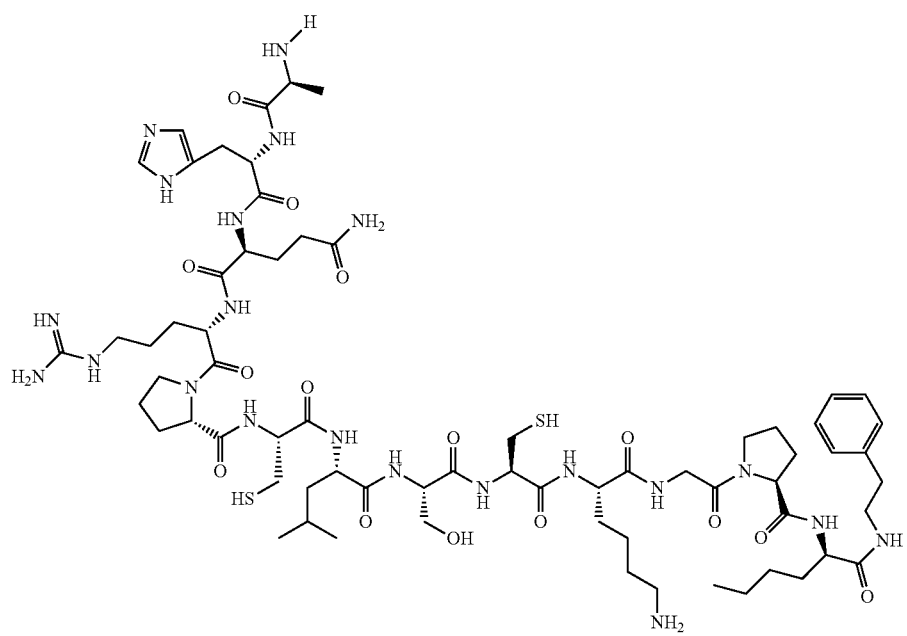

I-21B2

Intermediate 21B1 (276 mg, 0.1 mmol) was combined with 4 mL TFA solution (37 mL TFA, 1 mL H₂O, 1 mL TIPS, 3.06 g DTT) and shaken at r.t. for 3 hours. The solution was removed from the resin and precipitated into 40 mL cold Et₂O. The solution was vortexed and let stand over ice for 10 minutes before centrifuging at 4000 rpm for 5 minutes. The solvent was removed and the white solid was washed twice more with cold Et₂O (40 mL each time), centrifuged (5 minutes each time) and decanted. The solid was dried under vacuum overnight yielding Intermediate 21B2 (17.4 mg, 0.012 mmol). LCMS (SQ2 ProductAnalysis-Acidic-Peptide-Polar, Acquity UPLC BEH C18 column, 130 Å, 1.7 μm, 2.1 mm×50 mm, 50° C.): $R_t$=1.83 minutes, MS [M+H] 1513.5.

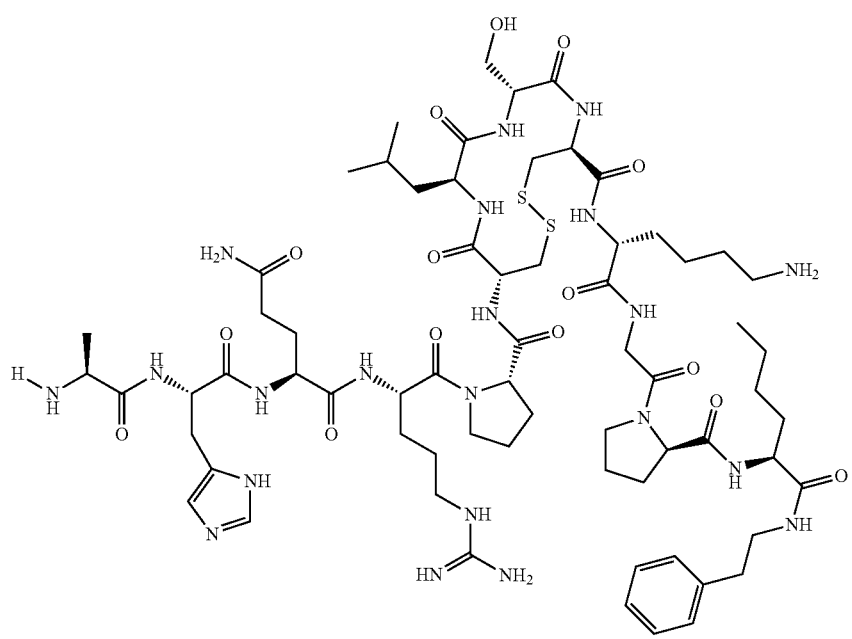

I-21B3

Step 3: Preparation of Intermediate 21B3 (Cyclization of Cysteine Residues)

Intermediate 21B1 (29.6 mg, 0.020 mmol) was dissolved in water (3 mL) and 10 drops of DMSO to give a slightly cloudy solution. Iodine (50 mM in HOAc, 0.783 mL, 0.039 mmol) was added slowly dropwise and the reaction was mixed at r.t. overnight. LCMS analysis of the crude reaction showed complete conversion of starting material. 0.5M ascorbic acid was added dropwise until color dissipated. The material was purified via MS-triggered HPLC. Lyophilization of the pooled fractions gave 7 mg of the desired product as a white powder (4.63 µmol, 24%). LCMS (SQ2 ProductAnalysis-Acidic-Peptide, Acquity UPLC BEH C18 column, 130 Å, 1.7 µm, 2.1 mm×50 mm, 50° C.): $R_t$=0.90 minutes, MS [M+H] 1511.8.

Step 4: Preparation of Conjugate Comprising Apelin A-H-Q-R-P-C-L-S-C-K-G-P-Dnle-Phenethyl Amine (SEQ ID NO: 32) and Intermediate 1-37 (N-Terminus Conjugation)-Example 21B UPLC BEH C18 column, 130 Å, 1.7 µm, 2.1 mm×50 mm, 50° C.): $R_t$=3.87 minutes, MS [M+H+2/2] 1533.1; [M+H+3/3] 1022.9.

Examples 22 to 24 Refers to Conjugates of a Fatty Acid with a siRNA

Kits for siRNA synthesis are commercially available, e.g., from New England Biolabs and Ambion. A siRNA agent can be constructed using chemical synthesis and enzymatic ligation reactions using procedures known in the art. For example, siRNA agent can be chemically synthesized using naturally-occurring nucleotides or variously modified nucleotides designed to decrease off-target effects, and/or increase the biological stability of the molecules or to increase the physical stability of the duplex formed between the antisense and sense nucleic acids, e.g., phosphorothioate derivatives and acridine substituted nucleotides can be used.

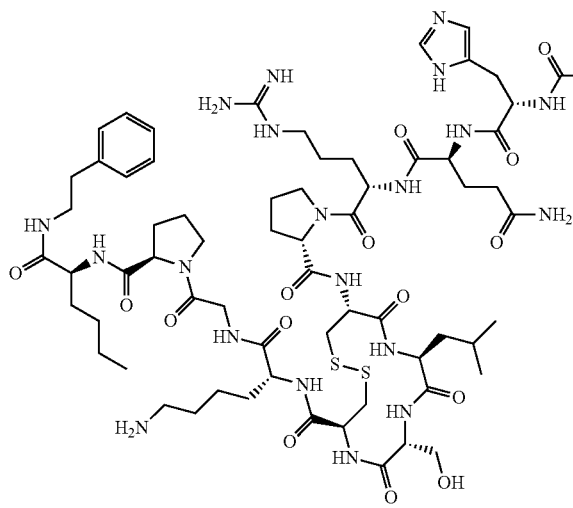
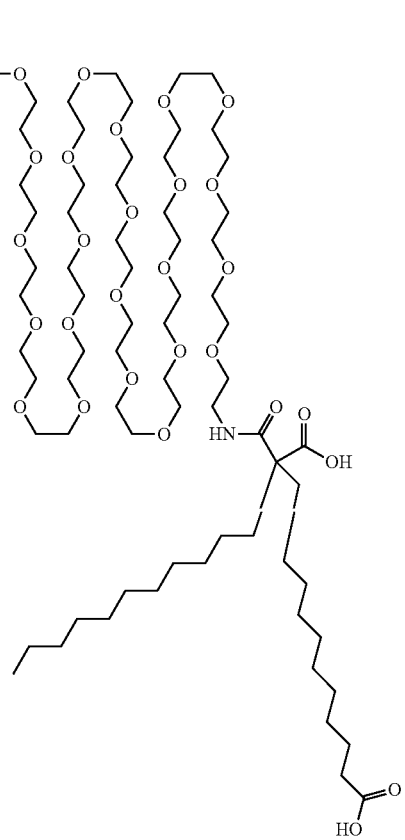

A 10 mg/mL solution of NHS-fatty acid was prepared in H$_2$O. Intermediate 21B3 (1.5 mg, 0.993 µmol) was dissolved in 30 mM pH4 NaOAc buffer (672 µL) and NHS-fatty acid (1-37: 0.850 mL, 5.10 µmol) was added. The reaction was mixed at r.t. for 16 hours at which point an additional 1.5 mg of NHS-fatty acid (10 mg/mL in H$_2$O) was added and the reaction mixed at r.t. for 16 hours. 8 mg of NHS-fatty acid (10 mg/mL in H$_2$O) was added and the reaction mixed at r.t. for 3 days and 1.7 mg of NHS-fatty acid (10 mg/mL in H$_2$O) was added. The mixture was shaken at r.t. for 16 hours and purified via M-triggered HPLC to give 1.7 mg of the title compound as a white powder (0.510 µmol, 51%). LCMS (SQ2 ProductAnalysis-Acidic-Peptide-Polar, Acquity "G," "C," "A," "T" and "U" each generally stand for a nucleotide that contains guanine, cytosine, adenine, thymidine and uracil as a base, respectively. However, the terms "ribonucleotide", "deoxynucleotide", or "nucleotide" can also refer to a modified nucleotide or a surrogate replacement moiety.

Those skilled in the art will appreciate that it is possible to synthesize and modify the siRNA as desired, using any conventional method known in the art (see Henschel et al. 2004 DEQOR: a web-based tool for the design and quality control of siRNAs. Nucleic Acids Research 32 (Web Server Issue): W113-W120).

Example 22

Conjugation of a Fatty Acid Moiety of Formula A3 to siRNA

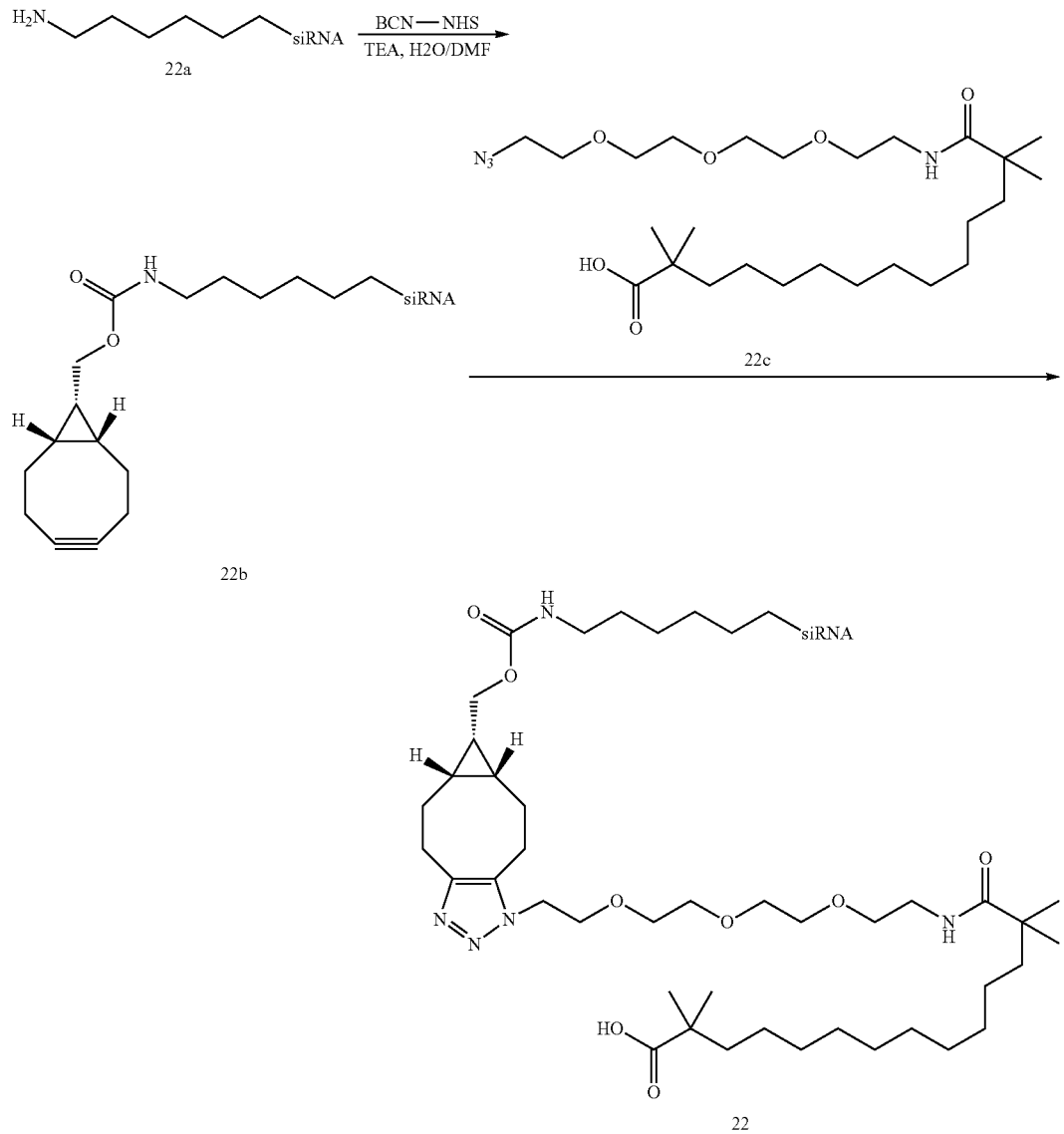

Preparation of Intermediate 22a:

From TTR siRNA [siRNA to transthyretin (TTR), synthesized using conventional methods known in the art] was converted to 22a using standard oligonucleotide procedures (e.g. reaction with 6-(4-Monomethoxytritylamino)hexyl-(2-cyanoethyl)-(N,N-diisopropyl)-phosphoramidite (Glen Research Catalog No: 10-1906))

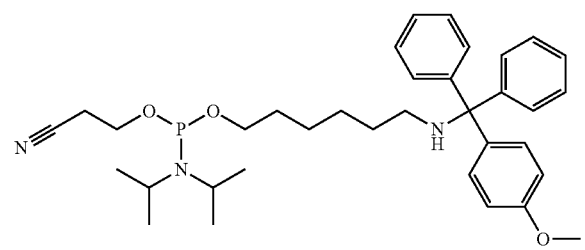 [SMILES: COc1ccc(C(NCCCCCCOP(OCCC#N)N(C(C)C)C(C)C)(c2ccccc2)c2ccccc2)cc1]

TTR siRNA:

Antisense strand:

(SEQ ID NO: 18)
P<u>uagagc</u>aaga<u>ac</u>acugu*u*rX058 wherein:

P is phosphate, lowercase letters indicate a 2'-OMe modified nucleotide, underlined letters indicate a 2'-F modified nucleotide, italics letters indicate a 2'-MOE modified nucleotide, r is abasic ribitol, * refers to a phosphorothioate linkage, and X058 is a non-nucleotidic 3' end cap of Formula:

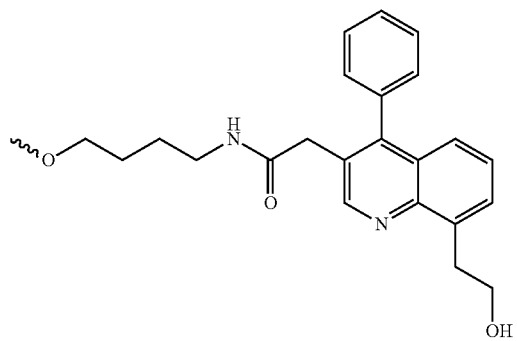

Sense Strand:

(SEQ ID NO: 19)
aac̲agug̲uuc̲uugc̲uc̲uar-C6OH.

refers to a phosphate; and C6OH (also known as C6) is a non-nucleotidic 3' end cap of Formula:

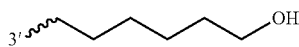

Preparation of Intermediate 22b:

To a 0.556 ml of a solution of siRNA 22a (TTR siRNA 14.02 mM in H2O, 7.79 μmol) at 0° C., 0.556 ml DMF was added and warmed up to room temperature. Then 208 μl TEA (0.3M in DMF, 62 μmol) was added and 260 μl BCN-NHS ((1R,8S,9s)-Bicyclo[6.1.0]non-4-yn-9-ylmethyl N-succinimidyl carbonate) (0.15M in DMF, 39 μmol). The resulted reaction stirred at room temperature for 1 hr. Analytical HPLC showed the disappearance of starting material 22a. The reaction was diluted to 10 ml with de-ionized H₂O and became cloudy. The above mixture was extracted with ethylacetate 5 times to remove small organic molecules. The aqueous layer was separated and lyophilized. The dried product solid (22b) was used as it was.

Preparation of Example 22:

Mixed 80 82 Compound 22b (12.3 mM in H₂O, 0.968 μmol) and 65 μbis fatty acid-N₃ (22c: step 2 of Example 15: 44.7 mM in DMSO, 2.90 μmol). The resulted mixture was cloudy, so 80 μl1:1 DMF/THF was added and the reaction was still slightly cloudy. Another 80 μDMSO was added to get a clear solution. The reaction stirred at room temperature for overnight. The reaction was diluted with de-ionized H₂O and purified over HPLC to afford 5.6 mg compound 22 (65.9% yield). HPLC conditions for purification: Column: Xselect Prep phenylhexyl 5 um OBD 19×50 mm; organic solvent: ACN modified with 100 mM TEA.HOAc; aqueous solvent: H₂O modified with 100 mM TEA.HOAc; Gradient: 5-60% AcCN/H₂O; Time: 10 min. Under LC-MS method H, the product showed a single peak with retention time of 5.44 min with the desired MW of 8778 after deconvolusion.

Example 23

Conjugation of a Fatty Acid Moiety of Formula A1 to siRNA Preparation of Compound 4

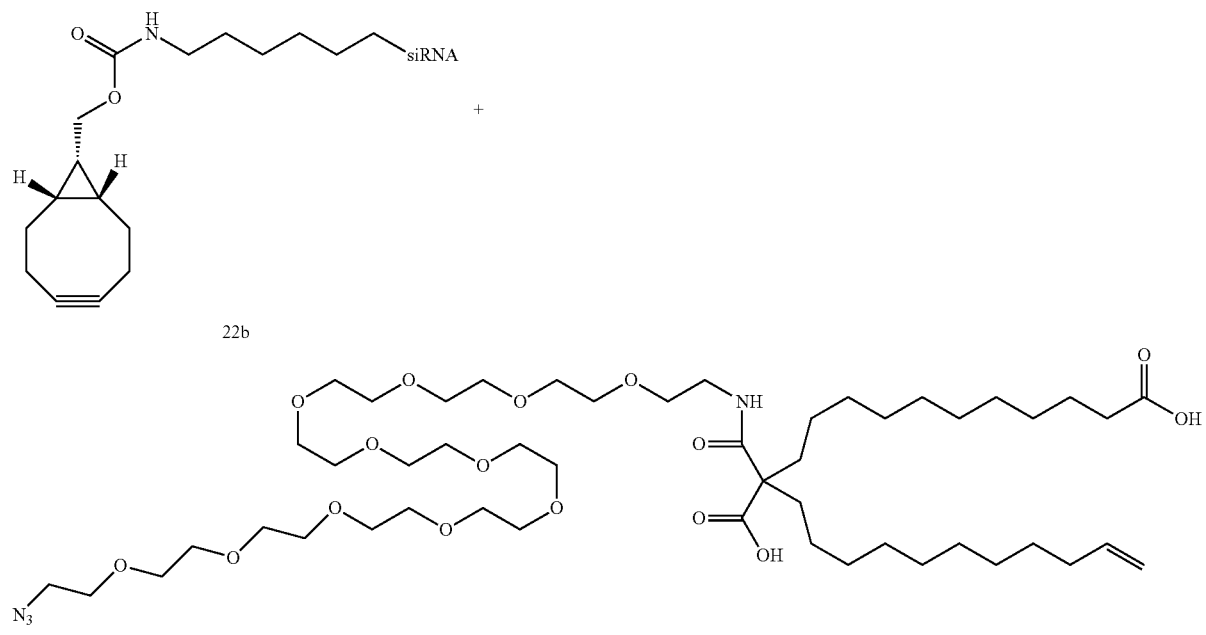

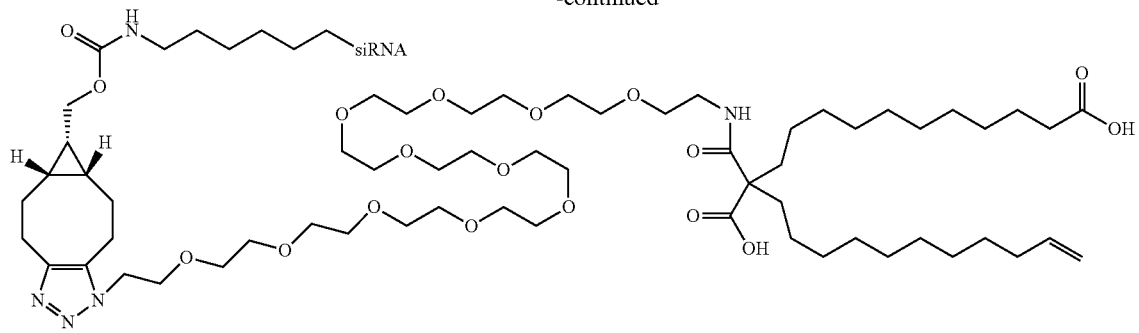

23

Example 23 was prepared using the same procedure as example 22.

Preparation of 23a:

To a solution NHS-fatty acid (20 mg) in DCM (16 mL) was added azido-peg7-amine (QuantaBiodesign, cat #10523) (31 mg) and DIPEA (52 uL) and the mixture was stirred at r.t. for 2 h. Complete conversion was observed by LC-MS analysis. The mixture was concentrated, re-dissolved in MeOH (3 mL) and purified by MS triggered HPLC with 0.1% TFA (rt=1.59 min, mass (M+1) expected: 818.062 mass observed: 817.9) to give clean product. Half material was lost due to 800 Da cut-off set in the HPLC MS system. 5-10 mg (17-33%) clean product was obtained.

Mixed 80 μl 22b (12.3 mM in H$_2$O, 0.968 μmol) and 65 μl tris fatty acid-N3 (23a: 44.7 mM in DMSO, 2.90 μmol). The reaction afforded 5.2 mg compound 23 (58.0% yield). Under LC-MS method H, the product showed a single peak with retention time of 5.87 min with the desired MW of 9257 after deconvolusion.

Example 24

Conjugation of Fatty Acid of Formula A3 to APOCIII siRNA

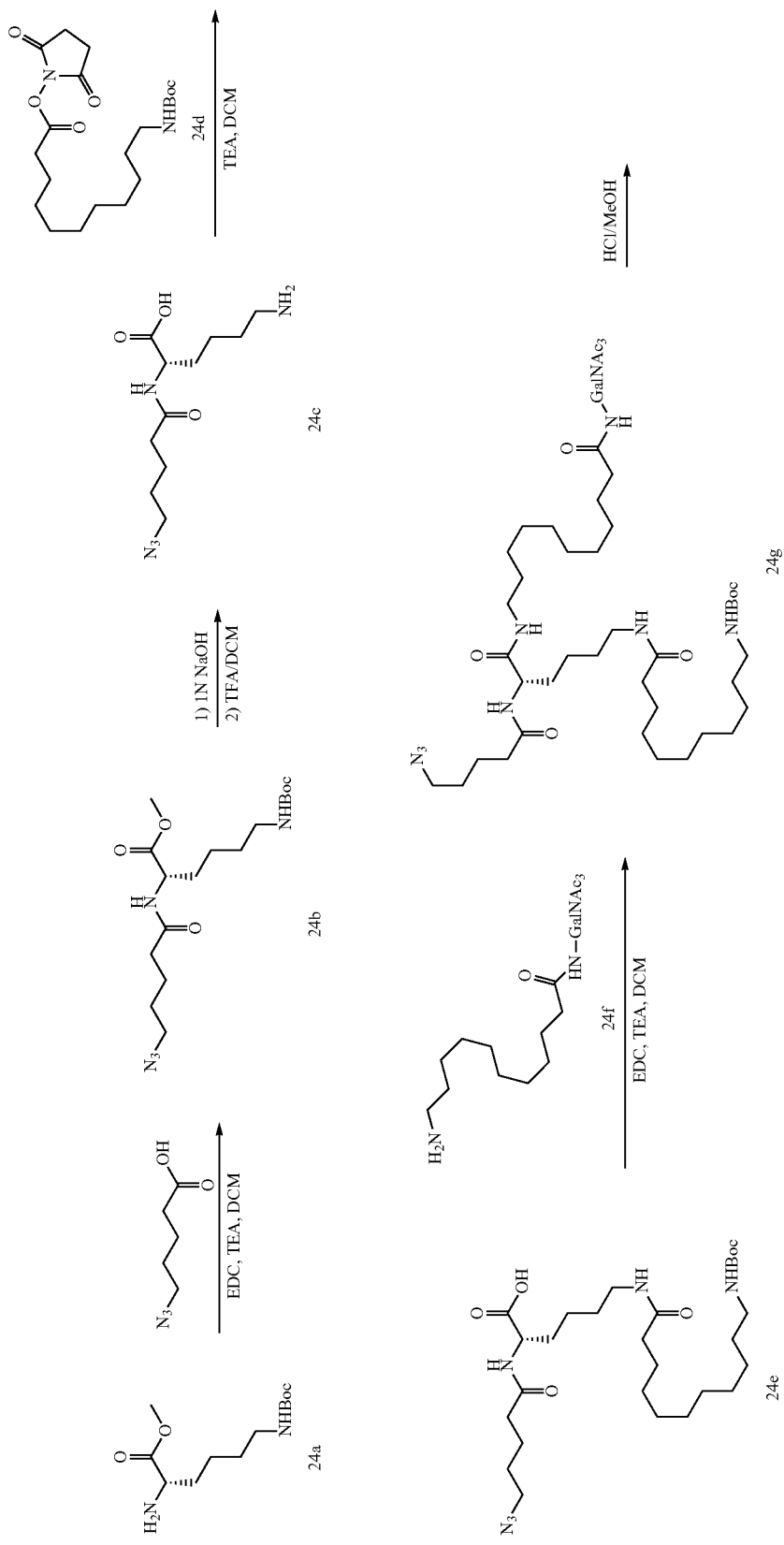

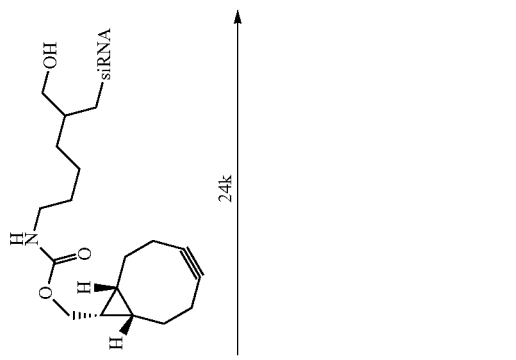
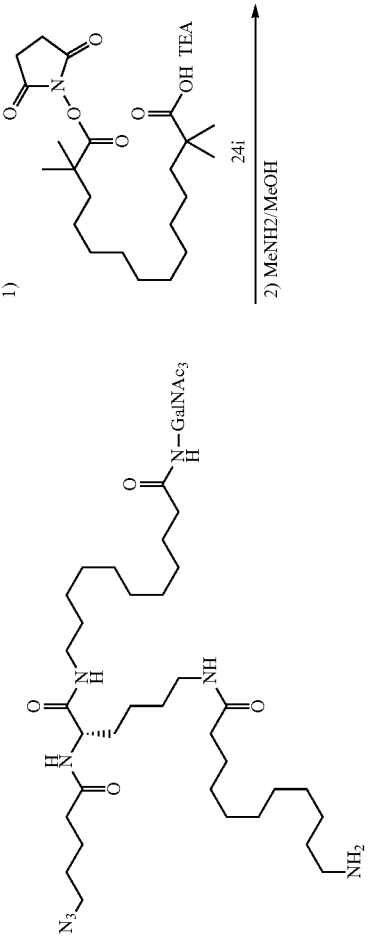
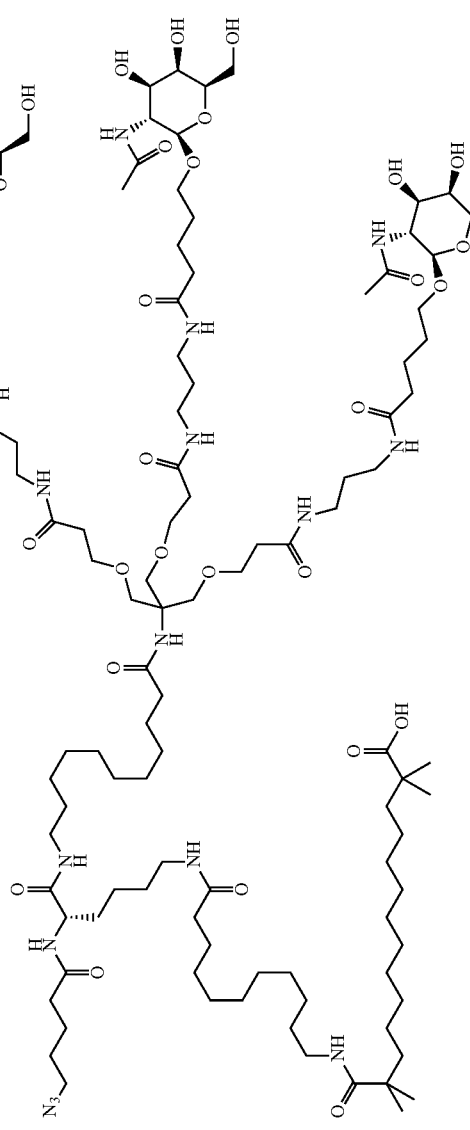

225 226
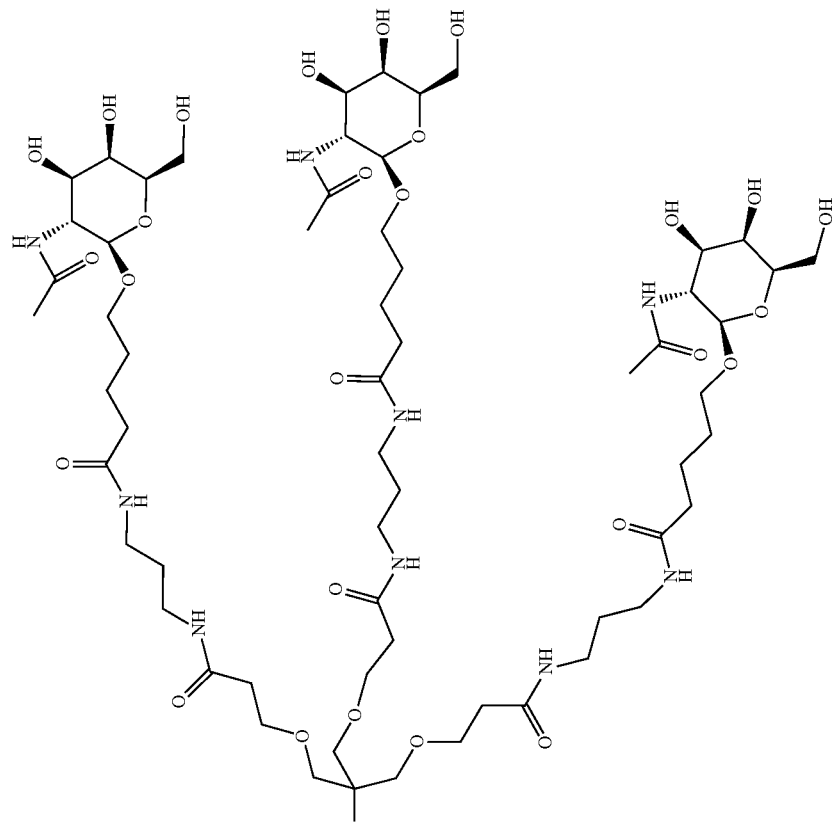
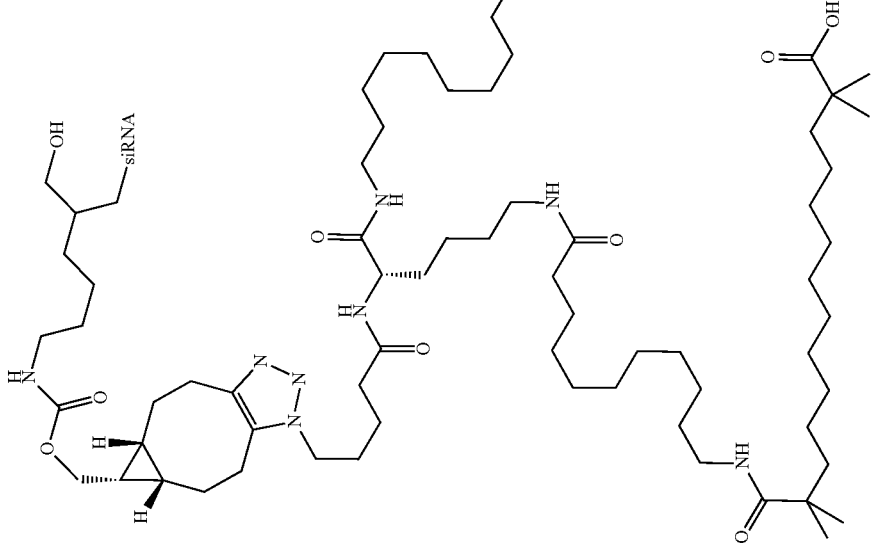

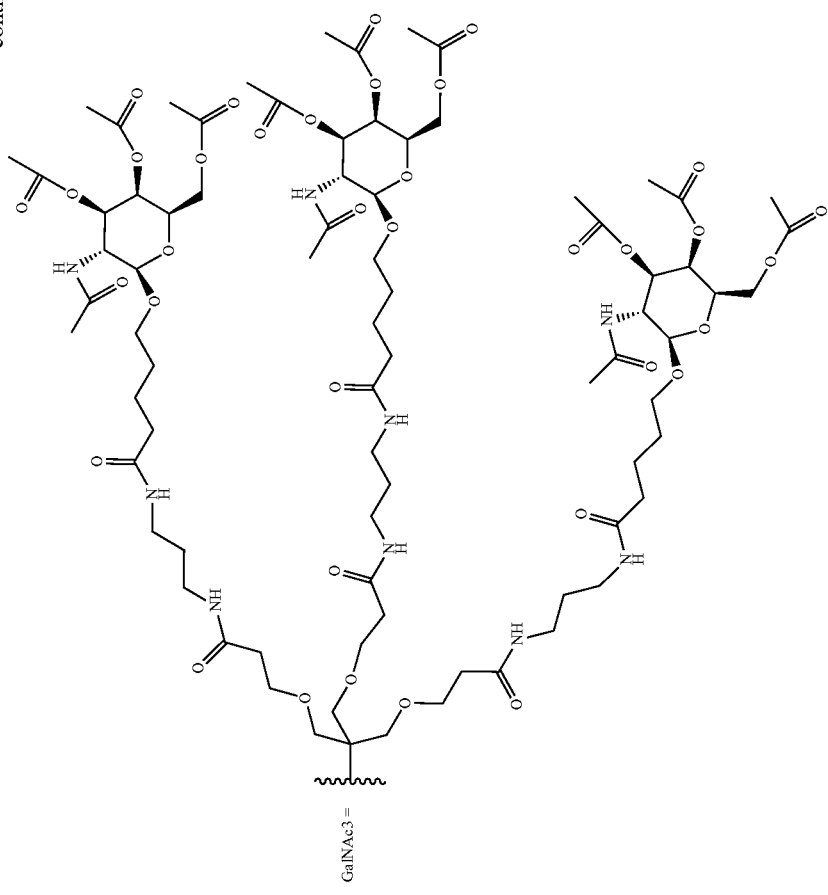

Preparation of 24b:

To a solution of 24a (1.244 g, 4.19 mmol) in 25 ml DCM, TEA (0.58 ml, 4.19 mmol) was added, followed by N3-pentanoic acid (500 mg, 3.49 mmol). EDC (804 mg, 4.19 mmol) was added at last. The reaction stirred at room temperature for 4 hr. The reaction was extracted between brine and DCM. Combined all organics, dried, concentrated and purified over SiO2 gel with 60% ethylacetate/heptane to afford 1.20 g compound 24b (89% yield). $^1$H NMR (CHLOROFORM-d, 400NHz) d: 5.88-6.37 (m, 1H), 4.60 (d, J=4.8 Hz, 2H), 3.77 (s, 3H), 3.33 (t, J=6.7 Hz, 2H), 3.13 (d, J=6.5 Hz, 2H), 2.30 (t, J=7.2 Hz, 2H), 1.81-1.95 (m, 1H), 1.63-1.81 (m, 5H), 1.48-1.57 (m, 2H), 1.46 (s, 9H), 1.36 (d, J=6.8 Hz, 2H)

Preparation of 24c

To a solution of 24b (860 mg, 2.23 mmol) in 12 ml THF, 1N NaOH (5.58 ml, 5.58 mmol) was added. The reaction stirred at room temperature for 0.5 hr. The reaction was diluted with brine and 20 ml DCM was added. The pH of aqueous layer was adjusted to pH ~5 with 1N HCl, then extracted with DCM. Combined all organics, dried, concentrated and the crude solid was redissolved into 6 ml DCM. 0.6 ml TFA was added and the reaction stirred at room temperature for 2 hr. The reaction was concentrated and afforded the crude 24c (400 mg, 54%), which was used directly without further purification. Under LC-MS method I, the product showed a major peak at 0.43 min. with a mass of 272.5 (M+H$^+$).

Preparation of 24e

To a solution of 24c (400 mg, 1.04 mmol) in 10 ml DCM, TEA (0.434 ml, 3.11 mmol) was added, followed by the addition of 24d (538 mg, 1.35 mmol). The reaction stirred at room temperature for 3 hr. The reaction was extracted between H$_2$O and DCM. Combined all organics, dried, concentrated and purified over SiO2 gel with 8% MeOH/DCM to afford 475 mg of 24e (82% yield). 1H NMR (CHLOROFORM-d, 400 MHz) d: 6.74-6.98 (m, 1H), 5.95-6.13 (m, 1H), 4.55 (dd, J=7.2, 2.4 Hz, 2H), 3.32 (t, J=6.7 Hz, 4H), 3.11 (d, J=5.8 Hz, 2H), 2.30-2.37 (m, 2H), 2.20-2.26 (m, 2H), 1.90 (br. s., 2H), 1.71-1.80 (m, 2H), 1.59-1.71 (m, 4H), 1.51-1.59 (m, 2H), 1.35-1.51 (m, 13H), 1.20-1.35 (m, 13H)

Preparation of 24f

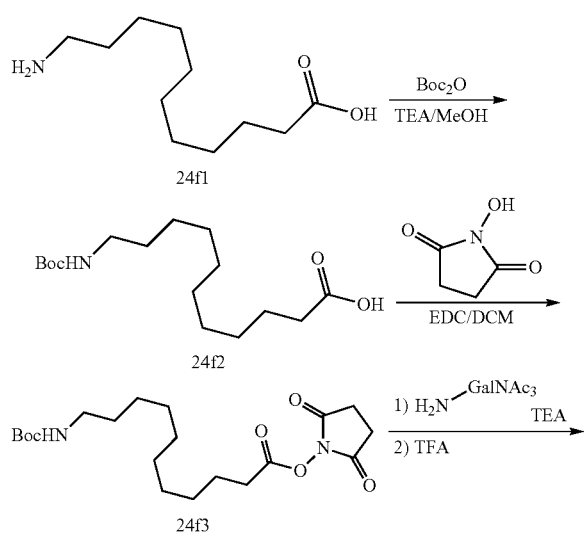

24f1

24f2

24f3

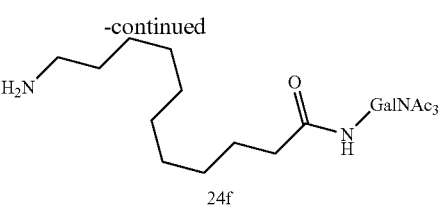

24f

Preparation of Intermediate 24f2

To a solution of 24f1 (1.0 g, 4.97 mmol) in MeOH (40 ml), TEA (1.04 ml, 7.45 mmol) was added, followed by di t-butyl dicarbonate (2.17 g, 9.94 mmol). The reaction was heated at 60° C. for 1.5 hr. The reaction was concentrated and purified over SiO2 column with 5% MeOH/DCM to afford 1.2 g compound 24f2 (80% yield). $^1$H NMR (CHLOROFORM-d, 400 MHz) d: 4.51 (br. s, 1H), 3.00-3.22 (m, 2H), 2.37 (t, J=7.4 Hz, 2H), 1.59-1.71 (m, 2H), 1.46 (s, 11H), 1.29 (br. s., 12H).

Preparation of Intermediate 24f3

To a solution of 24f2 (1.2 g, 3.98 mmol) in DCM (30 ml), N-hydroxyl scuccinimide (0.60 g, 5.18 mmol) was added, followed by EDC (1.0 g, 5.18 mmol). The solution was stirred at room temperature for overnight. The reaction was concentrated, directly loaded onto SiO2 column and purified with 40% ethylacetate/heptane to afford 1.46 g compound 24f3 (92% yield). 1H NMR (CHLOROFORM-d, 400 MHz) d: 4.49 (br. s, 1H), 3.04-3.19 (m, 2H), 2.86 (d, J=4.5 Hz, 4H), 2.62 (t, J=7.4 Hz, 2H), 1.70-1.82 (m, 2H), 1.37-1.53 (m, 13H), 1.30 (br. s., 10H)

Preparation of Intermediate 24f

To a solution of GalNAc3-NH2 (300 mg, 0.16 mmol) in DCM (1.5 ml), TEA (0.11 ml, 0.79 mmol) was added, followed by the addition of 24f3 (188 mg, 0.47 mmol). The reaction stirred at room temperature for overnight. Then trifluoroacetic acid (1.0 ml) was added. After 2 hrs, LC-MS showed the disappearance of the intermediate. The reaction was concentrated and purified on open access HPLC under acidic condition with ELSD as a detection. The HPLC fractions containing the product were collected and the solvent was evaporated to afford 220 mg compound 24f (67% yield). LC-MS showed that partial product lost one acetyl group. HPLC conditions for purification: column: Sunfire 30×100 mm 5 um column; organic solvent: ACN w/7.5% TFA; aqueous solvent: H$_2$O w/ 7.5% TFA; flow rate: 75 ml/min. Gradient: 15-40% H2O/AcCN; Time: 9.5 min. detection: ELSD (Evaporative Light Scattering Detector) as detection. Under LC-MS method 1, the product showed a peak at 0.83 min. with a mass of 989.9 (M/2+H$^+$).

Preparation of 24 g

To a solution of 24e (172 mg, 0.31 mmol) in 3 ml DCM, 24f (250 mg, 0.12 mmol) was added, followed by TEA (0.069 ml, 0.50 mmol). EDC (95 mg, 0.5 mmol) was added at last. The reaction stirred at room temperature for overnight. The reaction was concentrated and purified over SiO$_2$ column with 5% MeOH/DCM to afford 230 mg 24 g (74% yield). Under LC-MS method I, the product showed a peak 1.30 min. with a mass of 1258.2 (M/2+H$^+$).

Preparation of 24 h

To a solution of 24 g (230 mg, 0.091 mmol) in 1 ml THF, 0.457 ml 4N HCl (in dioxane, 1.83 mmol) was added. The reaction stirred at room temperature for 1 hr. The reaction was concentrated and purified over HPLC to afford 50 mg 24 h (23% yield), which lost one acetyl group on the sugar. HPLC conditions for purification: column: Sunfire 30×100 mm 5 um column; organic solvent: ACN w/ 7.5% TFA;

aqueous solvent: H₂O w/ 7.5% TFA; flow rate: 75 ml/min. Gradient: 15-40% H2O/AcCN; Time: 9.5 min. detection: ELSD (Evaporative Light Scattering Detector) as detection. Under LC-MS method I, the product showed a peak at 0.95 min. with a mass of 1187.1 (M/2+H⁺).

Preparation of 24i

To a solution of 2,2,13,13-tetramethyltetradecanedioic acid (40 mg, 0.127 mmol) in 2 ml DCM, N—OH succinimide (9.81 mg, 0.085 mmol) was added, followed by the addition of EDC (16.34 mg, 0.085 mmol). The reaction was stirred at room temperature for overnight. The reaction was concentrated and purified over HPLC to afford 20 mg 24i (38% yield). HPLC conditions for purification: column: Sunfire 30×100 mm 5 um column; organic solvent: ACN w/7.5% TFA; aqueous solvent: H₂O w/ 7.5% TFA; flow rate: 75 ml/min. Gradient: 45-70% H2O/AcCN; Time: 9.5 min. detection: ELSD (Evaporative Light Scattering Detector) as detection. Under LC-MS method 1, the product showed a peak at 1.55 min. with a mass of 434.3 (M+Na⁺).

Preparation of 24j

To a solution of 24 h (20 mg, 8.05 µmol) in 0.5 ml DCM, TEA (4.54 µl, 32 µmol) was added, followed by the addition of 24i (6.62 mg, 16 µmol) and DMAP (3.93 mg, 32 µmol). The reaction stirred at room temperature for overnight. Then 0.5 ml 2N MeNH₂/MeOH was added for the deprotection. The reaction stirred at room temperature for another overnight. The reaction was concentrated and acetone was added to precipitate the product and remove excess reagents and lipids to afforded 12 mg 24j (64% yield). Under LC-MS method I, the product showed a peak at 0.69 min. with a mass of 1166.9 (M/2+H⁺).

Preparation of 24K

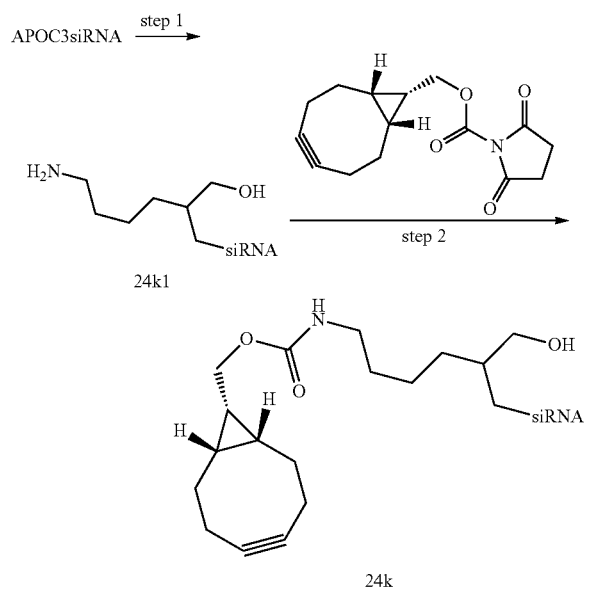

Step 1:

APOCIII siRNA [siRNA to gene APOCIII (also known as APOC3 or Apoc 3), synthesized using conventional methods known in the art]:

Annealing Oligonucleotides

General Procedure:

Each oligonucleotide pellet is briefly spinned down in a centrifuge and dissolved in Duplex Buffer (100 mM Potassium Acetate; 30 mM HEPES, pH 7.5) at high concentration (1-10 OD260 per 100 mL buffer). Heating (up to 94° C.) and vortexing may be used to facilitate resuspension. The sense and the antisense strands are then added together in equimolar amounts. The mixed oligonucleotides are then heated to 94° C. and gradually cooled down. For sequences with significant secondary structure, a more gradual cooling/annealing step may be employed. This is easily done by placing the oligo solution in a water bath or heat block and unplugging/turning off the machine. The resulting product will be in a stable, double-stranded form and can be stored at 4° C. or frozen.

Antisense strand of APOCIII siRNA comprises a sequence of APOCIII, wherein the 3' end of the strand terminates in a phosphate and further comprises, in 5' to 3' order, a ribitol, another phosphate, and a 3' end cap X058, a non-nucleotidic 3' end cap of Formula:

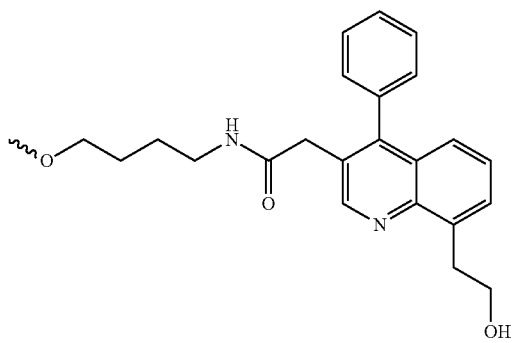

The sense strand comprises a sequence of APOCIII complementary to the antisense strand, wherein the 3' end of the strand terminates in a phosphate and further comprises, in 5' to 3' order, a ribitol, another phosphate, and a 3' end cap C6OH, a non-nucleotidic 3' end cap of Formula:

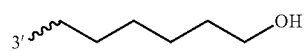

APOCIII siRNA was reacted with 2-Dimethoxytrityloxymethyl-6-fluorenylmethoxycarbonylamino-hexane-1-succinoyl-long chain alkylamino-CPG (Glen Research Catalog No 20-2957) to generate product 24k1.

Step 2

APOCIII siRNA (24k1: 401 µL, 11.2 mM in H₂O, 4.49 µmol) was mixed with 401 µl DMF to get a clear solution. Then TEA (180 µl, 0.25M in DMF, 45 µmol) was added, followed by BCN-NHS ((1R,8S,9s)-Bicyclo[6.1.0]non-4-yn-9-ylmethyl N-succinimidyl carbonate) (9.16 mg, 31 µmol). The reaction stirred at room temperature for 1 hr. The reaction was diluted with H₂O to 10 ml and extracted with ethylacetate 3times. The aqueous layer was separated and concentrated to ~5 ml and purified over PD-10 desalting column (GE healthcare).

Preparation of 24

24j (5.8 mg, 2.5 µmol) was added into 105 µl compound 24k (Apoc 3 siRNA 9.5 mM in H₂O, 0.993 µmol). After 1 hr, the reaction became viscous. So another 60 µl H₂O was added and the reaction stirred at room temperature for overnight. The reaction was diluted with H₂O and purified over HPLC to afford 5 mg conjugate 24 (57% yield). HPLC conditions for purification:

Column: Xselect Prep phenylhexyl 5 um OBD 19×50 mm; organic solvent: AcCN modified with 100 mM TEA.HOAc; aqueous solvent: H₂O modified with 100 mM TEA.HOAc; Gradient: 5-50% AcCN/H2O; Time: 10 min. Under LC-MS method H, the product showed a peak at 5.96 min. with the desired mass of 8896 after deconvolution.

Reference Example 3 siRNA Conjugated with GalNAc

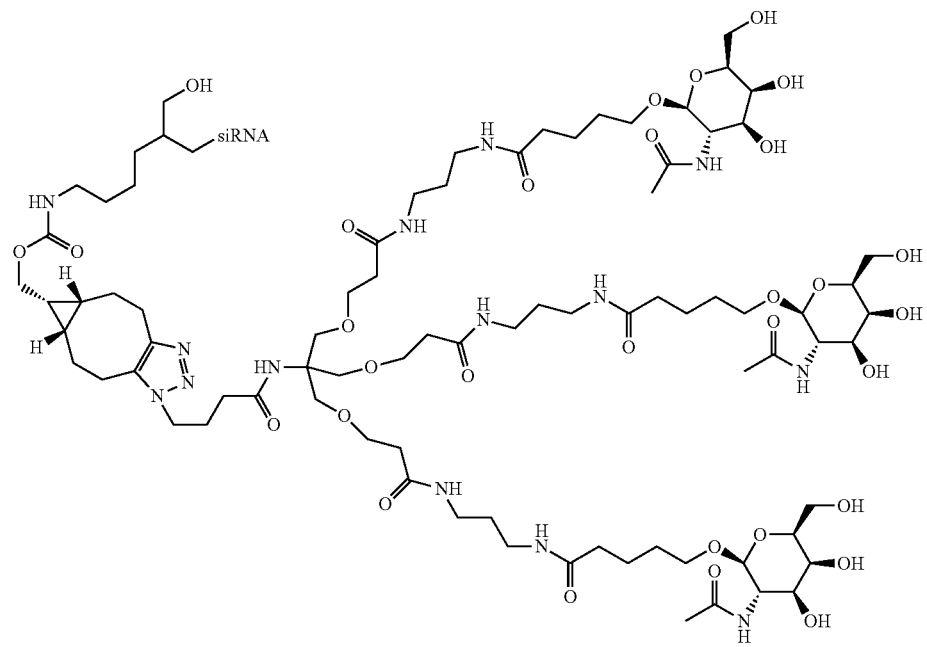

Reference Example 3 was prepared according to procedure of Example 24 (replacing 24j with GalNac3-N3 (below).

Preparation of GalNac3-N3

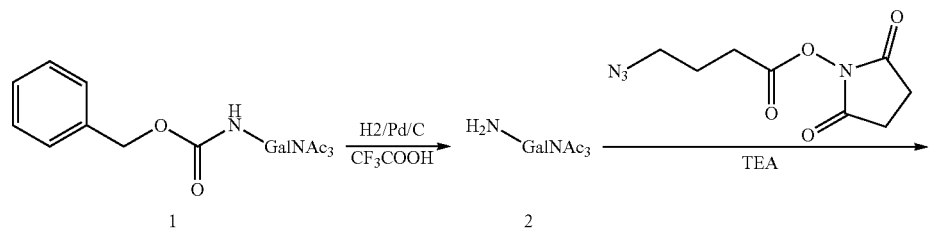

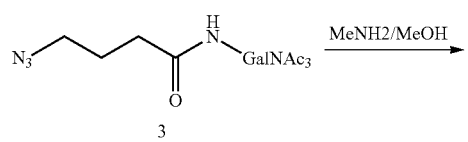

-continued

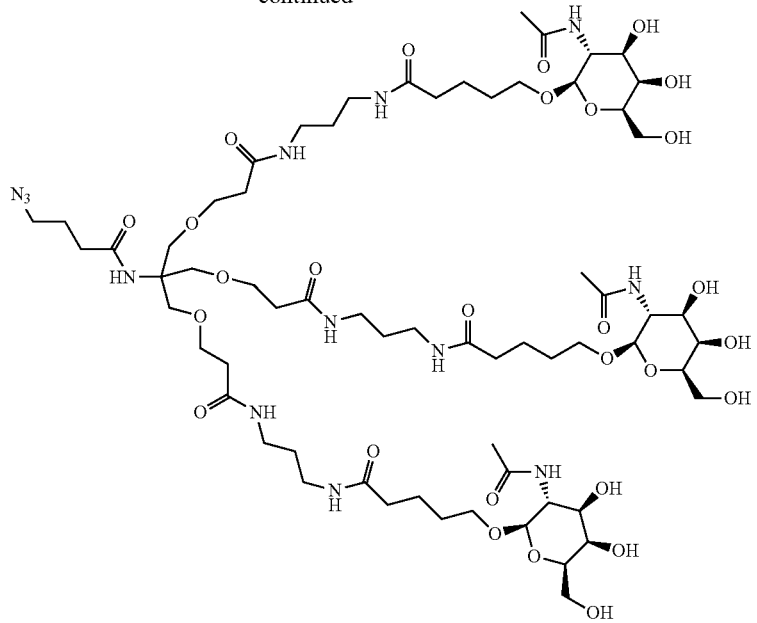

4

Preparation of intermediate 2

Compound 1 (2.06 g, 1.07 mmol) was dissolved in 20 ml ethanol, TFA (82 ul, 1.07 mmol) was added, followed by 10% Pd/C (0.114 g, 0.11 mmol). The reaction was treated under $H_2$ balloon for 6 hours. The reaction was filtered, washed with ethanol and concentrated to get white solid, which was used directly for next step. Under LC-MS method I, the product showed a peak at 0.81 min. with a mass of 898.5 ($M/2++H^+$).

Preparation of Intermediate 3

Compound 2 (4.848 g, 0.479 mmol) was dissolved in 10 ml anhdrous DMF, 2,5-dioxopyrrolidin-1-yl-4 azidobutanoate (0.325 g, 1.436 mmol) was added, followed by the addition of DIPEA (0.418 ml, 2.394 mmol). The reaction was to react overnight at room temperature. The reaction was concentrated with no heating, directly loaded onto a pre-equilibrated SiO2 column and purified with 0-20% methanol/DCM step gradient to afford 2.383 g compound 3 (49.25% yield).

Under LC-MS method I, the product showed a peak at 1.27 min. with a mass of 953.7 ($M/2+H^+$).

Preparation of Intermediate 4

Mixed compound 3 (1.33 g, 0.70 mmol) with MeNH2 (17.45 ml, 2.0M in Methanol, 34.9 mmol). The reaction stirred at room temperature for 2 hr. LC-MS only showed the product peak. The reaction was concentrated. Then the solid redissolved into ethanol and was precipitated with acetone to afford 1.0 g compound 4 (94% yield). Under LC-MS method 1, the product showed a peak at 0.53 min. with a mass of 764.5 ($M/2+H^+$).

Example 25

Conjugation of Carrier Protein (CRM197) and a Fatty Acid

Step 1: 2-((2,2-dimethyl-4-oxo-3,8,11,14,17,20,23,26,29,32,35,38-dodecaoxa-5-azatetracontan-40-yl)carbamoyl)-2-undecyltridecanedioic acid (25a)

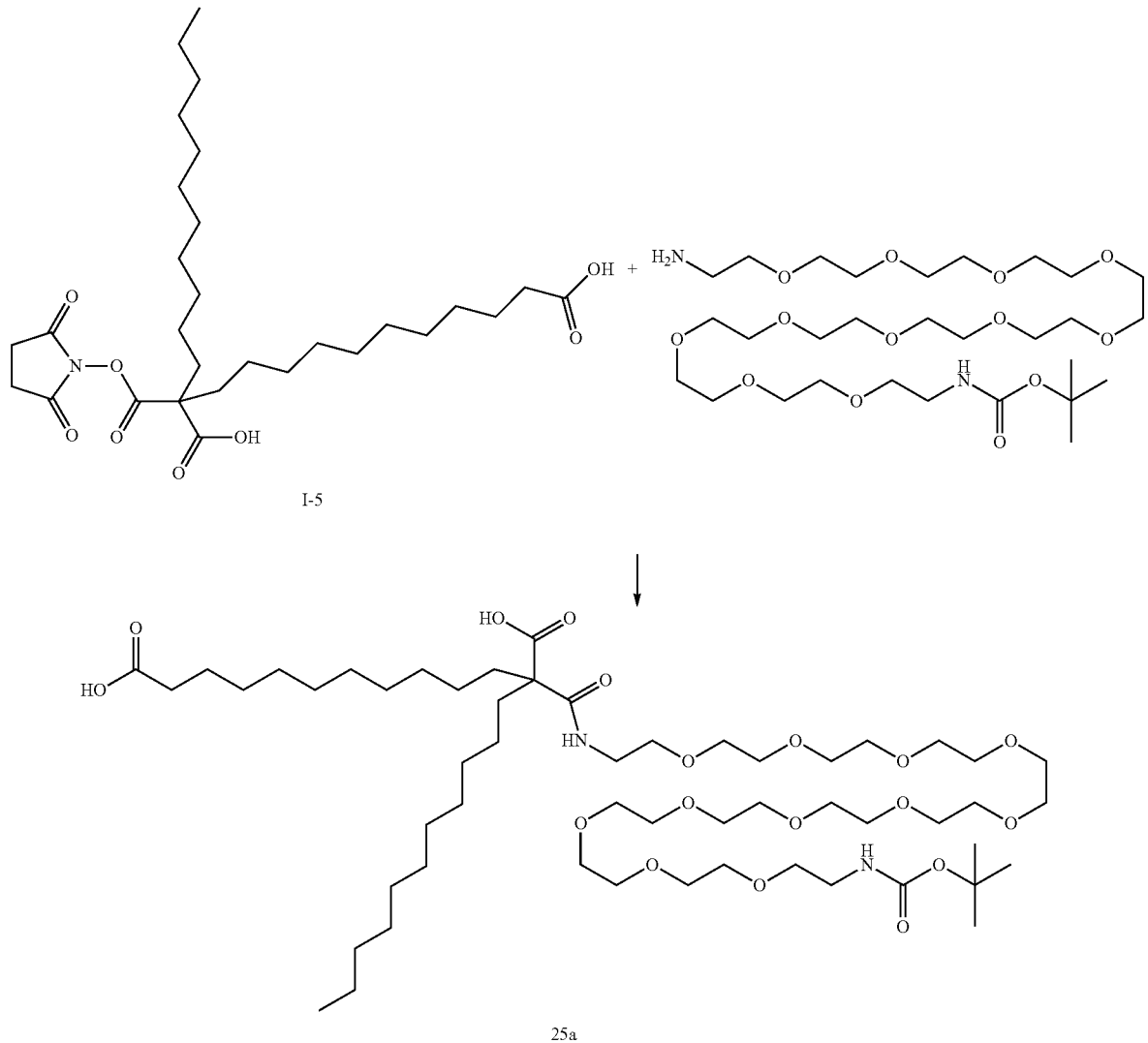

t-boc-N-amido-dPEG®₁₁-amine (100 mg, 0.155 mmol, Quanta Biodesign) and Intermediate 5 (80 mg, 0.148 mmol) were dissolved in THF (3 mL) and stirred at room temperature under nitrogen. After 30 minutes, DIPEA (0.05 mL, 0.286 mmol) was added and the reaction mixture stirred at room temperature overnight. Complete conversion was observed by LCMS (Acidic Eluent A: Water+0.05% Trifluoroacetic Acid, Eluent B: ACN, column Sunfire C18 3.5 μm 3.0×30 mm-40° C., 5-95% gradient 2 minutes, retention time 1.92 min). The reaction mixture was concentrated under reduced pressure, then dissolved in about 1.5 mL of acetonitrile. Purified on a MS-triggered HPLC (Sunfire 30×50 mm 5 um column ACN/H2O w/ 0.1% TFA 75 ml/min 1.5 ml injection, 65-95% ACN 3.5 min gradient, retention time 3.23 minutes) and the fractions pooled and lyophilized to give 85 mg clean product in 54% yield. Clear oil. LCMS: Method D Rt=1.18 min, M+H 1070.1; $^1$H NMR (400 MHz, ACETONITRILE-$d_3$) δ ppm 0.82-1.03 (m, 1 H) 1.11-1.37 (m, 10 H) 1.37-1.51 (m, 2 H) 1.51-1.64 (m, 1 H) 1.69-1.82 (m, 1 H) 1.90-2.04 (m, 66 H) 2.05-2.21 (m, 8 H) 2.21-2.42 (m, 1 H) 3.17-3.28 (m, 1 H) 3.40-3.68 (m, 13 H).

Step 2: 2-((35-amino-3,6,9,12,15,18,21,24,27,30,33-undecaoxapentatriacontyl)carbamoyl)-2-undecyltridecanedioic acid (25b)

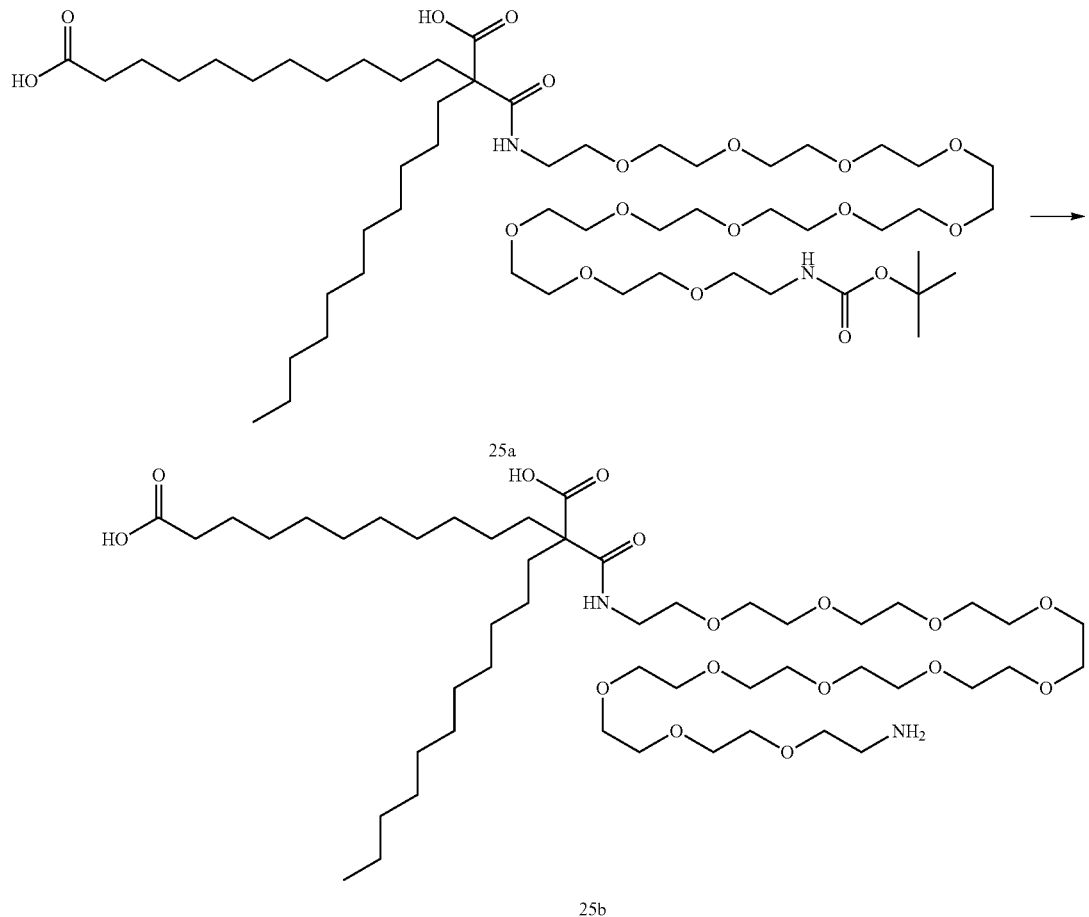

25a (5 mg, 4.68 μmol) was dissolved in DCM (Volume: 2 mL), then trifluoroacetic acid (25 μl, 0.324 mmol) was added. The reaction mixture was stirred at room temperature under nitrogen atmosphere for about 2 hours. Complete conversion was observed by LCMS (Acidic Eluent A: Water+0.05% Trifluoroacetic Acid, Eluent B: ACN, column Sunfire C18 3.5 μm 3.0×30 mm-40° C., 5-95% gradient 2 minutes, retention time 1.45 min). The reaction mixture was concentrated under reduced pressure, then rinsed with DCM and concentrated again 3 times. Dissolved in a mixture of acetonitrile and DMSO. Purified on a MS-triggered HPLC (Sunfire 30×50 mm 5 um column ACN/H2O w/ 0.1% TFA 75 ml/min 1.5 ml injection, 45-70% ACN 3.5 min gradient, retention time 2.50 minutes) and the fractions pooled and lyophilized to give 2.5 mg clean product in 55% yield. Clear oil.

Method A Rt=1.45 min, M+H 969.9; $^1$H NMR (400 MHz, ACETONITRILE-$d_3$) δ ppm 0.62-0.91 (m, 2 H) 0.91-1.10 (m, 3 H) 1.10-1.31 (m, 18 H) 1.46 (quin, J=7.21 Hz, 2 H) 1.59-1.89 (m, 35 H) 1.94-2.09 (m, 1 H) 2.16 (t, J=7.40 Hz, 2 H) 2.97-3.11 (m, 1 H) 3.24-3.37 (m, 1 H) 3.37-3.61 (m, 28 H) 3.61-3.89 (m, 2 H) 7.85 (br. s., 1 H).

Step 3: 2-(((S)-5-(3-amino-3-oxopropyl)-3,6-dioxo-1-phenyl-2,10,13,16,19,22,25,28,31,34,37,40-dodecaoxa-4,7-diazadotetracontan-42-yl)carbamoyl)-2-undecyltridecanedioic acid (25d)

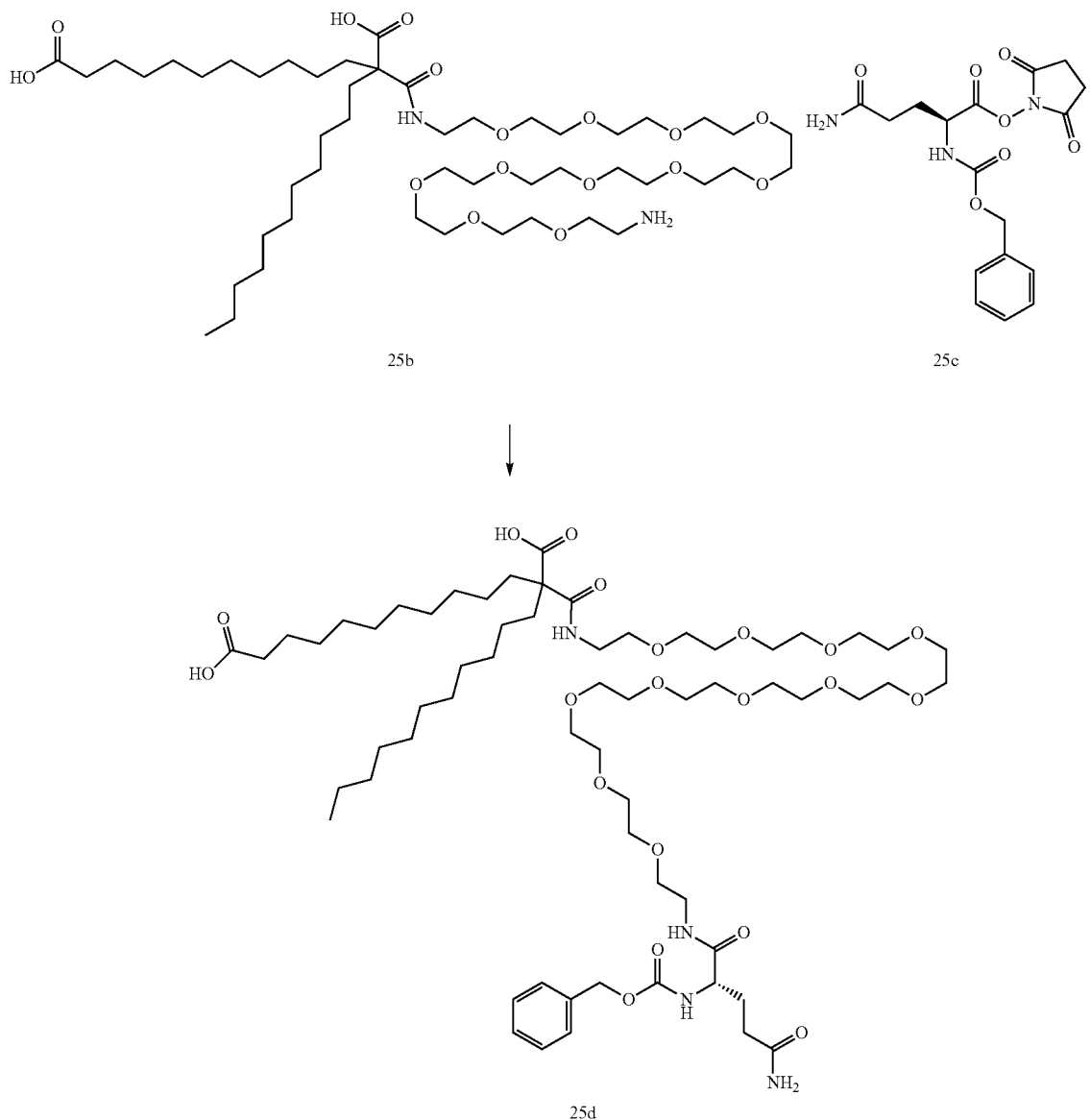

A solution of 25b (20 mg, 0.018 mmol) in THF (Volume: 2 mL) was added to Z-L-Gln-Osu 25c (Santa Cruz Biotechnology, CAS 34078-85-8, 11 mg, 0.029 mmol), then DIPEA (75 µl, 0.429 mmol) was added. Stirred at room temperature under a nitrogen atmosphere over weekend. Complete conversion was observed by LCMS (Acidic Eluent A: Water+ 0.05% Trifluoroacetic Acid, Eluent B: ACN, column Sunfire C18 3.5 µm 3.0×30 mm-40° C., 5-95% gradient 2 minutes, retention time 1.77 min). The reaction mixture was concentrated under reduced pressure, then dissolved in acetonitrile. Purified on a MS-triggered HPLC (Sunfire 30×50 mm 5 um column ACN/H2O w/ 0.1% TFA 75 ml/min 1.5 ml injection, 55-80% ACN 3.5 min gradient, retention time 2.70 minutes) and the fractions pooled and lyophilized to give 10.5 mg clean product in 46% yield as a clear colorless oil. Method C Rt=1.60 min, M+H 1232.4; $^1$H NMR (400 MHz, ACETONITRILE-$d_3$) δ ppm 0.67-0.93 (m, 2 H) 0.93-1.10 (m, 2 H) 1.10-1.32 (m, 15 H) 1.45 (quin, J=7.24 Hz, 1 H) 1.59-1.69 (m, 1 H) 1.75-1.93 (m, 30 H) 1.94-2.21 (m, 20 H) 3.23 (quin, J=5.26 Hz, 1 H) 3.28-3.51 (m, 23 H) 3.95 (td, J=7.73, 5.44 Hz, 1 H) 4.92-5.22 (m, 1 H) 5.78 (br. s., 1 H) 6.13-6.42 (m, 1 H) 6.88 (br. s., 1 H) 7.20-7.36 (m, 2 H) 7.42 (t, J=5.07 Hz, 1 H).

Step 4: mTGase-Mediated Labelling of CRM197 with Fatty Acid (Example 25)

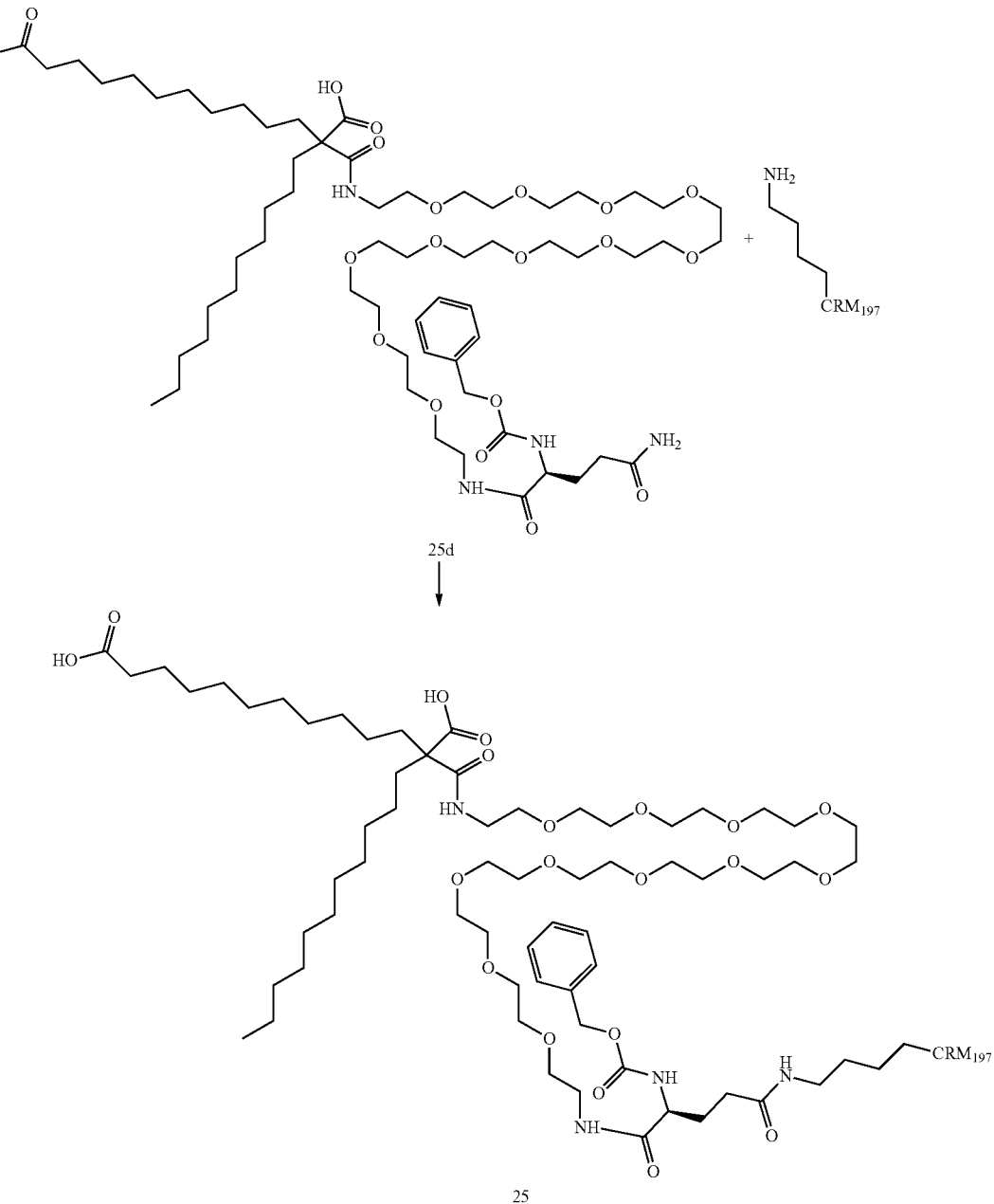

To a solution of 25d in 100 mM tris buffer pH 8 (8 mg/mL, 203 μL, 1.316 μmol) was added CRM197 (33 mg/mL, 1.515 μL, 0.00086 μmol) followed by a solution of transglutaminase enzyme (Ajinomoto) in PBS (50 mg/mL, 0.455 μL, 0.00060 μmol). The reaction was stirred at r.t. for 16 hours. The reaction mixture was exchanged into 100 mM tris buffer pH 8 using 10 kDa MWCO Amicon centrifugal filter by diluting and concentrating the reaction 5 times to a volume of 100 μL. LCMS analysis showed conversion to +1, +2, +3 and +4 products. LCMS QT2; Protein_35-70 kDa_3 min: $R_t$=1.45 min; MS [M+25d]: observed: 59625, calculated: 59624; MS [M+(2×25d)]: observed: 60839, calculated: 60838; MS [M+(3×25d)]: observed: 62054, calculated: 62052; MS [M+(4×25d)]: observed: 63270, calculated: 63266.

CRM197 Sequence:
(SEQ ID NO: 20)
GADDVVDSSK SFVMENFSSY HGTKPGYVDS IQKGIQKPKS

GTQGNYDDDW KEFYSTDNKY DAAGYSVDNE NPLSGKAGGV

VKVTYPGLTK VLALKVDNAE TIKKELGLSL TEPLMEQVGT

```
EEFIKRFGDG ASRVVLSLPF AEGSSSVEYI NNWEQAKALS

VELEINFETR GKRGQDAMYE YMAQACAGNR VRRSVGSSLS

CINLDWDVIR DKTKTKIESL KEHGPIKNKM SESPNKTVSE

EKAKQYLEEF HQTALEHPEL SELKTVTGTN PVFAGANYAA

WAVNVAQVID SETADNLEKT TAALSILPGI GSVMGIADGA

VHHNTEEIVA QSIALSSLMV AQAIPLVGEL VDIGFAAYNF

VESIINLFQV VHNSYNRPAY SPGHKTQPFL HDGYAVSWNT

VEDSIIRTGF QGESGHDIKI TAENTPLPIA GVLLPTIPGK

LDVNKSKTHI SVNGRKIRMR CRAIDGDVTF CRPKSPVYVG

NGVHANLHVA FHRSSSEKIH
```

| Degree of Labelling | Calculated | Observed | % | $R_t$ (min) |
|---|---|---|---|---|
| CRM197 | 58410 | n/a | 0 | n/a |
| CRM197 + 1 25d | 59624 | 59625 | 14 | 1.45 |
| CRM197 + 2 25d | 60838 | 60839 | 23 | 1.45 |
| CRM197 + 3 25d | 62052 | 62054 | 35 | 1.45 |
| CRM197 + 4 25d | 63266 | 63270 | 28 | 1.45 |

Peptide Mapping Experimental Summary:

Peptide Mapping Digestion: 5 μg modified CRM197 and positive control CRM197 samples were reduced with 20 mM DTT and digested with 1/30 (w/w) enzyme/protein at 26° C. overnight with trypsin. An aliquot of trypsin digested protein was further digested with GluC enzyme at 1/20 enzyme/protein ratio for 4 hr at 26° C.; note all enzymes purchased from Roche Diagnostics (Gmbh, Germany).

Reverse Phase LC-MS/MS Analysis: Resulting digested peptides were analyzed by liquid chromatography electrospray tandem mass spectrometry (LC-ESI MS/MS) on a Thermo LTQ Orbitrap Discovery (Thermo Fisher Scientific Inc., Waltham, Mass.) coupled to Agilent CapLC (Santa Clara, Calif.). Loaded ~10-15 μmole of CRM control and modified CRM197 digests on column at 40° C. (Waters Acuity BEH C18, 1.7 μm, 1×100 mm column). Ran 80 min total gradient at 10 μL/min stating at 0-1 min, 4% B, increased to 7% B at 1.1 min, 45% B at 55 min, then 95% B at 63 min, followed by washing and column equilibration. Mass spectrometer parameters included a full scan event using the FTMS analyzer at 30000 resolution from m/z 300-2000 for 30 ms. Collision Induced Dissociation MS/MS was conducted on the top seven intense ions (excluding 1+ions) in the ion trap analyzer, activated at 500 (for all events) signal intensity threshold counts for 30 ms.

Data Analysis and Database Searching: All mass spectra were processed in Qual Browser V 2.0.7 (Thermo Scientific). Mascot generic files (mgf) were generated with MS DeconTools (R.D. Smith Lab, PPNL) and searched using Mascot V2.3.01 (Matrix Science Inc., Boston, Mass.) database search against the provided protein sequence added to an in-house custom database and the SwissProt database (V57 with 513,877 sequences) for contaminating proteins. Search parameters included: enzyme: semitrypsin or trypsin/Glu-C, allowed up to three missed cleavage; variable modifications: added expected masses of small molecules (362.147787 Da and 463.206698 Da) to database called "CRM Tgase+alkyne 362 Da mod (CKR), CRM Tgase+alkyne 362 Da mod (N-term), CRM Tgase+azide 463 Da mod (CKR), CRM Tgase+azide 463 Da mod (N-term)"; peptide tolerance: ±20 ppm; MS/MS tolerance: ±0.6 Da. Sequence coverage and small molecule modification assessments were done on ions scores with >95% confidence. High-scoring peptide ions were then selected for manual MS/MS analysis using Qual Browser.

Positions at which lysine modification occurs can be determined according to the mapping experiment supra. According to similar conjugations described on CRM197 in US Application No: US 2015/0017192 filed on Jul. 11, 2014 (attorney docket number PAT055641-US-NP), we extrapolate that modification occurred on Lys37 or Lys39, Lys 33 and Lys440.

Example 26A

Conjugation of Oxytocin Derivative and a Fatty Acid

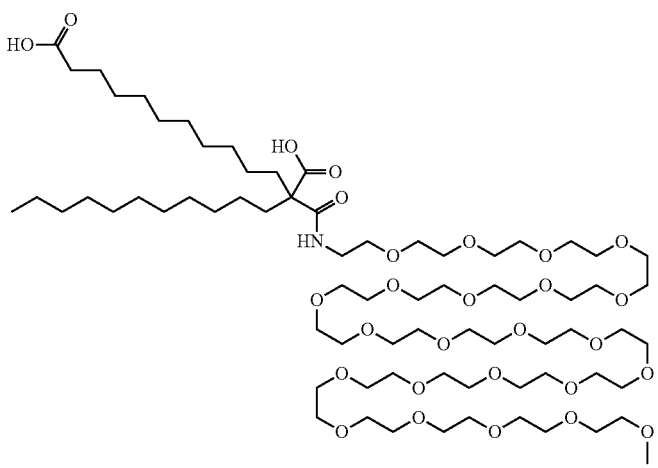

-continued
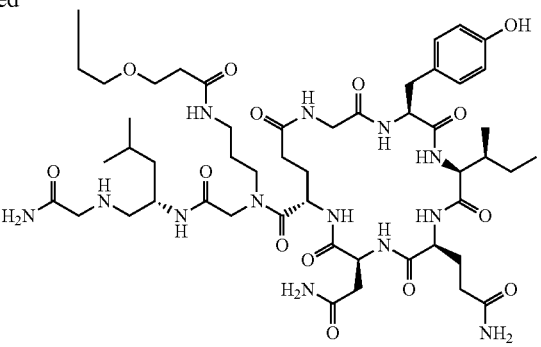
Oxytocin FA Conjugate
Step 1: Preparation of protected oxytocin on the resin
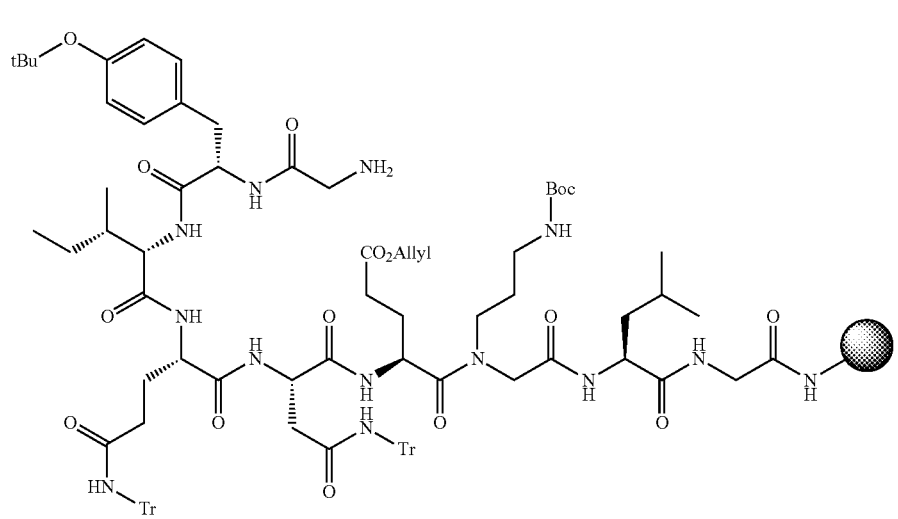
26a1
The protected from of oxytocin on the resin (26a1) was synthesized by analogy to Example 21B step 1.
Step 2: Allyl Deprotection, Cyclization, Cleavage from Resin
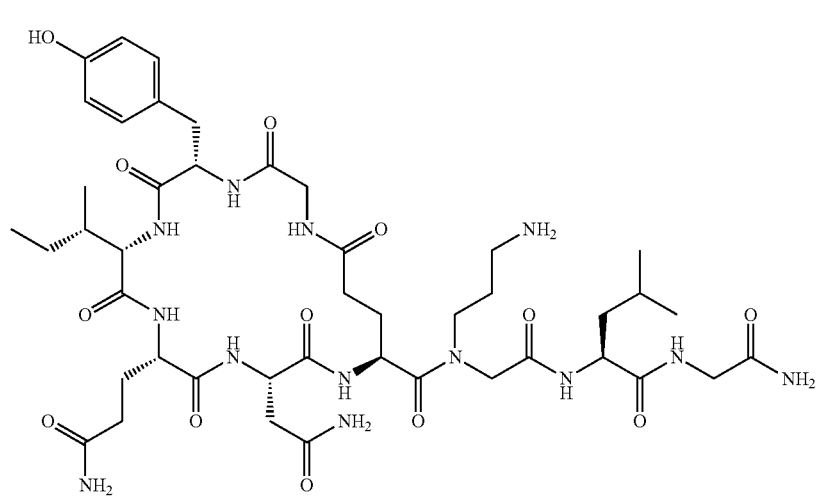
26a2

The protected intermediate (26a1) (0.2 mmol) was taken up in 6 ml of DCM containing phenylsilane (1 mmol) and Pd(PPh$_3$)$_4$ (0.02 mmol). The resin was agitated in this solution for 15 minutes and then filtered. This procedure was repeated twice with the phenylsilane/Pd(PPh$_3$)$_4$ in DCM solution. After the last agitation, the resin was filtered and washed with NMP (3 times), DCM (3 times), 0.5% DIEA/DCM (3 times) and finally NMP (3 times). The resulting washed resin was dried under vacuum. A portion of the dried resin (~0.1 mmol) was taken up in a solution of PyBOP (0.2 mmol), HOBt (0.4 mmol), and DIEA (0.5 mmol) in 6 mL of NMP. This reaction was agitated at room temperature for 20 hours. The resin was filtered and washed with EtOAc (3 times) and DCM (3 times). The resin was then taken up in 4 mL of 95/2.5/2.5 TFA/TIPS/H$_2$O and agitated for 2 hours. The TFA/TIPS/H$_2$O solution was then filtered into cold (<−20° C.) Et$_2$O to precipitate the cleaved peptide. After centrifugation, the Et$_2$O was decanted and the off-white residue was washed with Et$_2$O and centrifuged again. The resulting off-white solid was dried under N$_2$ overnight. This solid was purified on mass triggered prepatory HPLC (Waters Autopure HPLC System; Sunfire C18 30×50 mm 5 um column; mobile phase: 7.5-20% ACN in Water, 5 min gradient, 75 mL/min, modified with 0.1% TFA). Fractions corresponding to Intermediate (26a2) were combined, frozen, and lyophilized to a white solid (13.5 mg, 14%). HRMS-Analytic Method G: Rt=0.90 mins, MS m/z 988.5225 [M+H]+.

Step 3: Conjugation to the Fatty Acid

To a solution of Intermediate (26a2) (2.82 μmol) in 0.5 mL of pH=6.40 phosphate buffer was added a solution of I-37 (8.39 μmol) in 0.5 ml of pH=6.40 phosphate buffer. The reaction stirred at room temperature for 18 hours. The reaction mixture was then filtered through a 4.5 μm frit and purified on mass triggered prepatory HPLC (Waters Autopure HPLC System; Sunfire C18 30×50 mm 5 um column; mobile phase: 45-70% ACN in Water, 5 min gradient, 75 ml/min, modified with 0.1% TFA). Fractions corresponding to the Oxytocin-FA Conjugate (26A) were combined, frozen, and lyophilized to a white solid (1.71 mg, 24%). LCMS-Analytic Method G: Rt=3.07 mins, MS m/z 2540.5 [M+H]+.

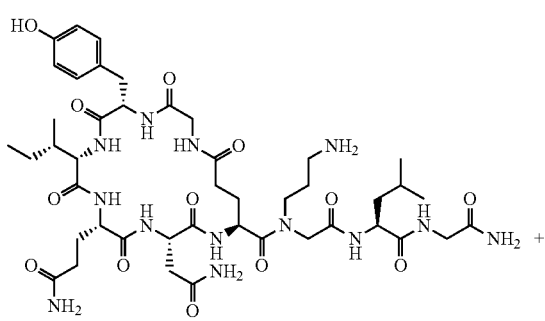

26a2

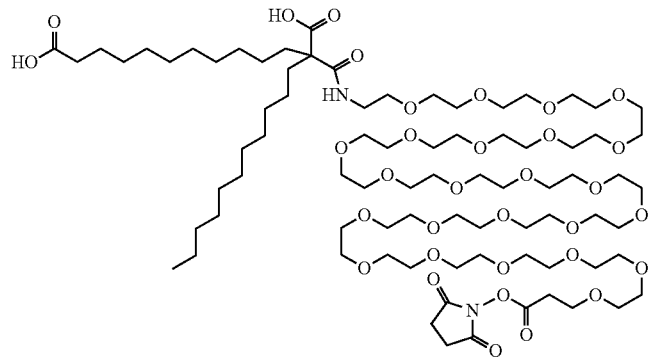

I-37

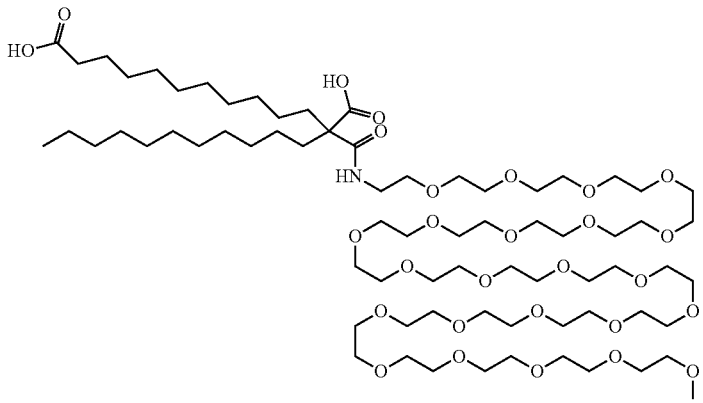

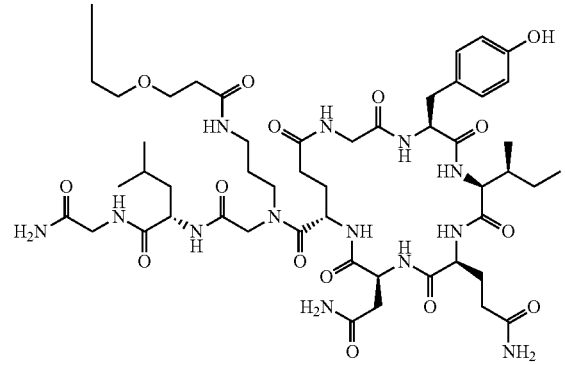

26A

Example 26B

Conjugation of Oxytocin Derivative and a Fatty Acid

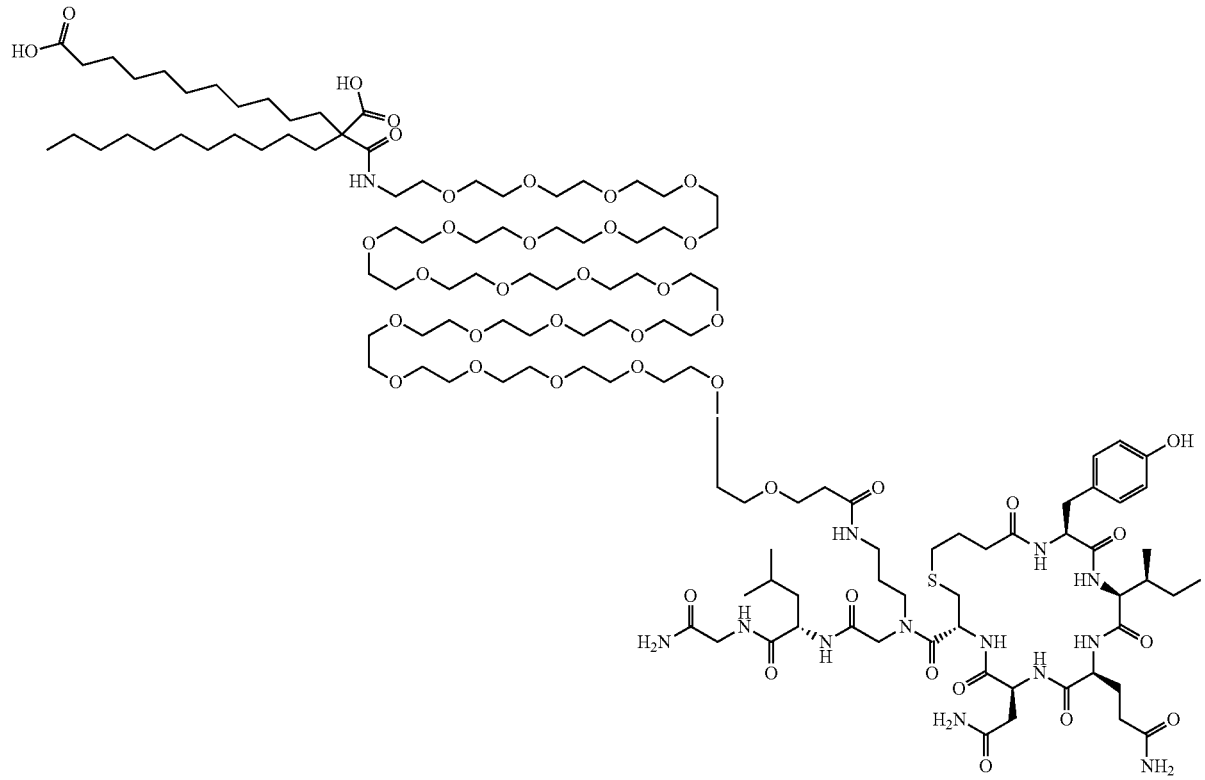

(26B)

The above example (26B) can be prepared according to the step 3 of Example 26A described above by reacting: SEQ ID NO: 33, *Butyrate-Tyr-Ile-Gln-Asn-Cys*-Gly(N-CH2CH2CH2NH2)-Leu-Gly-NH2*=sulfide bond (26b1):

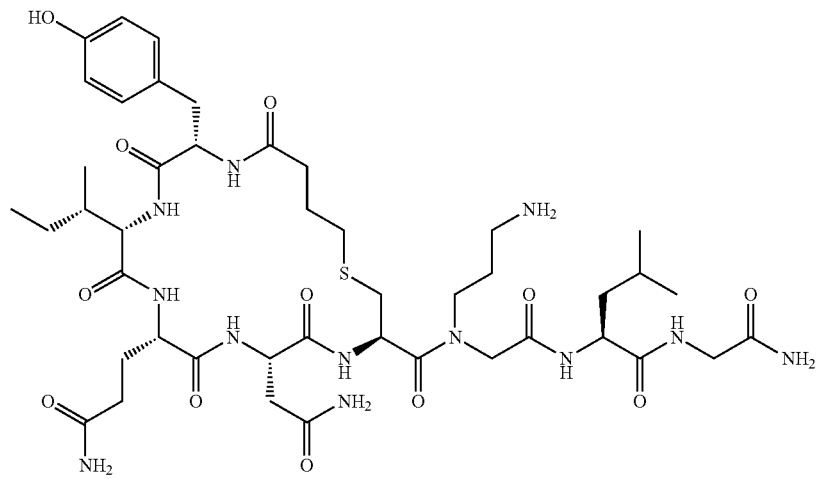

(26b1)

with intermediate I-37.

The cyclic peptide (26b1) was prepared by adapting the procedure of Example 41 disclosed in Wisniewski et al, J. Med. Chem. (2014), 57 5306-5317 which is incorporated by reference herein.

The peptide was synthesized manually on 1 mmol Fmoc-Rink Amide AMS resin via Fmoc chemistry. Protecting groups used for amino acids are: t-Butyl group for Tyr, Trt group for Gln and Asn. Two unusual amino acids, Fmoc-Cys(CH$_2$CH$_2$CH$_2$CO$_2$Allyl)-OH and Fmoc-[Nα—CH$_2$CH$_2$CH$_2$NH(Boc)]Gly-OH, were used. The peptide chain was assembled on resin by repetitive removal of the Fmoc protecting group and coupling of protected amino acid (3 eq) in DMF. HBTU and HOBt (3 eq: 3 eq) were used as coupling reagent; and N-methylmorpholine (NMM, 6 eq) was used as base. 20% piperidine in DMF (3 times of resin volume) was used as de-Fmoc reagent. Resin was washed by DMF (3 times of resin volume) after each coupling and de-Fmoc; Ninhydrin test was performed after each coupling to check the coupling efficiency.

Following the removal of the last Fmoc protecting group, the resin was washed with ethyl ether and dried under vacuum. The selective on-resin removal of allyl ester protecting group was performed by Pd(PPh3)4/5,5-dimethyl-1,3-cyclohexandione (1 eq/10 eq) in DCM/THF (1/1, 10 times of resin volume) for 3 hours. The resin was washed with DMF (3x) followed by 0.5% sodium diethyl dithiocarbamate in DMF (5x). In the final, on-resin cyclization was performed by HCTU/NMM (3 eq/6 eq) in DMF. The resin was washed and dried under vacuum to yield 3.2 grams of peptide resin which was treated with 32 ml TFA/TIS/DOT/$H_2O$(92.5/2.5/2.5/2.5, v/v) for 3 hours at room temperature to remove the side chain protecting groups and cleave the peptide from the resin. Crude peptide was precipitated from cold ether then collected by filtration and dried under high vacuum. Yield: 1.15 g (116%).

All crude of the peptide was purified on 2-inch C18 column with TFA buffer (buffer A, 0.1% TFA in water; buffer B, acetonitrile). Pooled fractions with purity >95% were lyophilized to dry. 84 mg of final peptide was obtained (TFA salt). MS: 991.6 $[M+H]^+$, HPLC ret time 9.49 min (method: flow rate 1.2 mL/min; Buffer A: 0.1% TFA in water; Buffer B: 0.1% TFA in acetonitrile; room temperature; column: Discovery, C18, 4.6 mm×250 mm, 5 micro; Gradient (linear) 15%-35% buffer B in 20 mins; injection volume 0.02 mL)

Example 27

Agouti-Related Protein (AgRP)-Fatty-Acid Conjugate

AgRP(83-132)-FA Conjugates:

Example 27A: mono fatty acid conjugate of AgRP (AgRP+1 FA) wherein the fatty acid is attached to the N-terminus of AgRP via a linker (PEG)

wherein AgRP(83-132) has the following sequence:
Ser-Ser-Arg-Arg-Cys-Val-Arg-Leu-His-Glu-Ser-Cys-Leu-Gly-Gln-Gln-Val-Pro-Cys-Cys-Asp-Pro-Cys-Ala-Thr-Cys-Tyr-Cys-Arg-Phe-Phe-Asn-Ala-Phe-Cys-Tyr-Cys-Arg-Lys-Leu-Gly-Thr-Ala-Met-Asn-Pro-Cys-Ser-Arg-Thr (SEQ ID NO: 21); which contains 5 disulfide bridges at positions C87&C102, C94&C108, C101&C119, C105&C129, C110&C117 Bridges.

Example 27B: di-fatty acid conjugate of AgRP(83-132) (AgRP+2 FA) wherein one fatty acid is attached to the N-terminus of AgRP (i.e. Serine 83) via a linker (PEG) and the other fatty acid is attached to the side chain of Lysine at position 121via a PEG linker.

To 0.90 ml of a 10 mg/ml solution of AgRP(83-132) (available from R&D Systems™) in pH 4.5 citrate buffer (9 mg, 1.585 µmol) was added 0.80 ml of pH=4.43 acetate buffer followed by a 1.30 ml of a 10 mg/ml solution of 1-37 in $H_2O$ (13 mg, 7.79 µmol). The reaction stirred at room temperature for 16 hours. HRMS (QT2) showed both AgRP+1 FA, m/z 7226.3 $[M+H]^+$ at 1.89 min, and AgRP+2FA, m/z 8778.4 $[M+H]^+$ at 2.41 min, present. The reaction was filtered through a 4.5 µm frit, combined with a second reaction ran as above (0.881 µmol AgRP, 2.64 µmol I-37), and purified on prepatory HPLC (Waters Autopure HPLC System; Waters Protein BEH C4 Column, 300 Angstrom, 5 um, 10×250 mm; mobile phase: 20-80% ACN in Water, 11 min gradient, 10 mL/min, modified with 0.1% TFA; run time: 15 min; fraction collection: UV 210 nm). Fractions corresponding to AgRP+1 FA and AgRP+2FA were isolated, frozen, and lyophilized to give the TFA salts of AgRP+1FA (27A) and AgRP+2FA (27B) as white solids (3.24 mg, 16% AgRP+1FA; 2.26 mg, 9% AgRP+2FA) LCMS-Analytic Method G: (AgRP+1FA) Rt=1.91 mins, MS m/z 7226.4 $[M+H]^+$; (AgRP+2FA) Rt=2.43 mins, MS m/z 8778.4 $[M+H]^+$.

Labeling Experiment to Determine Position of Attachment of the Fatty Acid.

Labeling at N-terminal Ser residue was confirmed by digesting the reaction mixture with Asp-N(Promega)

27A

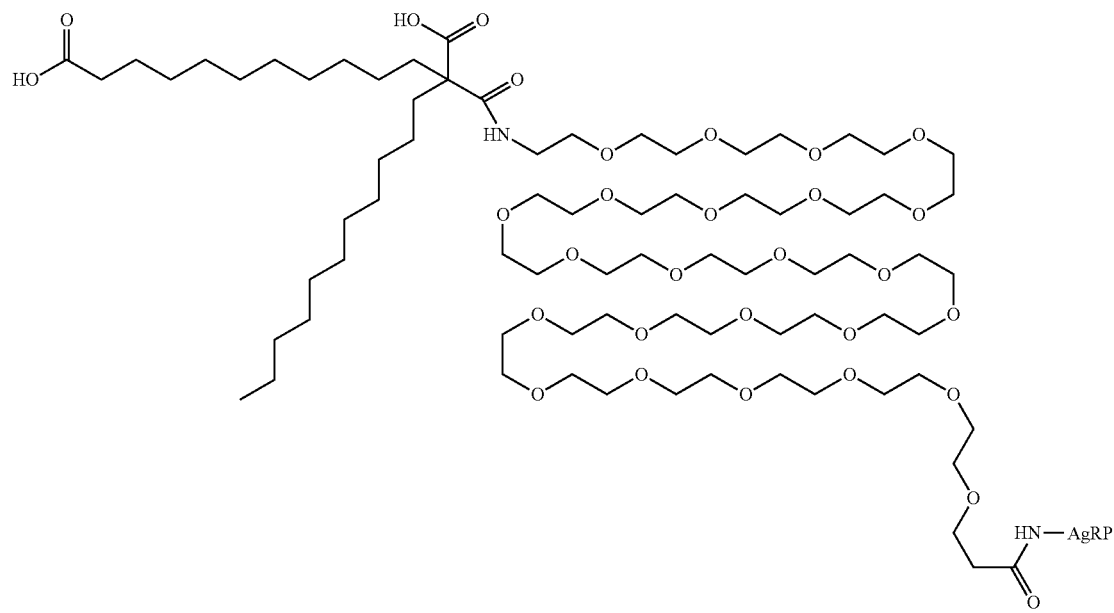

according to manufacturer protocol. All peptide mapping assays were achieved using a Thermo Dionex Ultimate 3000 LC coupled with a Bruker Maxis Impact Q-TOF mass spectrometer. The separation was performed on an ACQUITY UPLC BEH130 C18 column (2.1×150 mm, 1.7 μm, Waters) kept at 40° C. Flow rate was 0.1 mL/min with 0.1% FA in water as mobile phase A and 0.1% FA in acetonitrile as mobile phase B.

A solution of Asp-N(Promega Part# V162A) was reconstituted in 20 uL of HPLC/MS water (0.1 μg/μL). Around 10 μg of sample was diluted to a final volume of 25 μL in 6M urea, 10 mM dithiothreitol, 5 mM EDTA, and 50 mM Tris_HCl (pH=8.0). After reduction and alkylation, solutions were diluted six times with 50 mM Tris_HCl (pH=8.0), proteolysis was then performed with an additional 1 micrograms of Asp-N. The digests took place overnight at 37 degrees Celsius. LCMS analysis indicated that cleavage had occurred at the N-terminal D positions of wild AgRP and modified AgRP with one addition of fatty acid on each fragment as showed in the following table.

| peptide sequence | position | mass | RT | Expected m/z | Observed m/z | Charge |
|---|---|---|---|---|---|---|
| SSRRCVRLHESCLGQQVPCC (SEQ ID NO: 22) | A(1-20) | 2488.13 | 8.1 | 623.04 | 623.03 | 4 |
| DPCATCYCRFFNAFCYCRKL GTAMNPCSRT (SEQ ID NO: 23) | A(21-50) | 3783.58 | 10.1 | 757.72 | 757.72 | 5 |
| Modified SSRRCVRLHESCLGQQVPCC (SEQ ID NO: 22) + fa | A(1-20) | 4040.12 | 17.4 | 1011.04 | 1011.03 | 4 |
| DPCATCYCRFFNAFCYCRKL GTAMNPCSRT (SEQ ID NO: 23) + fa | A(21-50) | 5335.56 | 18.1 | 1068.12 | 1068.12 | 5 |

Example 28 (28a, 28B and 28C) Relates to Conjugates of hFGF23 Variant

FGF23 variants used

The sequence of a human FGF23 variant, used in and designated in this example as "hFGF23(R179Q)", ""hFGF23 R179"" or simply "hFGF23", is provided at SEQ ID NO: 10. This FGF23 variant lacks the signal peptide, but has a restored M at position 1, and has a mutation at R179 (R179Q). A conjugate comprising a fatty acid described herein was prepared with this FGF23 peptide (Example 28C) and shown to retain at least one FGF23 activity in table 8. Two other variants of human FGF23 were also used in this example (Examples 28A and 28B) to construct conjugates with fatty acids disclosed herein. Like the peptide of SEQ ID NO: 10, these lack the FGF23 signal peptide and have a mutation at R179, but have one or more additional mutations, but retain at least one FGF23 activity. These two FGF23 variants are used in and both designated in this example as a "hFGF23-variant" or "FGF23 variant" or the like.

The methods of producing conjugates described herein can be used with other FGF23 peptides, including FGF23, or a homolog, variant, fragment, or modified form thereof.

Protocol for FGF23 Variants Production

Transformation:

The hFGF23(R179) polypeptide were made by transient transfection of the pET28c-hFGF23 R179Q expression plasmid into BL21(DE3) competent cells, incubating on ice for 30 min, heat shocking at 42° C. for 45 sec, adding SOC media and incubating the bacteria in a 37° C. shaker for one hour. Thereafter, the bacterial culture was spread onto LB plates containing Kanamycin and incubated overnight at 37° C. Isolated colonies were transferred into LB media containing Kanamycin, incubated overnight at 37° C. with shaking and 25 mL aliquots transferred into new LB media containing Kanamycin and shaken at 37° C. for about 2.5 hours. When the cells were of sufficient density (OD of ~0.6), 1M IPTG was added to each culture with continued shaking at 37° C. to induce expression of the polypeptide. After four hours the cells were pelleted by centrifugation at 6000 rpm for 10 min and the pellet frozen down at −20° C. Subsequently, the pellet was re-suspended in lysis buffer (50 mM Tris, pH 8, 100 mM NaCl, 0.1% Triton X-100) and the cells lyzed using a microfluider. 10 mg lysozyme and 10 μL DNase (1 unit per mL, Invitrogen) were added per 100 mL of lysis mix and incubated at room temperature for 30 min, then spun down at 8000 rpm at 4° C. for 20 min, washed with three changes of 100 mL of lysis buffer and spinning, and the fourth time with lysis buffer without Triton X-100. The pellet (of inclusion bodies) from the final spin was immediately solubilized in 50 mM Tris, pH 7.4, 6M guanidine, 10 mM DTT, and the protein concentration determined and adjusted to 1 mg/ml before refolding.

Protein Refolding:

To refold the protein, 368 mg of reduced glutathione (GSSH) and 74 mg of oxidized glutathione (GSSG) were added to each 400 ml of solubilized inclusion body. The protein was dialyzed overnight at 4° C. against 4 L of 50 mM Tris, pH 8.0 and 250 mM of Arginine. Then 2L of dialysis buffer was removed and replaced with 2 L of water and dialysis continued for another 8 hours. The dialysis buffer was then changed to 20 mM Tris, pH8.0, 50 mM NaCl, 25 mM Arginine, and dialysis continued overnight.

Protein Purification:

To purify the protein, the dialyzed mix was spun down at 12000 rpm for 30 min, the supernatant loaded onto Heparin-Sepharose column equilibrated with the final dialysis buffer, and the column washed with 20× bed volume of 1×PBS. The refolded protein was eluted with 1×PBS supplemented with 0.5M NaCl, the purity of the protein assessed by SDS-PAGE gel, and protein concentration measured by its OD at 280 nm wavelength.

Example 28A
Conjugation of hFGF23 Variant with a Fatty Acid
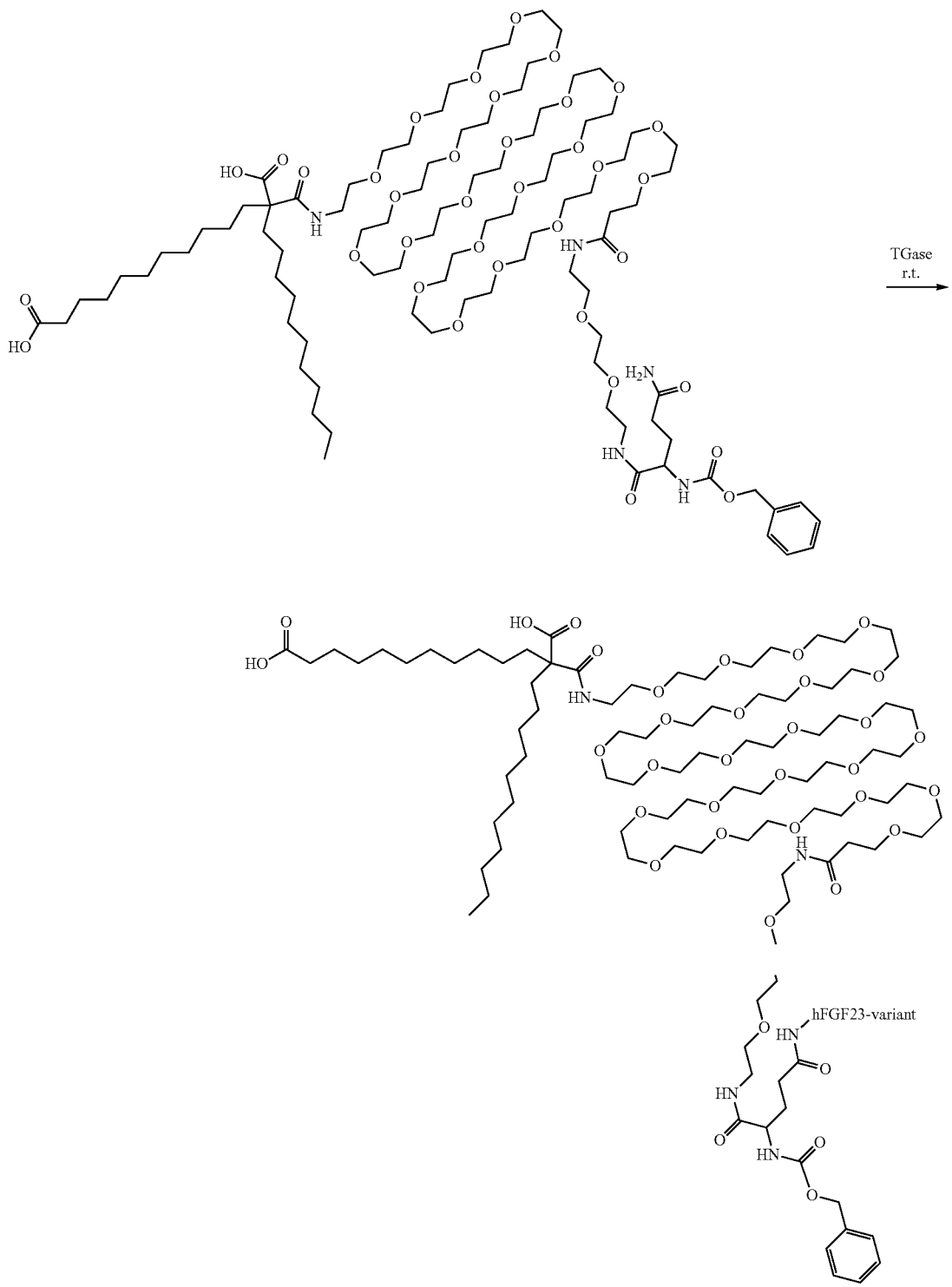
wherein the —NH$_2$ in hFGF23varian-NH$_2$— means the amino functionality of a lysine residue.

Step 1: Intermediate 28a

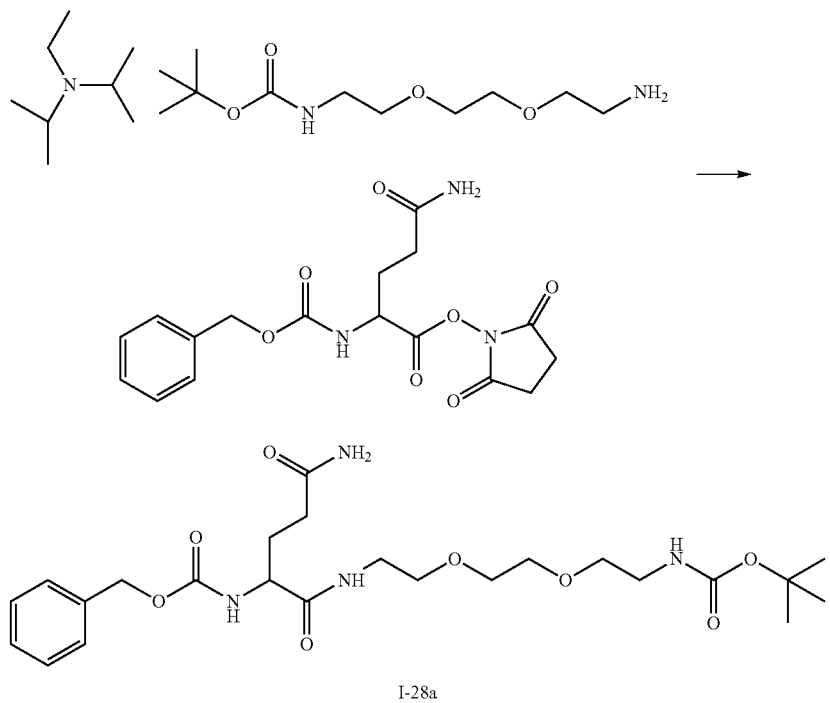

I-28a 2,5-dioxopyrrolidin-1-yl 5-amino-2-(((benzyloxy)carbonyl)amino)-5-oxopentanoate (0.5 g, 1.325 mmol) was dissolved in DMF (Volume: 9.96 ml) and tert-butyl (2-(2-(2-aminoethoxy)ethoxy)ethyl)carbamate (0.503 ml, 2.120 mmol) was added. DIPEA (0.274 g, 2.120 mmol) was added to the mixture and the reaction was stirred at r.t. for 2 hours at which point LCMS analysis showed formation of desired product and consumption of ZQ-NHS starting material (Method A, $R_t$=0.98 min, M+H 511.4). The reaction mixture was poured into DCM (100 mL) and washed with ice water (3×50 mL). The organic layer was dried over $Na_2SO_4$, filtered and concentrated to give 1.14 g of yellow oil. LCMS analysis indicated presence of desired product (Method M, Rt=1.82 min, M+H 511.4, 1.14 g). Material was carried on to next step without further purification.

Step 2: Intermediate 28b, benzyl (5-amino-1-((2-(2-(2-aminoethoxy)ethoxy)ethyl)amino)-1,5-dioxopentan-2-yl)carbamate

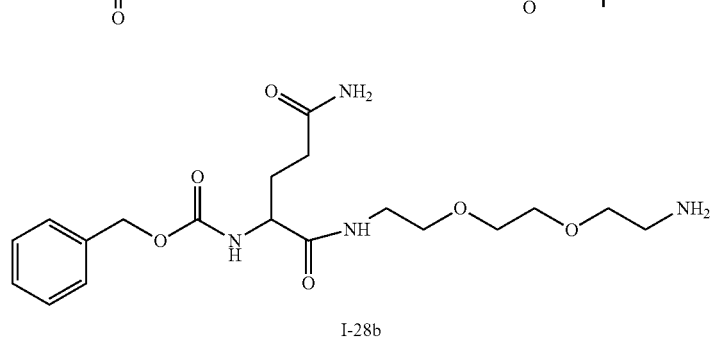

I-28b

Trifluoroacetic acid (10 mL, 2.233 mmol) was added to Intermediate 28a (1.14 g, 2.233 mmol) and stirred at r.t. for about one hour. LCMS analysis showed full conversion of starting material to desired product (Method A, $R_t$=0.56 min, M+H 411.3). The reaction mixture was taken up in DCM (30 mL) and concentrated to an oil twice. The oil was diluted with 1 mL ACN and 1 mL MeOH and purified by MS-triggered HPLC (Method N). Fractions with desired mass were pooled, frozen and lyophilized to afford Intermediate 28b as a white powder (Method 0, $R_t$=0.22 min, M+H 411.3, 160 mg, 18%)

Step 3: Intermediate 28c

Intermediate 28b (19.69 mg, 0.048 mmol) was dissolved in DMF (0.5 mL) and added to a solution of intermediate 37 (50 mg, 0.030 mmol) in DMF (1.0 mL). 3 drops of DIPEA was added and the reaction stirred at r.t. for 2 hours at which point LCMS analysis showed complete conversion to product (Method B, $R_t$=1.22 min, M+H+2/2 982.9). The reaction mixture was loaded on to a 20 g C-18 column for reverse phase chromatography. Using a solvent gradient from 100% Water (0.1% TFA) to 100% MeCN over a 20 minute period, fractions collected and analysed by LCMS. Fractions with desired mass were combined, frozen and lyophilized overnight to afford Intermediate 28c as a clear, colorless oil (Method C, $R_t$=1.21 min, M+H+2/2 982.9, M+H+3/3 655.5, 15.3 mg, 26%). Provisionally interpreted $^1$H-NMR indicates the presence of the amide bond formed at 6.29 ppm (1H, br m). $^1$H NMR (400 MHz, Chloroform-d) δ 7.52 (s, 1H), 7.35 (d, J=3.3 Hz, 5H), 5.10 (s, 2H), 4.30 (s, 1H), 3.77 (t, J=5.8 Hz, 2H), 3.69-3.49 (m, 94H), 3.46 (s, 4H), 2.59 (s, 3H), 2.32 (t, J=7.2 Hz, 25H), 2.08-1.94 (m, 4H), 1.79-1.65 (m, 2H), 1.65-1.52 (m, 2H), 1.40-1.06 (m, 31H), 0.94-0.82 (m, 3H).

Step 4: hFGF23-variant+Intermediate 28c

For this step, a human FGF23 (hFGF23) variant ("hFGF23-variant") was used, which lacks the signal peptide, but has one or more mutations relative to SEQ ID NO: 8 but retains at least one FGF23 activity, and wherein the "—$NH_2$" in "FGF23-variant-$NH_2$" indicates the amino functionality of a lysine residue.

A 50 mg/mL solution of TGase in 30 mM MES pH 6 and an 8 mg/mL solution of Intermediate 28c in 30 mM MES pH 6 buffer were prepared. The fatty acid solution turned cloudy in MES pH 6. To hFGF23-variant (0.3 mg/mL in 30 mM MES pH 6, 7.5 ml, 0.088 µmol) was added Intermediate 28c (217 µl, 0.883 µmol) followed by TGase (33.5 µl, 0.044 µmol). The reaction was mixed at r.t. for 18 hours and an additional 217 µL of Intermediate 28c was added. The reaction mixed at r.t. for 18 hours and an additional 217 µL of Intermediate 28c was added. The reaction mixed at r.t. for 18 hours and an additional 108.5 µL of Intermediate 28c was added. The reaction was mixed at r.t. for 4 hours at which point LCMS analysis showed complete conversion of starting material (Method P, $R_t$=1.55 min, M+H 27432). The reaction mixture was divided between two 4 mL 10 kDa MWCO Amicon centrifugal filters and buffer exchanged 3× with 30 mM MES pH 6 buffer, then concentrated to 1.5 mL. Material was stored in the refrigerator overnight. Some solid had settled in the bottom of the tube. Concentration of supernatant was measured by A280 (18730 cm-1M-1, 25485 g/mol) to be 0.43 mg/mL (27%).

Example 28B

Conjugation of hFGF23-Variant with a ZQG-PEG11-Fatty Acid

For this example, a conjugate was prepared comprising a fatty acid and a FGF23 variant which lacks the signal peptide and has one or more mutations relative to SEQ ID NO: 8, but the variants retains at least one FGF23 activity.

I-28c

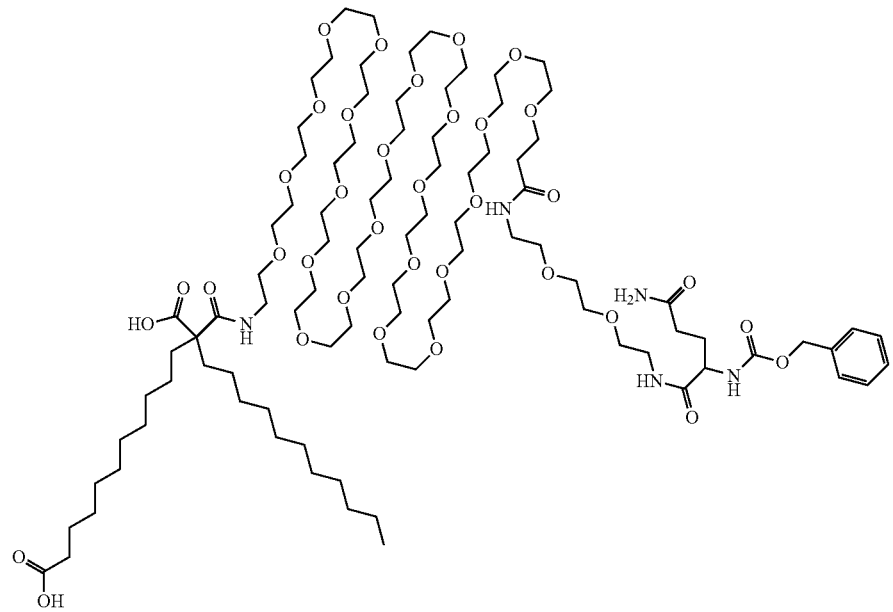

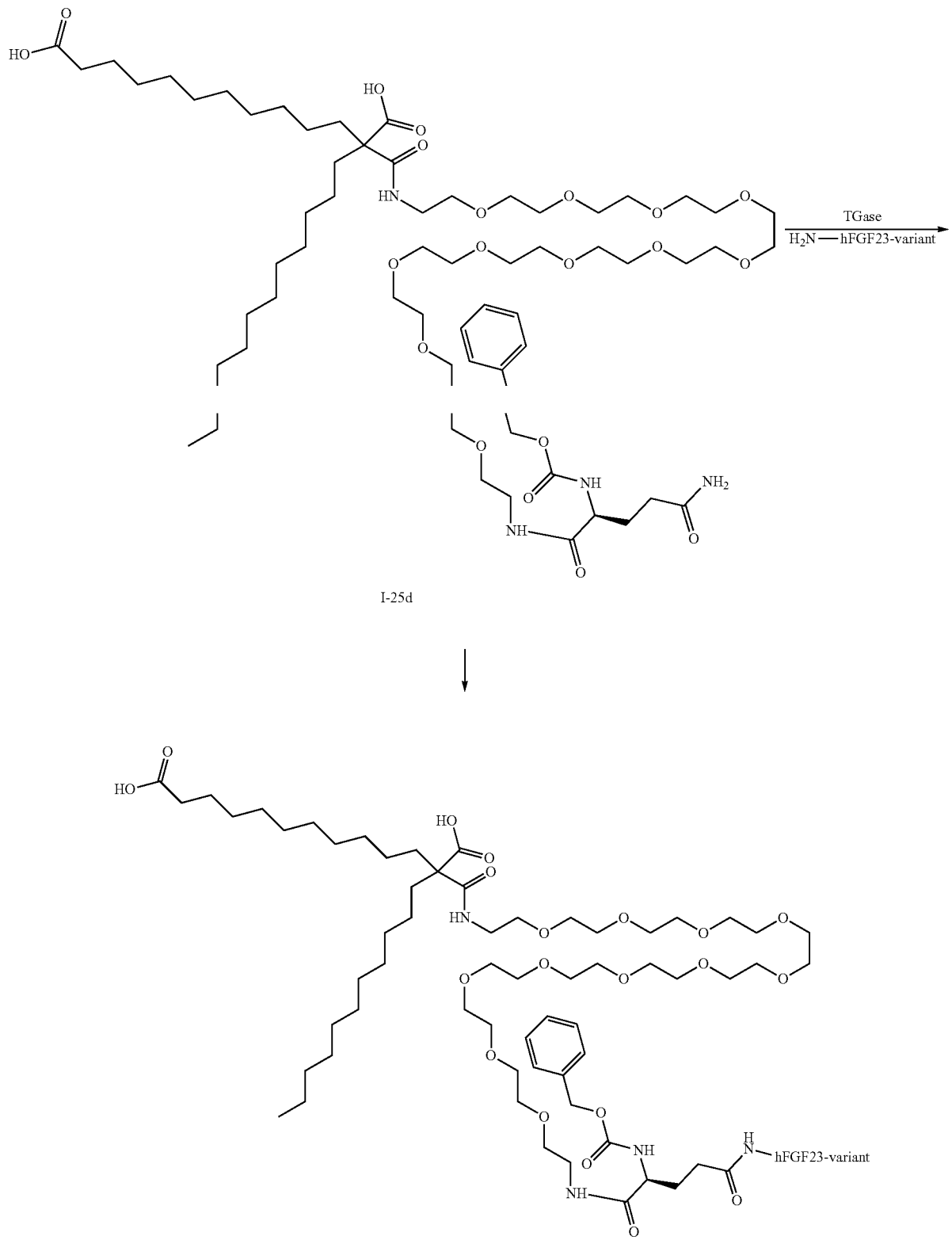

I-25d wherein the —NH₂ in hFGF23-variant-NH₂ means the amino functionality of a lysine residue.

An 8 mg/mL solution of intermediate 25d was prepared in 100 mM pH 8 tris buffer. A 50 mg/mL solution of TGase was prepared in H₂O. To a solution of hFGF23-variant (6.5 mL, 0.090 μmol) was added intermediate 25d (0.207 mL, 1.343 μmol) followed by TGase (0.136 mL, 0.179 μmol). The reaction was mixed at r.t. for three days and 90% conversion to +1 species was observed (LCMS Method Q, R$_t$=7.24 min, M+H 26616). The reaction mixture was exchanged into PBS 1× buffer using 10 kDa MWCO Amicon centrifugal filters by diluting and concentrating the reaction 6 times to a volume of 2 mL. The concentration was measured by A280 (18730 cm-1M-1, 26617 g/mol) to be 0.125 mg/mL (LCMS Method Q, $R_t$=7.24 min, M+H 26616).

Example 28C

Conjugation of h-FGF23 R179+ZQG-PEG11-Fatty Acid

For this example, a conjugate was prepared using the FGF23 variant "hFGF23 R179". This lacks the signal peptide and has a mutation at R179. The sequence is provided as SEQ ID NO: 10.
Calculated mass: 25463

An 8 mg/mL solution of intermediate 25d was prepared in 100 mM pH 8 tris buffer. A 50 mg/mL solution of TGase was prepared in $H_2O$. To a solution of hFGF23 R179 (2.50E+04 µl, 0.393 µmol) was added intermediate 25d (750 µl, 4.87 µmol) followed by TGase (597 µl, 0.785 µmol). The reaction was mixed at r.t. for two days at which point LCMS analysis showed complete conversion of starting material (Method P, $R_t$=1.58 min, M+H 26674). The reaction mixture was purified via ion exchange chromatography to give the +1 conjugate (Method R, $R_t$=3.87 min, M+H 26674):

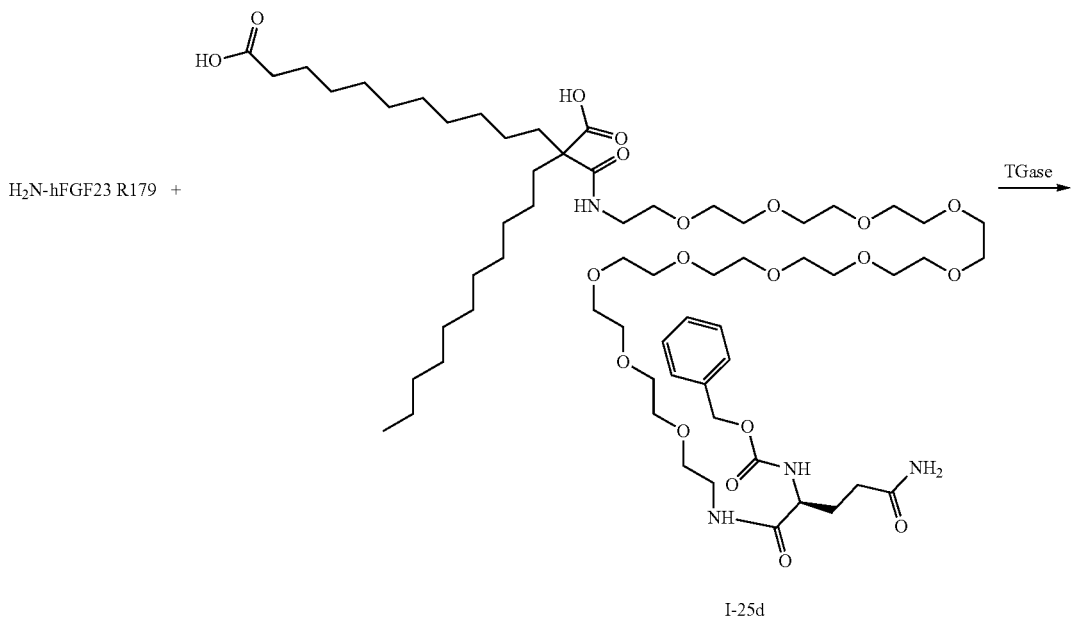

I-25d

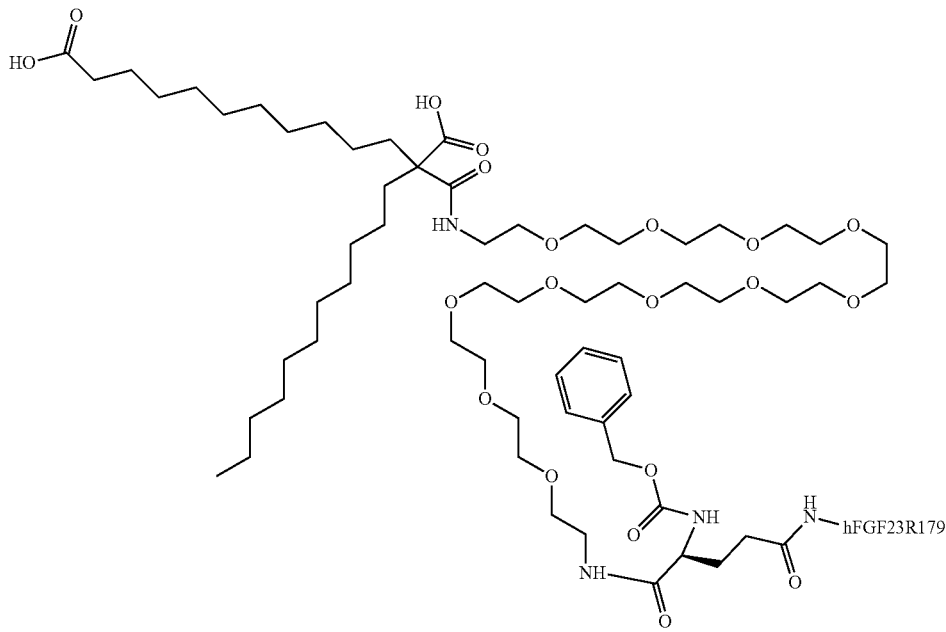

wherein the —NH$_2$ in hFGF23 R179-NH$_2$ means the amino functionality of a lysine residue.

Examples 29A and 29B Relate to Conjugates of Serelaxin

Example 29A

Serelaxin-Fatty Acid Conjugate (+1 Fatty Acid Conjugate)

Serelaxin-NH$_2$ $\xrightarrow{\text{I-25d}}$

Serelaxin+ZQG-PEG$_{11}$-fatty acid (Example 25d):
Serelaxin Sequence:
DSWMEEVIKLCGRELVRAQIAICGMSTWSC-FRALSRKTCGVHCCKNALASYLE (SEQ ID NO: 24); and
—NH2 in "serelaxin-NH2" means the reactive amino functionality at the side chain of lysine K17 as evidenced by the mapping experiment below; MW 5963 g/mol.

An 8 mg/mL solution of ZQG-PEG$_{11}$ fatty acid (Example 25d) was prepared in 100 mM tris pH 8 buffer. A 50 mg/mL solution of mTGase was prepared in H$_2$O. To a solution of serelaxin (211 µL, 0.168 µmol) in 100 mM tris pH 8 (1.018 mL, 0.5 mg/mL reaction) was added Example 25d (516 µl, 3.35 µmol) followed by mTGase (Ajinomoto, 255 µl, 0.335 µmol). The reaction was mixed at 37° C. for 3 days and then an additional 100 µL of ZQG-PEG$_{11}$ fatty acid was added. The reaction was mixed at 37° C. for 18 hours and then exchanged into PBS 1× buffer using 10 kDa MWCO Amicon centrifugal filter by diluting and concentrating the reaction 5 times to a volume of 0.7 mL. The material was purified via Method K and the fractions with the desired material were pooled, frozen and lyophilized to give a white powder. The material was dissolved in 1 mL 30 mM NaOAc buffer pH 5 and concentration was measured by A280 (5969 cm-1M-1, 7178 g/mol) to be 0.25 mg/mL (25%). LCMS Method L: R$_t$=1.65 min; MS [M+1+1FA]: observed: 7180, calculated: 7178.

Experimental Procedure for Serelaxin Mapping
Sample Proteolysis

Approximately 10 µg of protein was dissolved to a final volume of 25 µL in 6M urea, 10 mM dithiothreitol, 5 mM EDTA, and 50 mM Tris_HCl (pH=8.0) and maintained at 37° C. for 1 hour to reduce disulfide bonds. Iodoacetamide (500 mM, 1 uL) was added to alkylate free thiols and the solution was allowed to stand at room temperature for 1 hour in the dark. The solution was then diluted 6× with 50 mM Tris_HCl (pH=8.0), LysC (1 ug, Promega V107A) was added and the solution was maintained at 37° C. overnight to digest the protein. Formic acid (98%, 2 uL) was added to quench proteolysis and the resultant peptide mixture was analyzed by LC-MS/MS.

LC-MS/MS Analysis

Peptide mapping was done using a Thermo Dionex Ultimate 3000 HPLC coupled with a Bruker Maxis Impact Q-TOF mass spectrometer. The MS was controlled using Bruker Compass v. 1.7 and Bruker otofControl v. 3.4 software, with instrument parameters set as follows: mass range 300-2,000 Da; spray voltage 4.0 kV; capillary temperature 200° C.; drying gas flow 5.0 L/min. Fractionation was done with a Waters ACQUITY UPLC BEH130 C18 column (2.1×100 mm, 1.7 µm) maintained at 40° C. Mobile phases were 0.1% formic acid in water and acetonitrile, respectively, and flow rate was 100 uL/min. The gradient used was 0-2 min, 2% B; 2-3 min, 2%-8% B; 3-10 min, 8%-29% B; 10-14 min, 29%-33% B; 14-16 min, 33%-37% B; 16-20 min, 37%-73% B; 20-22 min, 73%-95% B; 22-25 min, 95% B; 25-26 min, 95%-2% B; 26-30 min, 2% B. Data processing was done using Bruker DataAnalysis v. 4.2.

The mapping experiment indicated that the fatty acid addition to serelaxin occurs primarily at Lysine K17 based on the peptide assigned as [CCHVGCTK$_{17}$(fa)RSLARFC-2H$_2$O; SEQ ID NO: 34], mass: 3088.56 Da, Charge: 5, Rt=13.4 min, Observed m/z 618.71, Expected m/z 618.72.

Example 29B

Serelaxin-Fatty Acid Conjugate (Mixture of +1FA, +2FA and +3FA Conjugate as Described Below)

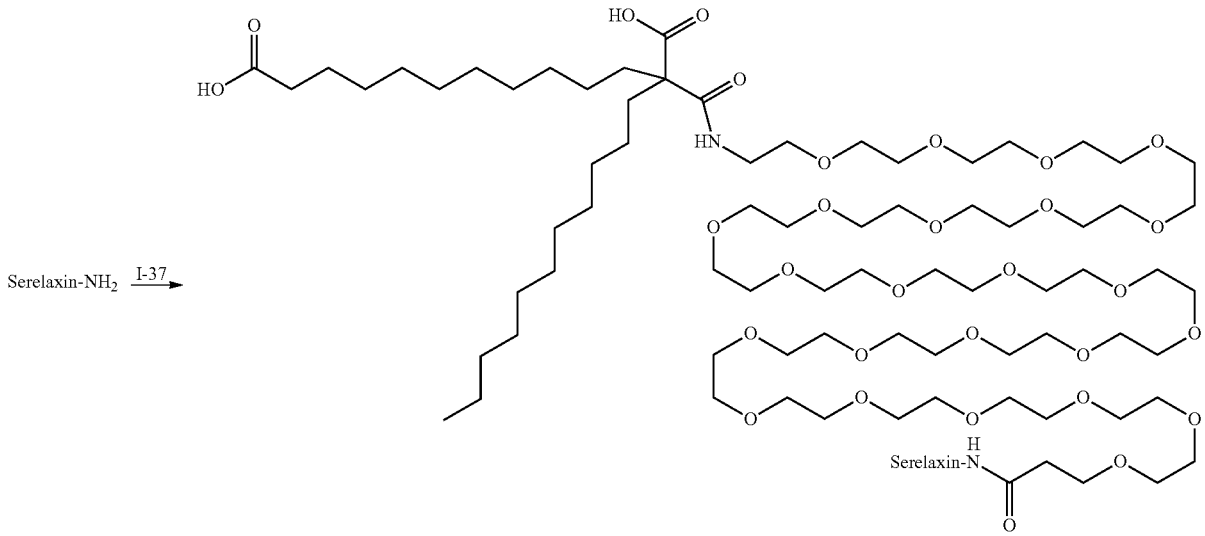

wherein the —NH$_2$ in "serelaxin-NH$_2$" means the reactive amino functionality at the side chain of a lysine.

Serelaxin+Intermediate 37: Example 29B was Tested as the Mixture Below

| Degree of Labelling | Calculated | Observed | % |
|---|---|---|---|
| serelaxin | 5963 | 5964 | 3 |
| serelaxin + 1 FA | 7517 | 7516 | 19 |
| serelaxin + 2 FA | 9071 | 9069 | 52 |
| serelaxin + 3 FA | 10625 | 10622 | 25 |

Sequence:

(SEQ ID NO: 24)
DSWMEEVIKLCGRELVRAQIAICGMSTWSCFRALSRKTCGVHCCKNA

LASYLpE

A 10 mg/mL solution of fatty acid intermediate 37 was prepared in H$_2$O. To a solution of serelaxin (105 µL, 0.084 µmol, 4.75 mg/mL) in 30 mM NaOAc buffer pH 4 (755 µL) was added fatty acid intermediate 37 (140 µL, 0.839 µmol). The reaction was mixed at r.t. for 16 hours at which point LCMS analysis showed 90% conversion of starting material. An additional 70 µL of intermediate 37 was added and the reaction mixed for 16 hours at r.t. at which point MALDI analysis indicated >95% conversion. The solution was exchanged into PBS 1× buffer using 3 kDa MWCO Amicon centrifugal filter by diluting and concentrating the reaction 4 times to a volume of 0.2 mL. The concentration was measured by A$_{280}$ (5969M-1 cm-1; 9068 g/mol) to be 2.61 mg/mL. LCMS Method L: R$_t$=1.56 min; MS [M+1+1 FA]: observed: 7516, calculated: 7517; R$_t$=1.65 min; MS [M+1+2 FA]: observed: 9069, calculated: 9071; R$_t$=1.74 min; MS [M+1+3 FA]: observed: 10622, calculated: 10625.

Example 30

Conjugation of M-his-hPIP with Fatty Acid Construct (1-37)-(Mixture of +1 FA Conjugate, and +2 FA Conjugates as Described Below)

M-His-hPIP (29-146) Sequence:

(SEQ ID NO: 13)
MHHHHHHQDNTRKIIIKNFDIPKSVRPNDEVTAVLAVQTELKECMVVKT

YLISSIPLQGAFNYKYTACLCDDNPKTFYWDFYTNRTVQIAAVVDVIRE

LGICPDDAAVIPIKNNRFYTIEILKVE

Expressed from
Expressed Protein sequence:

(SEQ ID NO: 25)
METDTLLLWVLLLWVPGSTGMHHHHHHQDNTRKIIIKNFDIPKSVRPND

EVTAVLAVQTELKECMVVKTYLISSIPLQGAFNYKYTACLCDDNPKTFY

WDFYTNRTVQIAAVVDVIRELGICPDDAAVIPIKNNRFYTIEILKVE

Nucleotide sequence:

(SEQ ID NO: 26)
GCTAGCCACCATGGAGACTGATACTTTGTTGTTGTGGGTACTGTTGCTT

TGGGTGCCCGGTAGTACCGGTATGCATCACCACCACCATCACCAGGACA

ACACCCGGAAGATCATCATCAAGAACTTCGACATCCCTAAGAGCGTGCG

CCCAAACGATGAAGTCACCGCGGTGCTGGCAGTGCAGACTGAGCTGAAG

GAGTGCATGGTGGTCAAGACGTACCTGATTTCGTCCATCCCGCTGCAAG

GCGCCTTCAACTACAAGTACACTGCCTGCCTCTGTGACGACAACCCCAA

GACCTTTTACTGGGACTTCTACACCAATAGAACTGTCCAGATTGCTGCC

GTGGTGGATGTGATCAGGGAATTGGGAATTTGCCCCGACGATGCGGCCG

TGATTCCGATCAAGAACAACCGCTTCTATACCATCGAGATCCTTAAAGT

GGAATGAGAATTC

PIP Expression Vector:

A mammalian expression vector encoding human PIP was generated by standard cloning methods. A fragment containing the mouse Ig kappa chain signal sequence followed by a MHHHHH (SEQ ID NO: 27) sequence then mature PIP with 5'-NheI (followed by a Kozak sequence) and 3'-EcoRI sites was codon optimized and synthesized (DNA2.0). This sequence was then cloned into unique 5'-NheI and 3'-EcoRI sites of a pcDNA3.1 (Invitrogen) based vector downstream of the CMV promoter.

PIP Expression and Purification:

The PIP expression plasmid DNA was transfected into HEK293T cells at a density of $1 \times 10^6$ cells per ml using standard polyethylenimine methods. 500 ml cultures were then grown in FreeStyle 293 Medium (Life Technologies) in 3 L flasks for 4 days at 37° C. with a humidified atmosphere of 8% $CO_2$. PIP protein was purified from clarified conditioned media.

| Degree of Labelling | Calculated | Observed | % |
| --- | --- | --- | --- |
| M-His-PIP | 14476 | 14472 | 4 |
| M-His-PIP + glycosylation |  | 18139 | 30 |
| M-His-PIP + 1 FA | 16030 | 16031 | 7 |
| M-His-PIP + 1 FA + glycosylation |  | 19692 | 37 |
| M-His-PIP + 2 FA | 17584 | 17578 | 15 |
| M-His-PIP + 2 FA + glycosylation |  | 21242 | 7 |

Experimental procedure for PIP mapping

Sample Proteolysis

Approximately 10 µg of protein was dissolved to a final volume of 25 µL in 6M urea, 10 mM dithiothreitol, 5 mM EDTA, and 50 mM Tris_HCl (pH=8.0) and maintained at 37° C. for 1 hour to reduce disulfide bonds. Iodoacetamide (500 mM, 1 uL) was added to alkylate free thiols and the solution was allowed to stand at room temperature for 1 hour in the dark. The solution was then diluted 6× with 50 mM

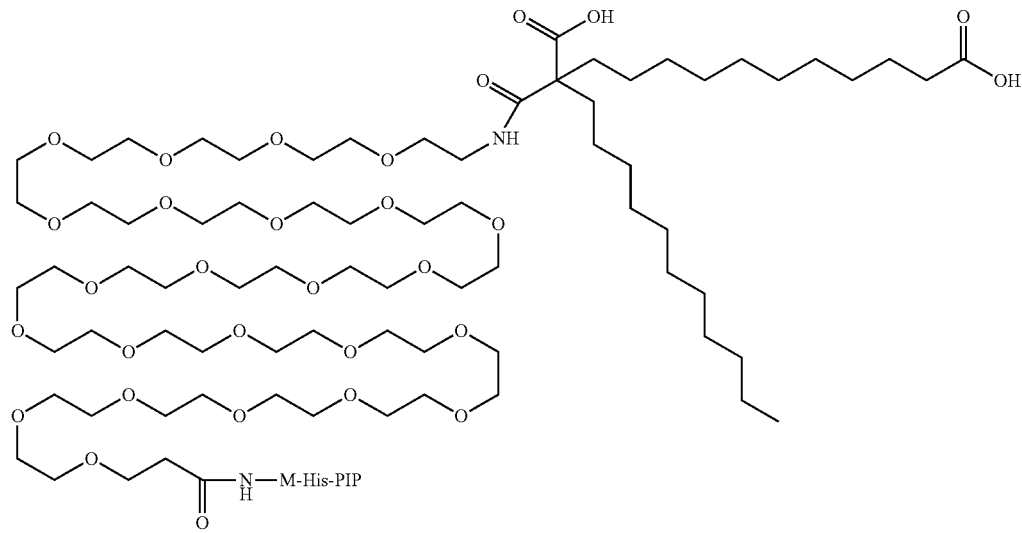

wherein M-His-PIP has SEQ ID NO: 12 and "M-his" is MHHHHHH (SEQ ID NO: 16).

Conjugation:

A 10 mg/mL solution of fatty acid-linker construct #1 was prepared in $H_2O$. M-His-hPIP (0.700 mL, 0.048 µmol) was diluted with 30 mM NaOAc buffer pH 4 (619 µL. 0.5 mg/mL reaction) and Intermediate 37 (0.081 mL, 0.484 µmol) was added. The reaction was mixed at r.t. for 18 hours at which point LCMS analysis showed 70% conversion to +1 (50%) and +2 (20%) products. The material was then exchanged into PBS 1× buffer using 3 kDa MWCO Amicon centrifugal filter by diluting and concentrating the reaction 5 times to a volume of 350 µL. Concentration was measured by $A_{280}$ (13850 cm-1M-1, 14472 g/mol) to be 1.7 mg/mL (70%). LCMS Method L, $R_t$=1.46 min; MS [M+1]: observed: 14472, calculated: 14476. $R_t$=1.57 min; MS [M+1+1 FA deglycosylated]: observed: 16025, calculated: 16030. $R_t$=1.69 min; MS [M+1+2FA deglycosylated]: observed: 17578, calculated: 17584.

M-His-hPIP+fatty acid-linker construct 1-37: Example 30 was tested as the mixture below Tris_HCl (pH=8.0), LysC (1 ug, Promega) or Trypsin/Lys C mix (1 ug, Promega) was added and the solution was maintained at 37° C. overnight to digest the protein. Formic acid (98%, 2 uL) was added to quench proteolysis and the resultant peptide mixture was analyzed by LC-MS/MS.

LC-MS/MS Analysis

Peptide mapping was done using a Thermo Dionex Ultimate 3000 HPLC coupled with a Bruker Maxis Impact Q-TOF mass spectrometer. The MS was controlled using Bruker Compass v. 1.7 and Bruker otofControl v. 3.4 software, with instrument parameters set as follows: mass range 300-2,000 Da; spray voltage 4.0 kV; capillary temperature 200° C.; drying gas flow 5.0 L/min. Fractionation was done with a Waters ACQUITY UPLC BEH130 C18 column (2.1×100 mm, 1.7 µm) maintained at 40° C. Mobile phases were 0.1% formic acid in water and acetonitrile, respectively, and flow rate was 100 uL/min. The gradient used was 0-2 min, 2% B; 2-3 min, 2%-8% B; 3-10 min, 8%-29% B; 10-14 min, 29%-33% B; 14-16 min, 33%-37% B; 16-20 min, 37%-73% B; 20-22 min, 73%-95% B; 22-25 min, 95%

B; 25-26 min, 95%-2% B; 26-30 min, 2% B. Data processing was done using Bruker DataAnalysis v. 4.2. The mapping experiment indicated that the fatty acid addition to MH$_6$-PIP occurs preferentially at the N-terminus as evidenced by [fa-MHHHHHHQDNTRK; SEQ ID NO: 35], mass: 3265.76 Da, Charge: 4, Rt=23.4 min, Observed m/z: 817.44, Expected m/z: 817.45.

A small degree of fatty acid addition occurs at lysine K42 as evidenced by peptide fragment [SVRPNDEVTAV-LAVQTELK(fa)ECMVVK; SEQ ID NO: 36], mass: 4366.45 Da, Charge 3, Rt=23.5 min, Observed m/z:1456.49, Expected m/z: 1456.49. Addition of the fatty acid at K42 blocks trypsin cleavage adjacent to this lysine, serving to confirm location of the addition.

Example 31

Conjugation of NPFF with Fatty Acid Using Click Chemistry

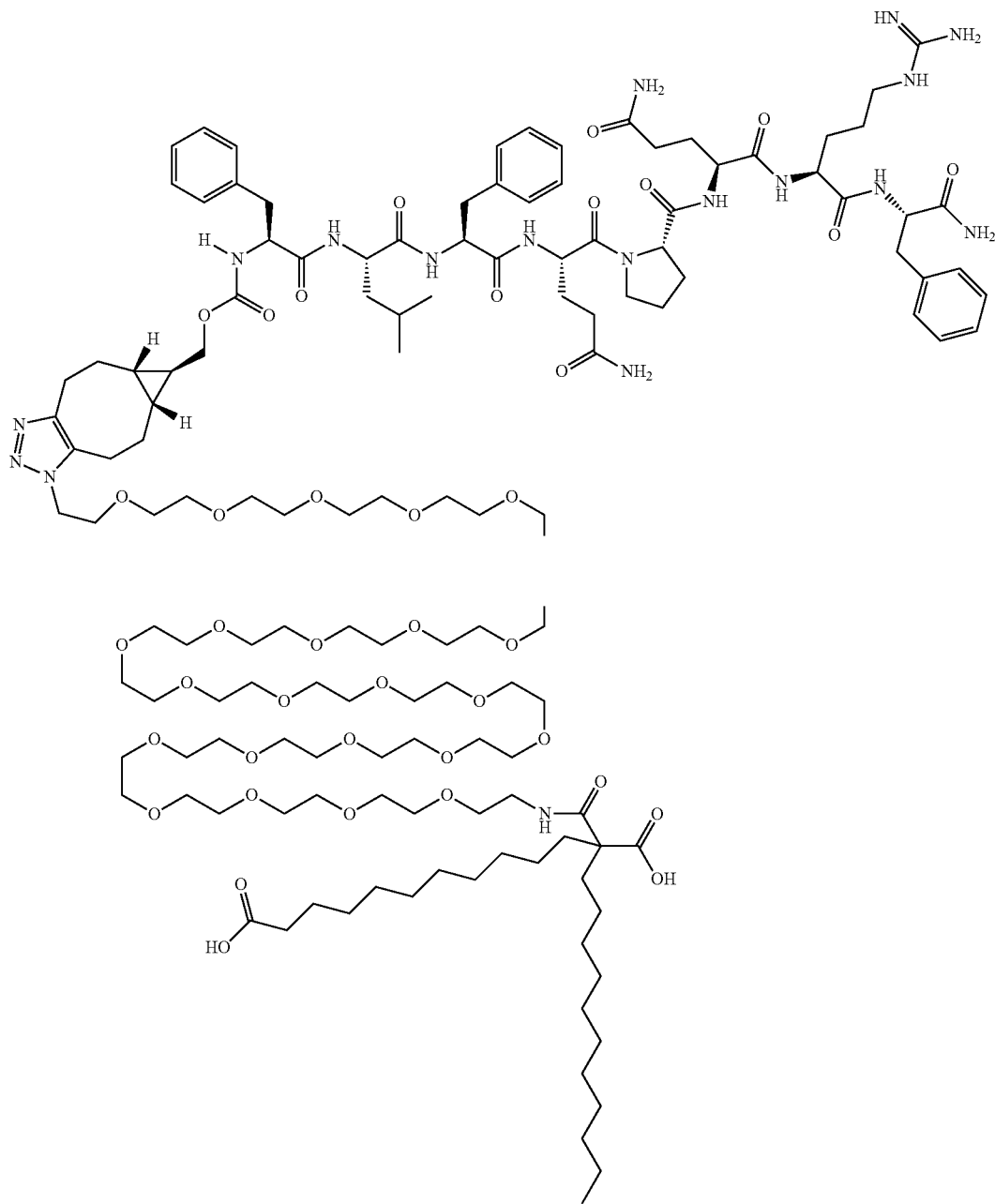

Step 1: Preparation of NPFF Click Chemistry Handle

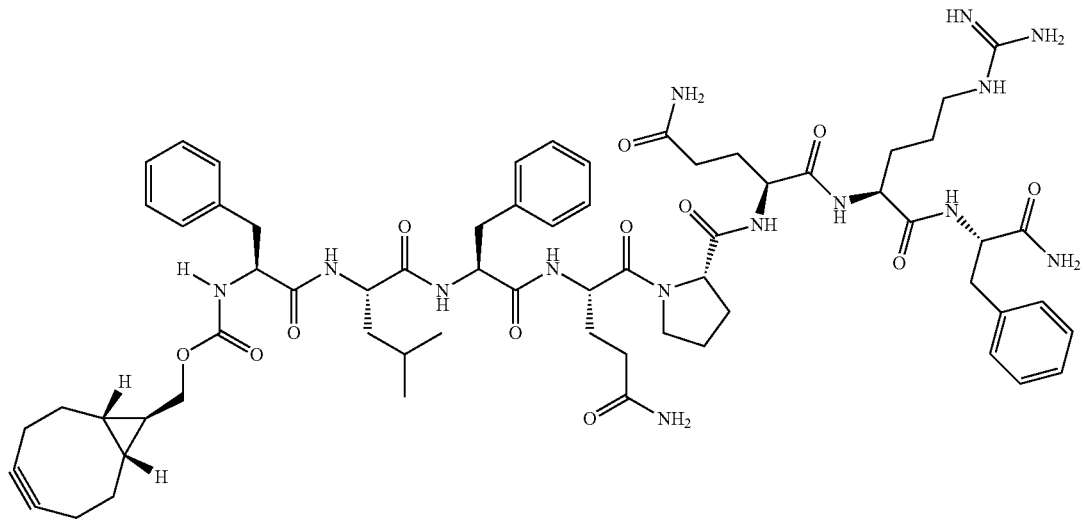 [SMILES: CC(C)C[C@H](NC(=O)[C@H](Cc1ccccc1)NC(=O)OC[C@H]1[C@@H]2CCC#CCC[C@@H]21)C(=O)N[C@@H](Cc1ccccc1)C(=O)N[C@@H](CCC(N)=O)C(=O)N1CCC[C@H]1C(=O)N[C@@H](CCC(N)=O)C(=O)N[C@@H](CCCNC(=N)N)C(=O)N[C@@H](Cc1ccccc1)C(N)=O]

Calc. MH+1258.8

To a solution of NPFF (Alfa Aesar, J66509, 5 mg, 3.82 µmol) in DMSO (1 mL) was added triethylamine (5.32 µl, 0.038 mmol) and then (1R,8S,9r)-bicyclo[6.1.0]non-4-yn-9-ylmethyl (2,5-dioxopyrrolidin-1-yl) carbonate (1.335 mg, 4.58 µmol). The reaction mixture was stirred at room temperature. Upon completion the reaction mixture was taken on as crude to the next reaction step.

Step 2: Conjugation

To the crude reaction mixture from Step 1 was added Intermediate 6 (1-6). The reaction mixture was shaken at room temperature. Upon completion the reaction mixture was purified using reverse phase chromatography (System: Agilent Bioinert SystemDate; Column: Waters Protein BEH C4 Column, 300 Angstrom, 5 um, 10×250 mm; Column for UPLC method development is BEH C4m, 300A, 1.7 um, 2.1×50 mm; Mobile Phase: 46-56% ACN gradient in 6 min, Modified with 0.1% TFA A: Water, B: Acetonitrile; Flow Rate: 2.0 mL/min; Run time: 15 min; Fraction collection: UV 210 nm) to afford the titled compound, a white solid as a TFA salt;

LCMS: Method S: ELSD: Rt 1.46 mins; MS m/z 928.3 [(M/3)$^+$H]$^+$

It can be seen that the conjugates of the invention have similar or improved efficacy as compared to the non-conjugated biomolecule but additionally the conjugates of the invention have improved plasma stability compared to the non-conjugated biomolecule. The conjugates in the examples above have been found to have a plasma stability higher than 5 h, higher than 10 h, higher than 20 h, higher than 30 h, higher than 40 h, and in some cases higher than 50 h.

Having thus described exemplary embodiments of the present invention, it should be noted by those of ordinary skill in the art that the within disclosures are exemplary only and that various other alternatives, adaptations, and modifications may be made within the scope of the present invention. Accordingly, the present invention is not limited to the specific embodiments as illustrated therein.

What is claimed is:

1. A conjugate comprising a biomolecule linked to a fatty acid via a linker
   wherein the fatty acid has the following Formulae A1:

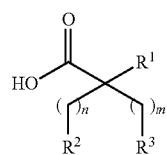

$$A1$$

wherein:
$R^1$ is $CO_2H$;
$R^2$, $R^3$ and are independently of each other H, OH, $CO_2H$, —CH=$CH_2$ or —C≡CH; and n and m are independently of each other an integer between 6 and 30; and
wherein the biomolecule is MH(199-308)hGDF15 (SEQ ID NO: 4), MHA(200-308)hGDF15 (SEQ ID NO: 6), AHA(200-308)hGDF15 (SEQ ID NO: 7), AH(199-308)hGDF15 (SEQ ID NO: 5), MHHHHHHM-hGDF15 (SEQ ID NO: 2), MHHHHHH-hGDF15 (SEQ ID NO: 1), or his-hGDF15; or a dimer thereof, wherein his-hGDF15 is hGDF15(197-308) wherein a tag, comprising 1 to 6 histidine amino acids and optionally 1 or 2 methionine amino acids, has been added to the N-terminus of hGDF15;
or an amide, ester, or pharmaceutically acceptable salt thereof.

2. The conjugate according to claim 1, wherein the fatty acid is selected from:

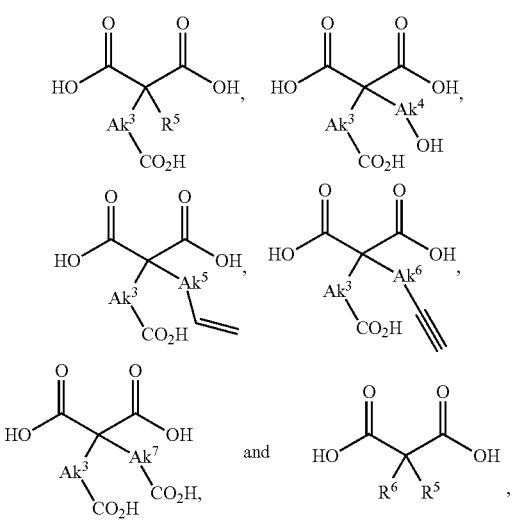

wherein $Ak^3$, $Ak^4$, $Ak^5$, $Ak^6$ and $Ak^7$ are independently a ($C_{8-20}$)alkylene, and $R^5$ and $R^6$ are independently linear ($C_{8-20}$)alkyl, or an amide, an ester or a pharmaceutically acceptable salt thereof.

3. The conjugate according to claim 1, wherein the fatty acid is selected from:

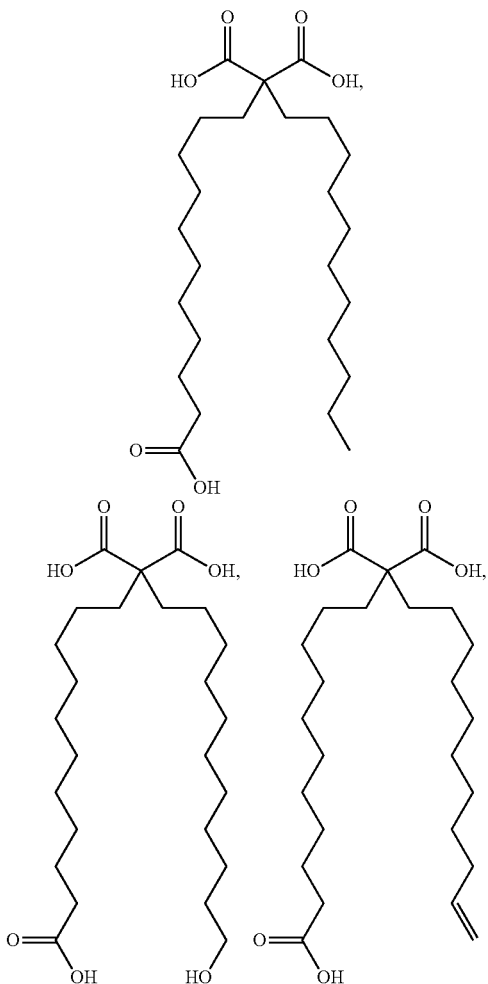

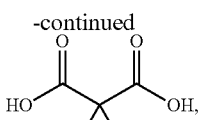

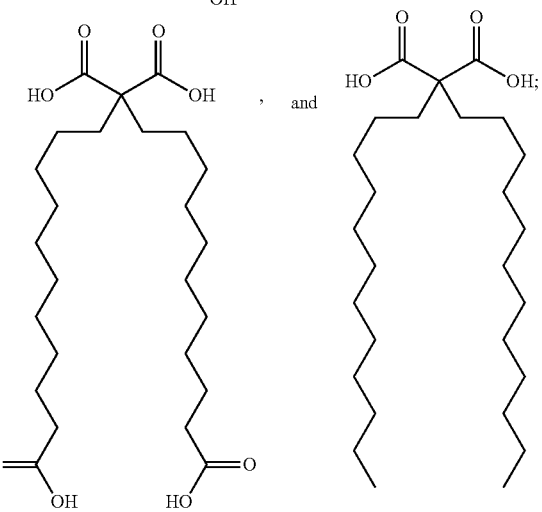

or an amide, ester, or a pharmaceutically acceptable salt thereof.

4. The conjugate according to claim 1, wherein the linker comprises alkyl, alkenyl, cycloalkyl, aryl, heteroaryl, heterocyclyl, polyethylene glycol, or one or more natural or unnatural amino acids, or combination thereof, wherein each of the alkyl, alkenyl, cycloalkyl, aryl, heteroaryl, heterocyclyl, polyethylene glycol and/or the natural or unnatural amino acids are optionally combined and linked together or linked to the biomolecule and/or to the fatty acid moiety via a chemical group selected from —C(O)O—, —OC(O)—, —NHC(O)—, —C(O)NH—, —O—, —NH—, —S—, —C(O)—, —OC(O)NH—, —NHC(O)—O—, =NH—O—, =NH—NH — and =NH—N(alkyl)-; or an amide, ester or a pharmaceutically acceptable salt thereof.

5. The conjugate according to claim 1, wherein the linker comprises an unbranched oligo ethylene glycol moiety of Formula:

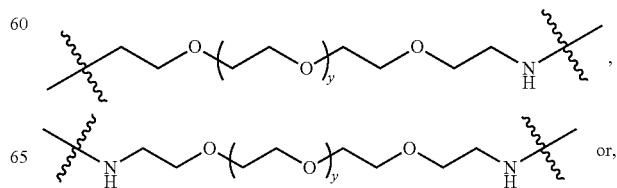

307

-continued

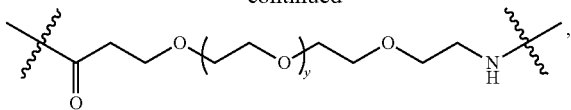

wherein y is 0 to 34; or an amide, an ester or a pharmaceutically acceptable salt thereof.

6. The conjugate according to claim 1, wherein the linker comprises a heterocyclic moiety of the following Formula:

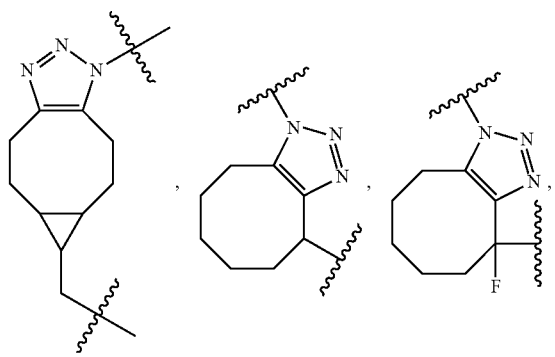

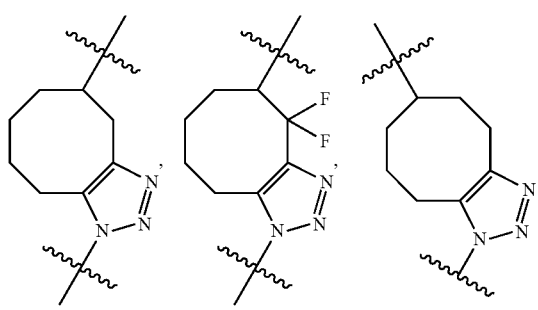

308

-continued

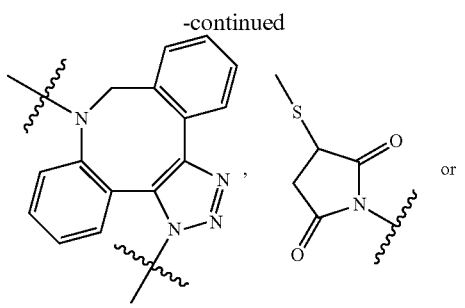
or

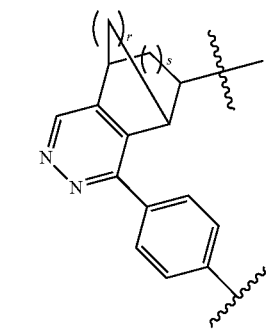

wherein r is an integer of 0 to 2 and s is an integer of 0 to 3;
or an amide, an ester or a pharmaceutically acceptable salt thereof.

7. The conjugate according to claim 1, wherein the linker comprises one or more amino acids independently selected from histidine, methionine, alanine, glutamine, asparagine and glycine; or an amide, an ester or a pharmaceutically acceptable salt thereof.

8. A conjugate according to claim 1, wherein the biomolecule linked to the fatty acid via a linker has one of the following Formulae:

FORMULA C

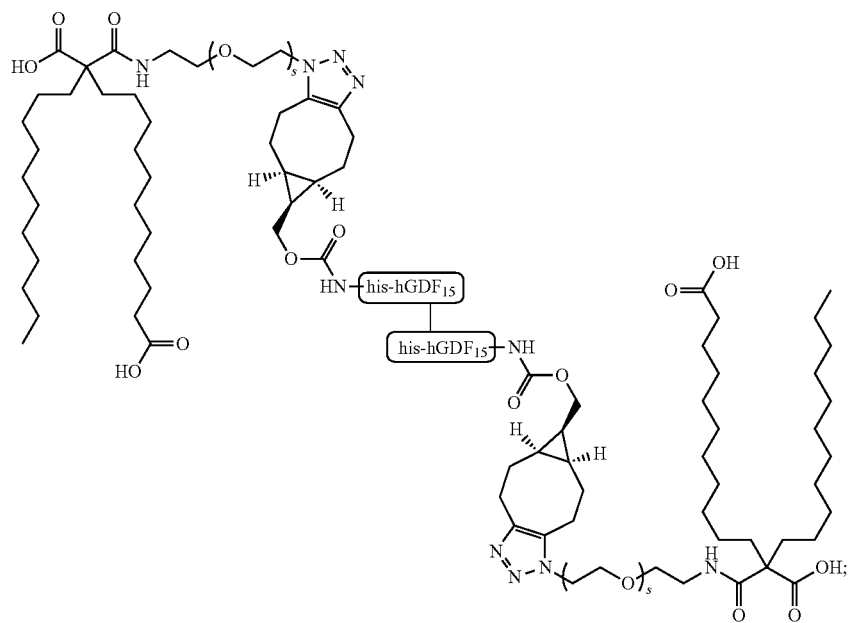

FORMULA D

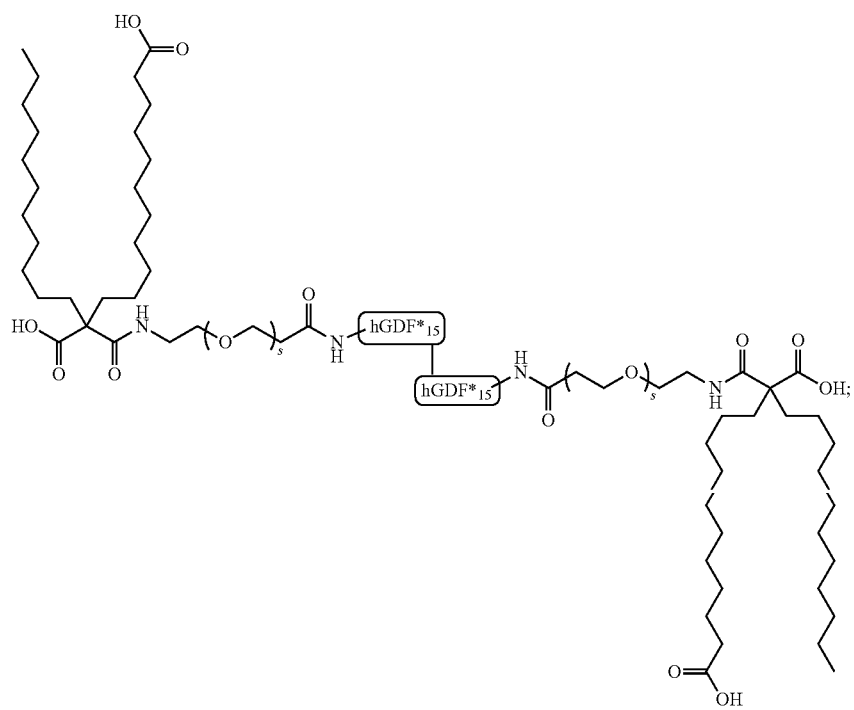

FORMULA E

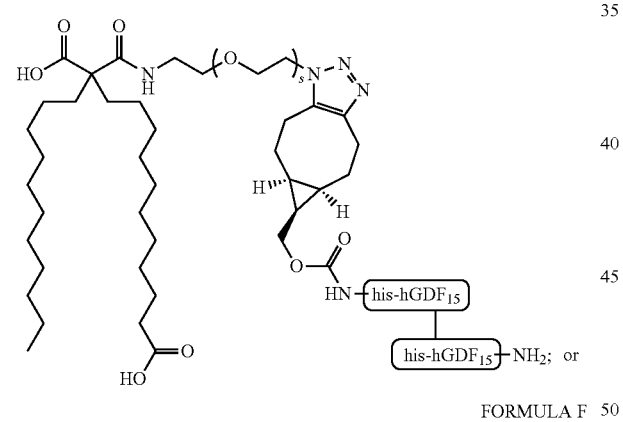

FORMULA F

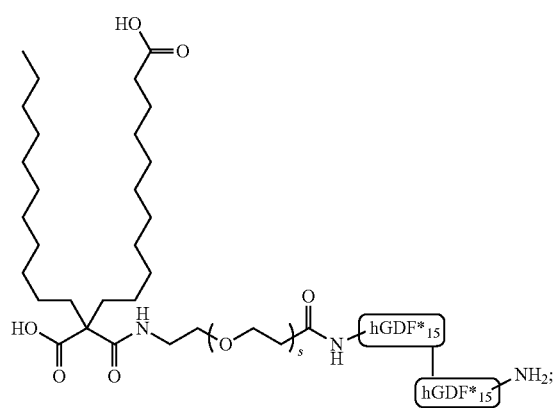

wherein in Formulae C and D, both monomeric units of his-hGDF15 or of hGDF15* are linked to the fatty acid moiety via a linker at the N-terminus of each his-hGDF15 monomeric unit and at the N-terminus of each hGDF15* monomeric unit;

wherein in Formulae E and F, only one of the monomeric unit of his-hGDF15 or of hGDF15* is linked to the fatty acid moiety via a linker at the N-terminus; and wherein in Formulae D and F, hGDF15* is MH(199-308) hGDF15 (SEQ ID NO:4), MHA(200-308)hGDF15 (SEQ ID NO:6), AHA(200-308)hGDF15 (SEQ ID NO:7), AH(199-308)hGDF15 (SEQ ID NO:5), MHH-HHHH-hGDF15 (SEQ ID NO:2), or MHHHHHH-hGDF15 (SEQ ID NO:1);

wherein in Formulae C, D, E and F, s is an integer between 20-30; and wherein in Formulae C, D, E and F, the line between the 2 monomeric units of his-hDGF15 or the 2 monomeric units of hGDF15* represent a disulfide bond.

9. A mixture comprising the conjugate according to claim 8 having Formula C and the conjugate according to claim 8 having Formula E or a mixture comprising the conjugate according to claim 8 having Formula D and the conjugate according to claim 8 having Formula F.

10. The conjugate according to claim 8, wherein the biomolecule linked to a fatty acid via a linkers is Of Formula G or of Formula H:

Formula G

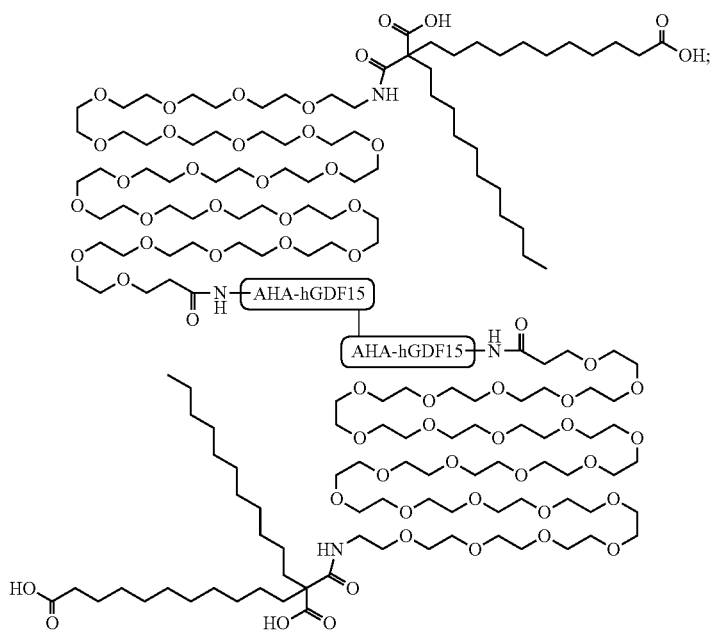

FORMULA H

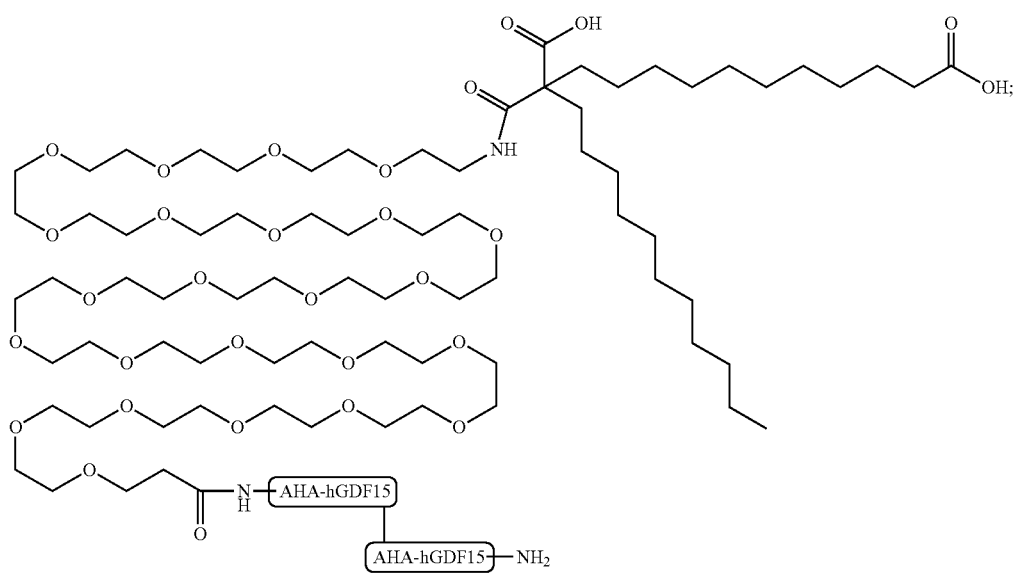

wherein AHA-hGDF15 is AHA(200-308)hGDF15 (SEQ ID NO: 7) and the fatty acid is linked via a linker at the N-terminus of one AHA-hGDF15 monomeric unit in Formula H or via a linker at both the N-terminus of each of the of two AHA-hGDF15 monomeric units in Formula G, and wherein the line between the two AHA-hGDF15 units represent a disulfide bond.

11. A mixture comprising the conjugate according to claim 10 having Formula G and the conjugate according to claim 10 having Formula H.

12. The conjugate according to claim 1, wherein the fatty acid moiety is attached the N-terminus of the biomolecule via a linker; or an amide, an ester or a pharmaceutically acceptable salt thereof.

13. The conjugate according to claim 1, wherein the conjugate has a plasma stability half-life of more than 10 hours, more than 20 hours or more than 30 hours.

14. The conjugate according to claim 1, where the improvement of plasma stability compared to the non-conjugated biomolecule is 2 fold, 5 fold, 10 fold, 20 fold, 30 fold, 40 fold, 50 fold, or 75 fold.

15. A combination comprising a therapeutically effective amount of a conjugate according to claim 1, or an amide, an ester or a pharmaceutically acceptable salt thereof; and one or more therapeutically active co-agent.

16. The combination according to claim 15, wherein the co-agent is selected from antidiabetic agent, hypolipidemic agent, anti-obesity agents, anti-hypertensive agents, and agonists of peroxisome proliferator-activator receptors.

17. The combination according to claim 16, wherein the co-agent is selected from insulin, insulin derivatives and mimetics; insulin secretagogues; glyburide, glimepiridine; insulinotropic sulfonylurea receptor ligands; thiazolidinediones, pioglitazone, balaglitazone, rivoglitazone, netoglitazone, troglitazone, englitazone, ciglitazone, adaglitazone, darglitazone, Cholesteryl ester transfer protein (CETP) inhibitors, GSK3 (glycogen synthase kinase-3) inhibitors; Retinoid X receptor ligands; sodium-dependent glucose cotransporter inhibitors; glycogen phosphorylase A inhibitors; biguanides; alpha-glucosidase inhibitors, GLP-1 (glucagon like peptide-1), GLP-1 analogs, GLP-1 mimetics; DPPIV (dipeptidyl peptidase IV) inhibitors, 3-hydroxy-3-methyl-glutaryl coenzyme A (HMG-CoA) reductase inhibitors; squalene synthase inhibitors; FXR (farnesoid X receptor), LXR (liver X receptor) ligands; cholestyramine; fibrates; nicotinic acid, aspirin; orlistat or rimonabant; loop diuretics, furosemide, torsemide; angiotensin converting enzyme (ACE) inhibitors; inhibitors of the Na-K-ATPase membrane pump; neutralendopeptidase (NEP) inhibitors; ACE/NEP dual inhibitors; angiotensin II antagonists; renin inhibitors; β-adrenergic receptor blockers; inotropic agents, dobutamine, milrinone; calcium channel blockers; aldosterone receptor antagonists; aldosterone synthase inhibitors; fenofibrate, pioglitazone, rosiglitazone, tesaglitazar, BMS-298585, and L-796449.

18. A pharmaceutical composition comprising a therapeutically effective amount of a conjugate according to claim 1; or an amide, an ester or a pharmaceutically acceptable salt thereof, and one or more pharmaceutically acceptable carriers.

19. A combination comprising a therapeutically effective amount of a mixture of conjugates according to claim 11; and one or more therapeutically active co-agent.

20. The combination according to claim 19, wherein the co-agent is selected from antidiabetic agent, hypolipidemic agent, anti-obesity agents, anti-hypertensive agents, and agonists of peroxisome proliferator-activator receptors.

21. The combination according to claim 20, wherein the co-agent is selected from insulin, insulin derivatives and mimetics; insulin secretagogues; glyburide, glimepiridine; insulinotropic sulfonylurea receptor ligands; thiazolidinediones, pioglitazone, balaglitazone, rivoglitazone, netoglitazone, troglitazone, englitazone, ciglitazone, adaglitazone, darglitazone, Cholesteryl ester transfer protein (CETP) inhibitors, GSK3 (glycogen synthase kinase-3) inhibitors; Retinoid X receptor ligands; sodium-dependent glucose cotransporter inhibitors; glycogen phosphorylase A inhibitors; biguanides; alpha-glucosidase inhibitors, GLP-1 (glucagon like peptide-1), GLP-1 analogs, GLP-1mimetics; DPPIV (dipeptidyl peptidase IV) inhibitors, 3-hydroxy-3-methyl-glutaryl coenzyme A (HMG-CoA) reductase inhibitors; squalene synthase inhibitors; FXR (farnesoid X receptor), LXR (liver X receptor) ligands; cholestyramine; fibrates; nicotinic acid, aspirin; orlistat or rimonabant; loop diuretics, furosemide, torsemide; angiotensin converting enzyme (ACE) inhibitors; inhibitors of the Na-K-ATPase membrane pump; neutralendopeptidase (NEP) inhibitors; ACE/NEP dual inhibitors; angiotensin II antagonists; renin inhibitors; β-adrenergic receptor blockers; inotropic agents, dobutamine, milrinone; calcium channel blockers; aldosterone receptor antagonists; aldosterone synthase inhibitors; fenofibrate, pioglitazone, rosiglitazone, tesaglitazar, BMS-298585, and L-796449.

22. A pharmaceutical composition comprising a therapeutically effective amount of a mixture of conjugates according to claim 11, and one or more pharmaceutically acceptable carriers.

23. The conjugate according to claim 1, wherein the biomolecule is MH(199-308)hGDF15 (SEQ ID NO:4), MHA(200-308)hGDF15 (SEQ ID NO:6), AHA(200-308) hGDF15 (SEQ ID NO:7) or AH(199-308)hGDF15 (SEQ ID NO:5); or a dimer thereof.

24. The mixture of claim 11, wherein the mixture is a 1:1 molar ratio of a conjugate of Formula G and a conjugate of Formula H.

* * * * *

UNITED STATES PATENT AND TRADEMARK OFFICE
CERTIFICATE OF CORRECTION

Page 1 of 1

PATENT NO. : 10,588,980 B2
APPLICATION NO. : 14/738272
DATED : March 17, 2020
INVENTOR(S) : Bruce et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 543 days.

Signed and Sealed this
First Day of September, 2020

Andrei Iancu
*Director of the United States Patent and Trademark Office*